United States Patent
Nicolaou et al.

(10) Patent No.: US 11,584,754 B2
(45) Date of Patent: Feb. 21, 2023

(54) DERIVATIVES OF THAILANSTATIN A, METHODS OF TREATMENT AND METHODS OF SYNTHESIS THEREOF

(71) Applicant: WILLIAM MARSH RICE UNIVERSITY, Houston, TX (US)

(72) Inventors: Kyriacos C. Nicolaou, Houston, TX (US); Derek Rhoades, Houston, TX (US); Soundarapandian M. Kumar, Houston, TX (US); Manas R. Pattanayak, Paris (FR); Manjunath Lamani, Boston, MA (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 16/308,334

(22) PCT Filed: Jun. 8, 2017

(86) PCT No.: PCT/US2017/036589
§ 371 (c)(1),
(2) Date: Dec. 7, 2018

(87) PCT Pub. No.: WO2017/214423
PCT Pub. Date: Dec. 14, 2017

(65) Prior Publication Data
US 2020/0024283 A1 Jan. 23, 2020

Related U.S. Application Data

(60) Provisional application No. 62/347,448, filed on Jun. 8, 2016.

(51) Int. Cl.
| | |
|---|---|
| C07D 493/10 | (2006.01) |
| A61K 47/68 | (2017.01) |
| A61P 35/00 | (2006.01) |
| A61K 31/35 | (2006.01) |
| A61K 31/352 | (2006.01) |
| A61K 31/453 | (2006.01) |
| A61K 31/5377 | (2006.01) |
| C07D 407/06 | (2006.01) |

(52) U.S. Cl.
CPC ............ *C07D 493/10* (2013.01); *A61K 31/35* (2013.01); *A61K 31/352* (2013.01); *A61K 31/453* (2013.01); *A61K 31/5377* (2013.01); *A61K 47/6803* (2017.08); *A61K 47/6851* (2017.08); *A61P 35/00* (2018.01); *C07D 407/06* (2013.01)

(58) Field of Classification Search
CPC .. C07D 309/10; C07D 405/12; C07D 493/20; A61K 31/35; A61K 31/352; A61K 31/435; A61K 31/5377
See application file for complete search history.

(56) References Cited

U.S. PATENT DOCUMENTS

| | | |
|---|---|---|
| 2008/0096879 A1 | 4/2008 | Koide et al. |
| 2014/0134193 A1 | 5/2014 | Dirico et al. |
| 2014/0221207 A1 | 8/2014 | Asolkar et al. |

FOREIGN PATENT DOCUMENTS

| | | | |
|---|---|---|---|
| WO | WO 2009/031999 | 3/2009 | |
| WO | WO 2014/068443 | 5/2014 | |
| WO | WO-2014068443 A1 * | 5/2014 | ............ A61K 31/35 |
| WO | WO 2015/077370 | 5/2015 | |

OTHER PUBLICATIONS

Liu (Journal of Natural Products vol. 76 pp. 685-693. Published 2013) (Year: 2013).*
Liu et al (Journal of Natural Products vol. 76 p. 685-693. Published 2013). (Year: 2013).*
Extended European Search Report issued in European Application No. 17811026.8, dated Oct. 29, 2019.
He et al., "Cytotoxic Spliceostatins from Burkholderia sp. and Their Semisynthetic Analogue," *Journal of Natural Products*, 77:1864-1870, 2014.
Liu et al., "Genomics-Guided Discovery of Thailanstatins A, B, and C as Pre-mRNA Splicing Inhibitors and Antiproliferative Agents from Burkholderia thailandensis MSMB43," *Journal of Natural Products*, 76:685-693, 2013.
Liu et al., "Isolation and characterization of spliceostatin B, a new analogue of FR901464, from *Pseudomonas* sp. No. 2663," *Journal of Antibiotics*, 66:555-558, 2013.
PCT International Preliminary Report on Patentability issued in PCT/US2017/036589, dated Dec. 11, 2018.
PCT Search Report and Written Opinion issued in PCT/US2017/036589, dated Nov. 28, 2017.

* cited by examiner

*Primary Examiner* — Theodore R. Howell
*Assistant Examiner* — George W Kosturko
(74) *Attorney, Agent, or Firm* — Parker Highlander PLLC

(57) ABSTRACT

In one aspect, the present disclosure provides analogs of thailanstatin of the formula wherein the variables are as defined herein. In another aspect, the present disclosure also provides methods of preparing the compounds disclosed herein. In another aspect, the present disclosure also provides pharmaceutical compositions and methods of use of the compounds disclosed herein.

(I)

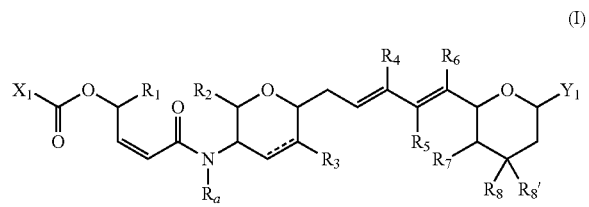

4 Claims, 8 Drawing Sheets

DERIVATIVES OF THAILANSTATIN A, METHODS OF TREATMENT AND METHODS OF SYNTHESIS THEREOF

This application is a national phase application under 35 U.S.C. § 371 of International Application No. PCT/US2017/036589 filed on Jun. 8, 2017 and claims the benefit of priority to U.S. Provisional Application No. 62/347,448, filed on Jun. 8, 2016, the entire contents of which are hereby incorporated by reference.

BACKGROUND

The development of this disclosure was funded in part by the Cancer Prevention and Research Institute of Texas (CPRIT) under Grant No. R1226 and the Welch Foundation under Grant No. C-1819.

1. Field

This disclosure relates to the fields of medicine, pharmacology, chemistry, and oncology. In particular, new compounds, compositions, methods of treatment, and methods of synthesis relating to analogs of thailanstatin and drug conjugates thereof are disclosed.

2. Related Art

Thailanstatin A is a natural product isolated from *Thailandensis burkholderia* MSMB43 which is shown to be active in a number of cancer cell lines and is believed to target the spliceosome (Liu, et al., 2013; He, et al., 2014). Given this unique mechanism, this series of compounds represents a unique combination of high activity and different mode of action. Therefore, the development of new analogs of these compounds is of commercial interest. Development of such analogs has been limited by the reliance on the natural product which has only been available from the source.

Furthermore, improving the synthetic pathway to obtain these compounds may allow access to additional analogs with groups which might be incompatible with the previous methods. These methods can allow access to compounds which contain functional handles for conjugating to cell targeting moieties such as antibodies. Thus, new methods of preparing these compounds as well as new analogs are needed.

SUMMARY

The present disclosure provides compounds of the formula:

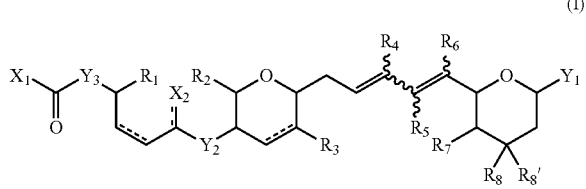

(I)

wherein:

$X_1$ is amino or alkyl$_{(C \leq 8)}$, cycloalkyl$_{(C \leq 8)}$, aryl$_{(C \leq 12)}$, heteroaryl$_{(C \leq 12)}$, heterocycloalkyl$_{(C \leq 12)}$, alkylamino$_{(C \leq 12)}$, dialkylamino$_{(C \leq 12)}$, arylamino$_{(C \leq 12)}$, alkylarylamino$_{(C \leq 18)}$, diarylamino$_{(C \leq 18)}$, or a substituted version of any of these groups;

$X_2$ is hydrogen, hydroxy, or oxo;

$Y_1$ is alkyl$_{(C \leq 8)}$, substituted alkyl$_{(C \leq 8)}$, or -A-$R_9$; wherein:

A is alkanediyl$_{(C \leq 6)}$, alkenediyl$_{(C \leq 6)}$, or a substituted version of either of these groups; and $R_9$ is amino, carboxy, or hydroxy, or heteroaryl$_{(C \leq 8)}$, substituted heteroaryl$_{(C \leq 8)}$, alkylamino$_{(C \leq 8)}$, substituted alkylamino$_{(C \leq 8)}$, dialkylamino$_{(C \leq 8)}$, substituted dialkylamino$_{(C \leq 8)}$, or —C(O)$R_b$, wherein:

$R_b$ is amino, hydroxy, or alkoxy$_{(C \leq 8)}$, aryloxy$_{(C \leq 8)}$, aralkoxy$_{(C \leq 8)}$, alkylamino$_{(C \leq 8)}$, dialkylamino$_{(C \leq 8)}$, cycloalkylamino$_{(C \leq 8)}$, dicycloalkylamino$_{(C \leq 12)}$, or a substituted version of any of these groups;

$Y_2$ and $Y_3$ are —O— or —NR$_a$—;

$R_a$, $R_1$, $R_2$, $R_3$, $R_4$, $R_5$ and $R_6$ are each independently selected from hydrogen, alkyl$_{(C \leq 8)}$, or substituted alkyl$_{(C \leq 8)}$;

$R_7$ is amino, halo, hydroxy, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 12)}$, or substituted dialkylamino$_{(C \leq 12)}$, or -$A_2$-$R_e$, wherein $A_2$ is —O— or —NR$_d$—, wherein $R_d$ is hydrogen, alkyl$_{(C \leq 8)}$, or substituted alkyl$_{(C \leq 8)}$; and $R_e$ is —C(O)$R_e$, wherein $R_e$ is amino, hydroxy, or alkyl$_{(C \leq 8)}$, heterocycloalkyl$_{(C \leq 8)}$, alkoxy$_{(C \leq 8)}$, alkylamino$_{(C \leq 8)}$, or dialkylamino$_{(C \leq 8)}$, or a substituted version of these five groups;

$R_8$ and $R_8'$ are each independently hydrogen, hydroxy, alkyl$_{(C \leq 8)}$, substituted alkyl$_{(C \leq 8)}$, or $R_8$ and $R_8'$ are taken together and are oxo, alkylidene$_{(C \leq 8)}$, substituted alkylidene$_{(C \leq 8)}$, or form a cycloalkyl or heterocycloalkyl group consisting of three to eight ring members;

provided that the compound is not:

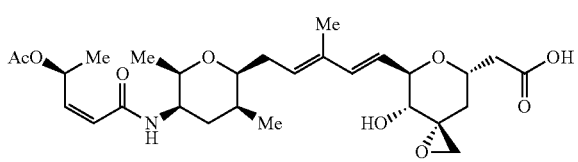 [SMILES: CC(=O)O[C@@H](C)/C=C\C(=O)N[C@@H]1C[C@H](C)[C@H](C/C=C(C)/C=C/[C@H]2O[C@H](CC(=O)O)C[C@@]3(CO3)[C@@H]2O)O[C@@H]1C]

or a pharmaceutically acceptable salt thereof.

In some embodiments,

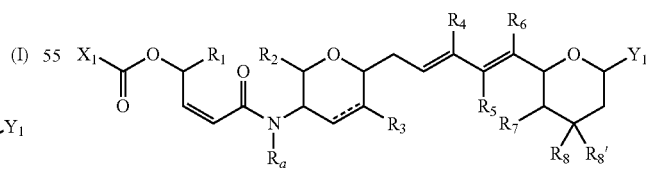

(II)

wherein:

$X_1$ is amino or alkyl$_{(C \leq 8)}$, cycloalkyl$_{(C \leq 8)}$, aryl$_{(C \leq 12)}$, heteroaryl$_{(C \leq 12)}$, heterocycloalkyl$_{(C \leq 12)}$, alkylamino$_{(C \leq 12)}$, dialkylamino$_{(C \leq 12)}$, arylamino$_{(C \leq 12)}$, alkylarylamino$_{(C \leq 18)}$, diarylamino$_{(C \leq 18)}$, or a substituted version of any of these groups;

$Y_1$ is alkyl$_{(C≤8)}$, substituted alkyl$_{(C≤8)}$, or -A-R$_9$; wherein:
A is alkanediyl$_{(C≤6)}$ or substituted alkanediyl$_{(C≤6)}$; and
R$_9$ is amino, carboxy, or hydroxy, or alkylamino$_{(C≤8)}$, substituted alkylamino$_{(C≤8)}$, dialkylamino$_{(C≤8)}$, substituted dialkylamino$_{(C≤8)}$, or —C(O)R$_b$, wherein:
R$_b$ is amino, hydroxy, or alkoxy$_{(C≤8)}$, aryloxy$_{(C≤8)}$, aralkoxy$_{(C≤8)}$, alkylamino$_{(C≤8)}$, dialkylamino$_{(C≤8)}$, cycloalkylamino$_{(C≤8)}$, dicycloalkylamino$_{(C≤12)}$, or a substituted version of any of these groups;

R$_a$, R$_1$, R$_2$, R$_3$, R$_4$, R$_5$ and R$_6$ are each independently selected from hydrogen, alkyl$_{(C≤8)}$, or substituted alkyl$_{(C≤8)}$;

R$_7$ is amino, halo, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤12)}$, or substituted dialkylamino$_{(C≤12)}$;

R$_8$ and R$_8$' are each independently hydroxy, alkyl$_{(C≤8)}$, substituted alkyl$_{(C≤8)}$, or R$_8$ and R$_8$' are taken together and are alkylidene$_{(C≤8)}$, substituted alkylidene$_{(C≤8)}$, or form a heterocycloalkyl group consisting of three to eight ring members;

provided that the compound is not:

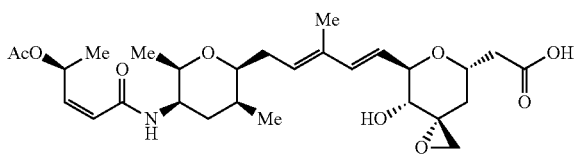 [SMILES: CC(=O)O[C@@H](C)/C=C\C(=O)N[C@@H]1C[C@H](C)[C@H](C/C=C(C)/C=C/[C@H]2O[C@H](CC(=O)O)C[C@@]3(CO3)[C@@H]2O)O[C@@H]1C]

or a pharmaceutically acceptable salt thereof. In some embodiments, the compounds are further defined as:

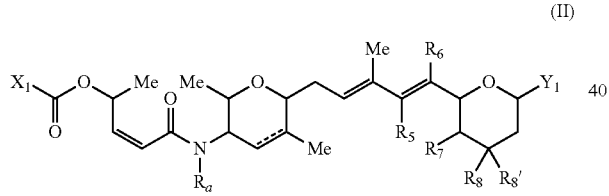

(II)

wherein:
X$_1$ is amino or alkyl$_{(C≤8)}$, cycloalkyl$_{(C≤8)}$, aryl$_{(C≤12)}$, heteroaryl$_{(C≤12)}$, heterocycloalkyl$_{(C≤12)}$, alkylamino$_{(C≤12)}$, dialkylamino$_{(C≤12)}$, arylamino$_{(C≤12)}$, alkylarylamino$_{(C≤18)}$, diarylamino$_{(C≤18)}$, or a substituted version of any of these groups;

Y$_1$ is alkyl$_{(C≤8)}$, substituted alkyl$_{(C≤8)}$, or -A-R$_9$; wherein:
A is alkanediyl$_{(C≤6)}$ or substituted alkanediyl$_{(C≤6)}$; and
R$_9$ is amino, carboxy, or hydroxy, or alkylamino$_{(C≤8)}$, substituted alkylamino$_{(C≤8)}$, dialkylamino$_{(C≤8)}$, substituted dialkylamino$_{(C≤8)}$, or —C(O)R$_b$, wherein:
R$_b$ is amino, hydroxy, or alkoxy$_{(C≤8)}$, aryloxy$_{(C≤8)}$, aralkoxy$_{(C≤8)}$, alkylamino$_{(C≤8)}$, dialkylamino$_{(C≤8)}$, cycloalkylamino$_{(C≤8)}$, dicycloalkylamino$_{(C≤12)}$, or a substituted version of any of these groups;

R$_a$, R$_5$, and R$_6$ are each independently selected from hydrogen, alkyl$_{(C≤8)}$, or substituted alkyl$_{(C≤8)}$;

R$_7$ is amino, halo, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤12)}$, or substituted dialkylamino$_{(C≤12)}$;

R$_8$ and R$_8$' are each independently hydroxy, alkyl$_{(C≤8)}$, substituted alkyl$_{(C≤8)}$, or R$_8$ and R$_8$' are taken together and are alkylidene$_{(C≤8)}$, substituted alkylidene$_{(C≤8)}$, or form a heterocycloalkyl group consisting of three to eight ring members; or wherein:
X$_1$ is amino or alkyl$_{(C≤8)}$, cycloalkyl$_{(C≤8)}$, aryl$_{(C≤12)}$, heteroaryl$_{(C≤12)}$, heterocycloalkyl$_{(C≤12)}$, alkylamino$_{(C≤12)}$, dialkylamino$_{(C≤12)}$, arylamino$_{(C≤12)}$, alkylarylamino$_{(C≤18)}$, diarylamino$_{(C≤18)}$, or a substituted version of any of these groups;

Y$_1$ is alkyl$_{(C≤8)}$, substituted alkyl$_{(C≤8)}$, or -A-R$_9$; wherein:
A is alkanediyl$_{(C≤6)}$, alkenediyl$_{(C≤6)}$, or a substituted version of either of these groups; and
R$_9$ is amino, carboxy, or hydroxy, or heteroaryl$_{(C≤8)}$, substituted heteroaryl$_{(C≤8)}$, alkylamino$_{(C≤8)}$, substituted alkylamino$_{(C≤8)}$, dialkylamino$_{(C≤8)}$, substituted dialkylamino$_{(C≤8)}$, or —C(O)R$_b$, wherein:
R$_b$ is amino, hydroxy, or alkoxy$_{(C≤8)}$, aryloxy$_{(C≤8)}$, aralkoxy$_{(C≤8)}$, alkylamino$_{(C≤8)}$, dialkylamino$_{(C≤8)}$, cycloalkylamino$_{(C≤8)}$, dicycloalkylamino$_{(C≤12)}$, or a substituted version of any of these groups;

R$_a$, R$_5$, and R$_6$ are each independently selected from hydrogen, alkyl$_{(C≤8)}$, or substituted alkyl$_{(C≤8)}$;

R$_7$ is amino, halo, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤12)}$, or substituted dialkylamino$_{(C≤12)}$, or -A$_2$-R$_e$, wherein A$_2$ is —O— or —NR$_d$—, wherein R$_d$ is hydrogen, alkyl$_{(C≤8)}$, or substituted alkyl$_{(C≤8)}$; and R$_e$ is —C(O)R$_e$, wherein R$_e$ is amino, hydroxy, or alkyl$_{(C≤8)}$, heterocycloalkyl$_{(C≤8)}$, alkoxy$_{(C≤8)}$, alkylamino$_{(C≤8)}$, or dialkylamino$_{(C≤8)}$, or a substituted version of these five groups;

R$_8$ and R$_8$' are each independently hydrogen, hydroxy, alkyl$_{(C≤8)}$, substituted alkyl$_{(C≤8)}$, or R$_8$ and R$_8$' are taken together and are oxo, alkylidene$_{(C≤8)}$, substituted alkylidene$_{(C≤8)}$, or form a cycloalkyl or heterocycloalkyl group consisting of three to eight ring members;

provided that the compound is not:

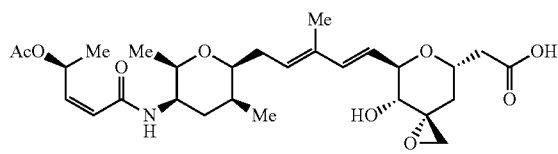 [SMILES: CC(=O)O[C@@H](C)/C=C\C(=O)N[C@@H]1C[C@H](C)[C@H](C/C=C(C)/C=C/[C@H]2O[C@H](CC(=O)O)C[C@@]3(CO3)[C@@H]2O)O[C@@H]1C]

or a pharmaceutically acceptable salt thereof. In some embodiments, the compounds are further defined as:

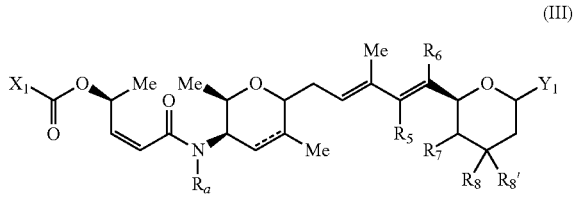

(III)

wherein:
X$_1$ is amino or alkyl$_{(C≤8)}$, cycloalkyl$_{(C≤8)}$, aryl$_{(C≤12)}$, heteroaryl$_{(C≤12)}$, heterocycloalkyl$_{(C≤12)}$, alkylamino$_{(C≤12)}$, dialkylamino$_{(C≤12)}$, arylamino$_{(C≤12)}$, alkylarylamino$_{(C≤18)}$, diarylamino$_{(C≤18)}$, or a substituted version of any of these groups;

$Y_1$ is alkyl$_{(C\leq8)}$, substituted alkyl$_{(C\leq8)}$, or -A-R$_9$; wherein:
A is alkanediyl$_{(C\leq6)}$ or substituted alkanediyl$_{(C\leq6)}$; and
R$_9$ is amino, carboxy, or hydroxy, or alkylamino$_{(C\leq8)}$, substituted alkylamino$_{(C\leq8)}$, dialkylamino$_{(C\leq8)}$, substituted dialkylamino$_{(C\leq8)}$, or —C(O)R$_b$, wherein:
R$_b$ is amino, hydroxy, or
alkoxy$_{(C\leq8)}$, aryloxy$_{(C\leq8)}$, aralkoxy$_{(C\leq8)}$, alkylamino$_{(C\leq8)}$, dialkylamino$_{(C\leq8)}$, cycloalkylamino$_{(C\leq8)}$, dicycloalkylamino$_{(C\leq12)}$, or a substituted version of any of these groups;
R$_a$, R$_5$, and R$_6$ are each independently selected from hydrogen, alkyl$_{(C\leq8)}$, or substituted alkyl$_{(C\leq8)}$;
R$_7$ is amino, halo, hydroxy, alkoxy$_{(C\leq8)}$, substituted alkoxy$_{(C\leq8)}$, alkylamino$_{(C\leq8)}$, substituted alkylamino$_{(C\leq8)}$, dialkylamino$_{(C\leq12)}$, or substituted dialkylamino$_{(C\leq12)}$;
R$_8$ and R$_8$' are each independently hydroxy, alkyl$_{(C\leq8)}$, substituted alkyl$_{(C\leq8)}$, or R$_8$ and R$_8$' are taken together and are alkylidene$_{(C\leq8)}$, substituted alkylidene$_{(C\leq8)}$, or form a heterocycloalkyl group consisting of three to eight ring members;
wherein:
X$_1$ is amino or alkyl$_{(C\leq8)}$, cycloalkyl$_{(C\leq8)}$, aryl$_{(C\leq12)}$, heteroaryl$_{(C\leq12)}$, heterocycloalkyl$_{(C\leq12)}$, alkylamino$_{(C\leq12)}$, dialkylamino$_{(C\leq12)}$, arylamino$_{(C\leq12)}$, alkylarylamino$_{(C\leq18)}$, diarylamino$_{(C\leq18)}$, or a substituted version of any of these groups;
Y$_1$ is alkyl$_{(C\leq8)}$, substituted alkyl$_{(C\leq8)}$, or -A-R$_9$; wherein:
A is alkanediyl$_{(C\leq6)}$, alkenediyl$_{(C\leq6)}$, or a substituted version of either of these groups; and
R$_9$ is amino, carboxy, or hydroxy, or heteroaryl$_{(C\leq8)}$, substituted heteroaryl$_{(C\leq8)}$, alkylamino$_{(C\leq8)}$, substituted alkylamino$_{(C\leq8)}$, dialkylamino$_{(C\leq8)}$, substituted dialkylamino$_{(C\leq8)}$, or —C(O)R$_b$, wherein:
R$_b$ is amino, hydroxy, or
alkoxy$_{(C\leq8)}$, aryloxy$_{(C\leq8)}$, aralkoxy$_{(C\leq8)}$, alkylamino$_{(C\leq8)}$, dialkylamino$_{(C\leq8)}$, cycloalkylamino$_{(C\leq8)}$, dicycloalkylamino$_{(C\leq12)}$, or a substituted version of any of these groups;
R$_a$, R$_5$, and R$_6$ are each independently selected from hydrogen, alkyl$_{(C\leq8)}$, or substituted alkyl$_{(C\leq8)}$;
R$_7$ is amino, halo, hydroxy, alkoxy$_{(C\leq8)}$, substituted alkoxy$_{(C\leq8)}$, alkylamino$_{(C\leq8)}$, substituted alkylamino$_{(C\leq8)}$, dialkylamino$_{(C\leq12)}$, or substituted dialkylamino$_{(C\leq12)}$, or -A$_2$-R$_e$, wherein A$_2$ is —O— or —NR$_d$—, wherein R$_d$ is hydrogen, alkyl$_{(C\leq8)}$, or substituted alkyl$_{(C\leq8)}$; and R$_e$ is —C(O)R$_e$, wherein R$_e$ is amino, hydroxy, or alkyl$_{(C\leq8)}$, heterocycloalkyl$_{(C\leq8)}$, alkoxy$_{(C\leq8)}$, alkylamino$_{(C\leq8)}$, or dialkylamino$_{(C\leq8)}$, or a substituted version of these five groups;
R$_8$ and R$_8$' are each independently hydrogen, hydroxy, alkyl$_{(C\leq8)}$, substituted alkyl$_{(C\leq8)}$, or R$_8$ and R$_8$' are taken together and are oxo, alkylidene$_{(C\leq8)}$, substituted alkylidene$_{(C\leq8)}$, or form a cycloalkyl or heterocycloalkyl group consisting of three to eight ring members;
provided that the compound is not:

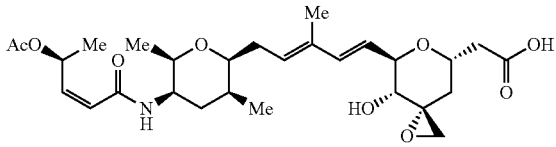 [SMILES: CC(=O)O[C@@H](C)/C=C\C(=O)N[C@@H]1C[C@H](C)[C@H](C/C=C(C)/C=C/[C@H]2O[C@H](CC(=O)O)C[C@@]3(CO3)[C@@H]2O)O[C@@H]1C]

or a pharmaceutically acceptable salt thereof. In some embodiments, the compounds are further defined as:

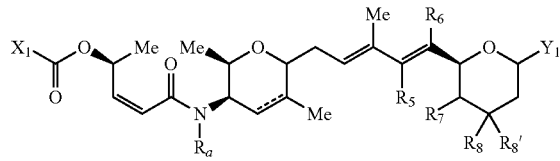

(IV)

wherein:
X$_1$ is amino or alkyl$_{(C\leq8)}$, cycloalkyl$_{(C\leq8)}$, aryl$_{(C\leq12)}$, heteroaryl$_{(C\leq12)}$, heterocycloalkyl$_{(C\leq12)}$, alkylamino$_{(C\leq12)}$, dialkylamino$_{(C\leq12)}$, arylamino$_{(C\leq12)}$, alkylarylamino$_{(C\leq18)}$, diarylamino$_{(C\leq18)}$, or a substituted version of any of these groups;
Y$_1$ is alkyl$_{(C\leq8)}$, substituted alkyl$_{(C\leq8)}$, or -A-R$_9$; wherein:
A is alkanediyl$_{(C\leq6)}$ or substituted alkanediyl$_{(C\leq6)}$; and
R$_9$ is amino, carboxy, or hydroxy, or alkylamino$_{(C\leq8)}$, substituted alkylamino$_{(C\leq8)}$, dialkylamino$_{(C\leq8)}$, substituted dialkylamino$_{(C\leq8)}$, or —C(O)R$_b$, wherein:
R$_b$ is amino, hydroxy, or
alkoxy$_{(C\leq8)}$, aryloxy$_{(C\leq8)}$, aralkoxy$_{(C\leq8)}$, alkylamino$_{(C\leq8)}$, dialkylamino$_{(C\leq8)}$, cycloalkylamino$_{(C\leq8)}$, dicycloalkylamino$_{(C\leq12)}$, or a substituted version of any of these groups;
R$_a$, R$_5$, and R$_6$ are each independently selected from hydrogen, alkyl$_{(C\leq8)}$, or substituted alkyl$_{(C\leq8)}$;
R$_7$ is amino, halo, hydroxy, alkoxy$_{(C\leq8)}$, substituted alkoxy$_{(C\leq8)}$, alkylamino$_{(C\leq8)}$, substituted alkylamino$_{(C\leq8)}$, dialkylamino$_{(C\leq12)}$, or substituted dialkylamino$_{(C\leq12)}$;
R$_8$ and R$_8$' are each independently hydroxy, alkyl$_{(C\leq8)}$, substituted alkyl$_{(C\leq8)}$, or R$_8$ and R$_8$' are taken together and are alkylidene$_{(C\leq8)}$, substituted alkylidene$_{(C\leq8)}$, or form a heterocycloalkyl group consisting of three to eight ring members;
wherein:
X$_1$ is amino or alkyl$_{(C\leq8)}$, cycloalkyl$_{(C\leq8)}$, aryl$_{(C\leq12)}$, heteroaryl$_{(C\leq12)}$, heterocycloalkyl$_{(C\leq12)}$, alkylamino$_{(C\leq12)}$, dialkylamino$_{(C\leq12)}$, arylamino$_{(C\leq12)}$, alkylarylamino$_{(C\leq18)}$, diarylamino$_{(C\leq18)}$, or a substituted version of any of these groups;
Y$_1$ is alkyl$_{(C\leq8)}$, substituted alkyl$_{(C\leq8)}$, or -A-R$_9$; wherein:
A is alkanediyl$_{(C\leq6)}$, alkenediyl$_{(C\leq6)}$, or a substituted version of either of these groups; and
R$_9$ is amino, carboxy, or hydroxy, or heteroaryl$_{(C\leq8)}$, substituted heteroaryl$_{(C\leq8)}$, alkylamino$_{(C\leq8)}$, substituted alkylamino$_{(C\leq8)}$, dialkylamino$_{(C\leq8)}$, substituted dialkylamino$_{(C\leq8)}$, or —C(O)R$_b$, wherein:
R$_b$ is amino, hydroxy, or
alkoxy$_{(C\leq8)}$, aryloxy$_{(C\leq8)}$, aralkoxy$_{(C\leq8)}$, alkylamino$_{(C\leq8)}$, dialkylamino$_{(C\leq8)}$, cycloalkylamino$_{(C\leq8)}$, dicycloalkylamino$_{(C\leq12)}$, or a substituted version of any of these groups;
R$_a$, R$_5$, and R$_6$ are each independently selected from hydrogen, alkyl$_{(C\leq8)}$, or substituted alkyl$_{(C\leq8)}$;
R$_7$ is amino, halo, hydroxy, alkoxy$_{(C\leq8)}$, substituted alkoxy$_{(C\leq8)}$, alkylamino$_{(C\leq8)}$, substituted alkylamino$_{(C\leq8)}$, dialkylamino$_{(C\leq12)}$, or substituted dialkylamino$_{(C\leq12)}$, or -A$_2$-R$_e$, wherein A$_2$ is —O— or —NR$_d$—, wherein R$_d$ is hydrogen, alkyl$_{(C\leq8)}$, or substituted alkyl$_{(C\leq8)}$; and R$_e$ is —C(O)R$_e$, wherein R$_e$ is amino, hydroxy, or alkyl$_{(C\leq8)}$, heterocycloalkyl$_{(C\leq8)}$, alkoxy$_{(C≤8)}$, alkylamino$_{(C≤8)}$, or dialkylamino$_{(C≤8)}$, or a substituted version of these five groups;

$R_8$ and $R_8'$ are each independently hydrogen, hydroxy, alkyl$_{(C≤8)}$, substituted alkyl$_{(C≤8)}$, or $R_8$ and $R_8'$ are taken together and are oxo, alkylidene$_{(C≤8)}$, substituted alkylidene$_{(C≤8)}$, or form a cycloalkyl or heterocycloalkyl group consisting of three to eight ring members;

provided that the compound is not:

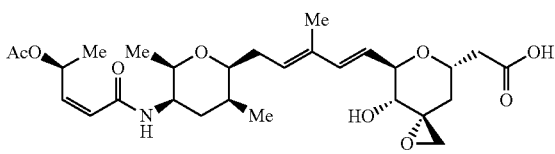 [SMILES: CC(=O)O[C@@H](C)/C=C\C(=O)N[C@@H]1C[C@H](C)[C@H](C/C=C(C)/C=C/[C@H]2O[C@H](CC(=O)O)C[C@@]3(CO3)[C@@H]2O)O[C@@H]1C]

or a pharmaceutically acceptable salt thereof. In some embodiments, the compounds are further defined as:

(V)

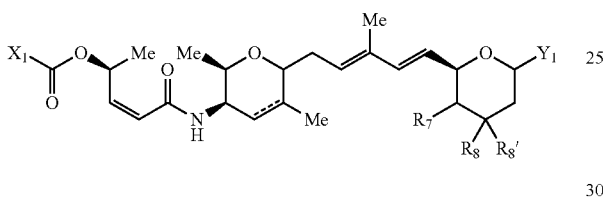

wherein:

$X_1$ is amino or alkyl$_{(C≤8)}$, cycloalkyl$_{(C≤8)}$, aryl$_{(C≤12)}$, heteroaryl$_{(C≤12)}$, heterocycloalkyl$_{(C≤12)}$, alkylamino$_{(C≤12)}$, dialkylamino$_{(C≤12)}$, arylamino$_{(C≤12)}$, alkylarylamino$_{(C≤18)}$, diarylamino$_{(C≤18)}$, or a substituted version of any of these groups;

$Y_1$ is alkyl$_{(C≤8)}$, substituted alkyl$_{(C≤8)}$, or -A-$R_9$; wherein:
A is alkanediyl$_{(C≤6)}$ or substituted alkanediyl$_{(C≤6)}$; and
$R_9$ is amino, carboxy, or hydroxy, or alkylamino$_{(C≤8)}$, substituted alkylamino$_{(C≤8)}$, dialkylamino$_{(C≤8)}$, substituted dialkylamino$_{(C≤8)}$, or —C(O)$R_b$, wherein:
$R_b$ is amino, hydroxy, or
alkoxy$_{(C≤8)}$, aryloxy$_{(C≤8)}$, aralkoxy$_{(C≤8)}$, alkylamino$_{(C≤8)}$, dialkylamino$_{(C≤8)}$, cycloalkylamino$_{(C≤8)}$, dicycloalkylamino$_{(C≤12)}$, or a substituted version of any of these groups;

$R_7$ is amino, halo, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤12)}$, or substituted dialkylamino$_{(C≤12)}$;

$R_8$ and $R_8'$ are each independently hydroxy, alkyl$_{(C≤8)}$, substituted alkyl$_{(C≤8)}$, or $R_8$ and $R_8'$ are taken together and are alkylidene$_{(C≤8)}$, substituted alkylidene$_{(C≤8)}$, or form a heterocycloalkyl group consisting of three to eight ring members;

wherein:

$X_1$ is amino or alkyl$_{(C≤8)}$, cycloalkyl$_{(C≤8)}$, aryl$_{(C≤12)}$, heteroaryl$_{(C≤12)}$, heterocycloalkyl$_{(C≤12)}$, alkylamino$_{(C≤12)}$, dialkylamino$_{(C≤12)}$, arylamino$_{(C≤12)}$, alkylarylamino$_{(C≤18)}$, diarylamino$_{(C≤18)}$, or a substituted version of any of these groups;

$Y_1$ is alkyl$_{(C≤8)}$, substituted alkyl$_{(C≤8)}$, or -A-$R_9$; wherein:
A is alkanediyl$_{(C≤6)}$, alkenediyl$_{(C≤6)}$, or a substituted version of either of these groups; and
$R_9$ is amino, carboxy, or hydroxy, or heteroaryl$_{(C≤8)}$, substituted heteroaryl$_{(C≤8)}$, alkylamino$_{(C≤8)}$, substituted alkylamino$_{(C≤8)}$, dialkylamino$_{(C≤8)}$, substituted dialkylamino$_{(C≤8)}$, or —C(O)$R_b$, wherein:
$R_b$ is amino, hydroxy, or
alkoxy$_{(C≤8)}$, aryloxy$_{(C≤8)}$, aralkoxy$_{(C≤8)}$, alkylamino$_{(C≤8)}$, dialkylamino$_{(C≤8)}$, cycloalkylamino$_{(C≤8)}$, dicycloalkylamino$_{(C≤12)}$, or a substituted version of any of these groups;

$R_7$ is amino, halo, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤12)}$, or substituted dialkylamino$_{(C≤12)}$, or -$A_2$-$R_e$ wherein $A_2$ is —O— or —N$R_d$—, wherein $R_d$ is hydrogen, alkyl$_{(C≤8)}$, or substituted alkyl$_{(C≤8)}$; and $R_e$ is —C(O)$R_e$, wherein $R_e$ is amino, hydroxy, or alkyl$_{(C≤8)}$, heterocycloalkyl$_{(C≤8)}$, alkoxy$_{(C≤8)}$, alkylamino$_{(C≤8)}$, or dialkylamino$_{(C≤8)}$, or a substituted version of these five groups;

$R_8$ and $R_8'$ are each independently hydrogen, hydroxy, alkyl$_{(C≤8)}$, substituted alkyl$_{(C≤8)}$, or $R_8$ and $R_8'$ are taken together and are oxo, alkylidene$_{(C≤8)}$, substituted alkylidene$_{(C≤8)}$, or form a cycloalkyl or heterocycloalkyl group consisting of three to eight ring members;

provided that the compound is not:

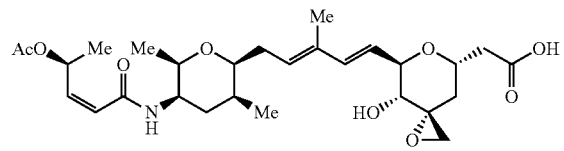 [SMILES: CC(=O)O[C@@H](C)/C=C\C(=O)N[C@@H]1C[C@H](C)[C@H](C/C=C(C)/C=C/[C@H]2O[C@H](CC(=O)O)C[C@@]3(CO3)[C@@H]2O)O[C@@H]1C]

or a pharmaceutically acceptable salt thereof.

In some embodiments, $X_1$ is alkyl$_{(C≤8)}$ or substituted alkyl$_{(C≤8)}$ such as methyl. In other embodiments, $X_1$ is alkylarylamino$_{(C≤8)}$ or substituted alkylarylamino$_{(C≤8)}$ such as N-methyl-N-phenylamino. In other embodiments, $X_1$ is heterocycloalkyl$_{(C≤8)}$ or substituted heterocycloalkyl$_{(C≤8)}$ such as pyrrolidinyl, piperidinyl, piperazinyl, or morpholinyl.

In some embodiments, $X_2$ is oxo. In other embodiments, $X_2$ is hydrogen.

In some embodiments, $Y_1$ is alkyl$_{(C≤8)}$ or substituted alkyl$_{(C≤8)}$ such as methyl. In other embodiments, $Y_1$ is -A-$R_9$; wherein:
A is alkanediyl$_{(C≤6)}$, alkenediyl$_{(C≤6)}$, or a substituted version of either of these groups; and
$R_9$ is amino, carboxy, or hydroxy, or heteroaryl$_{(C≤8)}$, substituted heteroaryl$_{(C≤8)}$, alkylamino$_{(C≤8)}$, substituted alkylamino$_{(C≤8)}$, dialkylamino$_{(C≤8)}$ substituted dialkylamino$_{(C≤8)}$, or —C(O)$R_b$, wherein:
$R_b$ is amino, hydroxy, or
alkoxy$_{(C≤8)}$, aryloxy$_{(C≤8)}$, aralkoxy$_{(C≤8)}$, alkylamino$_{(C≤8)}$, dialkylamino$_{(C≤8)}$, cycloalkylamino$_{(C≤8)}$, dicycloalkylamino$_{(C≤12)}$, or a substituted version of any of these groups.

In some embodiments, $Y_1$ is -A-$R_9$; wherein:
A is alkanediyl$_{(C≤6)}$ or substituted alkanediyl$_{(C≤6)}$; and
$R_9$ is amino, carboxy, or hydroxyl, or alkylamino$_{(C≤8)}$, substituted alkylamino$_{(C≤8)}$, dialkylamino$_{(C≤8)}$, substituted dialkylamino$_{(C≤8)}$, or —C(O)$R_b$, wherein:
$R_b$ is amino, hydroxyl, or
alkoxy$_{(C≤8)}$, aryloxy$_{(C≤8)}$, aralkoxy$_{(C≤8)}$, alkylamino$_{(C≤8)}$, dialkylamino$_{(C≤8)}$, cycloalkylamino$_{(C≤8)}$, dicycloalkylamino$_{(C≤12)}$, or a substituted version of any of these groups.

In some embodiments, A is alkenediyl$_{(C≤6)}$ such as methylene. In other embodiments, A is substituted alkenediyl$_{(C≤6)}$ such as difluoromethylene. In some embodiments, $R_9$ is amino. In other embodiments, $R_9$ is —C(O)OH. In other embodiments, $R_9$ is —C(O)$R_b$, wherein:

$R_b$ is amino, hydroxy, or alkoxy$_{(C\leq8)}$, aryloxy$_{(C\leq8)}$, aralkoxy$_{(C\leq8)}$, alkylamino$_{(C\leq8)}$, dialkylamino$_{(C\leq8)}$, cycloalkylamino$_{(C\leq8)}$, dicycloalkylamino$_{(C\leq12)}$, or a substituted version of any of these groups.

In some embodiments, $R_b$ is amino. In other embodiments, $R_b$ is hydroxy. In other embodiments, $R_b$ is alkoxy$_{(C\leq8)}$ or substituted alkoxy$_{(C\leq8)}$ such as methoxy. In other embodiments, $R_b$ is aryloxy$_{(C\leq8)}$ or substituted aryloxy$_{(C\leq8)}$. In other embodiments, $R_b$ is alkylamino$_{(C\leq8)}$ or substituted alkylamino$_{(C\leq8)}$ such as N-methylaminoethylamino or 2-carboxyethylamino. In other embodiments, $R_b$ is cycloalkylamino$_{(C\leq8)}$ or substituted cycloalkylamino$_{(C\leq8)}$ such as cyclopropylamino. In some embodiments, $Y_2$ is —NR$_a$— such as —NH—.

In some embodiments, $R_7$ is hydroxy. In other embodiments, $R_7$ is halo such as fluoro. In other embodiments, $R_7$ is -$A_2$-$R_c$, wherein $A_2$ is —O— or —NR$_d$—, wherein $R_d$ is hydrogen, alkyl$_{(C\leq8)}$, or substituted alkyl$_{(C\leq8)}$; and $R_c$ is —C(O)$R_e$, wherein $R_e$ is amino, hydroxy, or alkyl$_{(C\leq8)}$, heterocycloalkyl$_{(C\leq8)}$, alkoxy$_{(C\leq8)}$, alkylamino$_{(C\leq8)}$, or dialkylamino$_{(C\leq8)}$, or a substituted version of these five groups. In some embodiments, $A_2$ is —O—. In some embodiments, $R_e$ is alkyl$_{(C\leq8)}$, heterocycloalkyl$_{(C\leq8)}$, alkylamino$_{(C\leq8)}$, or dialkylamino$_{(C\leq8)}$, or a substituted version of these four groups.

In some embodiments, $R_8$ is alkyl$_{(C\leq6)}$ or substituted alkyl$_{(C\leq6)}$ such as fluoromethyl. In some embodiments, $R_8'$ is hydroxy. In other embodiments, $R_8$ and $R_8'$ are taken together and are alkylidene$_{(C\leq6)}$ or substituted alkylidene$_{(C\leq6)}$ such as $R_8$ and $R_8'$ are taken together and are =CH$_2$. In other embodiments, $R_8$ and $R_8'$ are taken together and are heterocycloalkyl$_{(C\leq6)}$ or substituted heterocycloalkyl$_{(C\leq6)}$ such as $R_8$ and $R_8'$ are taken together and are oxirane or oxetane.

In some embodiments, $R_a$ is hydrogen. In other embodiments, $R_a$ is alkyl$_{(C\leq6)}$ or substituted alkyl$_{(C\leq6)}$ such as methyl. In some embodiments, $R_5$ is hydrogen. In other embodiments, $R_5$ is alkyl$_{(C\leq6)}$ or substituted alkyl$_{(C\leq6)}$ such as methyl. In some embodiments, $R_6$ is hydrogen. In other embodiments, $R_6$ is alkyl$_{(C\leq6)}$ or substituted alkyl$_{(C\leq6)}$ such as methyl.

In some embodiments, $R_1$ is alkyl$_{(C\leq6)}$ or substituted alkyl$_{(C\leq6)}$ such as methyl. In some embodiments, $R_2$ is alkyl$_{(C\leq6)}$ or substituted alkyl$_{(C\leq6)}$ such as methyl. In some embodiments, $R_3$ is alkyl$_{(C\leq6)}$ or substituted alkyl$_{(C\leq6)}$ such as methyl. In some embodiments, $R_4$ is alkyl$_{(C\leq6)}$ or substituted alkyl$_{(C\leq6)}$ such as methyl. In some embodiments, the compound is further defined as:

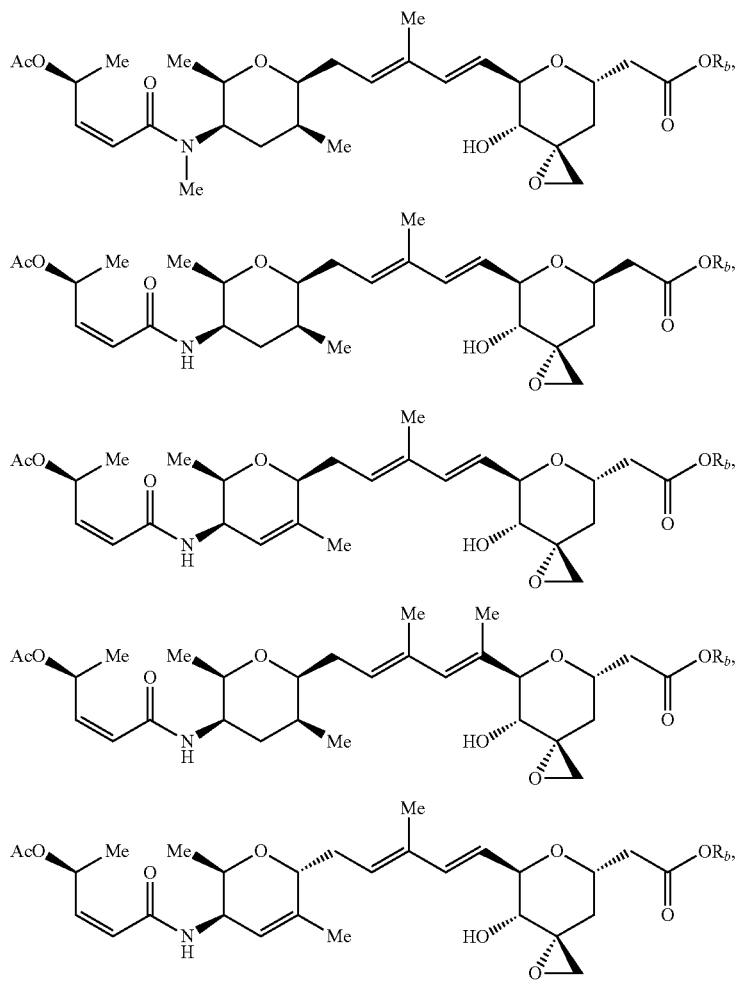

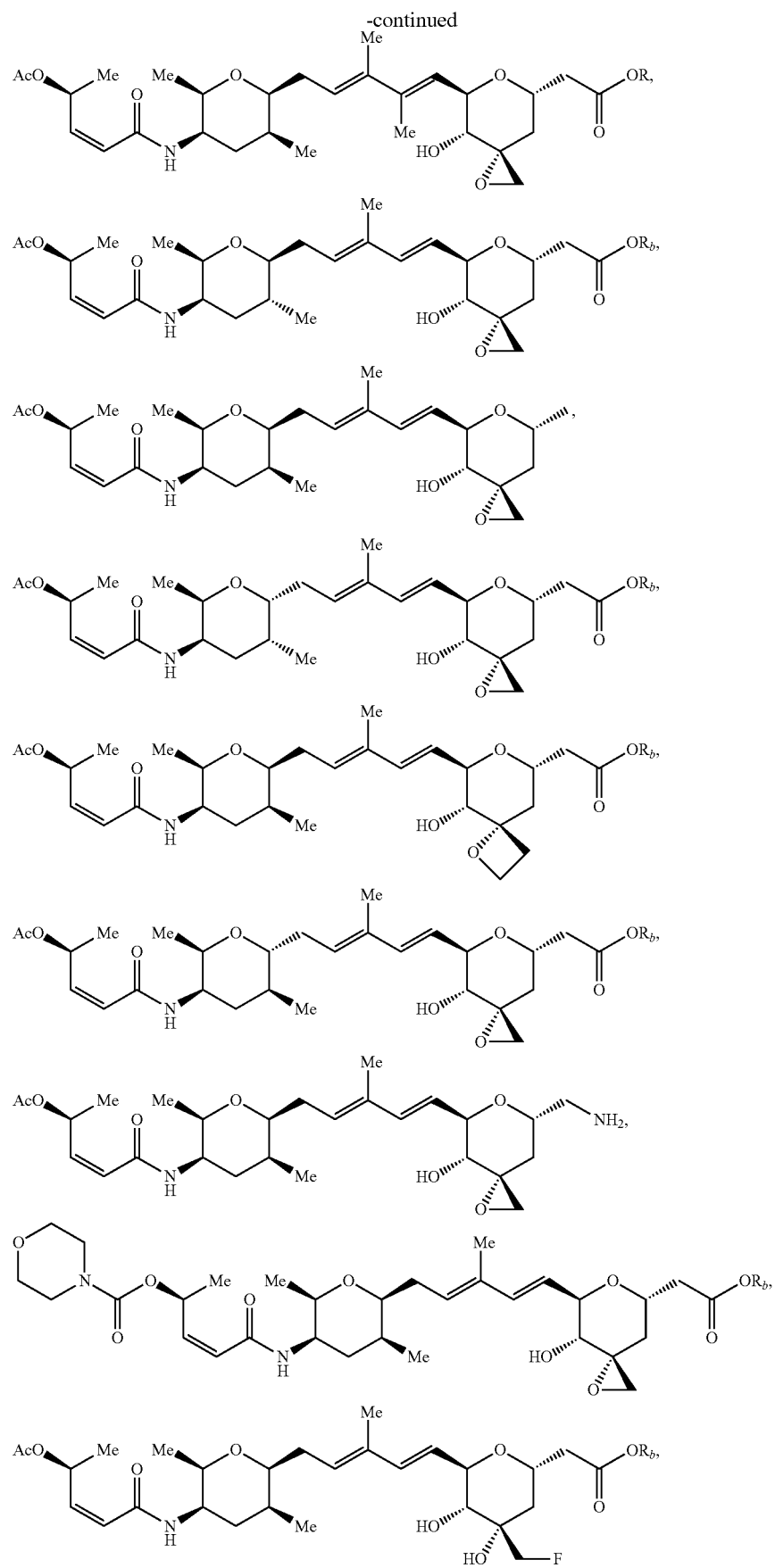

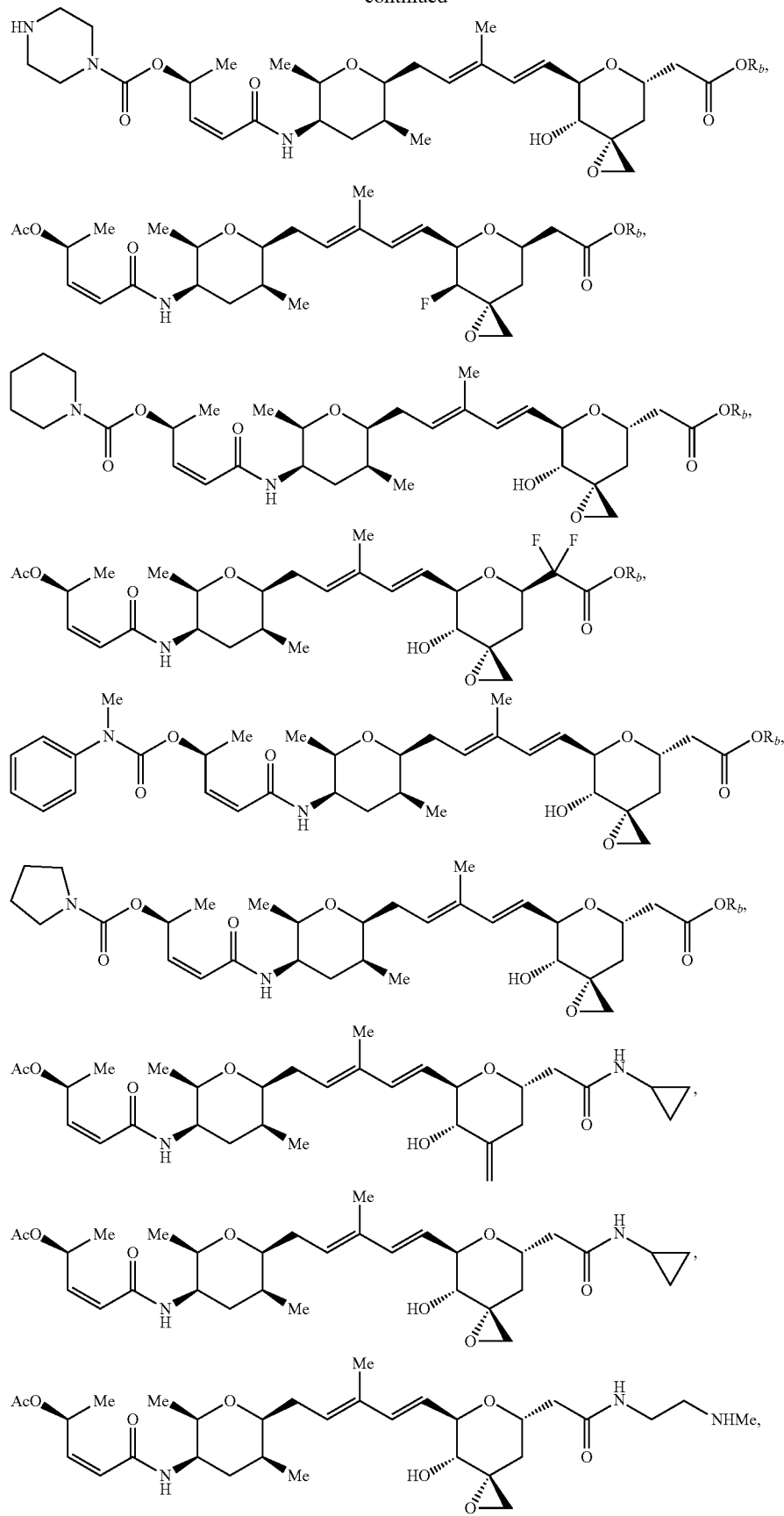

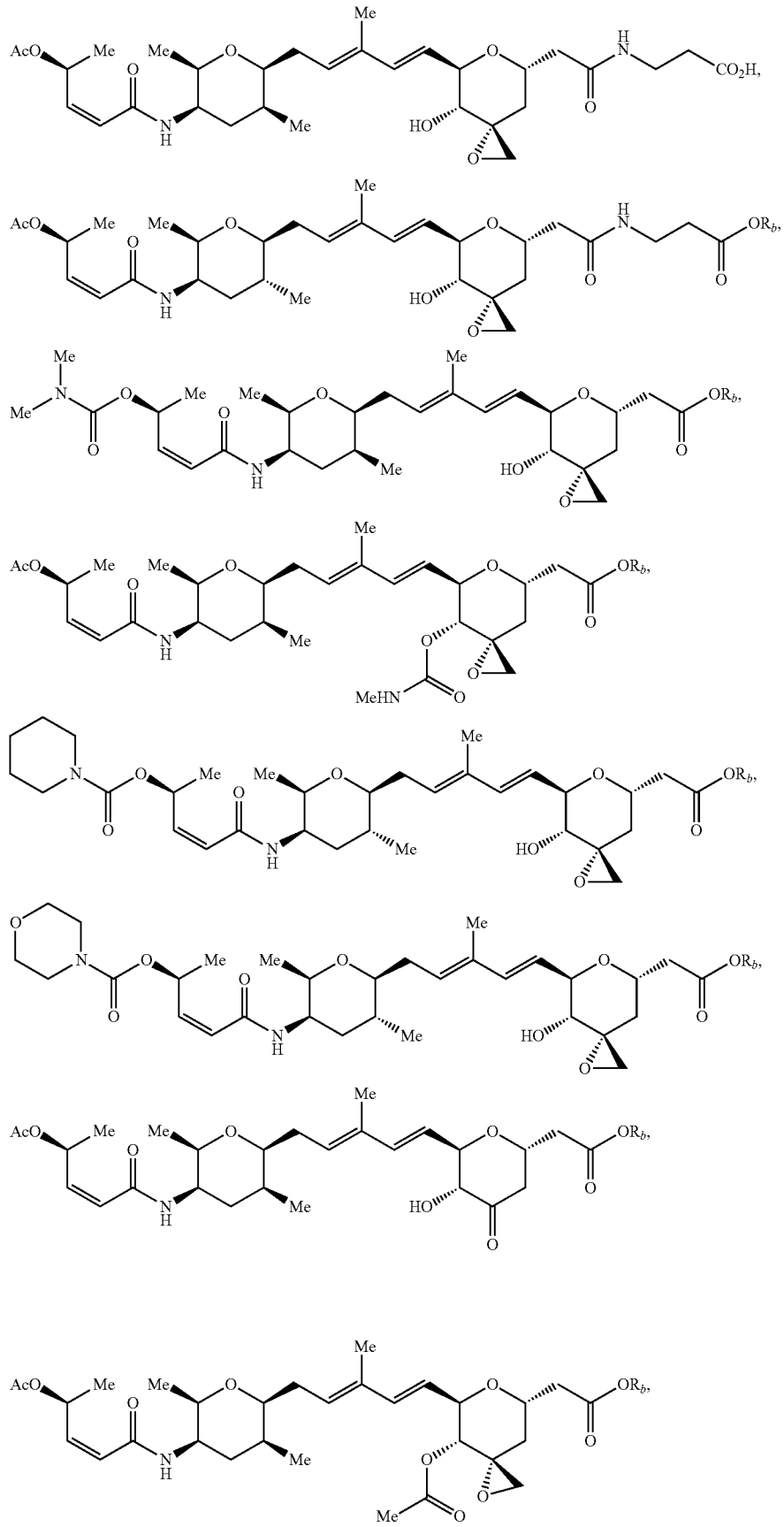

-continued
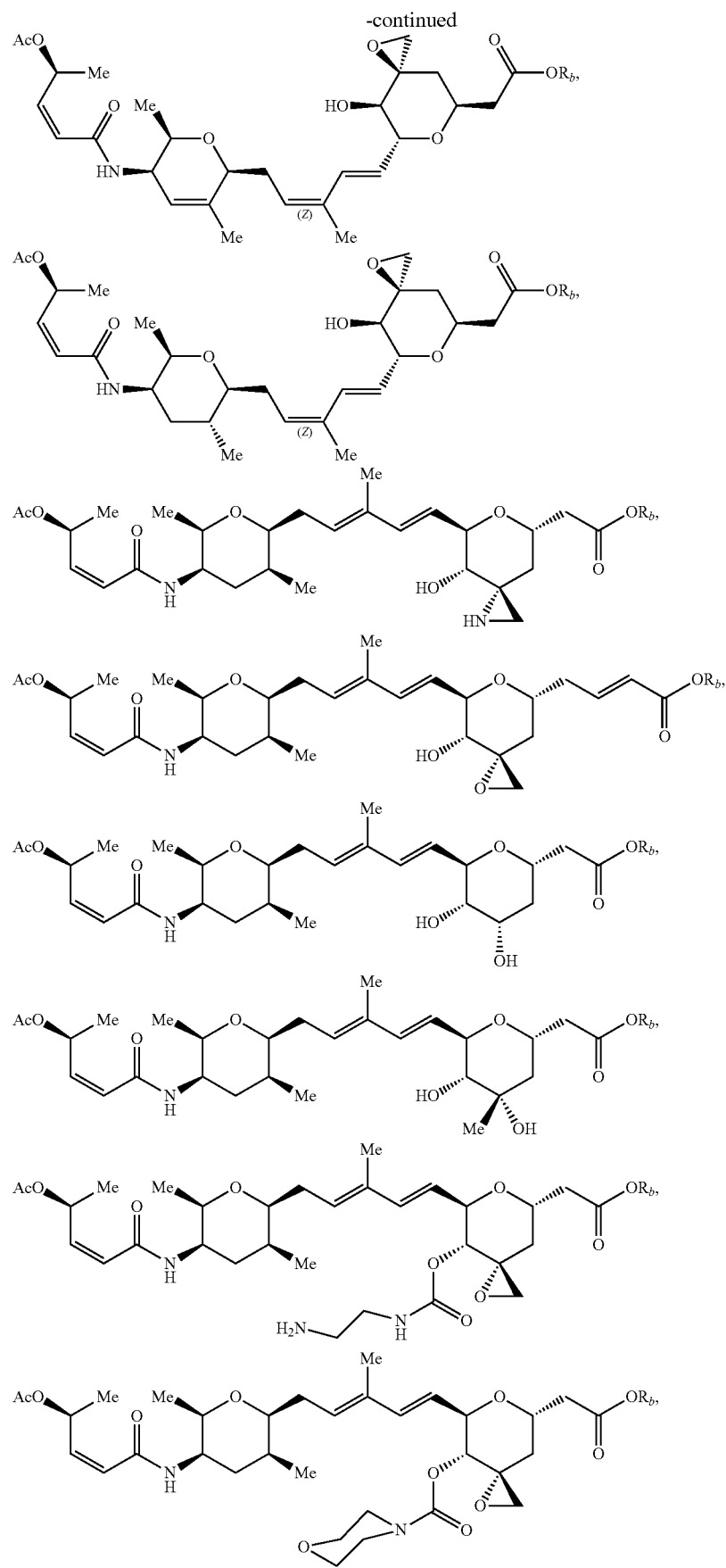

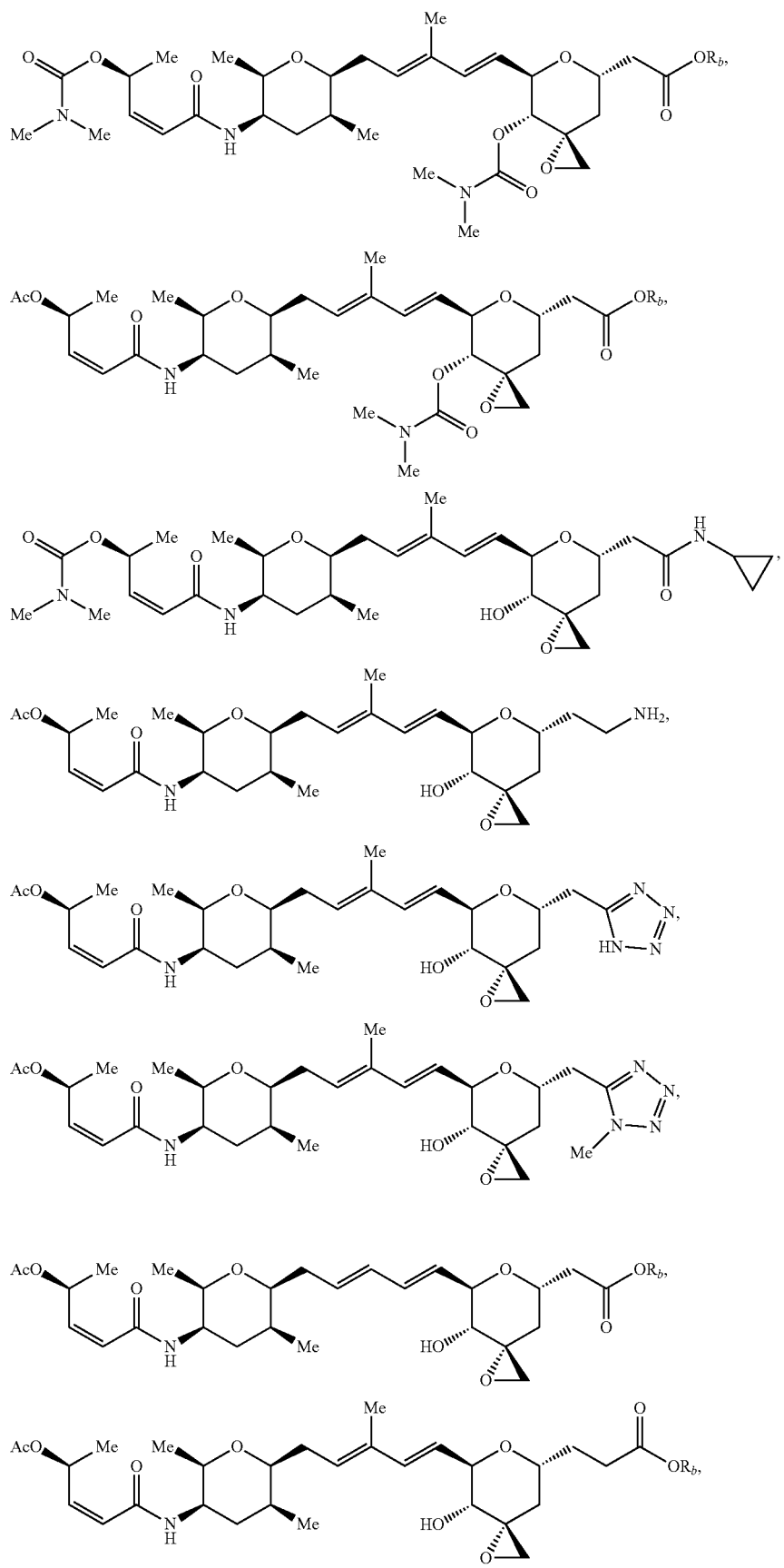

-continued

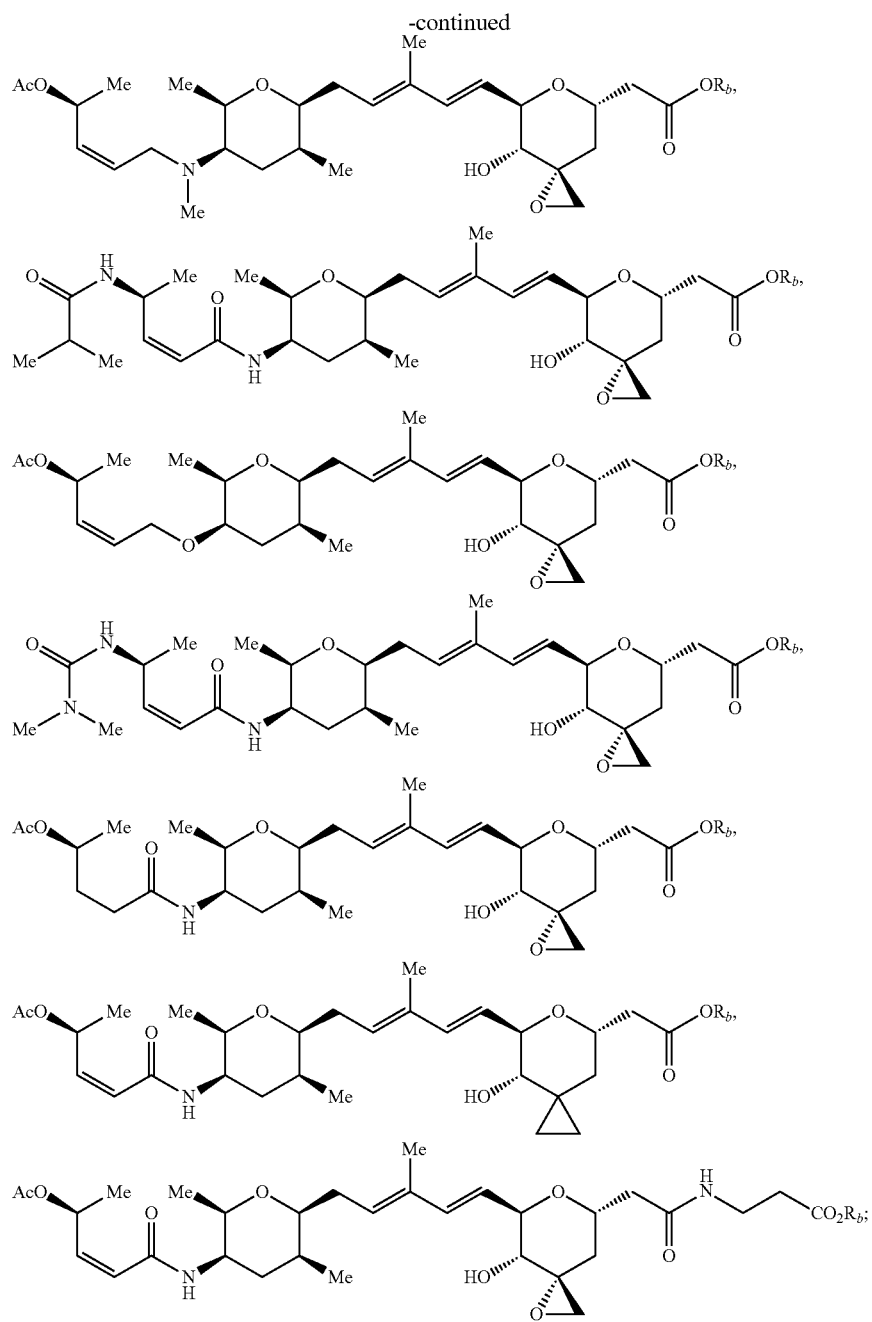

wherein:

$R_b$ is hydrogen, alkyl$_{(C\leq 6)}$, substituted alkyl$_{(C\leq 6)}$, aryl$_{(C\leq 8)}$, substituted aryl$_{(C\leq 8)}$, aralkyl$_{(C\leq 6)}$, or substituted aralkyl$_{(C\leq 6)}$; or a pharmaceutically acceptable salt thereof.

or a pharmaceutically acceptable salt thereof. In some embodiments, $R_b$ is alkyl$_{(C\leq 6)}$ such as methyl, ethyl, or isopropyl. In other embodiments, $R_b$ is hydrogen. In some embodiments, $R_b$ is methyl.

In yet another aspect, the present disclosure provides cell targeting linked compositions comprising:

(a) a compound described herein;
(b) a cell targeting moiety;

wherein the cell targeting moiety is linked to the compound.

In some embodiments, the cell targeting moiety is linked to the compound through a linker such as a linker which is degradable in vivo. In some embodiments, the linker is a peptide. In some embodiments, the cell targeting moiety is an antibody. In some embodiments, the cell targeting moiety is an antibody for a cell surface receptor or surface protein which is overexpressed in a cancer cell.

In still yet another aspect, the present disclosure provides pharmaceutical compositions comprising:

(a) a compound described herein; and
(b) a pharmaceutically acceptable carrier.

In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical compositions are formulated as a unit dose.

In yet another aspect, the present disclosure provides method of treating a disease or disorder in a patient comprising administering to the patient in need thereof a therapeutically effective amount of a compound or composition described herein. In some embodiments, the disease or disorder is cancer. The cancer may be a carcinoma, sarcoma, lymphoma, leukemia, melanoma, mesothelioma, multiple myeloma, or seminoma. The cancer may be a cancer of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

In some embodiments, the cancer is a breast cancer, a colon cancer, a gastric cancer, a lung cancer, an ovarian cancer, or a prostate cancer. In some embodiments, the cancer is a breast cancer such as a breast adenocarcinoma. In other embodiments, the cancer is a colon cancer such as a drug resistant colon cancer. In other embodiments, the cancer is a gastric cancer. In other embodiments, the cancer is a lung cancer such as a non-small cell lung cancer or a squamous cell lung cancer. In other embodiments, the cancer is an ovarian cancer. In other embodiments, the cancer is a prostate cancer.

In some embodiments, the methods further comprise a second cancer therapy. In some embodiments, the second cancer therapy is a second chemotherapeutic compound, surgery, radiotherapy, or immunotherapy. In some embodiments, the methods comprise administering the compound or composition to the patient once. In other embodiments, the methods comprise administering the compound or composition to the patient two or more times. In some embodiments, the patent is a mammal such as a human.

In still yet another aspect, the present disclosure provides methods of preparing a compound of the formula:

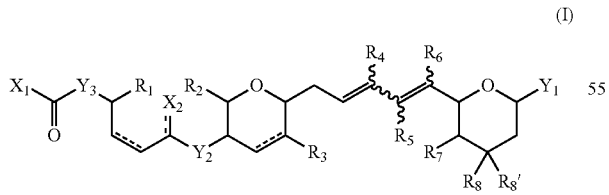

(I)

wherein:
$X_1$ is amino or alkyl$_{(C \leq 8)}$, cycloalkyl$_{(C \leq 8)}$, aryl$_{(C \leq 12)}$, heteroaryl$_{(C \leq 12)}$, heterocycloalkyl$_{(C \leq 12)}$, alkylamino$_{(C \leq 12)}$, dialkylamino$_{(C \leq 12)}$, arylamino$_{(C \leq 12)}$, alkylarylamino$_{(C \leq 18)}$, diarylamino$_{(C \leq 18)}$, or a substituted version of any of these groups;
$X_2$ is hydrogen, hydroxy, or oxo;

$Y_1$ is alkyl$_{(C \leq 8)}$, substituted alkyl$_{(C \leq 8)}$, or -A-$R_9$; wherein:
A is alkanediyl$_{(C \leq 6)}$, alkenediyl$_{(C \leq 6)}$, or a substituted version of either of these groups; and
$R_9$ is amino, carboxy, or hydroxy, or heteroaryl$_{(C \leq 8)}$, substituted heteroaryl$_{(C \leq 8)}$, alkylamino$_{(C \leq 8)}$, substituted alkylamino$_{(C \leq 8)}$, dialkylamino$_{(C \leq 8)}$, substituted dialkylamino$_{(C \leq 8)}$, or —C(O)$R_b$, wherein:
$R_b$ is amino, hydroxy, or
alkoxy$_{(C \leq 8)}$, aryloxy$_{(C \leq 8)}$, aralkoxy$_{(C \leq 8)}$, alkylamino$_{(C \leq 8)}$, dialkylamino$_{(C \leq 8)}$, cycloalkylamino$_{(C \leq 8)}$, dicycloalkylamino$_{(C \leq 12)}$, or a substituted version of any of these groups;
$Y_2$ and $Y_3$ are —O— or —NR$_a$—;
$R_a$, $R_1$, $R_2$, $R_3$, $R_4$, $R_5$ and $R_6$ are each independently selected from hydrogen, alkyl$_{(C \leq 8)}$, or substituted alkyl$_{(C \leq 8)}$;
$R_7$ is amino, halo, hydroxy, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 12)}$, or substituted dialkylamino$_{(C \leq 12)}$, or -$A_2$-$R_e$, wherein $A_2$ is —O— or —NR$_d$—, wherein $R_d$ is hydrogen, alkyl$_{(C \leq 8)}$, or substituted alkyl$_{(C \leq 8)}$; and $R_c$ is —C(O)$R_e$, wherein $R_e$ is amino, hydroxy, or alkyl$_{(C \leq 8)}$, heterocycloalkyl$_{(C \leq 8)}$, alkoxy$_{(C \leq 8)}$, alkylamino$_{(C \leq 8)}$, or dialkylamino$_{(C \leq 8)}$, or a substituted version of these five groups;
$R_8$ and $R_8'$ are each independently hydrogen, hydroxy, alkyl$_{(C \leq 8)}$, substituted alkyl$_{(C \leq 8)}$, or $R_8$ and $R_8'$ are taken together and are oxo, alkylidene$_{(C \leq 8)}$, substituted alkylidene$_{(C \leq 8)}$, or form a cycloalkyl or heterocycloalkyl group consisting of three to eight ring members;
comprising reacting a compound of the formula:

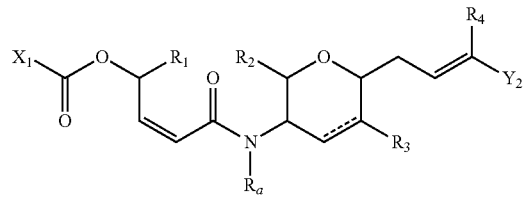

(VII)

wherein: $X_1$, $R_1$, $R_2$, $R_3$, $R_a$, and $R_4$ are as defined above; and
$Y_2$ is halo or a boron containing group;
with a compound of the formula:

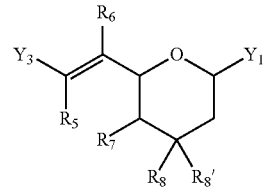

(VIII)

wherein: $Y_1$, $R_5$, $R_6$, $R_7$, $R_8$, and $R_8'$ are as defined above; and
$Y_3$ is halo or a boron containing group;
in the presence of a transition metal catalyst and a base; provided that when $Y_2$ is a boron containing group, then $Y_3$ is halo; and when $Y_2$ is halo, then $Y_3$ is a boron containing group.

In some embodiments, the transition metal catalyst is a palladium catalyst such as Pd(PPh$_3$)$_4$ or Pd(dppf)

Cl₂.CH₂Cl₂. In some embodiments, the base is a metal alkoxide such as thallium ethoxide. In other embodiments, the base is a metal phosphate salt such as K₃PO₄.

In some embodiments, the methods comprise adding from about 0.1 equivalents to about 5 equivalent of the base relative to the compound of formula VII such as adding about 1 equivalents of the base. In some embodiments, the methods comprise adding from about 0.5 equivalents to about 3 equivalent of the compound of formula VI relative to the compound of formula VII such as adding about 1.1 equivalents of the compound of formula VII. In some embodiments, the method comprises heating the reaction to a temperature from about 0° C. to about 50° C. such as about 25° C.

In yet another aspect, the present disclosure provides methods of preparing a compound of the formula:

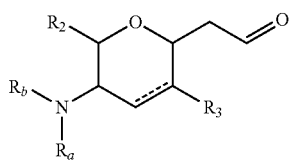

wherein:

$R_2$ and $R_3$ are each independently selected from hydrogen, alkyl$_{(C \leq 8)}$, or substituted alkyl$_{(C \leq 8)}$; and $R_a$ and $R_b$ are each independently selected from hydrogen, alkyl$_{(C \leq 8)}$, substituted alkyl$_{(C \leq 8)}$, a monovalent amino protecting group, or $R_a$ and $R_b$ are taken together and are a divalent amino protecting group;

comprising reacting a compound of the formula:

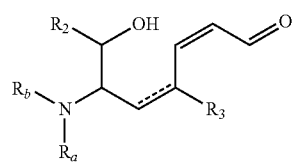

wherein: $R_2$, $R_3$, $R_a$, and $R_n$ are as defined above;

in the presence of a weak acid and a catalyst of the formula:

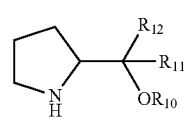

wherein:

$R_{10}$ is hydrogen, alkylsilyl$_{(C \leq 12)}$, or substituted alkylsilyl$_{(C \leq 12)}$; and $R_{11}$ and $R_{12}$ are each independently selected from aryl$_{(C \leq 12)}$ or substituted aryl$_{(C \leq 12)}$.

In some embodiments, $R_{10}$ is alkylsilyl$_{(C \leq 12)}$ such as trimethylsilyl. In some embodiments, $R_{11}$ is 2,4-ditrifluoromethylphenyl. In some embodiments, $R_{12}$ is 2,4-ditrifluoromethylphenyl. In some embodiments, the catalyst is:

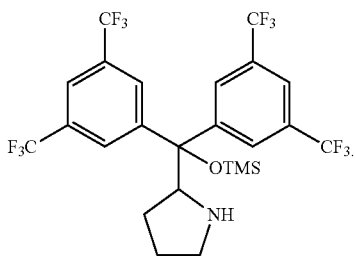

In some embodiments, the weak acid has a p$K_a$ of less than 7. In some embodiments, the weak acid has a p$K_a$ greater than −1. In some embodiments, the weak acid is an acid with one or more carboxylic acid group. In some embodiments, the weak acid is an arylcarboxylic acid$_{(C \leq 12)}$ such as benzoic acid.

In some embodiments, the methods comprise adding from about 0.05 equivalents to about 1 equivalent of the catalyst of formula X relative to the compound of formula IX such as adding about 0.2 equivalents of the catalyst of formula X. In some embodiments, the methods comprise adding from about 0.05 equivalents to about 1 equivalent of the weak acid relative to the compound of formula IX such as adding about 0.2 equivalents of the weak acid. In some embodiments, the methods comprise heating the reaction to a temperature from about −20° C. to about 25° C. such as the temperature is about 0° C.

In some embodiments, the methods described herein may further comprise one or more deprotection steps. In some embodiments, the methods described herein may further comprise one or more purification steps. In some embodiments, the purification step comprises purification through chromatography, distillation, extraction, or precipitation. In some embodiments, the chromatography is column chromatography or high performance liquid chromatography (HPLC).

It is contemplated that any method or composition described herein can be implemented with respect to any other method or composition described herein. For example, a compound synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

FIG. 1 shows the X-ray derived structure of 16a.

DESCRIPTION OF ILLUSTRATIVE EMBODIMENTS

Figure 1:
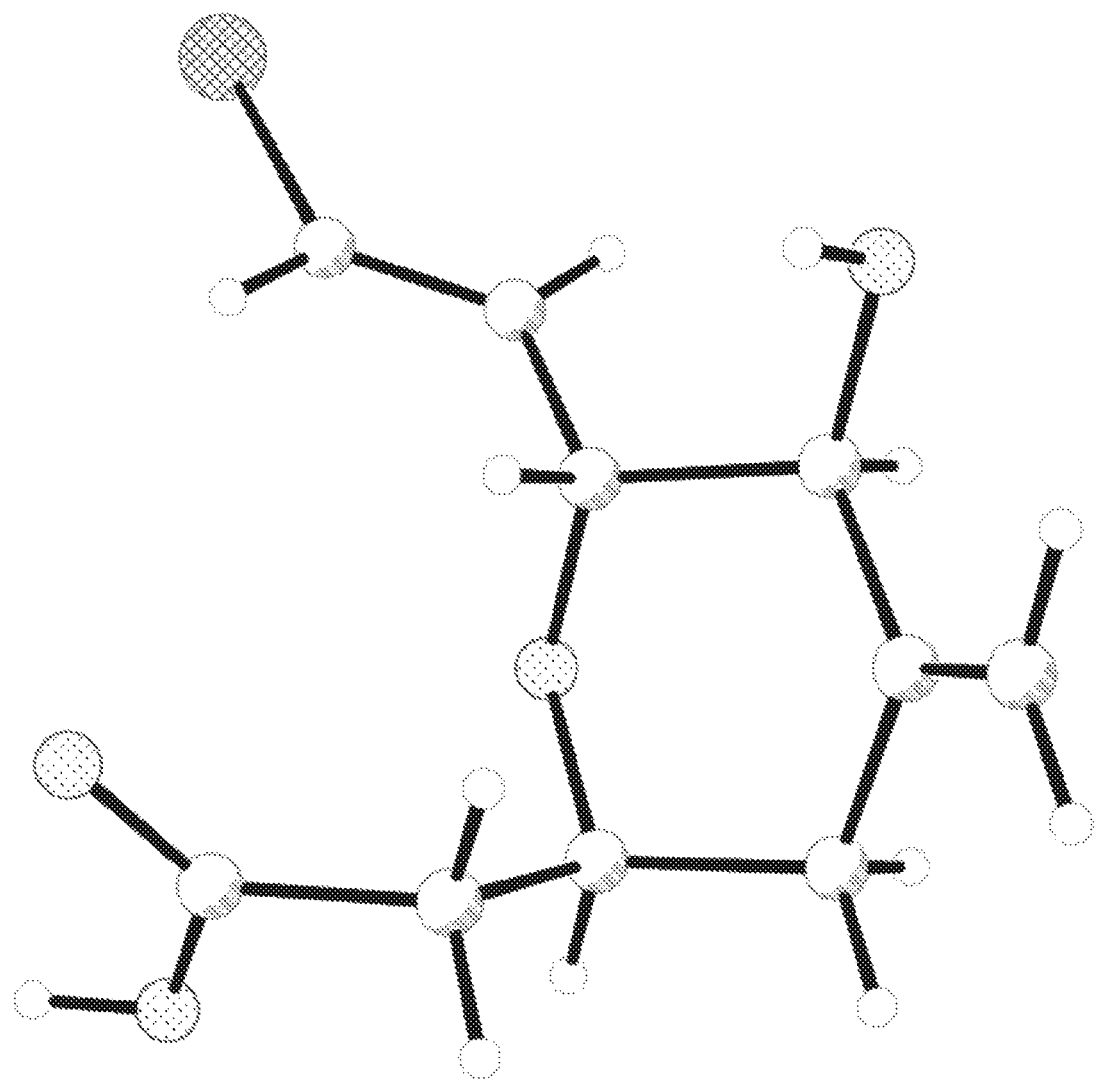

The present disclosure relates to analogs of thailanstatin. These compounds may be used in the treatment of patients including the treatment of cancer. Also provided herein are modular methods of synthesis for these compounds which may allow increased access to other analogs including analogs which contain a reactive group which can be linked to a cell targeting moiety such as an antibody. These methods may show an improved yield or reduced number of steps to obtain the desired final product.

I. COMPOUNDS AND FORMULATIONS THEREOF

A. Compounds

The thailanstatin A methyl ester and analogs thereof provided by the present disclosure are shown, for example, above in the summary of the disclosure section and in the examples and claims below. They may be made using the methods outlined in the Examples section. The thailanstatin A methyl ester and analogs thereof described herein can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The thailanstatin A methyl ester and analogs thereof described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the (S) or the (R) configuration.

Chemical formulas used to represent the thailanstatin A methyl ester and analogs thereof described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The thailanstatin A methyl ester and analogs thereof described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the thailanstatin A methyl ester and analogs thereof described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

The thailanstatin A methyl ester and analogs thereof described herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the thailanstatin A methyl ester and analogs thereof described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the thailanstatin A methyl ester and analogs thereof described herein are within the scope of the disclosure. It will also be appreciated by those skilled in organic chemistry that many organic compounds can exist in more than one crystalline form. For example, crystalline form may vary from solvate to solvate. Thus, all crystalline forms of the thailanstatin A methyl ester and analogs thereof described herein are within the scope of the present disclosure.

B. Formulations

In some embodiments of the present disclosure, the compounds described herein are used in a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly (lactic acid), poly(glycolic acid) or poly(ortho esters) or combinations thereof).

Formulations for oral use include tablets containing the active ingredient(s) (e.g., the thailanstatin A methyl ester and analogs thereof described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. CANCER AND OTHER HYPERPROLIFERATIVE DISEASES

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the thailanstatin A methyl ester and analogs thereof described herein may be used to lead to decreased cell counts and as such can potentially be used to treat a variety of types of cancer lines. In some aspects, it is anticipated that the thailanstatin A methyl ester and analogs thereof described herein may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; in situ pulmonary adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant;

neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. CELL TARGETING MOIETIES

In some aspects, the present disclosure provides thailanstatin A methyl ester and analogs thereof conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. For instance, a cell targeting moiety according the embodiments may bind to a liver cancer cell such as a Hep3B cell. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example is the cell targeting agents described in U.S. Patent Publication No. 2004/005647 and in Winthrop et al. (2003) that bind to MUC-1, an antigen that is expressed on a variety cancer types. Thus, it will be understood that in certain embodiments, cell targeting constructs according to the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used may include a cofactor, a sugar, a drug molecule, an imaging agent, or a fluorescent dye. Many cancerous cells are known to overexpress folate receptors and thus folic acid or other folate derivatives may be used as conjugates to trigger cell-specific interaction between the conjugates of the present disclosure and a cell (Campbell et al., 1991; Weitman et al., 1992).

Since a large number of cell surface receptors have been identified in hematopoietic cells of various lineages, ligands or antibodies specific for these receptors may be used as cell-specific targeting moieties. IL-2 may also be used as a cell-specific targeting moiety in a chimeric protein to target IL-2R+ cells. Alternatively, other molecules such as B7-1, B7-2 and CD40 may be used to specifically target activated T cells (The Leucocyte Antigen Facts Book, 1993, Barclay et al. (eds.), Academic Press). Furthermore, B cells express CD19, CD40 and IL-4 receptor and may be targeted by moieties that bind these receptors, such as CD40 ligand, IL-4, IL-5, IL-6 and CD28. The elimination of immune cells such as T cells and B cells is particularly useful in the treatment of lymphoid tumors.

Other cytokines that may be used to target specific cell subsets include the interleukins (IL-1 through IL-15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor [Thompson (ed.), 1994, The Cytokine Handbook, Academic Press, San Diego]. In some aspects, the targeting polypeptide is a cytokine that binds to the Fn14 receptor, such as TWEAK (see, e.g., Winkles, 2008; Zhou et al., 2011 and Burkly et al., 2007, incorporated herein by reference).

A skilled artisan recognizes that there are a variety of known cytokines, including hematopoietins (four-helix bundles) {such as EPO (erythropoietin), IL-2 (T-cell growth factor), IL-3 (multicolony CSF), IL-4 (BCGF-1, BSF-1), IL-5 (BCGF-2), IL-6, IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor); interferons (such as IFN-γ, IFN-α, and IFN-β); immunoglobin superfamily [such as B7.1 (CD80), and B7.2 (B70, CD86)]; TNF family [such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)]; and those unassigned to a particular family (such as TGF-β, IL 1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)]. Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated against virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

Additionally, it is contemplated that the compounds described herein may be conjugated to a nanoparticle or other nanomaterial. Some non-limiting examples of nanoparticles include metal nanoparticles such as gold or silver nanoparticles or polymeric nanoparticles such as poly-L-lactic acid or poly(ethylene) glycol polymers. Nanoparticles and nanomaterials which may be conjugated to the instant compounds include those described in U.S. Patent Publications Nos. 2006/0034925, 2006/0115537, 2007/0148095, 2012/0141550, 2013/0138032, and 2014/0024610 and PCT Publication Nos. 2008/121949, 2011/053435, and 2014/087413, each incorporated herein by reference.

IV. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, intracranial, intrathecal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

For oral administration the thailanstatin A methyl ester and analogs thereof described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA's Division of Biological Standards and Quality Control of the Office of Compliance and Biologics Quality.

B. Methods of Treatment

In particular, the compositions that may be used in treating cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation. In some embodiments, amounts of the thailanstatin A methyl ester and analogs thereof used to induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the thailanstatin A methyl ester and analogs thereof may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the thailanstatin A methyl ester and analogs thereof described herein may be used in combination therapies with one or more cancer therapies or a compound which mitigates one or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the thailanstatin A methyl ester and analogs thereof described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are also contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin $\gamma_1$ and calicheamicin $\omega_1$; dynemicin, including dynemicin A; uncialamycin and derivatives thereof; bisphosphonates, such as clodronate; an esperamicin; as well as neocarzinostatin chromophore and related chromoprotein enediyne antiobiotic chromophores, aclacinomycins, actinomycin, authrarnycin, azaserine, bleomycins, cactinomycin, carubicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozotocin, tubercidin, ubenimex, zinostatin, or zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosourea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabine, navelbine, farnesyl-protein tansferase inhibitors, transplatinum, 5-fluorouracil, vincristine, vinblastine and methotrexate and pharmaceutically acceptable salts, acids or derivatives of any of the above.

2. Radiotherapy

Radiotherapy, also called radiation therapy, is the treatment of cancer and other diseases with ionizing radiation Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 12.9 to 51.6 mC/kg for prolonged periods of time (3 to 4 wk), to single doses of 0.516 to 1.55 C/kg. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ, IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believed to be particularly efficacious in reducing the reoccurance of the tumor. Additionally, the compounds of the present disclosure can also be used in a neoadjuvant setting.

5. Other Agents

It is contemplated that other agents may be used with the present disclosure. These additional agents include immunomodulatory agents, agents that affect the upregulation of cell surface receptors and gap junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon α, β, and γ; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increased intercellular signaling by elevating the number of gap junctions would increase the anti-hyperproliferative effects on the neighboring hyperproliferative cell population. In other embodiments, cytostatic or differentiation agents may be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 41.1° C.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA's Division of Biological Standards and Quality Control of the Office of Compliance and Biologics Quality.

It also should be pointed out that any of the foregoing therapies may prove useful by themselves in treating cancer.

V. SYNTHETIC METHODS

In some aspects, the compounds of this disclosure can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of the thailanstatin A methyl ester and analogs thereof described herein.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; "hydrazine" means —NHNH$_2$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "hydroxysulfonyl" means —SO₃H, "sulfonyl" means —S(O)₂—; and "sulfinyl" means —S(O)—.

In the context of chemical formulas, the symbol "—" means a single bond, "=" means a double bond, and "≡" means triple bond. An "epoxidized double bond" represents the group:

The symbol "----" represents an optional bond, which if present is either single, double, or an epoxided double bond. The symbol "====" represents a single bond or a double bond. Thus, for example, the formula

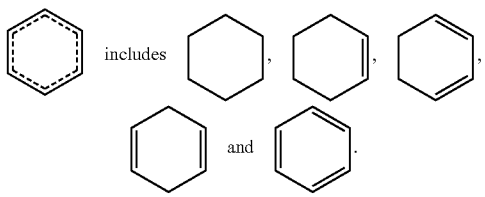

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⁓", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⋯▥" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

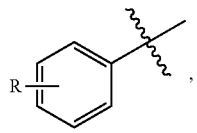

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

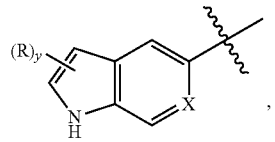

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$, and —CH$_2$CH$_2$CH$_2$, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forms part of one or more non-aromatic ring structures, a cyclo or cyclic structure, no carbon-carbon double or triple bonds, and no atoms other than carbon and hydrogen. Non-limiting examples of cycloalkyl groups include: —CH(CH$_2$)$_2$ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, said carbon atom(s) forms part of one or more non-aromatic ring structures, a cyclo or cyclic structure, no carbon-carbon double or triple bonds, and no atoms other than carbon and hydrogen.

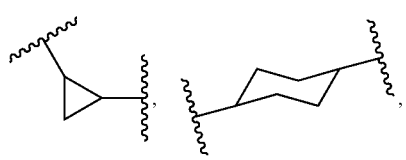

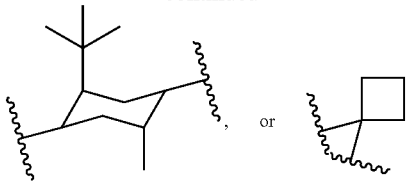

are non-limiting examples of cycloalkanediyl groups. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted cycloalkyl groups: —C(OH)(CH$_2$)$_2$,

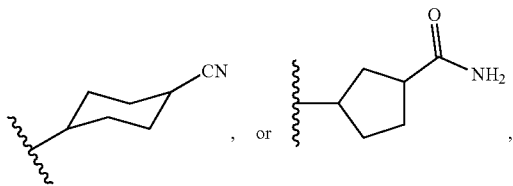 [SMILES: *C1CCC(C#N)CC1 ; *C1CCC(C(N)=O)C1]

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

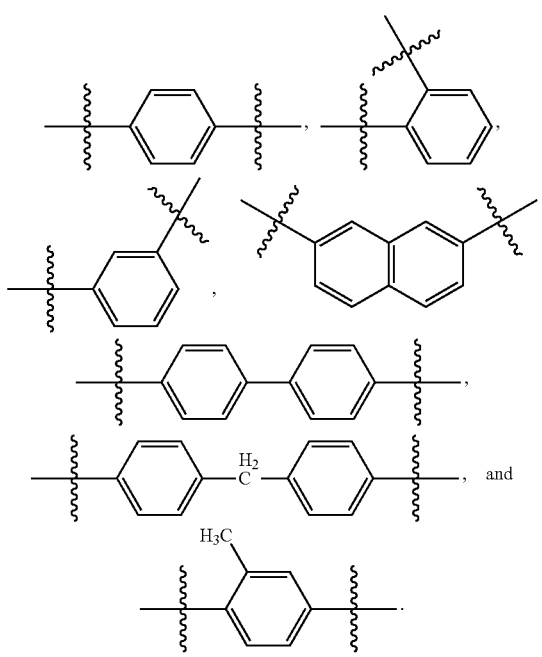

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl, isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. As the term is used herein, the term heteroaryl includes pyrimidine base and base analogs. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

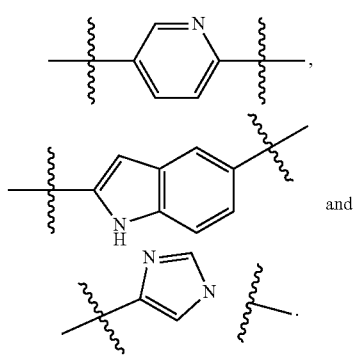

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is boron, nitrogen, oxygen or sulfur, and wherein the heterocycloalkyl group consists of no atoms other than carbon, hydrogen, nitrogen, oxygen and sulfur. Heterocycloalkyl rings may contain 1, 2, 3, or 4 ring atoms selected from nitrogen, oxygen, or sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. An "anhydride" is a group of the formula ROR', wherein R and R' are acyl groups as defined above. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples include: —OCH₃ (methoxy), —OCH₂CH₃ (ethoxy), —OCH₂CH₂CH₃, —OCH(CH₃)₂ (isopropoxy), and —OC(CH₃)₃ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alkylthiodiyl" refers to the divalent group —S-alkanediyl-, —S-alkanediyl-S—, or -alkanediyl-S-alkanediyl-. The term "alcohol" corresponds to an alkane, as defined above, wherein at least one of the hydrogen atoms has been replaced with a hydroxy group. The term "ether" corresponds to an alkane or cycloalkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "alkylamino" when used without the "substituted" modifier refers to the group —NHR, in which R is an alkyl, as that term is defined above. Non-limiting examples include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂ and —N(CH₃)(CH₂CH₃). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. Similarly, the term "alkylarylamino" or "alkylaralkylamino" when used without the "substituted" modifier refers to the group NRR', in which R and R' can be the same or different alkyl or aryl groups or the same or different alkyl and aralkyl groups, as those terms are defined above. A substituted version of any of these groups refers to a group in which one or more of the alkyl, aryl, or aralkyl groups is substituted as those terms are defined above. When any of these terms is used with the "substituted" modifier one or more hydrogen atom attached to a carbon atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups —NHC(O)OCH₃ and —NHC(O)NHCH₃ are non-limiting examples of substituted amido groups.

The term "alkylsilyl" when used without the "substituted" modifier refers to a monovalent group, defined as —SiH₂R, —SiHRR', or —SiRR'R", in which R, R' and R" can be the same or different alkyl groups, or any combination of two of R, R' and R" can be taken together to represent an alkanediyl. The groups, —SiH₂CH₃, —SiH(CH₃)₂, —Si(CH₃)₃ and —Si(CH₃)₂C(CH₃)₃, are non-limiting examples of unsubstituted alkylsilyl groups. The terms arylsilyl and aralkylsilyl refer to a monovalent group in which R, R' and R" as shown above are aryl and aralkyl groups, respectively. The term "substituted alkylsilyl" refers —SiH₂R, —SiHRR', or —SiRR'R", in which at least one of R, R' and R" is a substituted alkyl or two of R, R' and R" can be taken together to represent a substituted alkanediyl. When more than one of R, R' and R" is a substituted alkyl, they can be the same or different. Any of R, R' and R" that are not either substituted alkyl or substituted alkanediyl, can be either alkyl, either the same or different, or can be taken together to represent a alkanediyl with two or more saturated carbon atoms, at least two of which are attached to the silicon atom. The term "arylsilyl" or "aralkylsilyl" refers to the group as defined above where at least one of R, R', or R" is an aryl or aralkyl group as those groups are defined above. Similarly, the term "alkylarylsilyl" or "alkylaralkylsilyl" when used without the "substituted" modifier refer to monovalent groups, in which R, R' and R" can be the same or different alkyl or aryl groups or the same or different alkyl and aralkyl groups, as those terms are defined above. A substituted version of any of these groups refers to a group in which one or more of the alkyl, aryl, or aralkyl groups is substituted as those terms are defined above.

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular Immuno-Pharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof), multispecific antibodies (e.g., bi-specific antibodies) formed from at least two intact antibodies, and antibody fragments so long as they exhibit the desired biological activity. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting. As used herein the term antibody also encompasses an antibody fragment such as a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. An oxygen linked antibody is an antibody which has a chemical function group such that the linkage between the antibody and the linker or compound is joined via an oxygen atom. Similarly, a nitrogen linked antibody is an antibody which has a chemical function group such that the linkage between the antibody and the linker or compound is joined via an nitrogen atom.

An "acid" in the context of this application is a compound which has an empty orbital to accept a pair of electrons. Some non-limiting examples of acids include carboxylic acids, phenols, or mineral acids such as HCl, HBr, and $H_2SO_4$. Weak acids are compounds which have a $pK_a$ above −2 and below 7. Carboxylic acids are generally considered weak acids and may include any compound with a —$CO_2H$ group. Some non-limiting examples of carboxylic acids include acetic acid, citric acid, trifluoroacetic acid, benzoic acid, phenylacetic acid, lactic acid, succinic acid, or chloroacetic acid.

A "base" in the context of this application is a compound which has a lone pair of electron that can accept a proton. Non-limiting examples of a base can include triethylamine, a metal hydroxide, a metal alkoxide, a metal hydride, or a metal alkane. An alkyllithium or organolithium is a compound of the formula $alkyl_{(C\leq 12)}$-Li. A nitrogenous base is an alkylamine, dialkylamino, trialkylamine, nitrogen containing heterocycloalkane or heteroarene wherein the base can accept a proton to form a positively charged species. For example, but not limited to, a nitrogenous base could be 4,4-dimethylpyridine, pyridine, 1,8-diazabicyclo[5.4.0]undec-7-ene, diisopropylethylamine, or triethylamine. A metal alkoxide is an alkoxy group wherein the oxygen atom, which was the point of connectivity, has an extra electron and thus a negative charge which is charged balanced by the metal ion. For example, a metal alkoxide could be a sodium tert-butoxide or potassium methoxide. As used herein, the term "strong base" indicates a base which has a $pK_a$ of greater than 20. Alternatively, the term "weak base" indicates a base which has a $pK_a$ of less than 20.

A "boron containing group" is a functional group which contains a boron atom such as boronic acid or boronate esters. Some non-limiting examples of such functional groups include —$B(OH)_2$, —$B(OMe)_2$, or pinacol boronate ester.

A "metal" in the context of this application is a transition metal or a metal of groups I or II. It may also be an element of Group 13 such as, but not limited to, boron and aluminum.

A "linker" in the context of this application is divalent chemical group which may be used to join one or more molecules to the compound of the instant disclosure. Linkers may also be an amino acid chain wherein the carboxy and amino terminus serve as the points of attachment for the linker. In some embodiments, the linker contains a reactive functional group, such as a carboxyl, an amide, a amine, a hydroxy, a mercapto, an aldehyde, or a ketone on each end that be used to join one or more molecules to the compounds of the instant disclosure. In some non-limiting examples, —$CH_2CH_2CH_2CH_2$—, —$C(O)CH_2CH_2CH_2$—, —$OCH_2CH_2NH$—, —$NHCH_2CH_2NH$—, and —$(OCH_2CH_2)_n$—, wherein n is between 1-1000, are linkers.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropyl-methoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a protected hydroxy group is a group of the formula $PG_{A1}PG_{A2}N$— wherein $PG_{A1}$ and PG$_{A2}$ are an monovalent amine protecting group as described above or one of these two groups may be a hydrogen provided the other is a monovalent amine protecting group or the two groups are taken together to form a divalent amine protecting group.

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected hydroxy group is a group of the formula PG$_H$O wherein PG$_H$ is a hydroxyl protecting group as described above.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected thiol group is a group of the formula PG$_T$S wherein PG$_T$ is a thiol protecting group as described above.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedrally substituted carbon atoms), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Synthesis of Thailastatin A and Analogs Thereof

Depicted in Scheme 1 below is the retrosynthetic pathway of the developed synthetic strategy toward thailanstatin A (1).

Scheme 1: Thailanstatin Structure and Retrosynthesis
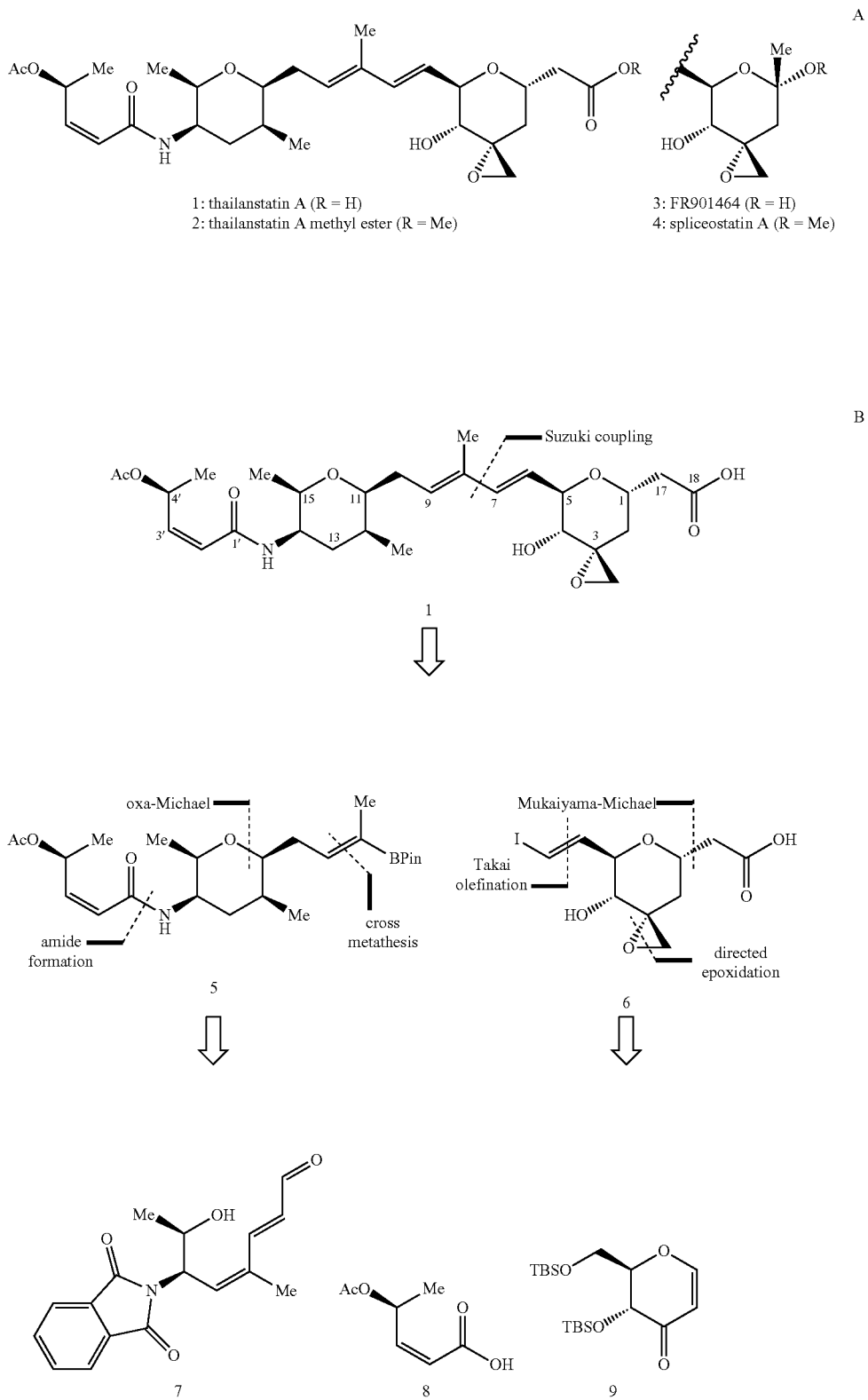
A: Molecular structures of thailanstatin A (1), its methyl ester (2), and related natural products FR901464 (3) and spliceostatin A (4). B: Retrosynthetic analysis of 1 through intermediates 5 and 6.

Beginning with the disconnection of 1, advanced intermediates vinyl boronate 5 and vinyl iodide 6 can be joined with Suzuki coupling. Further disconnection of 5 at the amide linkage (amide bond formation), the vinyl boronate olefinic bond (cross metathesis), and the tetrahydropyran system (oxa-Michael reaction) as indicated in Scheme 1 revealed doubly conjugated hydroxy aldehyde 7 and acetoxy carboxylic acid 8 as potential building blocks. Disassembly of 6 at the vinyl iodide (Takai olefination), epoxide (directed epoxidation) and tetrahydropyran (Mukaiyama-Michael reaction) sites traced this advanced intermediate back to the known and readily available starting material, pyranone 9.

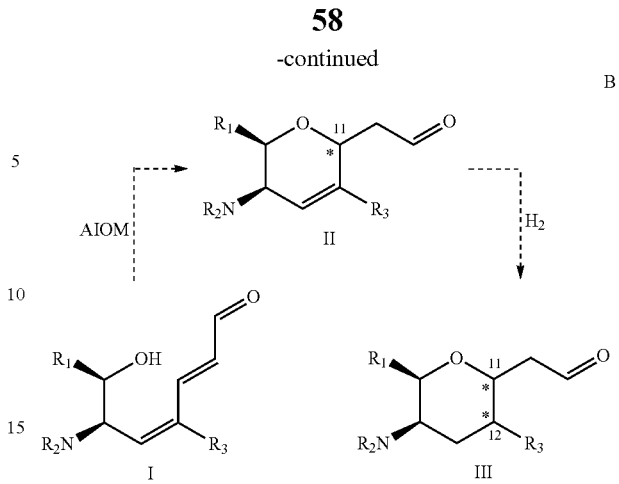

Scheme 2: Synthesis of Tetrahydropyran System of Thailanstatin

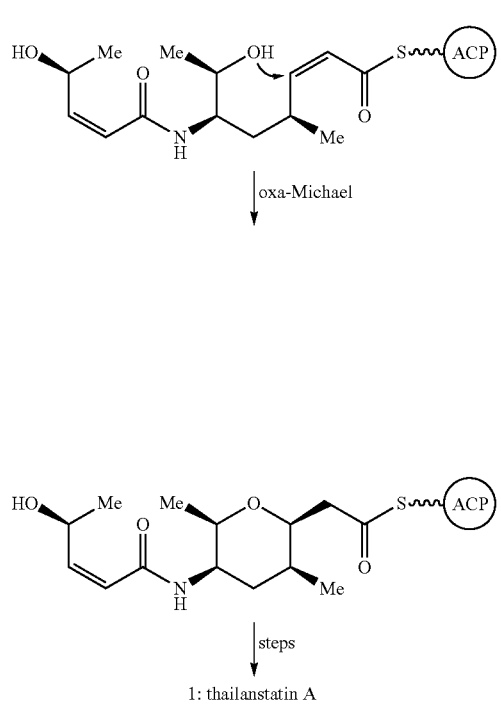

A: Biosynthetic formation of the tetrasubstituted tetrahydropyran system of thailanstatin A (1) through an oxa-Michael reaction. B: Proposed diastereodivergent approach to tetrasubstitued dihydropyrans II from α,β,γ,δ-unsaturated aldehyde I through asymmetric intramolecular oxa-Michael (AIOM) reaction and tetrasubstituted tetrahydropyrans III from II via hydrogenation.

Figure 2A:
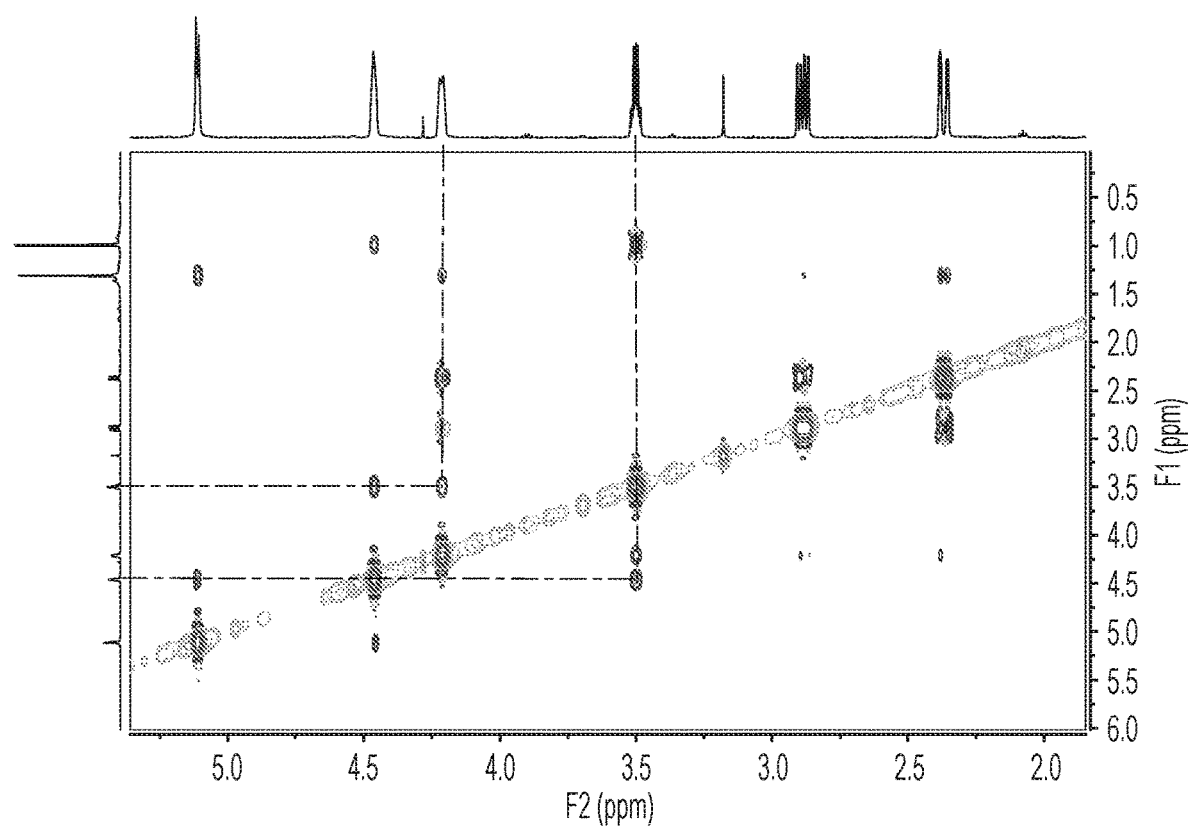
FIGS. 2A-2E show the 2D NOE NMR spectra of compound 24 (FIG. 2A), 11-epi-24 (FIG. 2B), 26 (FIG. 2C), 12-epi-26 (FIG. 2D), and 6a (FIG. 2E).
Figure 2B:
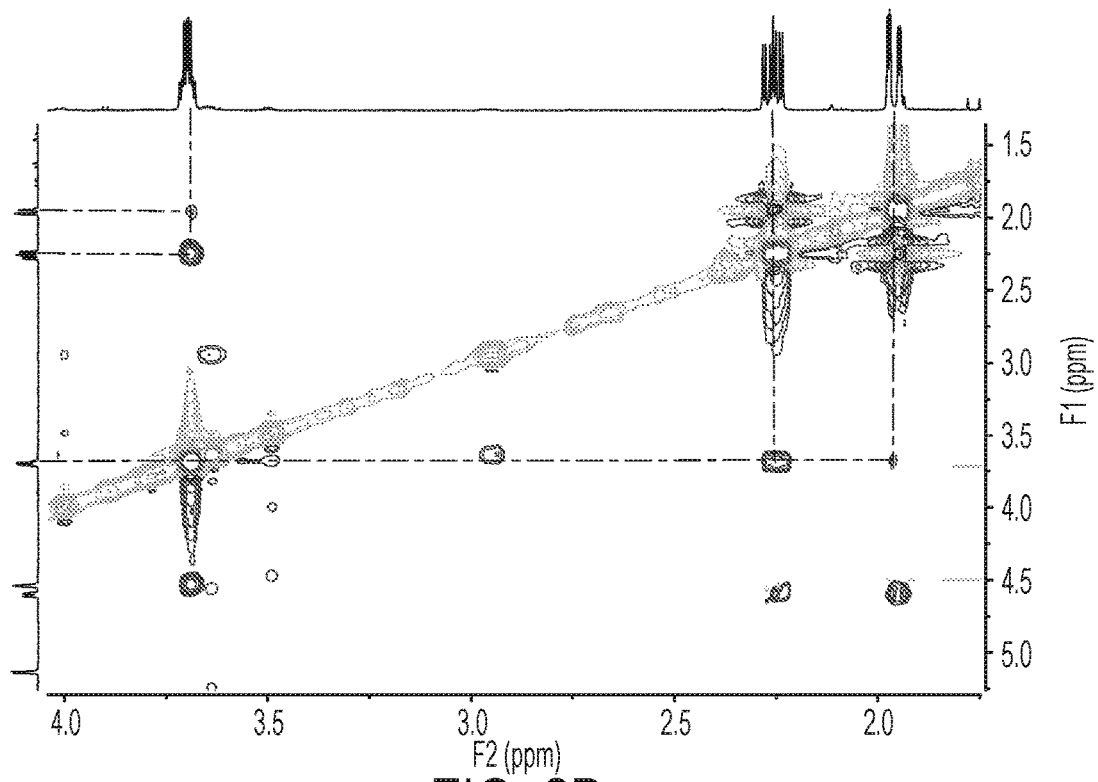

Beginning with the proposed biosynthesis of 1 (Scheme 2), which involves an intramolecular oxa-Michael reaction of an acyl carrier protein (ACP)-bound α,β-unsaturated thioester of a polyketide synthase (PKS) complex to obtain the 2,3,5,6-tetrasubstituted tetrahydropyran ring embedded within intermediate 5 (Liu, et al., 2013; Helfrich and Piel, 2016), but in an effort to preserve atom and step economy (Trost, 1995) and in order to establish a foundation for a diastereodivergent approach to highly functionalized tetrahydropyrans, the asymmetric intramolecular oxa-Michael (AIOM) reaction (Nising and Bräse, 2008; Nising and Bräse, 2012) was explored with an unprecedented substrate possessing an additional degree of unsaturation, such as an α,β,γ,δ-unsaturated aldehyde (I, Scheme 2). If successful, this methodology would constitute an entry to 2,6-syn or 2,6-anti tetrasubstituted dihydropyrans II (FIG. 2B) in a diastereoselective manner via catalyst control. Additionally, subsequent substrate-controlled hydrogenation could allow access to tetrasubstituted tetrahydropyrans III (FIG. 2B) with defined stereochemistry at C11 and C12, respectively.

Scheme 3: Synthesis of Vinyl Boronate 5$^a$

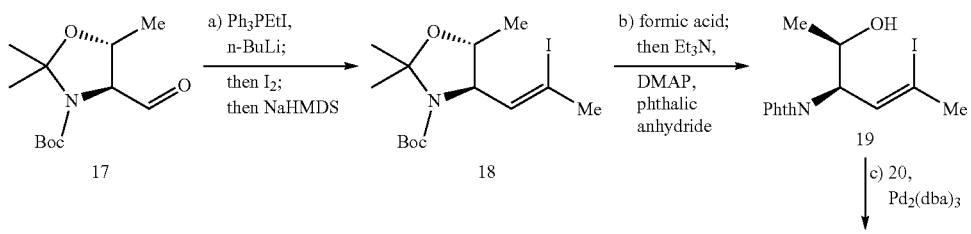

-continued

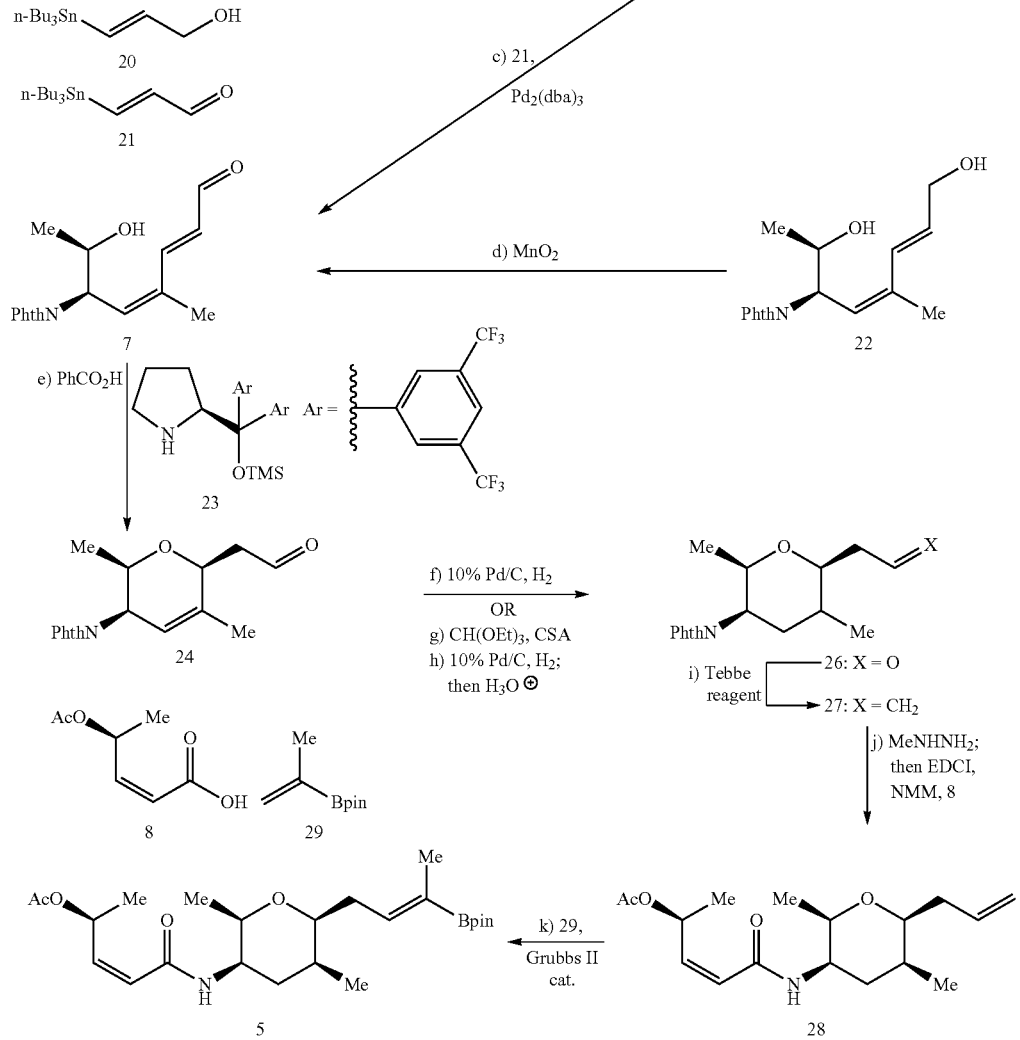

aReagents and conditions: (a) PPh3EtI (2.0 equiv), n-BuLi (2.0 equiv), THF, 25° C., 15 min; then I2 (1.9 equiv); then NaHMDS (1.9 equiv); then 17 (1.0 equiv), THF, −78 → −20 → −78° C., 1.5 h, 54% [(Z):(E) ca. 95:5]; (b) formic acid (neat), 25° C., 10 min; then phthalic anhydride (1.1 equiv), Et3N (20 equiv), DMAP (0.1 equiv), CHCl3, 70° C., 48 h, 80% overall; (c) 20 (1.2 equiv), Pd2(dba)3 (0.1 equiv), NMP, 25° C., 16 h, 73%; (c) 21 (2.0 equiv), Pd2(dba)3 (0.1 equiv), NMP, 25° C., 16 h, 60%; (d) MnO2 (20 equiv), CH2Cl2, 25° C. 1 h, 90%; (e) 23 (0.2 equiv), PhCO2H (0.2 equiv), CH2Cl2, 0° C., 6.5 h, 77%; (f) 10% Pd/C (50%, w/w), H2 (80 bar), HFIP, 25° C., 24 h, 93% (dr 7:3); (g) CH(OEt)3 (10 equiv), CSA (0.1 equiv), EtOH, 25° C., 2 h, 91%; (h) 10% Pd/C (35%, w/w), H2 (80 bar), EtOH, 25° C., 15 h; then 0.1M eq. HCl (3.0 equiv), acetone, 25° C., 10 min, 54% overall; (i) Tebbe reagent (1.0 equiv), THF, −20 → 0° C., 1 h, 76%; (j) MeNHNH2 (10 equiv), PhH, 25° C., 2 h; then EDCI (3.0 equiv), NMM (3.0 equiv), 8 (2.0 equiv), CH2Cl2, 25° C., 30 min, 73% overall; (k) 29 (5.0 equiv), Grubbs II cat. (0.1 equiv), ClCH2CH2Cl, 80° C., 1 h, 71%. Abbreviations: Boc = tert-butyloxycarbonyl; CSA = camphorsulfonic acid; dba = dibenzylideneacetone; DMAP = N,N-dimethylaminopyridine; EDCI = 1-(3-dimethylaminopropyl)-3-ethylcarbodiimide hydrochloride; HFIP = hexafluoroisopropanol; HMDS = hexamethyldisilazide; NMM = N-methylmorpholine; NMP = N-methyl-2-pyrrolidinone; Phth = phthaloyl; pin = pinacolato; TMS = trimethylsilyl.

The synthesis of vinyl boronate 5 from Garner aldehyde 17 (Dondoni and Perrone, 2004) is described above in Scheme 3. Then, α-methyliodomethylenation of 17 under Stork-Zhao conditions (Stork and Zhao, 1989; Chen, et al., 1994) furnished olefinic iodo-Boc derivative 18 [54% yield, (Z):(E) ca. 95:5, chromatographically separated] from which the desired iodo-Phth derivative 19 was generated through protecting group exchange (formic acid; then phthalic anhydride, Et3N, DMAP cat.) in an overall yield of 80%. Stille coupling of 19 with hydroxy stannane 20 [Pd2(dba)3, 73% yield] (Pilli, et al., 1998 or described in detail in Example 3 below) to obtain the desired diene 22, whose MnO2 oxidation afforded the desired (E,Z)-α,β,γ,δ-unsaturated aldehyde 7 in an excellent yield of 90%. The same aldehyde (7) could also be obtained in one step directly from iodide 19 and aldehyde stannane 21 (Johnson and Kadow, 1987) through Stille coupling [Pd2(dba)3, 60% yield]. Exposure of the resultant aldehyde 7 to diaryl prolinol catalyst 23 (0.2 equiv) in the presence of benzoic acid (0.2 equiv) in CH2Cl2 caused the desired asymmetric intramolecular oxa-Michael reaction, thus obtaining the desired 2,6-syn dihydropyran 24 in 77% yield (dr>20:1). Aldehyde 24 tended to resist the subsequent hydrogenation reaction. Optimal hydrogenation results were achieved by masking the aldehyde moiety as a diethoxy acetal [25, CH(OEt)3, CSA, 91% yield] which was followed by selective hydrogenation from the α-face of the ring system could be achieved with 10% Pd/C in ethanol under a H₂ atmosphere at high pressure (80 bar) to afford 2,3,5,6-syn tetrahydropyran 26 (54% yield) followed by mild aqueous acidic workup. Additionally, after extensive experimentation, aldehyde 24 was found be efficiently hydrogenated directly (H₂, 80 bar) in excellent yield with 10% Pd/C in hexafluoroisopropanol (HFIP) solvent, albeit with modest diastereoselectivity (93%, 7:3 dr, 65% yield for 26). Methylenation using Tebbe reagent of saturated aldehyde 26 provided the desired olefin 27 in 76% yield. Removal of the phthalimide moiety within 27 with methylhydrazine, followed by direct amide coupling with carboxylic acid 8 (He, et al., 2014 or see the detailed description in Example 3 below) using EDCI and NMM to afford amide 28 (73% yield), an advanced intermediate reported in the synthesis of FR901464 (Albert, et al., 2006). Cross metathesis of 28 with commercially available isopropenylboronic acid pinacol ester 29 using Grubbs II cat. in ClCH₂CH₂Cl afforded the advanced intermediate vinyl boronate 5 in 71% yield.

unsaturated aldehydes, esters, and amides generally favor the 2,6-syn tetrahydropyran product (Nising and Bräse, 2008; Nising and Bräse, 2012). Previous studies by Hong have also shown that olefin geometry such as (E) or (Z) α,β-unsaturated aldehydes can render AIOM reactions stereoselective as a consequence of substrate control, while catalyst control alone has rarely useful for high levels of 2,6-anti stereoselectivity (Lee, et al., 2011). As depicted in Scheme 4A, 2,6-syn dihydropyran 24 or 2,6-anti dihydropyran 11-epi-24 (half-chair structures confirmed by ¹H NOE spectroscopy, see FIGS. 2A & 2B for NOE spectral information) were found to be accessed in comparable yields with virtually complete stereoselectivity, based solely on catalyst control. In addition, complementary stereoselectivity in the hydrogenation of acetal substrate 25 could be achieved through the use of specific reaction conditions. Thus, as shown in Scheme 4B, treatment of 25 with [Ir(Py)(PCy₃)(COD)BARF] cat., (Lightfoot, et al., 1998) a counteranion analogue of Crabtree's catalyst, in CH₂Cl₂ under 1 atm of H₂ cleanly provided the resultant diasteoromer, Scheme 4: Diastereodivergent Synthesis of 2,3,5,6-Tetrasubstituted Tetrahydropyrans<sup>a</sup>

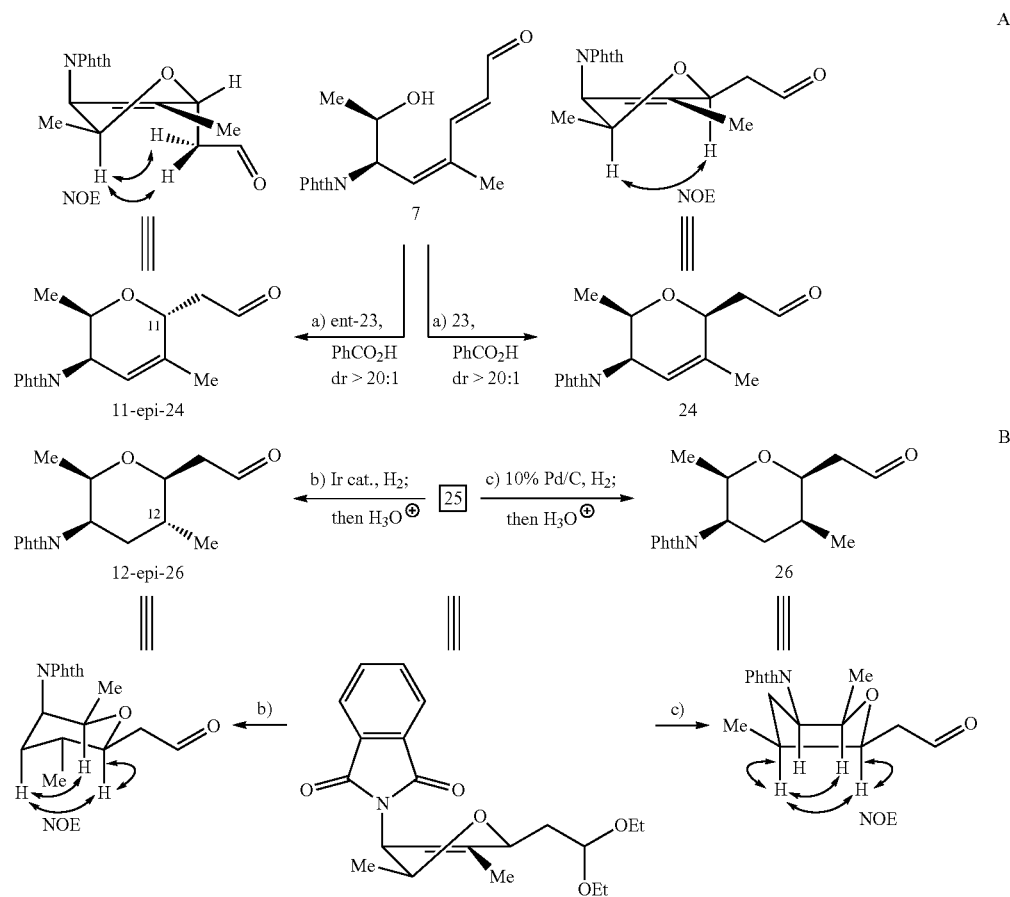

Ir cat. = [Ir(Py)(PCy₃)(COD)BARF]
<sup>a</sup>Reagents and conditions: (a) 23 or ent-23 (0.2 equiv), PhCO₂H (0.2 equiv), CH₂Cl₂, 0° C., 6.5 h, 77% for 24 (dr > 20:1), 64% for 11-epi-24 (dr > 20:1); (b) [Ir(Py)(PCy₃)(COD)BARF] (0.05 equiv), H₂ (1 atm), CH₂Cl₂, 25° C., 10 h; then 0.1M aq. HCl (3.0 equiv), acetone, 25° C., 10 min, 85% overall; (c) 10% Pd/C (35%, w/w), H₂ (80 bar), EtOH, 25° C., 24 h; then 0.1M aq. HCl (3.0 equiv), acetone, 25° C., 10 min, 54% overall.
Abbreviations: BARF = tetrakis[3,5-bis(trifluoromethyl)phenyl] borate; COD = 1,5-cyclooctadiene; Cy = cyclohexyl; Py = pyridine.

Figure 2C:
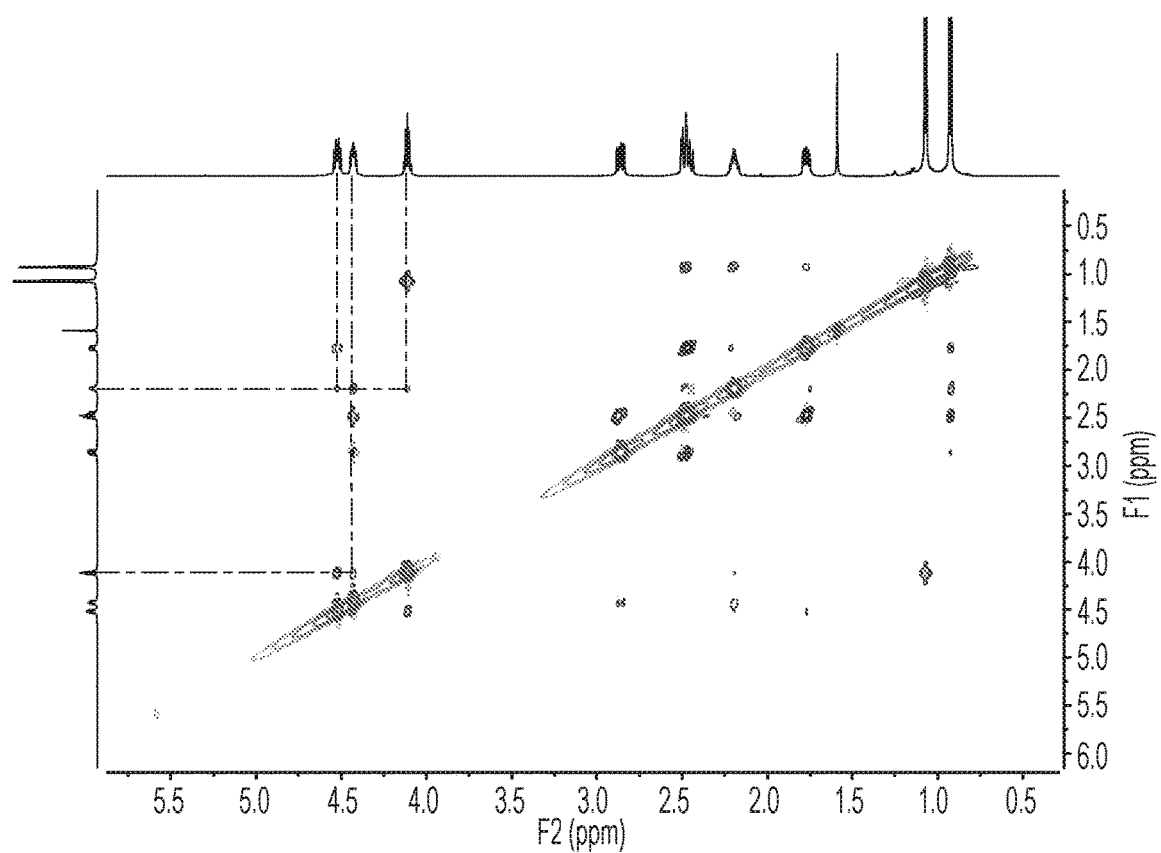
Figure 2D:
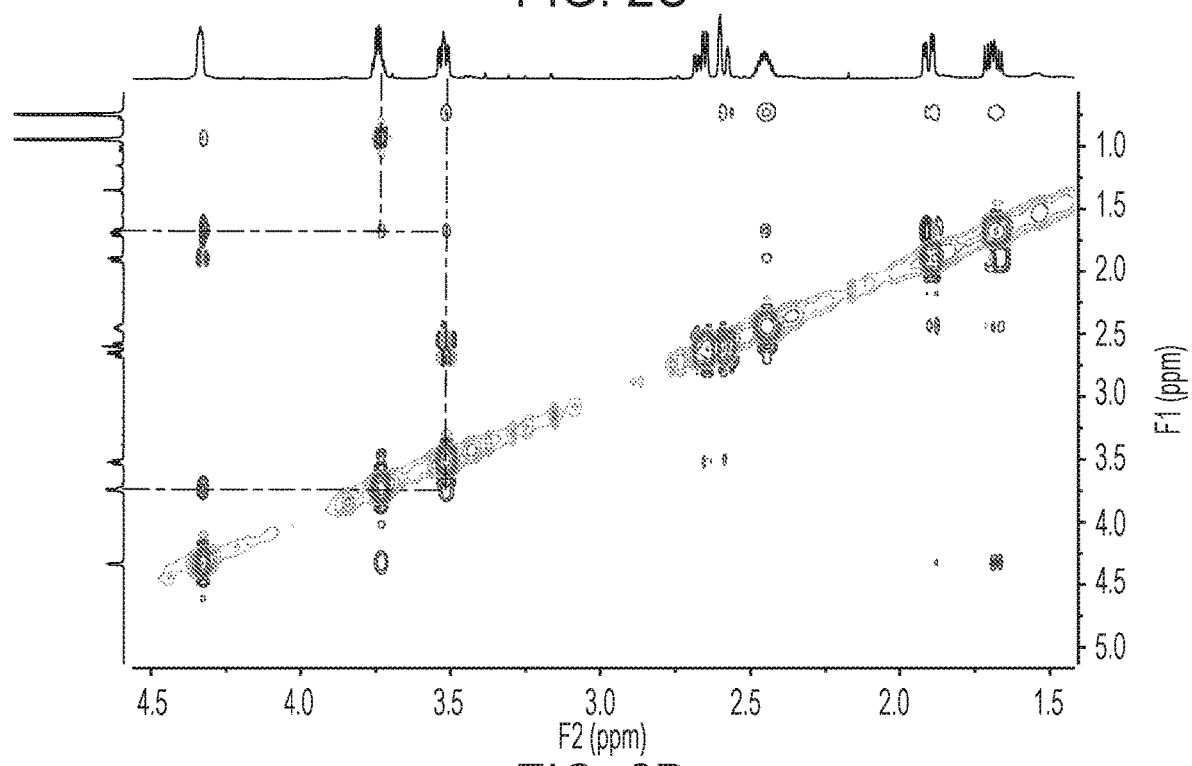

The oxa-Michael reaction of aldehyde 7 displays an unusually high degree of catalyst control, especially as compared with typical AIOM reactions, in which α,β-12-epi-26, after workup with dilute acid. Without wishing to be bound by any theory, it is believed that the delivery of the hydrogen atom to the β-face of 25 was likely facilitated by the O atom(s) of the acetal and/or the imide carbonyl O atom(s). Alternatively, the use of heterogeneous conditions led to 26, the product of $H_2$ delivery from the α-face of 25, as dictated by the hindered nature of its β-face. The relative configurations of 26 and 12-epi-26 were confirmed by $^1H$ NOE studies (FIGS. 2C & 2D), which revealed a chair conformation for 12-epi-26 but a boat conformation for 26, likely due to the large 1,3 diaxial interaction between the bulky N-phthaloyl moiety and the adjacent axial methyl group. This AIOM/hydrogenation approach may be used as a general method in the synthesis of highly substituted tetrahydropyrans within other systems as well as the current analogs of thailanstatin.

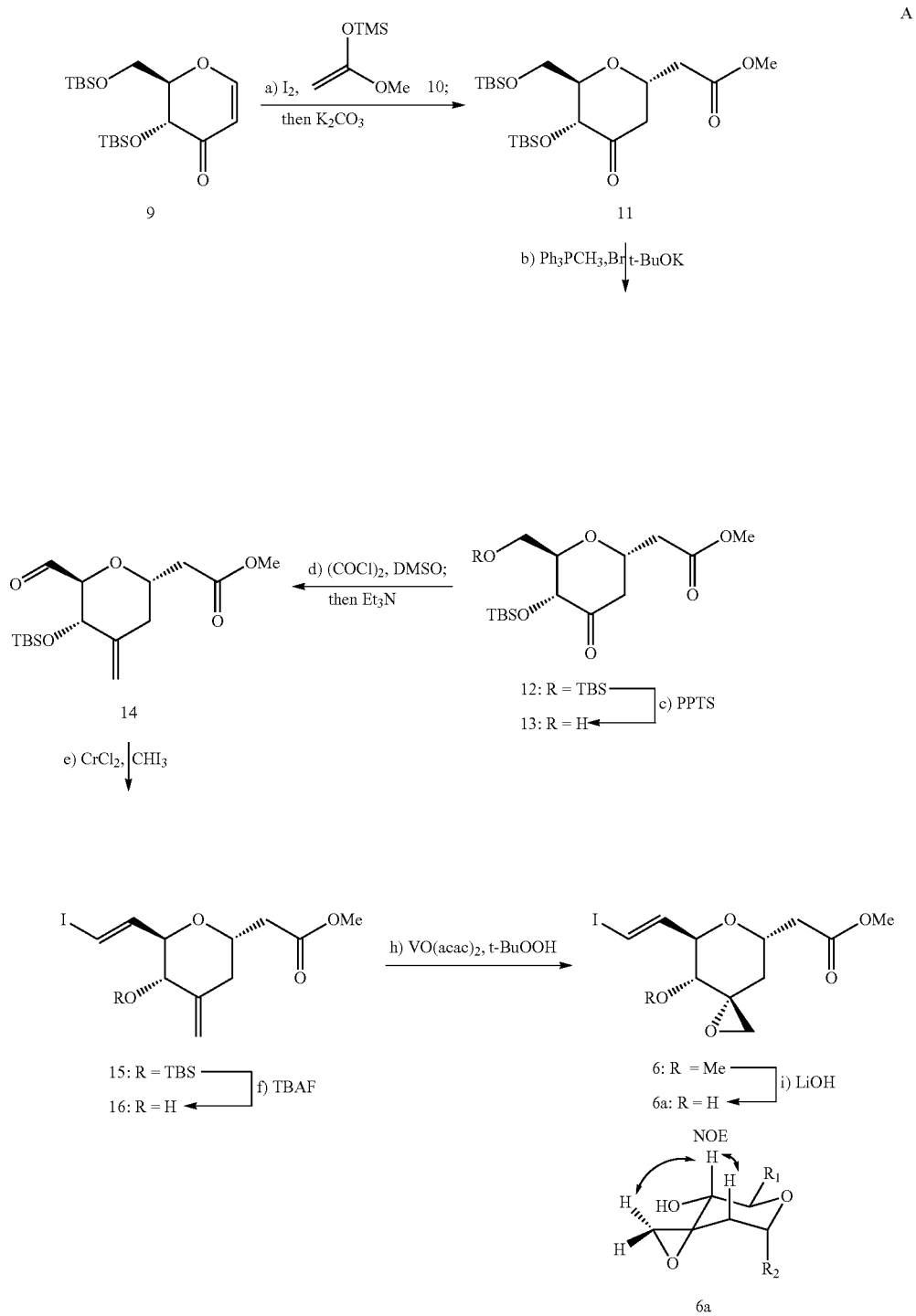

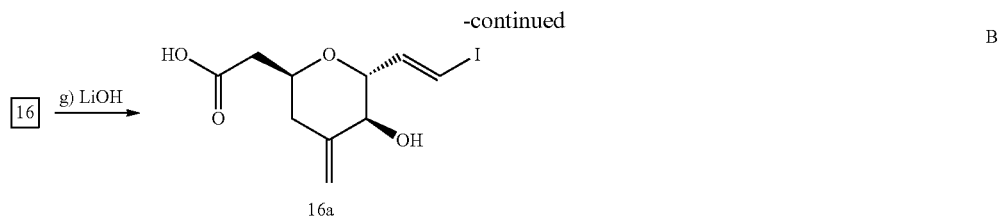

<sup>a</sup>Regents and conditions:
(a) 10 (2.0 equiv), I₂ (0.1 equiv), MeCN, -30 → -20° C., 30 min; then K₂CO₃ (0.1 equiv), MeOH, 25° C., 10 min, 98% overall;
(b) Ph₃PCH₃Br (2.5 equiv), t-BuOK (2.0 equiv), THF, 0° C., 1 h, 72%
(c) PPTS (1.0 equiv), MeOH, 25° C., 12 h, 98%;
(d) (COCl)₂ (1.5 equiv), DMSO (3.0 equiv), then Et₃N (5.0 equiv), CH₂Cl₂, -78 → -55° C., 3 h, 96%;
(e) CrCl₂ (6.0 equiv), CHI₃ (3.0 equiv), THF, 25° C., 12 h, 58%;
(f) TBAF (2.0 equiv), THF, 0 → 25° C., 30 min, 93%;
(g) LiOH (8.0 equiv), 1:1 THF/H₂O, 25° C., 12 h, 98%;
(h) VO(acac)₂ (0.1 equiv), t-BuOOH (2.1 equiv), CH₂Cl₂, 0 → 25° C., 10 h, 74%;
(i) LiOH (1.5 equiv), 10:1 THF/H₂O, 0 → 25° C., 12 h, 90%.
Abbreviations:
DMSO = dimethyl sulfoxide;
PPTS = pyridinium p-toluenesulfonate;
TBAF = n-tetrabutylammonium fluoride;
TBS = tert-butyldimethylsilyl.

Figure 2E:
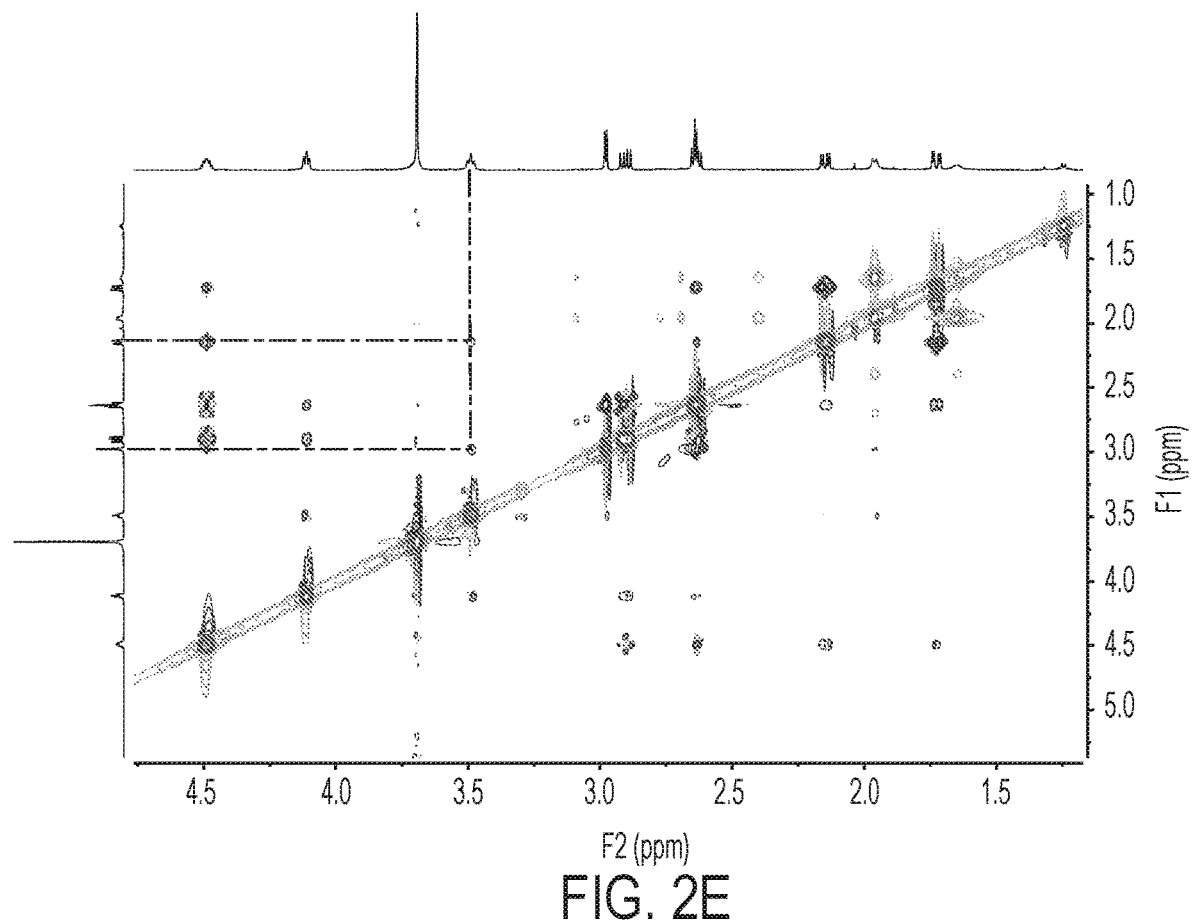
Figure 3A:
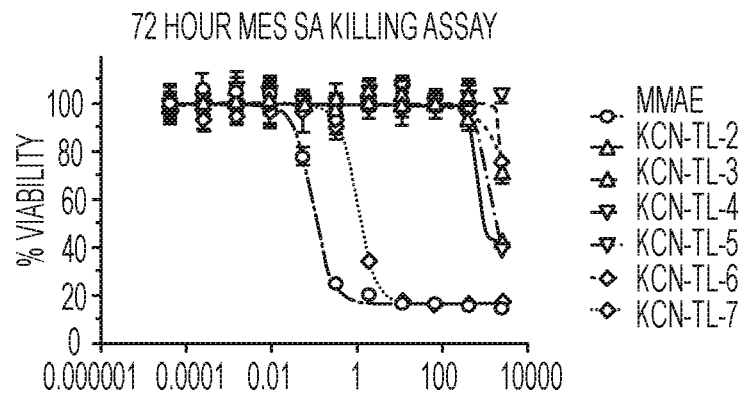
FIGS. 3A-3L show the 72 hour killing assay in MES SA for KCN-TL-2KCN-TL-7 (FIG. 3A), for KCN-TL-9KCN-TL-14 (FIG. 3D), for KCN-TL-8 (FIG. 3G), and for KCN-TL-19 (FIG. 3J); the 72 hour killing assay for MES SA DX for KCN-TL-2KCN-TL-7 (FIG. 3B), for KCN-TL-9KCN-TL-14 (FIG. 3E), for KCN-TL-8 (FIG. 3H), and for KCN-TL-19 (FIG. 3K); the 72 hour killing assay for 293T naive for KCN-TL-2KCN-TL-7 (FIG. 3C), for KCN-TL-9KCN-TL-14 (FIG. 3F), for KCN-TL-8 (FIG. 3I), and for KCN-TL-19 (FIG. 3L).
Figure 3B:
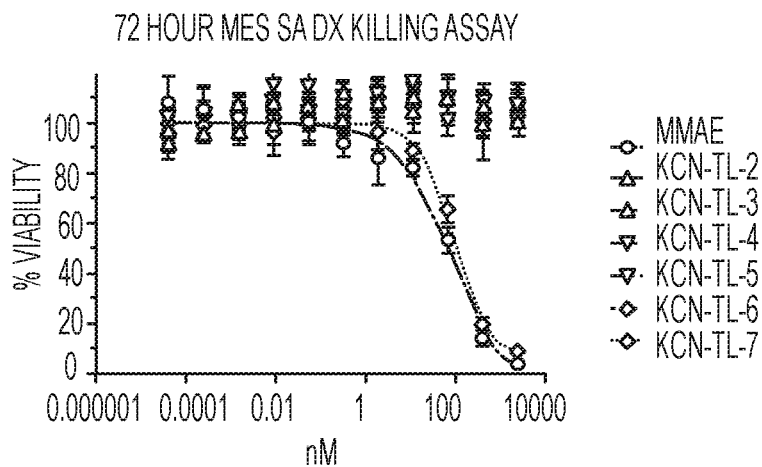
Figure 3C:
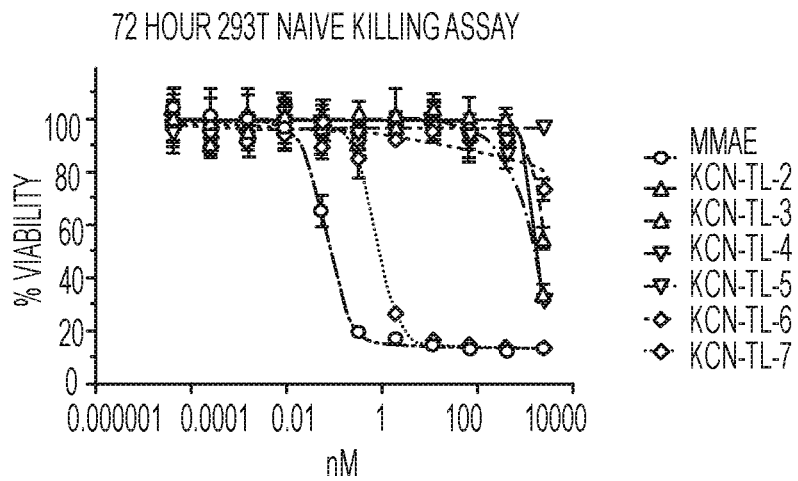
Figure 3D:
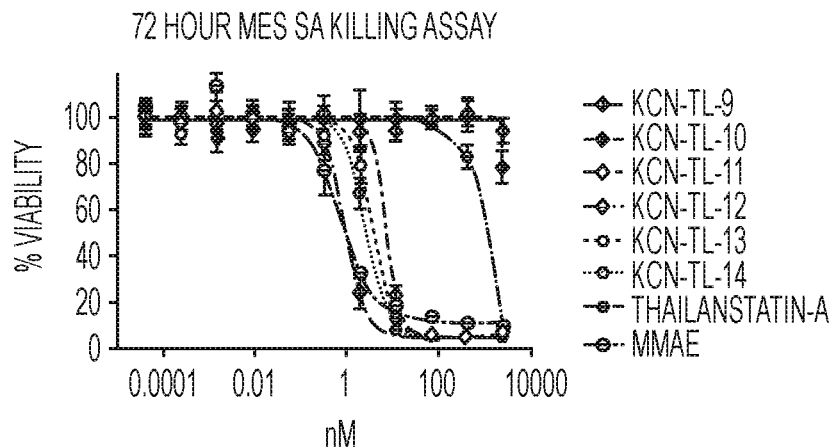
Figure 3E:
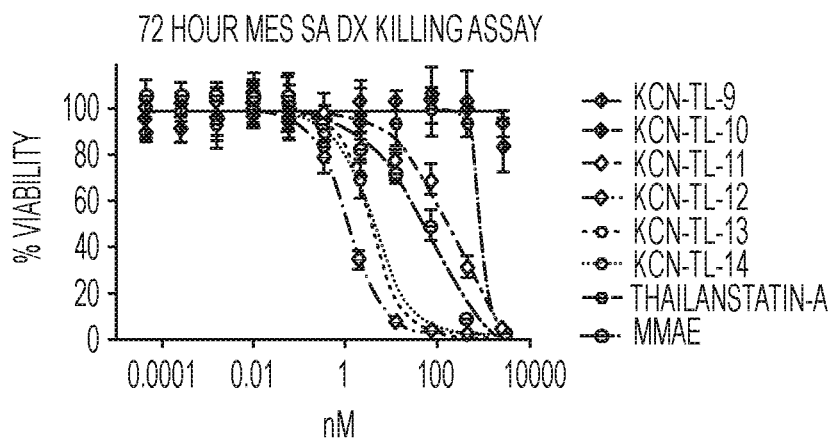
Figure 3F:
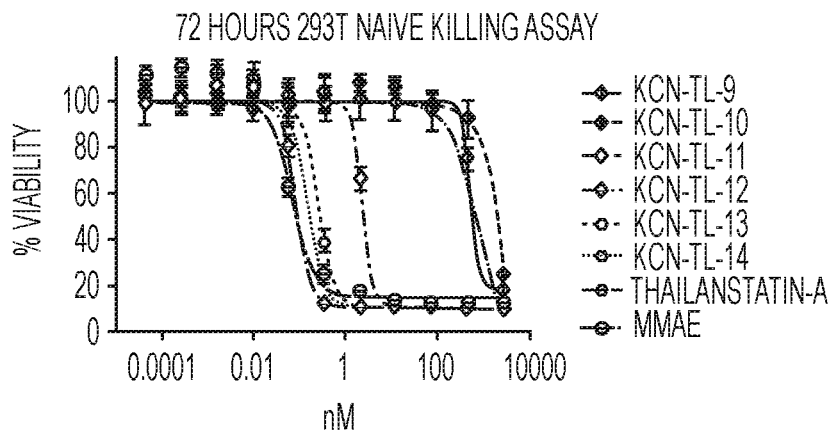
Figure 3G:
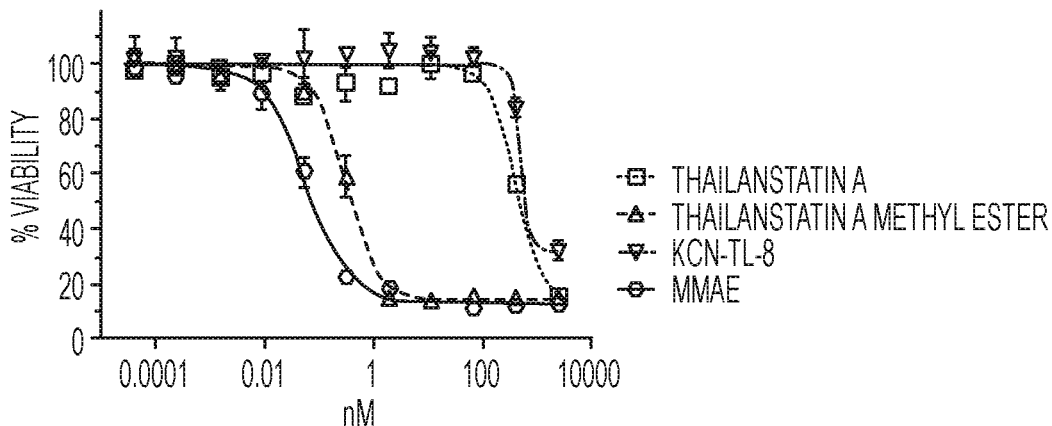
Figure 3H:
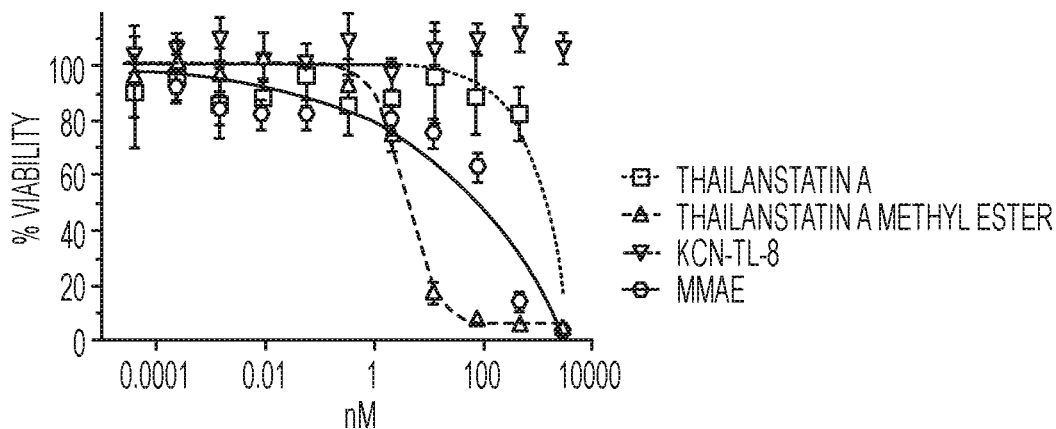
Figure 3I:
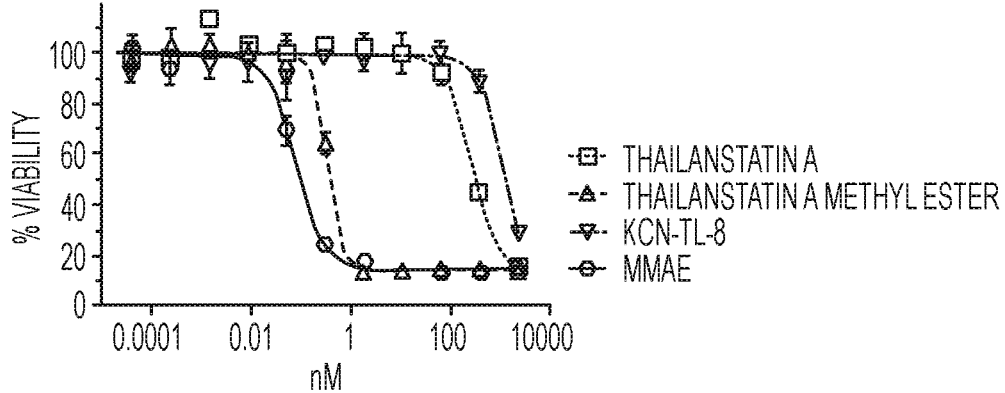
Figure 3J:
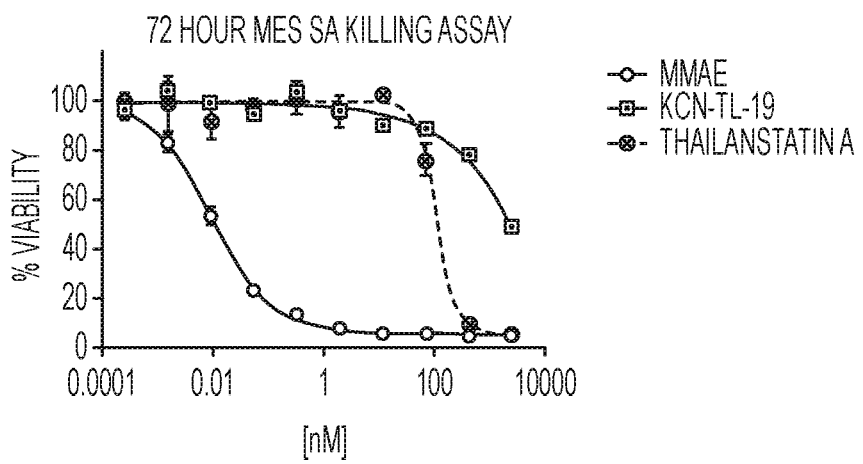
Figure 3K:
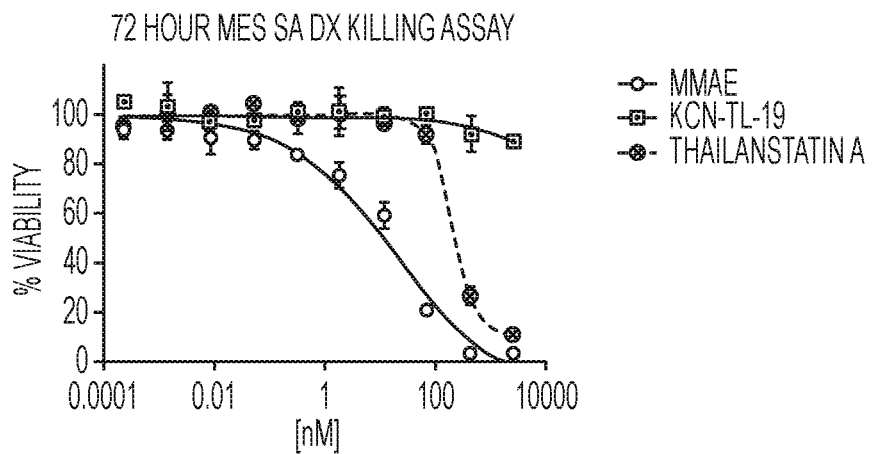
Figure 3L:
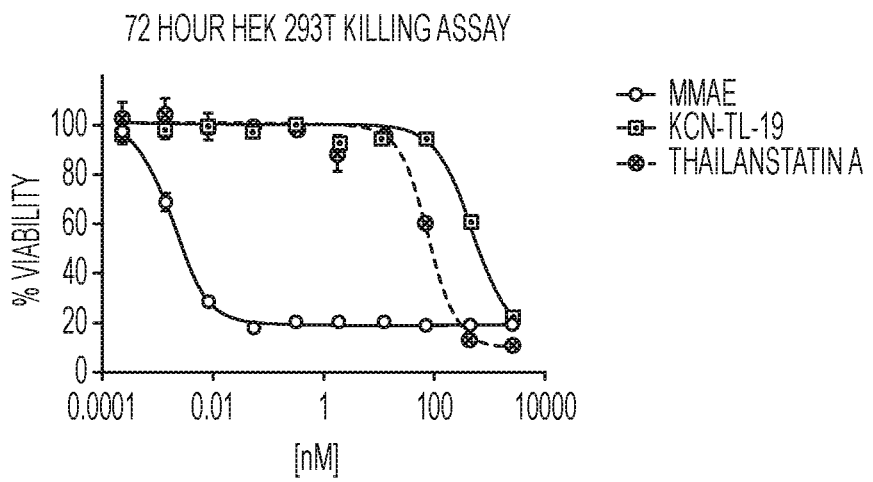

The syntheses of key vinyl iodide building blocks 6 and 6a are described in Scheme 5A. Previously synthesized pyrone derivative 9 (Fujiwara and Hayashi, 2008) was reacted with ketene silyl acetal 10 in the presence of iodine to afford stereoselectively, after treatment with methanolic K₂CO₃, ketone methyl ester 11 in 98% yield on a 10 g scale (Deuri and Phukan, 2012). Wittig reaction of 11 with the ylide derived from the phosphonium salt of MeBr and t-BuOK yielded terminal olefin 12 (80% yield), whose conversion to aldehyde 14 was achieved by selective monodesilylation (PPTS, 98% yield) to obtain primary alcohol 13 followed by oxidation. The primary alcohol 13 was converted by Swern oxidation [(COCl)₂, DMSO; Et₃N, 96% yield] to obtain aldehyde 14 (Dondoni and Perrone, 2004). Takai olefination (CrCl₂, CHI₃) (Takai, et al., 1986) of aldehyde 14 then led to the desired (E)-iodo-olefin 15 in 58% yield. Desilylation of 15 (TBAF, 93% yield) furnished allylic alcohol 16. To confirm the configuration, the methyl ester was saponification of 16 (LiOH) to afford acid 16a as a crystalline solid (m.p.=128-136° C., EtOAc). X-Ray crystallographic analysis (see ORTEP in FIG. 1) of the free acid 16a unambiguously confirmed the 2,6-anti configuration of the tetrahydropyran ring system. Directed expoxidation of 16 with t-BuOOH and catalytic VO(acac)₂ delivered the targeted hydroxy epoxide methyl ester 6a (74% yield), whose ¹H NOE analysis confirmed its relative stereochemistry (Scheme 3B, FIG. 2E) (Itoh, et al., 1979). Subsequent conversion of methyl ester 6 to carboxylic acid 6a was accomplished by saponification with LiOH (90% yield).

Scheme 6: Completion of the Total Synthesis of Thailanstatin A (1) and its Methyl Ester (2)<sup>a</sup>

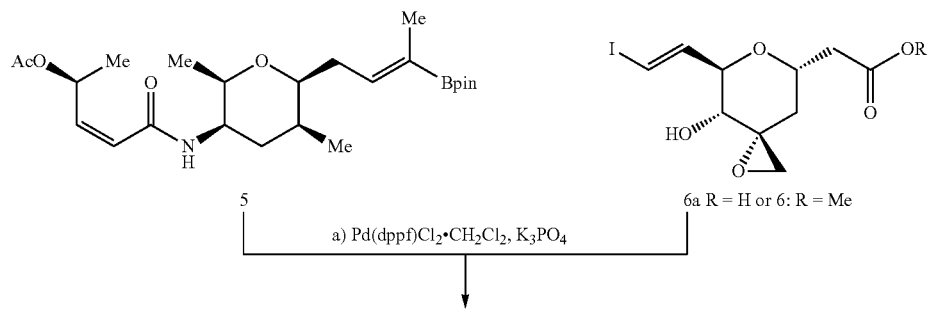

-continued

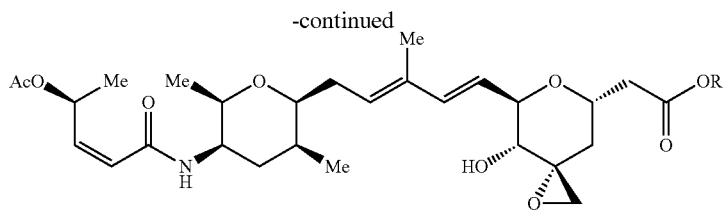

1: thailanstatin A (R = H)
2: thailanstatin A methyl ester (R = Me) ← b) TMSCHN₂

[a]Reagents and conditions:
(a) Pd(dppf)Cl₂·CH₂Cl₂ (0.02 equiv), K₃PO₄ (1.0 equiv), 5 (1.1 equiv), 6 or 6a (1.0 equiv), 1,4-dioxane/MeCN/H₂O (3:1:1), 25° C., 10 min, 52% for 1, 64% for 2;
(b) TMSCHN₂ (3.0 equiv), 3:2 PhMe/MeOH, 0 → 25° C., 3 h, quant.
Abbreviations: dppf = diphenylphosphinoferrocenyl.

Scheme 6 depicts the final coupling of the advanced intermediates vinyl iodides 6 and 6a with vinyl boronate 5 to afford the desired targets 1 and 2, respectively. At first, methyl ester 2 was obtained through Suzuki coupling utilizing catalytic Pd(PPh₃)₄ and Tl(OEt) as the base (Frank, et al., 2000). While the reaction was completed quickly (<15 min, 25° C.), the basic thallium(I) salts resulted in significant decomposition which are likely presumably due to epoxide and acetate ruptures. To circumvent this decomposition, the more stable Pd(dppf)Cl₂.CH₂Cl₂ complex was used with K₃PO₄ as the base in a biphasic system to deliver the desired thailanstatin A (1) and its methyl ester 2 (64% yield), respectively. Despite efforts to purify 1 by standard chromatographic techniques, semipreparative HPLC was utilized to affect its purification (see Example 3 for details). The yield was approximated, since the semipreparative HPLC purification required the treatment of crude 1 with TMSCHN₂ to generate chromatographically stable methyl ester 2 (52% overall yield).

Using the methods developed in the total synthesis of thailanstatin described above, the analogs described in Scheme 7 may also be prepared.

Scheme 7. Thailanstatin A (1), its methyl ester (2), and designed and synthesized analoges 30-47.

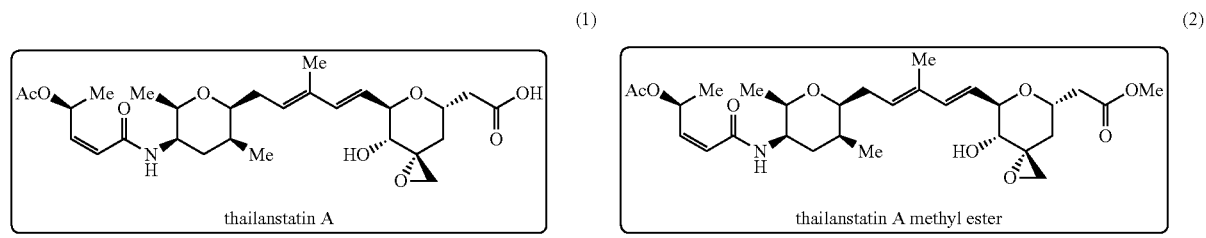

thailanstatin A (1)

thailanstatin A methyl ester (2)

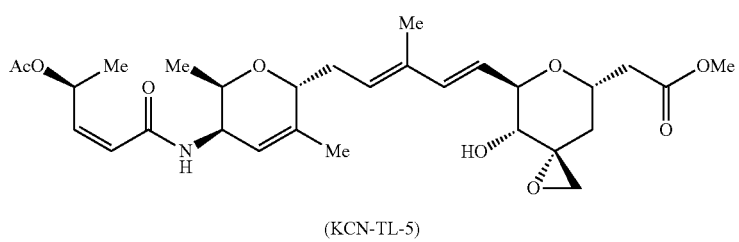

(KCN-TL-5) 30

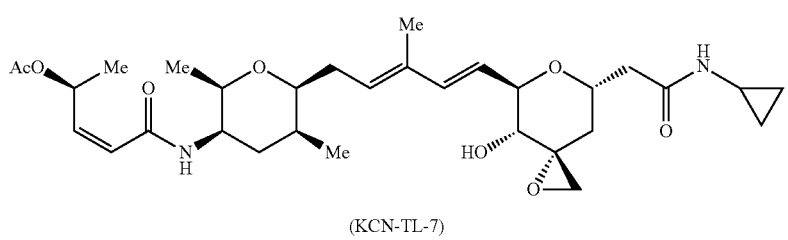

(KCN-TL-7) 31

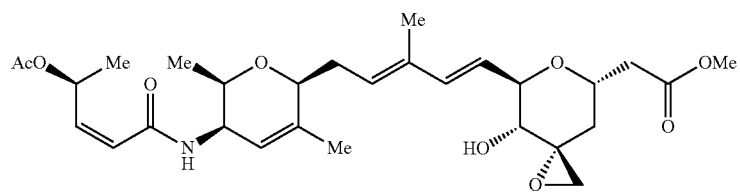
(KCN-TL-4)
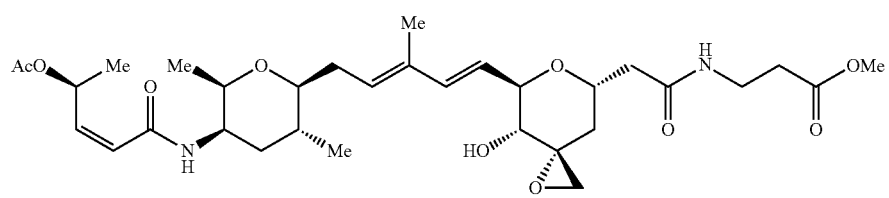
(KCN-TL-8)
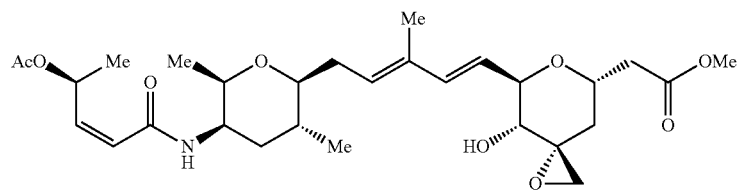
(KCN-TL-2)
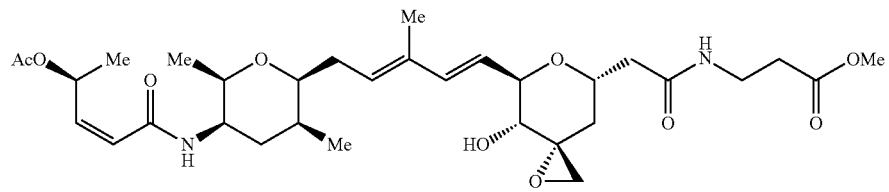
(KCN-TL-11)
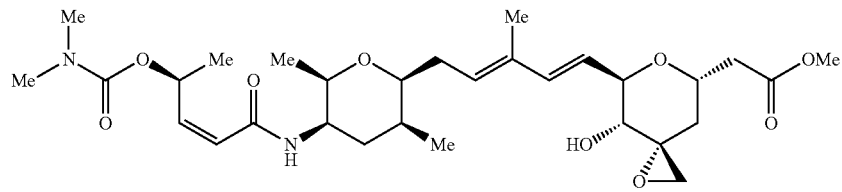
(KCN-TL-12)
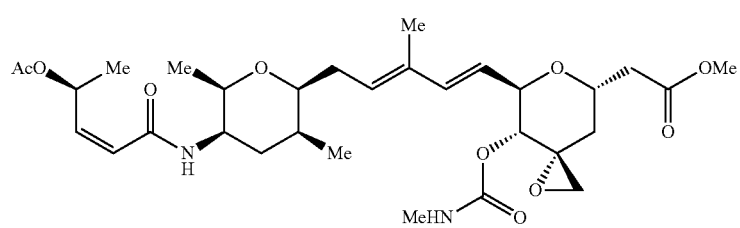
(KCN-TL-17)

-continued
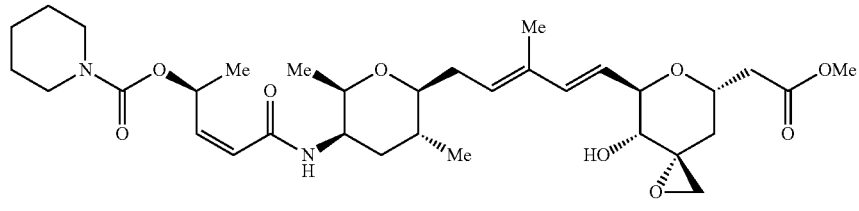
(KCN-TL-10)
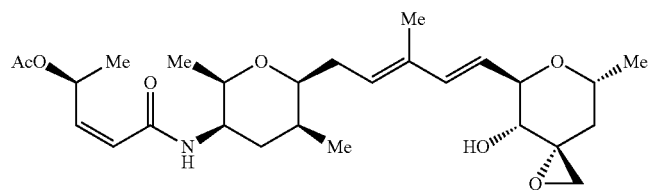
(KCN-TL-18)
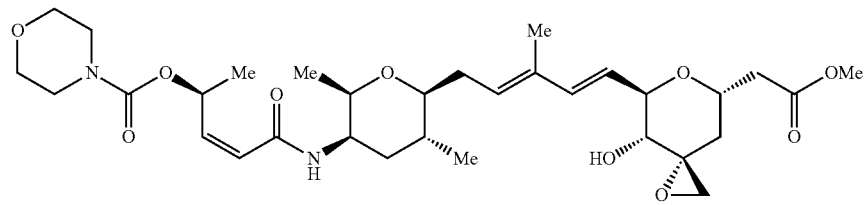
(KCN-TL-9)
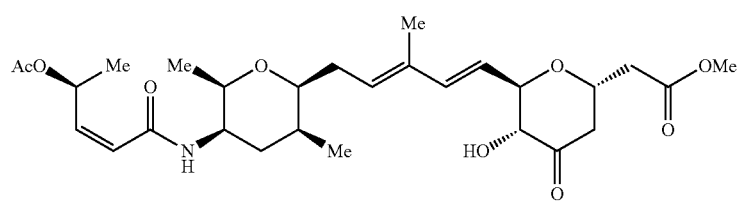
(KCN-TL-19)
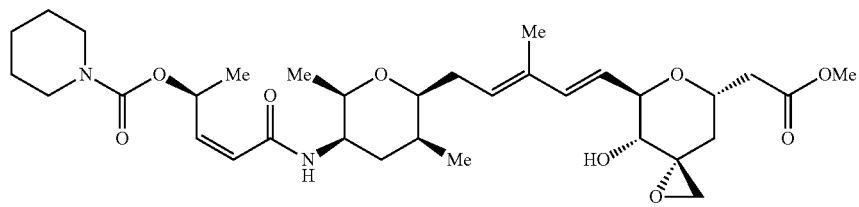
(KCN-TL-13)
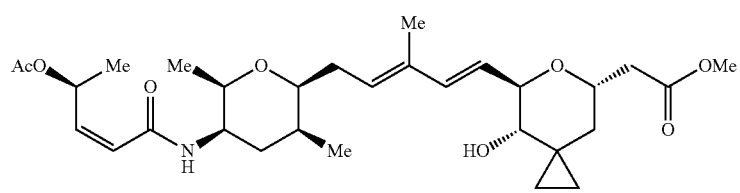
(KCN-TL-15)

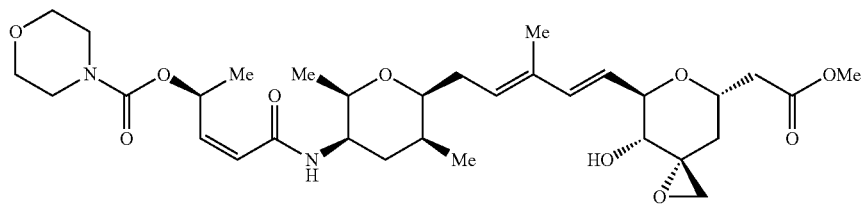
(KCN-TL-14) 44
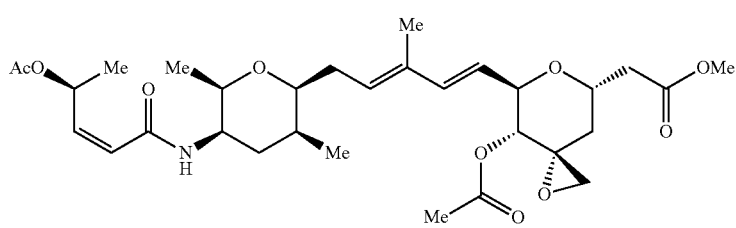
(KCN-TL-16) 45
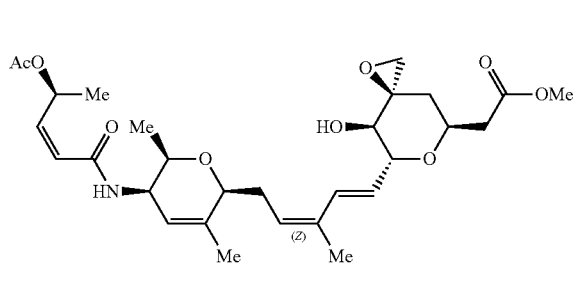
(KCN-TL-6) 46
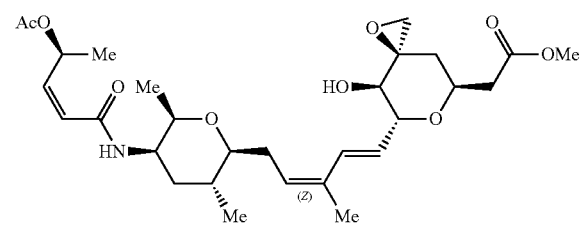
(KCN-TL-3) 47
Analogs 32 and 46 can be prepared using the methods described in Scheme 8 below. The preparation of the appropriate boronate coupling partner for vinyl iodide 6 to form analogs 32 and 46.
Scheme 8. Synthesis of thailanstatin A analogues 32 and 46.
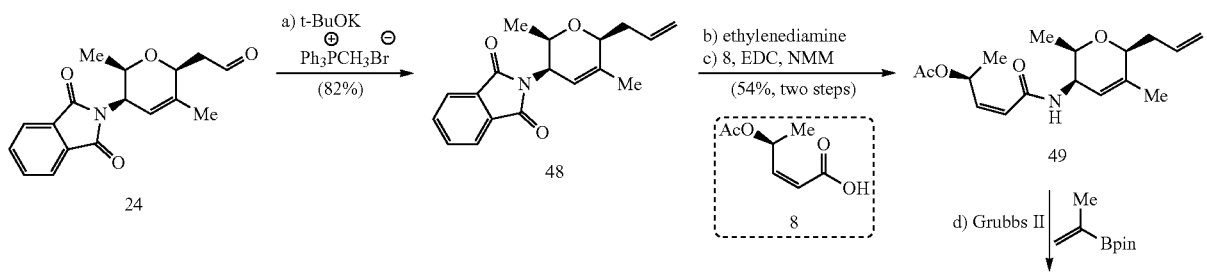

-continued

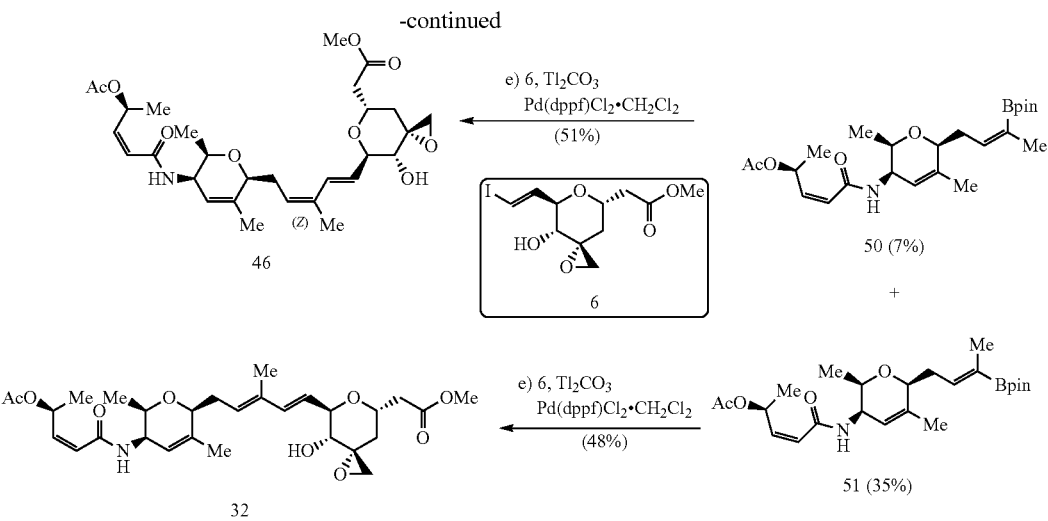

Reagents and conditions:
(a) t-BuOK (1.4 equiv), Ph$_3$P$^+$CH$_3$Br$^-$ (1.7 equiv), THF, 0° C., 2 h, 82%;
(b) ethylenediamine (2.0 equiv), EtOH, 80° C., 15 h;
(c) 8 (2.0 equiv), EDC (3.0 equiv), NMM (3.0 equiv), CH$_2$Cl$_2$, 25° C., 2 h, 54% for two steps;
(d) isopropenylBpin (10 equiv), Grubbs II (0.1 equiv), DCE, 80° C., 2 h, 7% for 50, 35% for 51;
(e) 6, Pd(dppf)Cl$_2$·CH$_2$Cl$_2$ (0.10 equiv), Tl$_2$CO$_3$ (5.0 equiv), THF:H$_2$O (3:1, v/v), 25° C., 3 h, 51% for 46, 48% for 32.

Abbreviations:
dppf = 1,1′-Bis(diphenylphosphino)ferrocene;
EDC = N-(3-dimethylaminopropyl)-N′-ethylcarbodiimide hydrochloride;
NMM = N-methylmorpholine;
isopropenylBpin = isopropenylboronic acid pinacol ester;
DCE = 1,2-dichloroethane,
THF = tetrahydrofuran.

Analog 30 was prepared as described in Scheme 9 from the epimer of 24 through similar borylation protocols using vinyl iodide 6.

Scheme 9. Synthesis of thailanstatin A analogue 30.

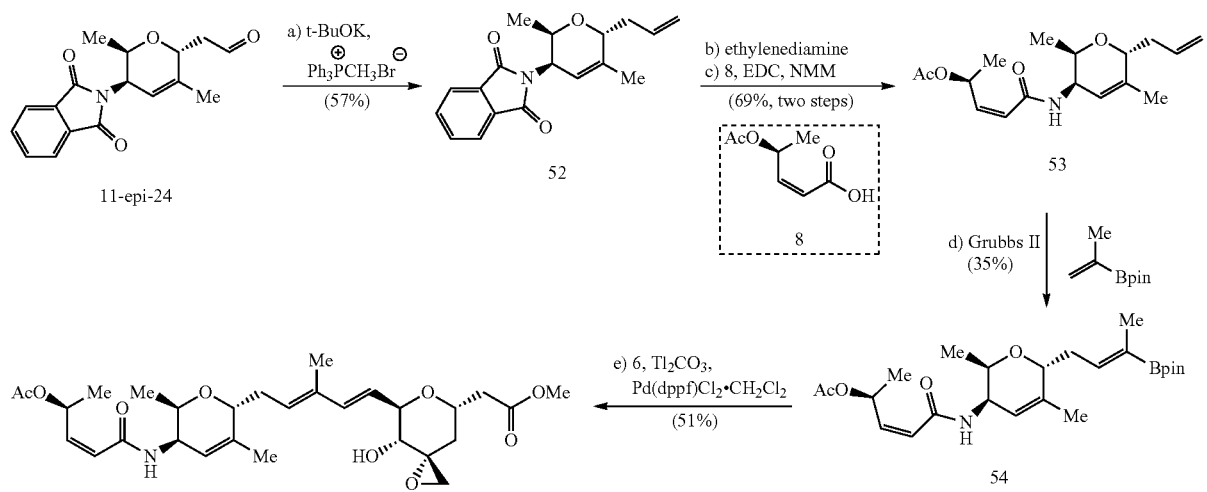

Reagents and conditions:
(a) KOt-Bu (1.7 equiv), Ph$_3$P$^+$CH$_3$Br$^-$ (2.0 equiv), THF, 0° C., 2 h, 57%;
(b) ethylenediamine (2.0 equiv), EtOH, 80° C., 15 h;
(c) 8 (1.5 equiv), EDC (3.0 equiv), NMM (3.0 equiv), CH$_2$Cl$_2$, 25° C., 2 h, 69% for two steps;
(d) isopropenylBpin (10 equiv), Grubbs II (0.1 equiv), DCE, 80° C., 2 h, 35%;
(e) 6, Pd(dppf)Cl$_2$·CH$_2$Cl$_2$ (0.10 equiv), Tl$_2$CO$_3$ (5.0 equiv), THF:H$_2$O (3:1, v/v), 25° C., 3 h 51%.

Scheme 10 shows the preparation of analogs 34 and 47 from the diastereomeric form 60 and 61 with the relevant vinyl iodide 6.

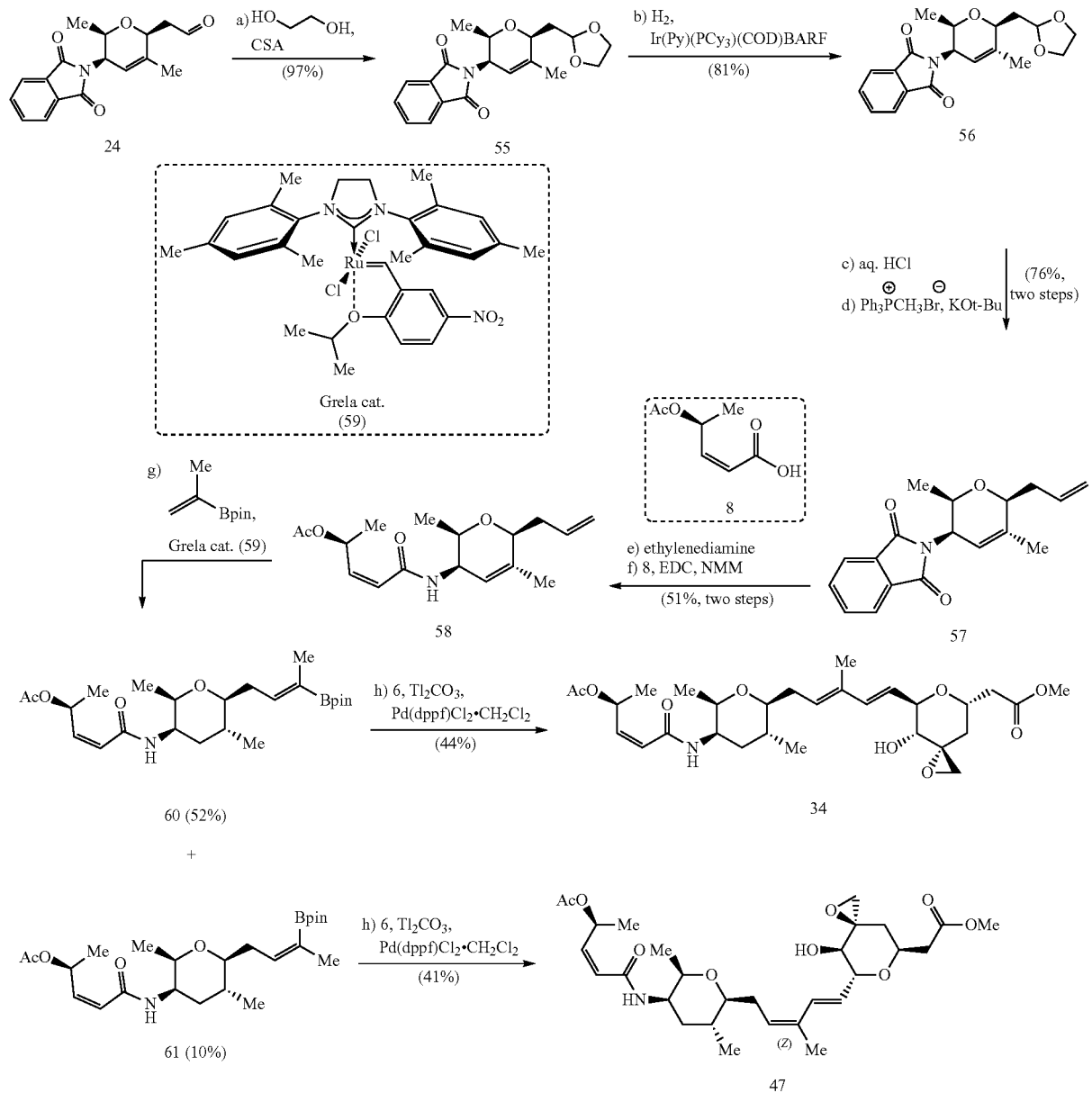

Scheme 10. Synthesis of thailanstatin A analogues 34 and 47.

Reagents and conditions:
(a) ethylene glycol (2.0 equiv), CSA (0.1 equiv), benzene, 80° C., 16 h, 97%;
(b) Ir(Py)(PCy3)(COD)BARF (0.05 eqiv), H2 (1 atm), CH2Cl2, 25° C., 15 h, 81%;
(c) 1 N aq. HCl (5.0 equiv), acetone, 25° C., 15 h;
(d) KOt-Bu (1.7 equiv), Ph3P+CH3Br− (2.0 equiv), THF, 0° C., 2 h, 76% for two steps;
(e) ethylenediamine (2.0 equiv), EtOH, 80° C., 15 h;
(f) 8 (3.0 equiv), EDC (3.0 equiv), NMM (6. equiv), CH2Cl2, 25° C., 2 h, 51%, for two steps;
(g) isopropenylBpin (10 equiv), Grela cat. (59 10 mol %), CH2Cl2, 50° C., 7 h, 52% for 60, 10% for 61;
(h) 6, Pd(dppf)Cl2·CH2Cl2 (0.10 equiv), Tl2CO3 (5.0 equiv), THF:H2O (3:1, v/v), 25° C., 3 h, 44% for 34, 41% for 47.
CSA = camphorsulfonic acid.

Scheme 11 shows the preparation of analogs 38 and 40 by converting the acetylated compound into the corresponding carbamate building block before reacting the boronate reagent with the vinyl iodide.

Scheme 11. Synthesis of thailanstatin A analogues 38 and 40.

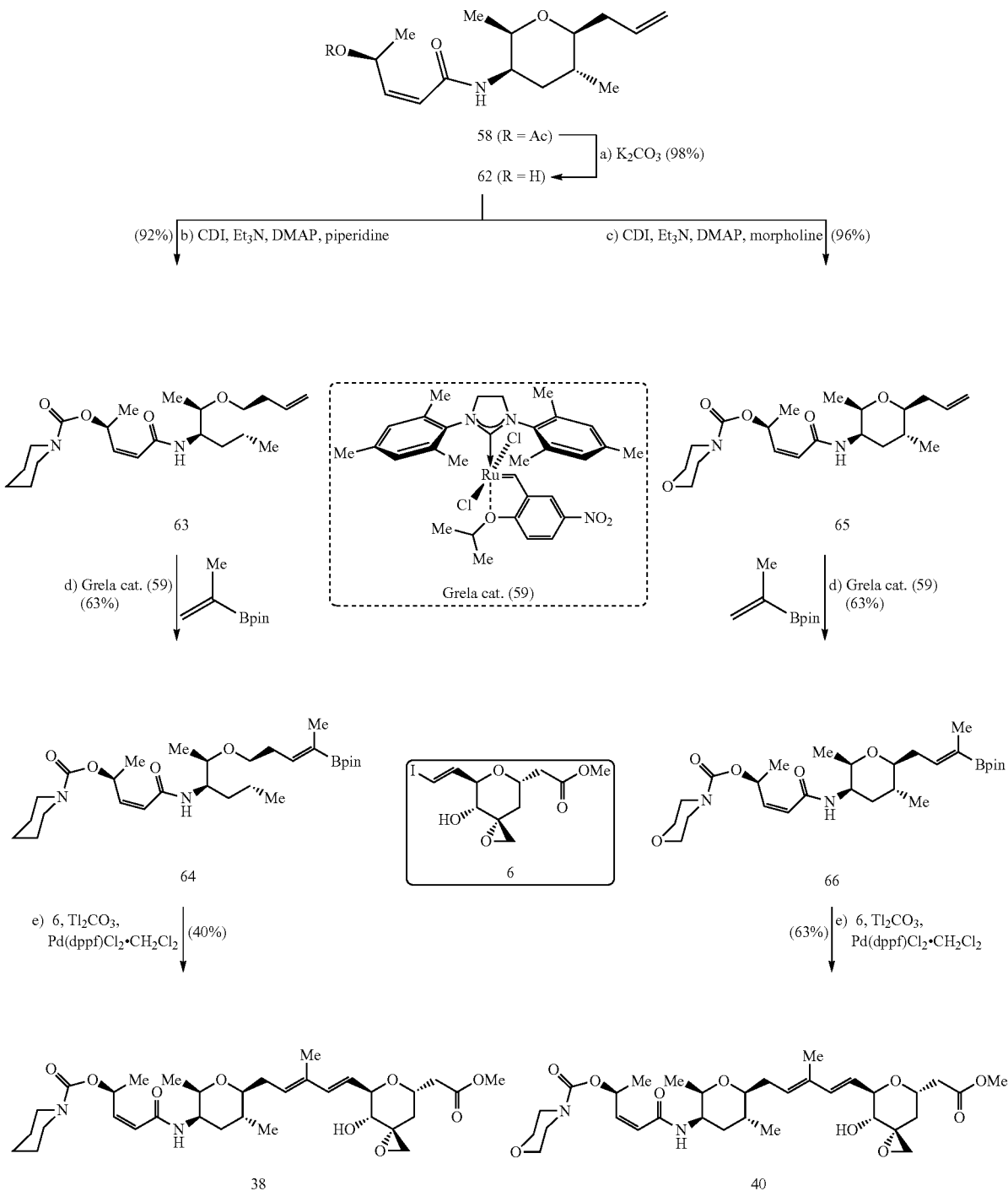

Reagents and conditions:
(a) K₂CO₃ (3.0 equiv), MeOH, 25° C., 2 h, 98%
(b) CDI (4.0 equiv), Et₃N (4.0 equiv), DMAP (0.2 equiv), CH₂Cl₂, 25° C., 2 h; then piperidine (20 equiv), 25° C., 3 h 92%;
(c) CDI (3.0 equiv), Et₃N (4.0 equiv), DMAP (0.2 equiv), CH₂Cl₂, 25° C., 2 h; then morpholine (10 equiv), 25° C., 15 h, 96%;
(d) isopropenylBpin (10 equiv), Grela cat. (59, 0.1 equiv), CH₂Cl₂, 50° C., 6 h, 63% for 64, 63% for 66;
(e) 6, Pd(dppf)Cl₂·CH₂Cl₂ (0.10 equiv), Tl₂CO₃ (5.0 equiv), THF:H₂O (3:1, v/v), 25° C., 6 h, 40% for 38, 63% for 40.
CDI = N,N'-carbonyldiimidazole; DMAP = N,N'-dimethylaminopyridine.

As described in Scheme 11, Scheme 12 shows the preparation of the relevant starting carbamate analog, which is coupled with vinyl iodide 6 to form analogs 36, 42, and 44.

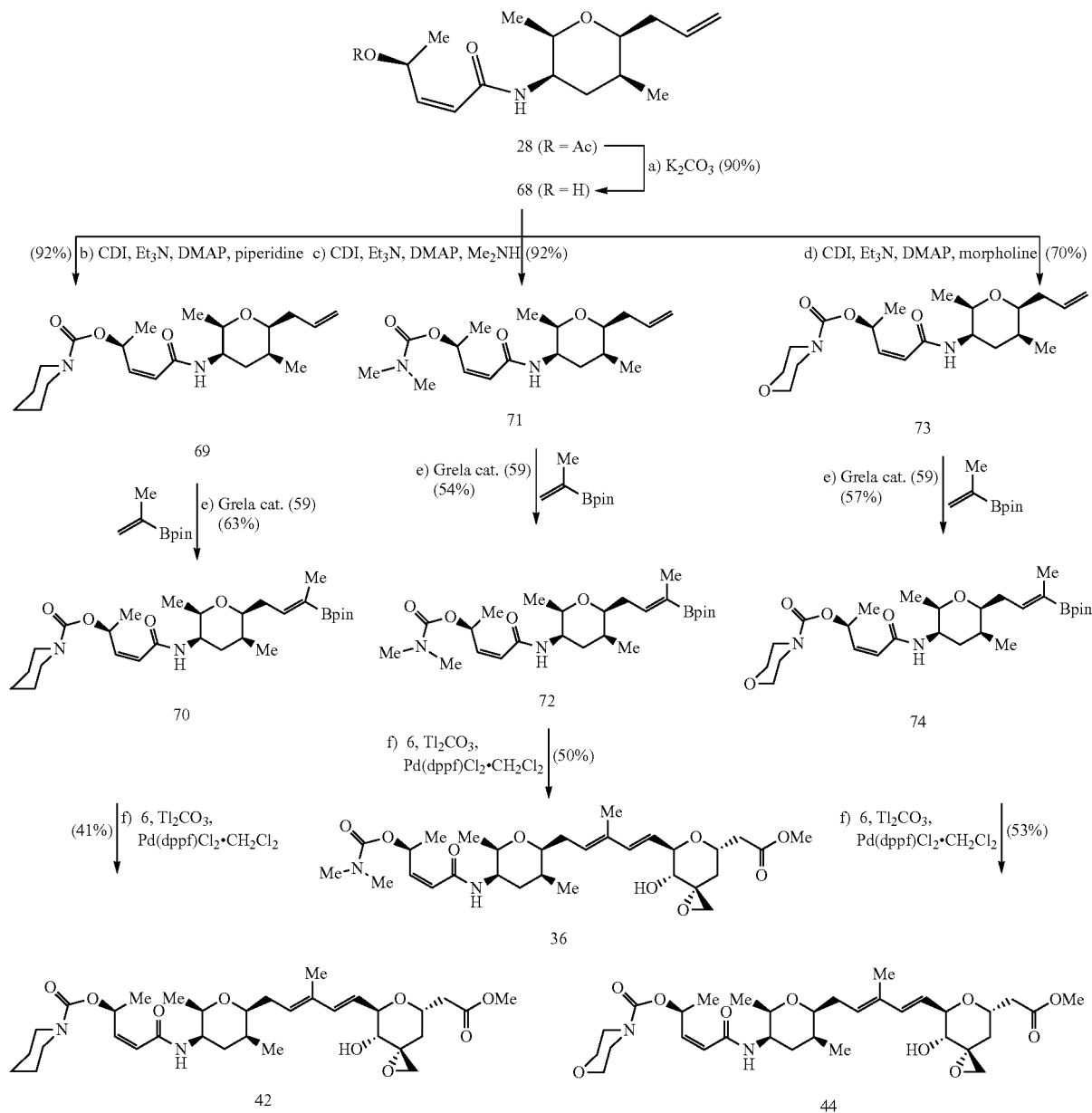

Scheme 12. Synthesis of thailanstatin A analogues 36, 42, and 44.

Reagents and conditions:
(a) K$_2$CO$_3$ (1.3 equiv), MeOH, 25° C., 1 h, 90%;
(b) CDI (3.0 equiv), Et$_3$N (4.0 equiv), DMAP (0.2 equiv), CH$_2$Cl$_2$, 25° C., 2 h; then piperidine (10 equiv), 25° C., 3 h, 92%
(c) CDI (3.0 equiv), Et$_3$N (4.0 equiv), DMAP (0.2 equiv), CH$_2$Cl$_2$, 25° C., 2 h, then dimethylamine (20 equiv), 25° C., 3 h, 92%;
(d) CDI (3.0 equiv), Et$_3$N (4.0 equiv), DMAP (0.2 equiv), CH$_2$Cl$_2$, 25° C., 2 h; then morpholine (20 equiv), 25° C., 15 h, 70%;
(e) isopropenylBpin (10 equiv), Grela cat. (59, 0.01 equiv), CH$_2$Cl$_2$, 50° C., 6 h, 63% for 70, 54% for 72, 57% for 74;
(f) 6, Pd(dppf)Cl$_2$•CH$_2$Cl$_2$ (0.20 equiv), Tl$_2$CO$_3$ (5.0 equiv), THF:H$_2$O (3:1, v/v), 25° C., 6 h, 41% for 42, 50% for 36, 53% for 44.

Scheme 13 show the formation of three different vinyl iodide analogs (76, 77, and 80) to form the "eastern half" of the thailanstatin analog which are later coupled to the relevant boronate to form additional analogs.

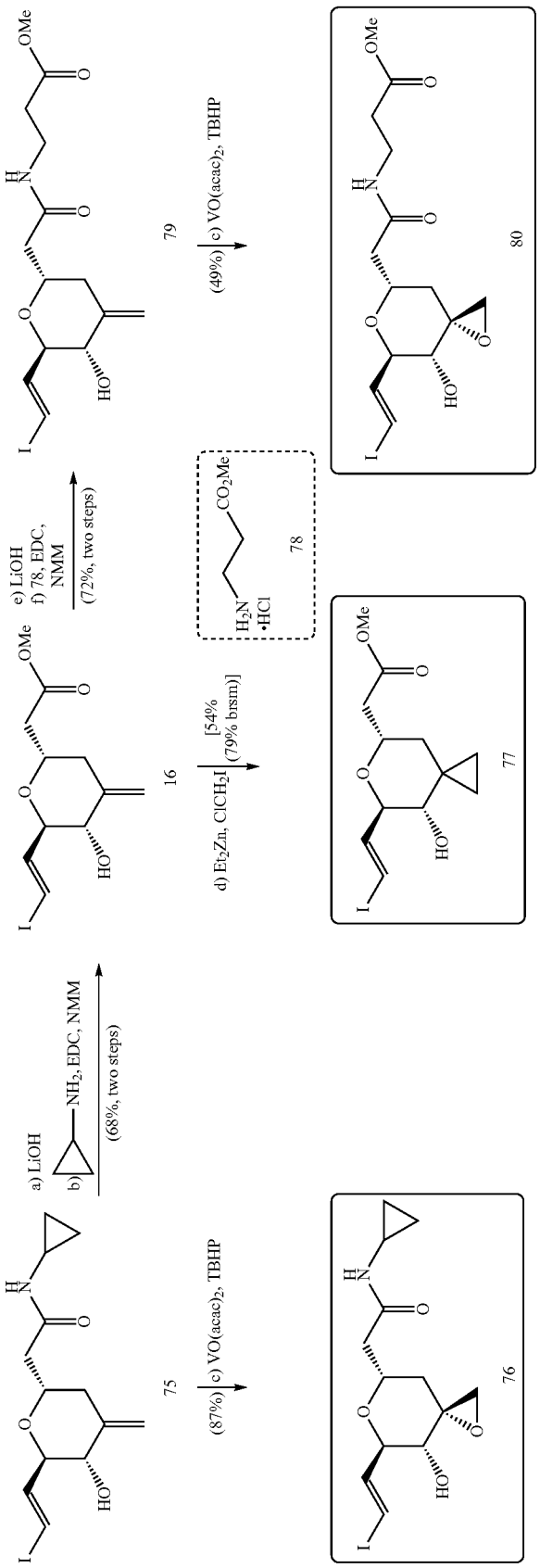

Scheme 13. Synthesis of vinyl iodides 76, 77, and 80 as building blocks for the "eastern half" of thailanstatin A analogues 31, 33, 35 and 43, respectively.

Reagents and conditions: (a) LiOH (8.0 equiv), THF:H$_2$O (4:1, v/v), 0→25° C., 15 h; (b) cyclopropylamine (2.0 equiv), NMM (3.0 equiv), EDC (2.0 equiv), CH$_2$Cl$_2$, 25° C., 15 h, 68% for two steps (c) VO(acac)$_2$ (0.10 equiv), TBHP (2.0 equiv), CH$_2$Cl$_2$, 0→25° C., 2 h, 87% for 76, 49% for 80; (d) Et$_2$Zn (2.0 equiv), ClCH$_2$I (2.0 equiv), CH$_2$Cl$_2$, 0° C., 2 h, 54% (79% brsm); (e) LiOH (8.0 equiv), THF:H$_2$O (4:1, v/v), 0→25° C., 10 h; (f) 78 (2.0 equiv), EDC (2.0 equiv), NMM (3.0 equiv), CH$_2$Cl$_2$, 25° C., 16 h, 72% for two steps. TBHP = tert-butyl hydroperoxide; brsm = based on recovered starting material.

Scheme 14 illustrates the preparation of vinyl iodide analogs 81 and 82 with modified hydroxyl groups by conversion of the free hydroxyl to the relevant carbamate and ester, respectively.

Scheme 14. Synthesis of vinyl iodides 81 and 82 as building blocks for the "eastern half" of thailanstatin A analogues 37 and 45, respectively.

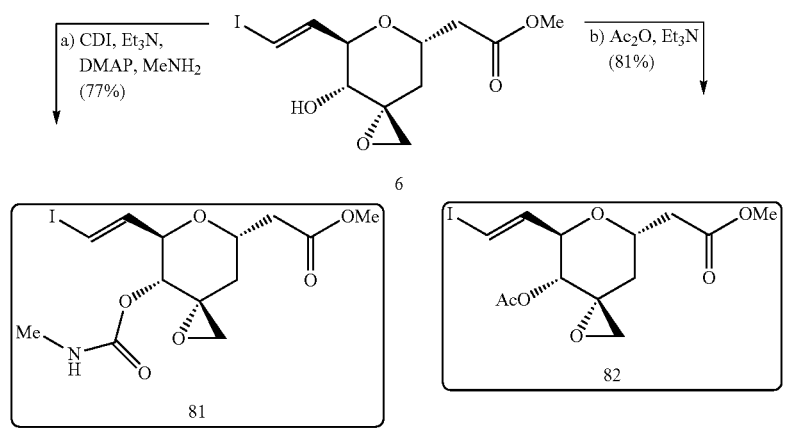

Reagents and conditions:
(a) CDI (3.0 equiv), Et₃N (4.0 equiv), DMAP (0.20 equiv), CH₂Cl₂, 25° C., 2 h; then methylamine (10 equiv), 25° C., 3 h, 77%:
(b) Ac₂O (2.0 equiv), Et₃N (3.0 equiv), CH₂Cl₂, 24° C., 1 h, 81%.

Furthermore, decarboxylated vinyl iodide analog 86 is prepared as shown in Scheme 15 by decarboxylating vinyl iodide derivative 15.

Scheme 15. Synthesis of vinyl iodide 86 as building block for the "eastern half" of thailanstatin A analogue 39.

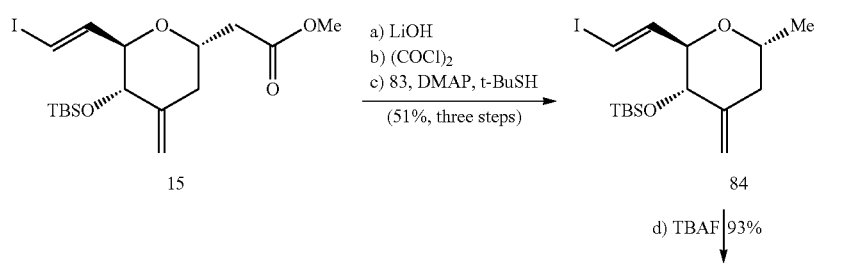

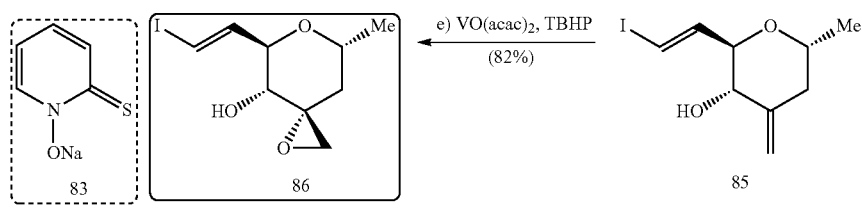

Reagents and conditions:
(a) LiOH (8.0 equiv), THF:H₂O (4:1, v/v) 0 → 25° C., 10 h;
(b) (COCl)₂ (3.0 equiv), CH₂Cl₂, 25° C., 20 min
(c) 83 (1.5 equiv), DMAP (0.1 equiv), t-BuSH (10 equiv), benzene, 25° C., hv, 1 h, 51% for three steps;
(d) TBAF (1.5 equiv), THF, 0 → 25° C., 2 h, 93%;
(e) VO(acac)₂ (0.1 equiv), TBHP (2.0 equiv), CH₂Cl₂, 0 → 25° C., 1.5 h, 82%. TBAF = tetra-n-butyl ammonium fluoride.

Scheme 16 shows the preparation of ketone containing vinyl iodide analog 90

Scheme 16. Synthesis of vinyl iodide 90 as building block for the "eastern half" of thailanstatin A analogue 41.

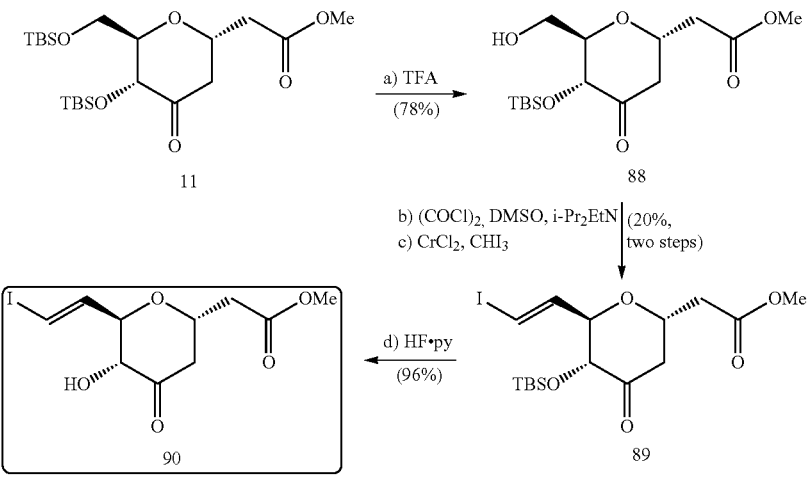

Reagents and conditions:
(a) TFA (10 equiv), CH$_2$Cl$_2$, 0 → 25° C., 7 h, 78%;
(b) (COCl)$_2$ (1.5 equiv), DMSO (3.0 equiv), iPr$_2$EtN (5.8 equiv), CH$_2$Cl$_2$, -78 → -45° C., 1.5 h;
(c) CrCl$_2$ (6.0 equiv), CHI$_3$ (3.0 equiv), THF, 25° C., 3 h, 20% for two steps;
(d) HF•py (xs), THF, 0 → 25° C., 20 h, 96%. TFA = trifluoroacetic acid; DMSO = dimethylsulfoxide.

Having obtained the relevant building boronate and vinyl iodide analogs, the final analogs 31, 33, 35, 37, 39, 41, 43, and 45 were prepared as described in Scheme 17.

Scheme 17. Synthesis of thailanstatin A analogues 31, 33, 35, 37, 39, 41, 43, and 45.

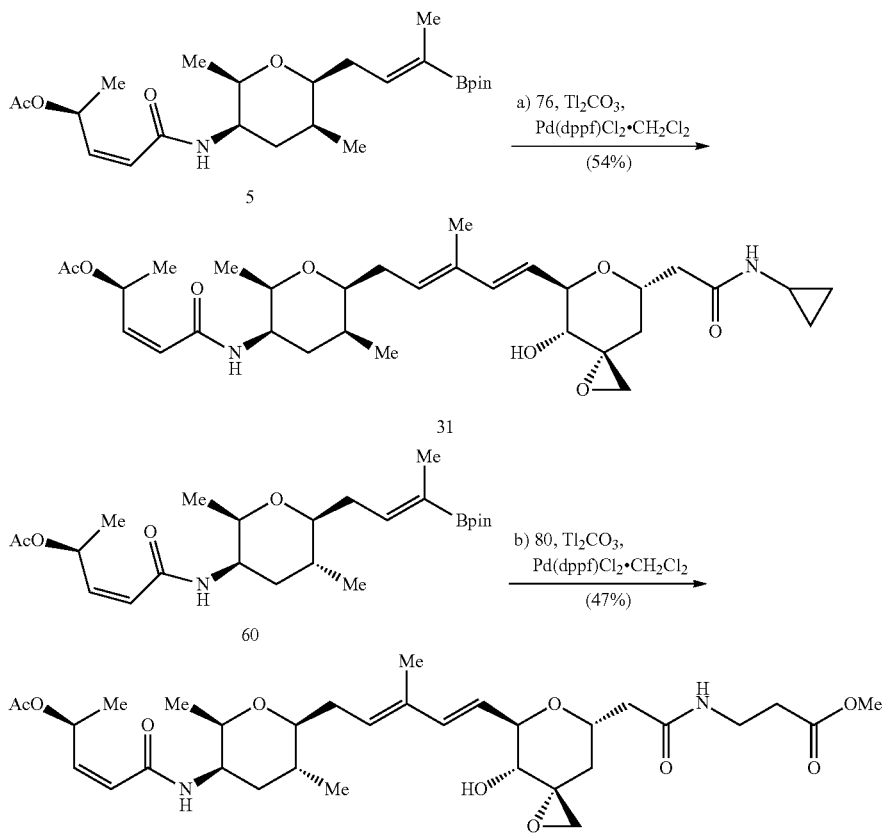

-continued
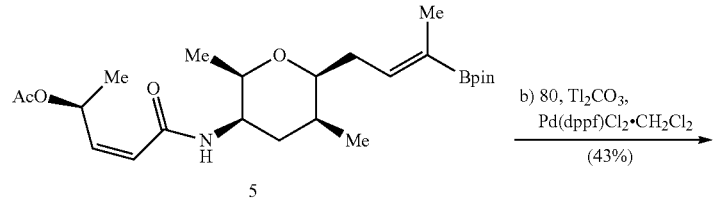
5
b) 80, Tl₂CO₃, Pd(dppf)Cl₂·CH₂Cl₂
(43%)
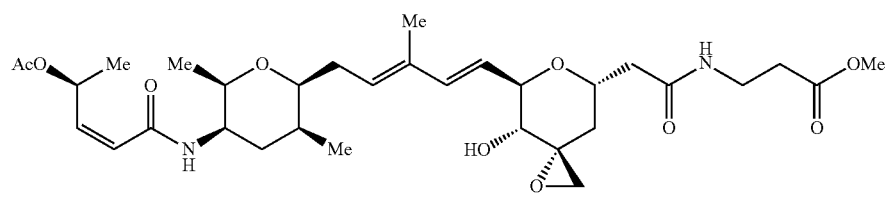
35
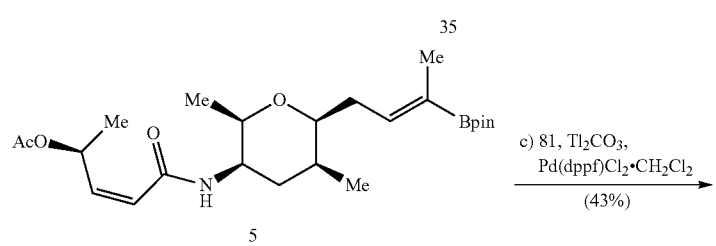
5
c) 81, Tl₂CO₃, Pd(dppf)Cl₂·CH₂Cl₂
(43%)
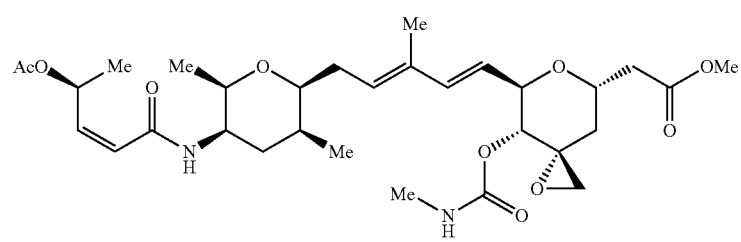
37
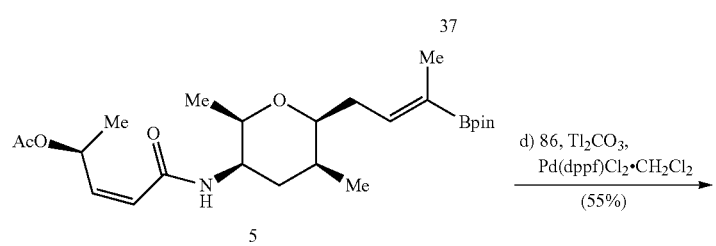
5
d) 86, Tl₂CO₃, Pd(dppf)Cl₂·CH₂Cl₂
(55%)
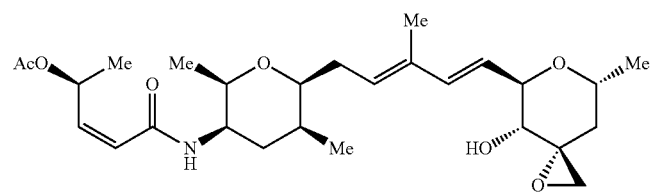
39
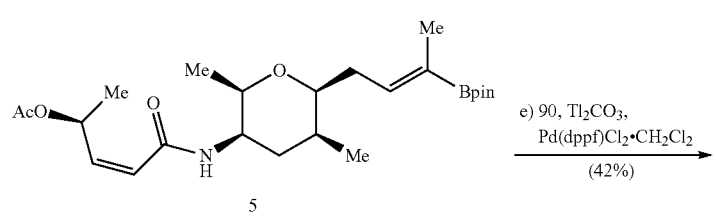
5
e) 90, Tl₂CO₃, Pd(dppf)Cl₂·CH₂Cl₂
(42%)

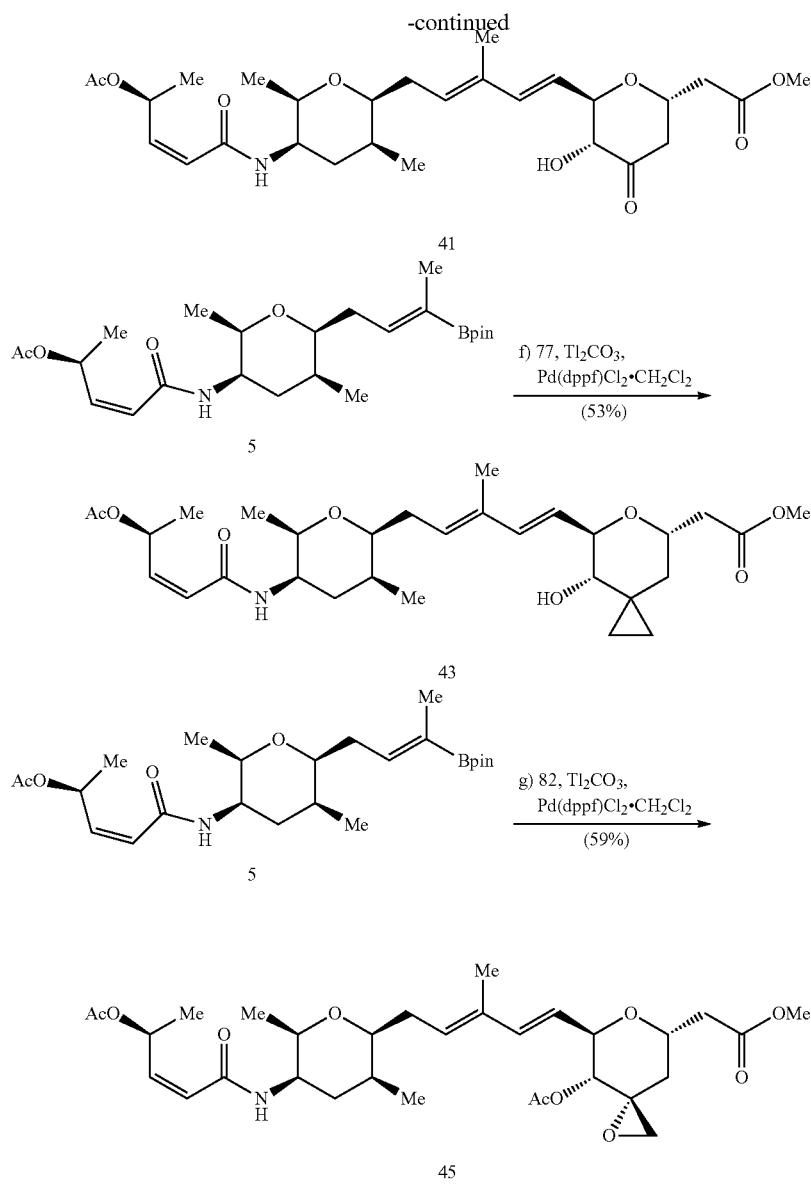

Reagents and conditions:
(a) 76, Pd(dppf)Cl$_2$•CH$_2$Cl$_2$ (0.1 equiv), Tl$_2$CO$_3$ (5.0 equiv), THF:H$_2$O (3:1, v/v), 25° C., 3 h, 54%;
(b) 80, Pd(dppf)Cl$_2$•CH$_2$Cl$_2$ (0.1 equiv), Tl$_2$CO$_3$ (5.0 equiv), THF:H$_2$O (3:1, v/v), 25° C., 3 h 47% for 33, 43% for 35;
(c) 81, Pd(dppf)Cl$_2$•CH$_2$Cl$_2$ (0.1 equiv), Tl$_2$CO$_3$ (5.0 equiv), THF:H$_2$O (3:1, v/v), 25° C., 3 h, 43%;
(d) 86, Pd(dppf)Cl$_2$•CH$_2$Cl$_2$ (0.1 equiv), Tl$_2$CO$_3$ (5.0 equiv), THF:H$_2$O (3:1, v/v), 25° C., 3 h 55%;
(e) 90, Pd(dppf)Cl$_2$•CH$_2$Cl$_2$ (0.1 equiv), Tl$_2$CO$_3$ (5.0 equiv), THF:H$_2$O (3:1, v/v), 25° C., 3 h, 42%;
(f) 77, Pd(dppf)Cl$_2$•CH$_2$Cl$_2$ (0.1 equiv), Tl$_2$CO$_3$ (5.0 equiv), THF:H$_2$O (3:1, v/v), 25° C., 3 h, 53%;
(g) 82, Pd(dppf)Cl$_2$•CH$_2$Cl$_2$ (0.1 equiv), Tl$_2$CO$_3$ (5.0 equiv), THF:H$_2$O (3:1, v/v), 25° C., 3 h, 59%.

Using the methods described above, additional analogs described in Scheme 18 may be prepared.

Scheme 18. Thailanstatin A analogues to be synthesized.

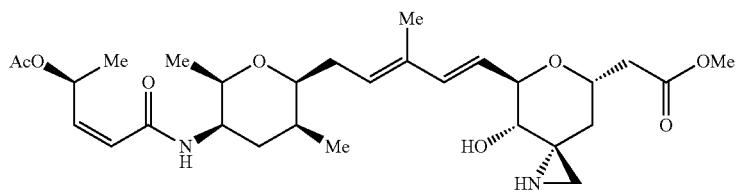

-continued
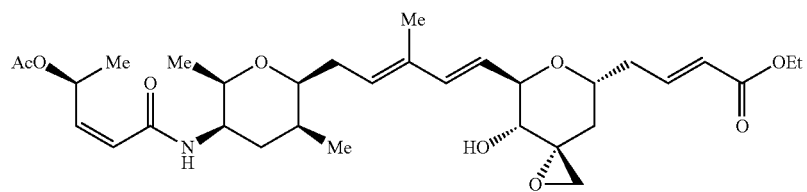
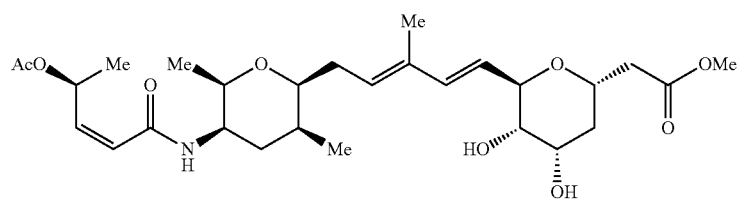
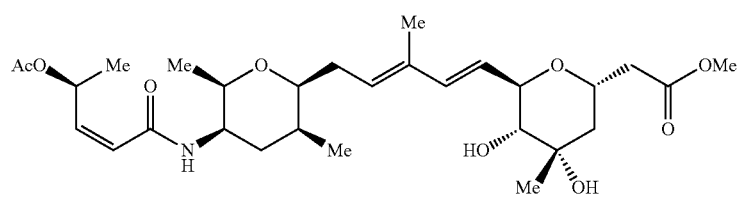
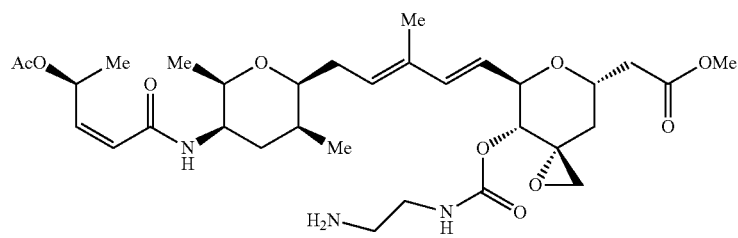
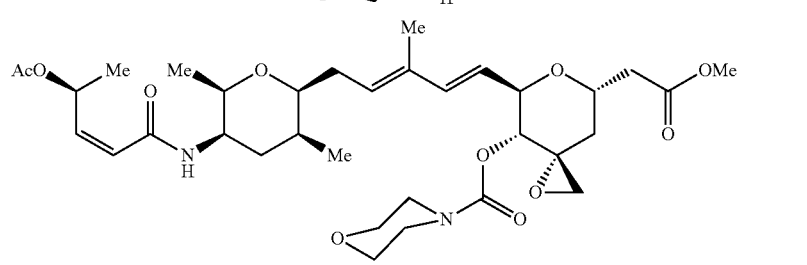
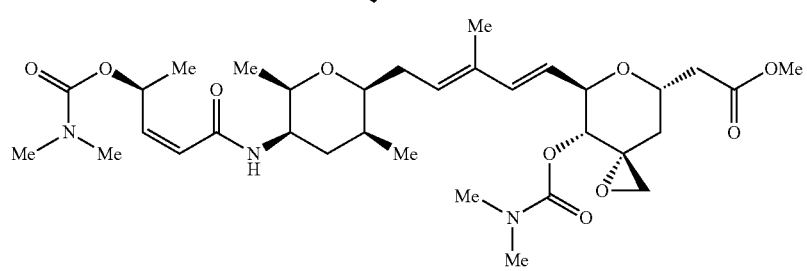
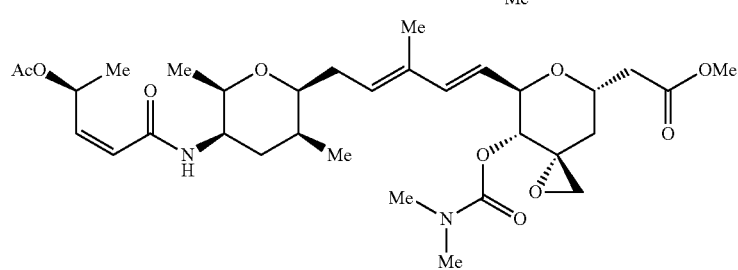

-continued
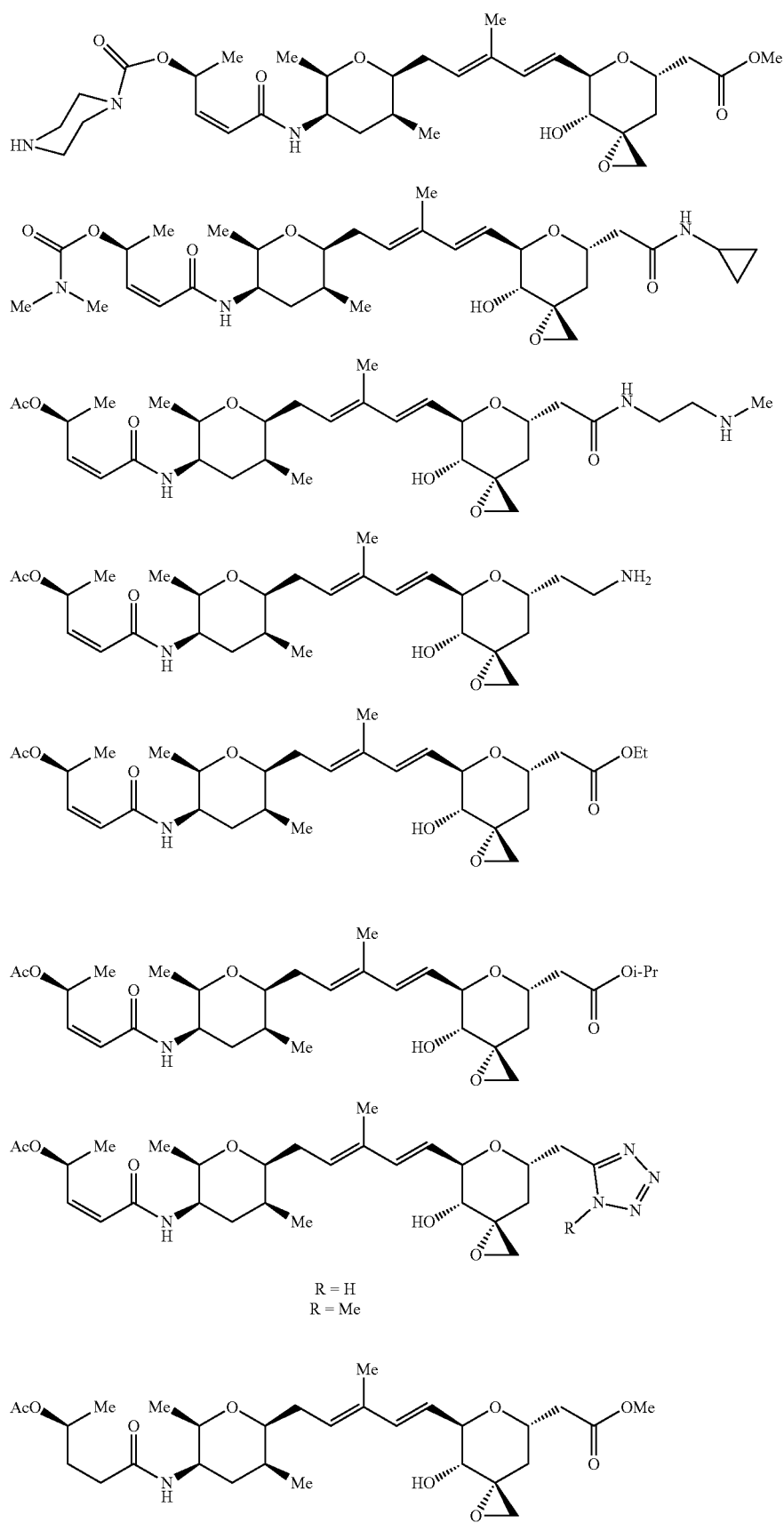
R = H
R = Me

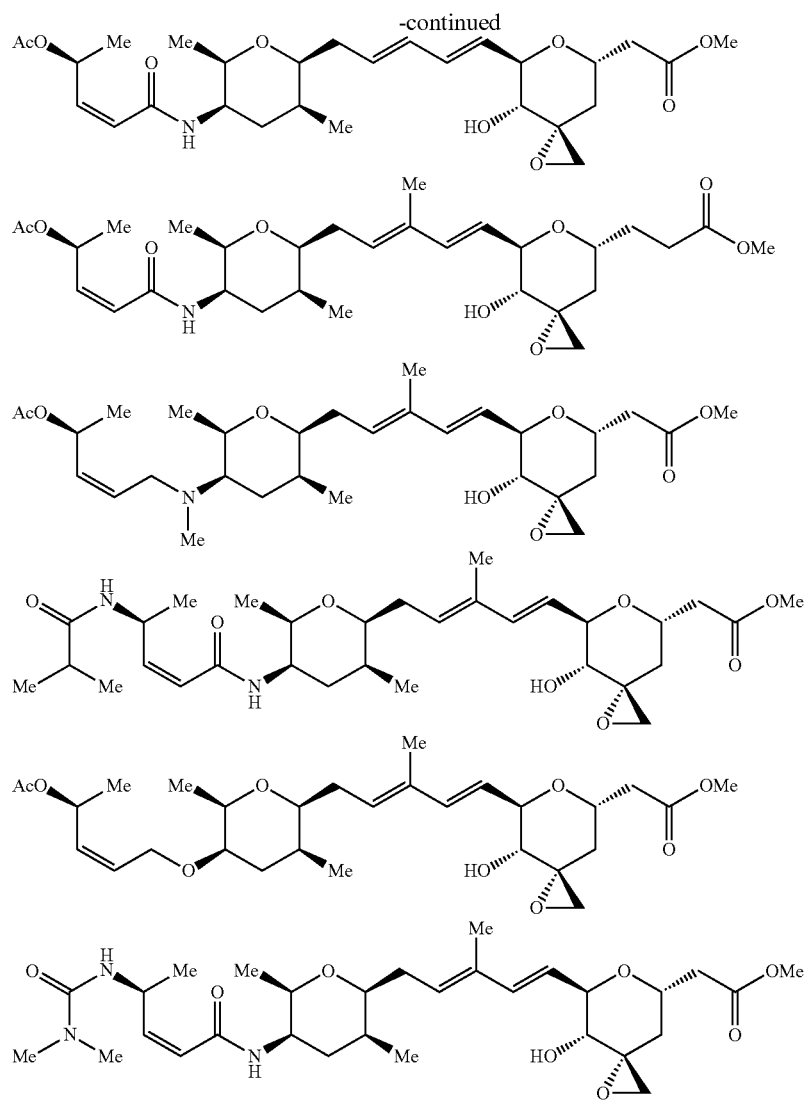

Example 2

General Methods and Materials

All reactions were carried out under an argon atmosphere with dry solvents under anhydrous conditions, unless otherwise noted. Dry acetonitrile (MeCN), diethyl ether (Et$_2$O), dimethylformamide (DMF), methylene chloride (CH$_2$Cl$_2$), tetrahydrofuran (THF), triethylamine (Et$_3$N), and toluene were obtained by passing commercially available pre-dried, oxygen-free formulations through activated alumina columns. Yields refer to chromatographically and spectroscopically ($^1$H NMR) homogeneous materials, unless otherwise stated. Reagents were purchased at the highest commercial quality and used without further purification, unless otherwise stated. Reactions were monitored by thin-layer chromatography (TLC) carried out on S-2 0.25 mm E. Merck silica gel plates (60E-254) using UV light as visualizing agent and an acidic aqueous solution of p-anisaldehyde, an aqueous solution of cerium sulfate, or a basic aqueous solution of potassium permanganate and heat as developing agents. E. Merck silica gel (60, particle size 0.040-0.063 mm) was used for flash column chromatography. NMR spectra were recorded on a Bruker DRX-600 instrument and calibrated using residual undeuterated solvent for $^1$H-NMR and deuterated solvent for $^{13}$C-NMR (CD$_2$Cl$_2$: $\delta_H$=5.32 ppm, $\delta_C$=53.84 ppm; CDCl$_3$: $\delta_H$=7.26 ppm, $\delta_C$=77.16 ppm; C$_6$D$_6$: $\delta_H$=7.16 ppm, $\delta_C$=128.06 ppm) as an internal reference. The following abbreviations were used to designate multiplicities: s=singlet, d=doublet, t=triplet, q=quartet, m=multiplet, qd=quartet of doublets, dd=doublet of doublets, ddd=doublet of doublet of doublets, dddd=doublet of doublet of doublet of doublets, dt=doublet of triplets, dq=doublet of quartets, ddq=doublet of doublet of quartets, br=broad. Infrared (IR) spectra were recorded on a PerkinElmer 100 FT-IR spectrometer. High-resolution mass spectra (HRMS) were recorded on an Agilent ESI-TOF (time of flight) mass spectrometer using MALDI (matrix-assisted laser desorption ionization) or ESI (electrospray ionization). Optical rotations were recorded on a POLARTRONIC M100 polarimeter at 589 nm, and are reported in units of 10$^{-1}$ (deg cm$^2$g$^{-1}$).

Example 3

Compound Characterization

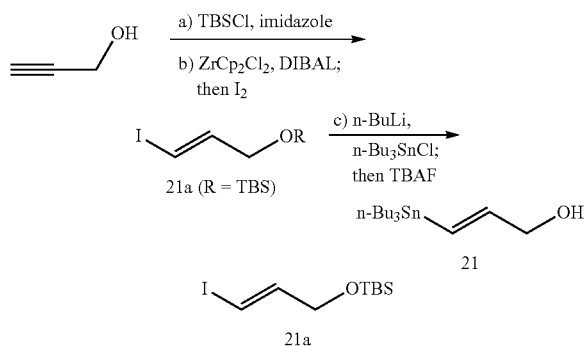

Vinyl iodide 21a: To a stirred solution of propargyl alcohol (1.95 g, 34.7 mmol, 1.0 equiv) in $CH_2Cl_2$ (116 mL) was added imidazole (4.72 g, 69.4 mmol, 2.0 equiv) followed by TBSCl (7.85 g, 52.1 mmol, 1.5 equiv) at 25° C. After 45 min, the reaction mixture was quenched with a saturated aqueous solution of ammonium chloride (75 mL), and the phases were separated. The aqueous layer was extracted with $CH_2Cl_2$ (25 mL), and the combined organic layers were dried with anhydrous sodium sulfate and concentrated in vacuo. The obtained residue was filtered through a short silica plug, thoroughly eluted with 2% $Et_2O$ in hexanes (350 mL), and concentrated in vacuo. The obtained colorless oil (5.9 g, 34.7 mmol, quant.) was used directly in the following step.

To a stirred suspension of $ZrCp_2Cl_2$ (17.2 g, 59 mmol, 1.7 equiv) in THF (30 mL) was added DIBAL (59 mL, 1.0 M in THF, 59 mmol, 1.7 equiv) dropwise at 0° C. After 30 min, a solution of TBS propargyl alcohol (5.9 g, 34.7 mmol, 1.0 equiv) in THF (35 mL) was added dropwise via cannula, the original flask was rinsed with additional THF (3×2 mL), and the reaction mixture was allowed to warm to 25° C. After stirring for an additional 1 h, the reaction mixture was cooled to −78° C., and iodine (16.7 g, 65.9 mmol, 1.9 equiv) was added in one portion. After 30 min, the reaction mixture was quenched with an aqueous solution of hydrochloric acid (1.0 M, 100 mL), and allowed to warm to 25° C. The phases were separated, the aqueous layer was extracted with $Et_2O$ (75 mL), and the combined organic layers were washed with a saturated aqueous solution of sodium thiosulfate (100 mL), a saturated aqueous solution of sodium bicarbonate (100 mL), and brine (100 mL). The combined organic layers were dried with anhydrous sodium sulfate and concentrated in vacuo. The obtained residue was purified by flash column chromatography (silica gel, hexanes→3% $Et_2O$ in hexanes) to afford vinyl iodide 21a (8.80 g, 29.5 mmol, 85% yield) as a colorless oil. The physical and spectral data were consistent with those reported (Huang and Negishi, 2006).

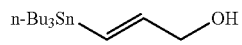

21

Stannane 21: To a stirred solution of vinyl iodide 21a (8.8 g, 29.5 mmol, 1.0 equiv) in $Et_2O$ (148 mL) was added n-butyllithium (17.7 mL, 2.5 M in hexanes, 44.3 mmol, 1.5 equiv) dropwise at −78° C. After 20 min, n-tributyltin chloride (12 mL, 44.3 mmol, 1.5 equiv) was added dropwise, and the reaction mixture was stirred for an additional 20 min. Then the reaction mixture was quenched with a saturated aqueous solution of ammonium chloride (50 mL), and allowed to warm to 25° C. The phases were separated, and the organic layer was dried with anhydrous sodium sulfate and concentrated in vacuo. The crude material was redissolved in a solution of n-tetrabutylammonium fluoride (148 mL, 1.0 M in THF, 148 mmol, 5.0 equiv) with vigorous stirring at 25° C. After 1 h, the reaction mixture was quenched with a saturated aqueous solution of ammonium chloride (70 mL), and the phases were separated. The organic layer was dried with anhydrous sodium sulfate and concentrated in vacuo. The obtained residue was purified by flash column chromatography (silica gel, 10% ethyl acetate in hexanes) to obtain 21 (9.00 g, 25.9 mmol, 88%) as a slightly yellow oil. The physical and spectral data were consistent with those reported (Pilli, et al., 1998).

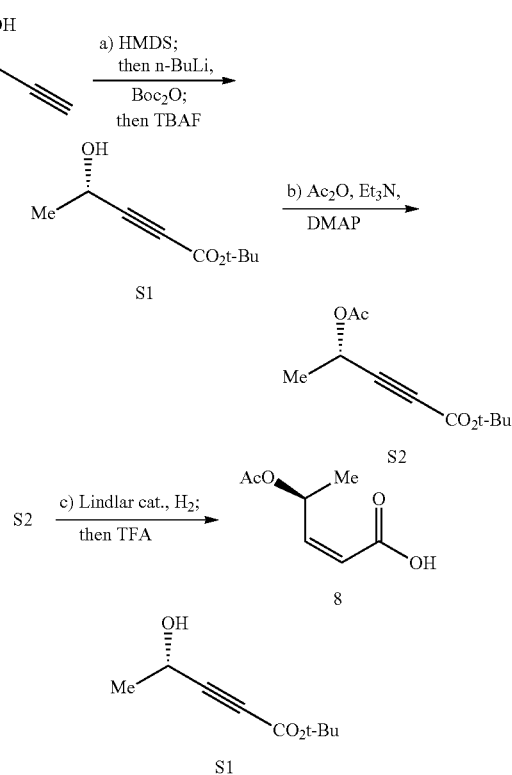

tert-Butyl ester S1: To a stirred solution of (S)-(−)-2-butynol (1.23 g, 17.5 mmol, 1.0 equiv) in THF (8.8 mL) was added HMDS (2.0 mL, 9.6 mmol, 0.55 equiv) followed by a drop (ca. 10 μL 0.18 mmol, 0.01 equiv) of concentrated sulfuric acid, and the reaction mixture was heated to 70° C. After 3 h, the reaction mixture was cooled to −78° C., and n-butyllithium (8.4 mL, 2.5 M in hexanes, 21 mmol, 1.2 equiv) was added dropwise over 15 min. After stirring for 30 min at the same temperature, a solution of di-tert-butyl dicarbonate (5.00 g, 22.8 mmol, 1.3 equiv) in THF (5 mL) was added dropwise over 10 min via cannula, the original flask was rinsed with additional THF (3×0.5 mL), and the reaction mixture was allowed to warm to 0° C. After 20 min, the reaction mixture was quenched with a saturated aqueous solution of ammonium chloride (20 mL), and allowed to warm to 25° C. The phases were separated, the aqueous layer was extracted with Et$_2$O (15 mL), and the combined organic layers were dried with anhydrous sodium sulfate and concentrated in vacuo. The crude material was redissolved in THF (70 mL) with stirring, and n-tetrabutylammonium fluoride (35 mL, 1.0 M in THF, 35 mmol, 2.0 equiv) was added dropwise at 25° C. After 20 min, the reaction mixture was quenched with a saturated aqueous solution of ammonium chloride (50 mL), the phases were separated, and the aqueous layer was extracted with ethyl acetate (3×15 mL). The combined organic layers were dried with anhydrous sodium sulfate and concentrated in vacuo. The obtained residue was purified by flash column chromatography (silica gel, 5→15% ethyl acetate in hexanes) to provide tert-butyl ester S1 (1.82 g, 10.7 mmol, 61%) as a colorless oil. S1: $R_f$=0.26 (silica gel, 20% ethyl acetate in hexanes); $[\alpha]_D^{25}$=−31.8 (c=1.0, CH$_2$Cl$_2$); FT-IR (neat) $\nu_{max}$=3407, 2982, 2936, 2876, 2231, 1841, 1705, 1478, 1457, 1394, 1369, 1255, 1154, 1126, 1063, 1037, 985, 895, 842, 808, 790, 754 cm$^{-1}$; $^1$H NMR (600 MHz, CDCl$_3$) δ 4.62 (qd, J=6.6, 0.7 Hz, 1H), 1.91 (d, J=4.3 Hz, 1H), 1.51 (d, J=6.8 Hz, 1H), 1.50 (s, 9H) ppm; $^{13}$C NMR (151 MHz, CDCl$_3$) δ 152.5, 86.0, 83.9, 77.3, 58.3, 28.1, 23.50 ppm; HRMS (ESI-TOF) calcd for C$_9$H$_{14}$O$_3$Na$^+$ [M+Na]$^+$ 193.0835, found 193.0833.

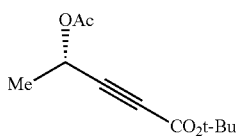

S2

Acetate S2: To a stirred solution of S1 (680 mg, 4.0 mmol, 1.0 equiv) in CH$_2$Cl$_2$ (80 mL) was added triethylamine (2.8 mL, 20.0 mmol, 5.0 equiv), followed by acetic anhydride (1.13 mL, 12.0 mmol, 3.0 equiv) and DMAP (98 mg, 0.8 mmol, 0.2 equiv) at 25° C. After 12 h, the reaction mixture was quenched with a saturated aqueous solution of ammonium chloride (50 mL), and the phases were separated. The aqueous layer was extracted with ethyl acetate (3×10 mL), and the combined organic layers were dried with anhydrous sodium sulfate and concentrated in vacuo. The obtained residue was purified by flash column chromatography (silica gel, 5% ethyl acetate in hexanes) to provide acetate S2 (679 mg, 3.2 mmol, 80%) as a colorless oil. S2: $R_f$=0.34 (silica gel, 10% ethyl acetate in hexanes); $[\alpha]_D^{25}$=−117 (c=1.0, CH$_2$Cl$_2$); FT-IR (neat) $\nu_{max}$=2983, 2939, 2875, 2237, 1748, 1708, 1479, 1457, 1370, 1337, 1277, 1260, 1226, 1157, 1137, 1101, 1051, 1013, 983, 938, 843, 753 cm$^{-1}$; $^1$H NMR (600 MHz, CDCl$_3$) δ 5.51 (q, J=6.8 Hz, 1H), 2.08 (s, 3H), 1.53 (d, J=6.8 Hz, 3H), 1.49 (s, 9H) ppm; $^{13}$C NMR (151 MHz, CDCl$_3$) δ 169.8, 152.2, 84.0, 82.5, 77.6, 59.6, 28.1, 21.0, 20.6 ppm; HRMS (ESI-TOF) calcd for C$_{11}$H$_{16}$O$_4$Na$^+$ [M+Na]$^+$ 235.0941, found 235.0938.

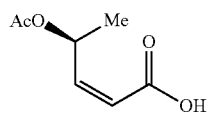

8

Acid 8: To a stirred solution of acetate S2 (512 mg, 2.41 mmol, 1.0 equiv) in EtOH (16 mL) was added quinoline (0.06 mL, 0.48 mmol, 0.2 equiv) and Lindlar's catalyst (102 mg, 5% Pd/CaCO$_3$ poisoned with lead, 20%, w/w) at 25° C. After 10 min, the reaction mixture was placed under an atmosphere of H$_2$ (1 atm), and stirring was continued for 4 h. Then the H$_2$ atmosphere was removed, and the reaction mixture was filtered through Celite® and concentrated in vacuo. The crude material was redissolved in a solution of trifluoroacetic acid (4.5 mL, 10% v/v in CH$_2$Cl$_2$) with stirring at 25° C. After 1 h, the reaction mixture was concentrated in vacuo, and the remaining trifluoroacetic acid was azeotropically removed in vacuo with ethyl acetate (3×5 mL). The obtained residue was purified by flash column chromatography (silica gel, 20→80% ethyl acetate in hexanes) to afford pure acid 8 (362 mg, 2.29 mmol, 95%) as a pale yellow oil. 8: $R_f$=0.56 (silica gel, ethyl acetate); $[\alpha]_D^{25}$=+18.1 (c=1.0, CH$_2$Cl$_2$); FT-IR (neat) $\nu_{max}$=3571, 3185, 3114, 3052, 2985, 2938, 2877, 2735, 2684, 2585, 1738, 1724, 1699, 1650, 1431, 1371, 1240, 1195, 1119, 1048, 1019, 956, 925, 866, 826, 741, 698 cm$^{-1}$; $^1$H NMR (600 MHz, CDCl$_3$) δ 6.31-6.15 (m, 2H), 5.82 (d, J=10.7 Hz, 1H), 2.06 (s, 3H), 1.38 (d, J=6.3 Hz, 3H) ppm; $^{13}$C NMR (151 MHz, CDCl$_3$) δ 170.6, 170.4, 150.8, 119.3, 68.9, 21.3, 19.7 ppm; HRMS (ESI-TOF) calcd for C$_7$H$_9$O$_4$Na$^+$ [M+Na]$^+$ 203.0291, found 203.0284.

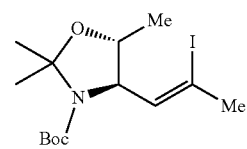

18

Vinyl Iodide 18: To a stirred suspension of triethylphosphonium iodide (27.9 g, 66.6 mmol, 2.0 equiv) in THF (333 mL) at 25° C. was added n-butyllithium (26.6 mL, 2.5 M in hexanes, 66.6 mmol, 2.0 equiv) dropwise. After stirring for 15 min, the resulting red orange solution was transferred to a stirred solution of iodine (16.1 g, 63.3 mmol, 1.9 equiv) in THF (450 mL) at −78° C. dropwise via cannula. The resulting thick yellow paste was warmed to −20° C., and NaHMDS (63.3 mL, 1.0 M in THF, 63.3 mmol, 1.9 equiv) was added dropwise, and stirring was continued for 10 min. The resulting deep red homogenous solution was cooled back down to −78° C., and a solution of aldehyde 17 (8.1 g, 33.3 mmol, 1.0 equiv) in THF (100 mL) was added dropwise via cannula, and the original flask was rinsed with additional THF (3×2 mL). After stirring for an additional 30 min, the reaction mixture was quenched with a saturated aqueous solution of ammonium chloride (300 mL) and allowed to warm to 25° C. The phases were separated, the aqueous layer was extracted with ethyl acetate (3×75 mL), and the combined organic layers were dried with anhydrous sodium sulfate and concentrated in vacuo. The obtained residue was purified by flash column chromatography (silica gel, 2→8% ethyl acetate in hexanes) to afford pure (Z)-vinyl iodide 18 (6.86 g, 18.0 mmol, 54%) as a white amorphous solid and a small amount of (E) isomer 18a (0.36 g, 0.94 mmol, 5%) as a colorless oil. 18: $R_f$=0.22 (silica gel, 5% ethyl acetate in hexanes); $[\alpha]_D^{25}$=+98.0 (c=1.0, CH$_2$Cl$_2$); FT-IR (neat) $\nu_{max}$=2977, 2933, 2871, 1698, 1654, 1475, 1454, 1428, 1376, 1365, 1338, 1274, 1253, 1213, 1177, 1163, 1127, 1083, 1063, 991, 979, 934, 860, 775 cm$^{-1}$; $^1$H NMR (600 MHz, CDCl$_3$) δ 5.36-5.34 (m, 1H), 4.06-3.97 (m, 1H), 3.85 (qd, J=6.1, 6.1 Hz, 1H), 2.54 (s, 3H), 1.61 (br s, 3H), 1.51 (br s, 3H), 1.43 (br s, 9H), 1.38 (d, J=6.0 Hz, 3H) ppm; $^{13}$C NMR (151 MHz, CDCl$_3$) δ 152.1, 134.7, 101.0, 94.4, 79.8, 75.2, 69.6, 34.0, 28.7, 26.6, 25.4, 18.2 ppm; HRMS (ESI-TOF) calcd for $C_{14}H_{24}INO_3Na^+$ [M+Na]$^+$ 404.0693, found 404.0706.

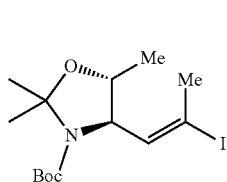

18a

Data for 18a: $R_f$=0.24 (silica gel, 5% ethyl acetate in hexanes); $[\alpha]_D^{25}$=−20.0 (c=1.0, CH$_2$Cl$_2$); FT-IR (neat) $\nu_{max}$=2977, 2932, 2872, 1699, 1641, 1552, 1476, 1455, 1387, 1376, 1365, 1348, 1289, 1256, 1213, 1176, 1137, 1121, 1081, 1062, 981, 935, 859, 778, cm$^{-1}$; $^1$H NMR (600 MHz, CDCl$_3$) δ 5.98-5.94 (m, 1H), 4.04-3.95 (m, 1H), 3.82 (qd, J=6.0, 6.0 Hz, 1H), 2.44 (br s, 3H), 1.59 (br s, 3H), 1.50 (br s, 3H), 1.44 (br s, 9H), 1.28 (d, J=6.0 Hz, 3H) ppm; $^{13}$C NMR (151 MHz, CDCl$_3$) δ 152.0, 140.5, 95.8, 94.4, 80.0, 74.4, 63.2, 28.5, 28.1, 26.5, 25.4, 17.5 ppm; HRMS (ESI-TOF) calcd for $C_{14}H_{24}INO_3Na^+$ [M+Na]$^+$ 404.0693, found 404.0706.

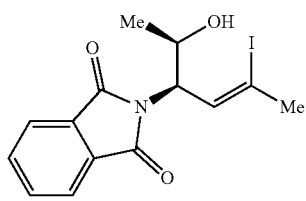

19

Alcohol 19: Vinyl iodide 18 (487 mg, 1.28 mmol, 1.0 equiv) was dissolved in formic acid (13 mL) with stirring at 25° C. After 20 min, the reaction mixture was concentrated in vacuo, and the remaining formic acid was azeotropically removed in vacuo with toluene (3×5 mL). The crude material was redissolved in CHCl$_3$ (13 mL), and triethylamine (3.6 mL, 25.6 mmol, 20 equiv), DMAP (16 mg, 0.13 mmol, 0.1 equiv), and phthalic anhydride (209 mg, 1.41 mmol, 1.1 equiv) were added with stirring, and the reaction mixture was heated to 70° C. After 48 h at the same temperature, the reaction mixture was allowed to cool to 25° C., and then concentrated in vacuo. The obtained residue was purified directly by flash column chromatography (silica gel, 10→30% ethyl acetate in hexanes) to afford alcohol 19 (386 mg, 1.04 mmol, 81%) as a white amorphous solid. 19: $R_f$=0.22 (silica gel, 30% ethyl acetate in hexanes); $[\alpha]_D^{25}$=+111 (c=0.2, CH$_2$Cl$_2$); FT-IR (neat) $\nu_{max}$=3466, 2970, 2917, 1773, 1704, 1646, 1612, 1467, 1427, 1386, 1359, 1334, 1221, 1188, 1174, 1150, 1127, 1085, 1050, 1034, 1012, 985, 917, 886, 865, 832, 794, 718, 700 cm$^{-1}$; $^1$H NMR (600 MHz, CDCl$_3$) δ 7.89-7.82 (m, 2H), 7.78-7.71 (m, 2H), 6.15 (dq, J=8.8, 1.5 Hz, 1H), 4.87 (dd, J=8.8, 7.2 Hz, 1H), 4.32 (qd, J=6.6, 6.6 Hz, 1H), 2.56 (d, J=1.5 Hz, 3H), 2.41 (d, J=8.4 Hz, 1H), 1.27 (d, J=6.4 Hz, 3H) ppm; $^{13}$C NMR (151 MHz, CDCl$_3$) δ 168.7, 134.3, 131.9, 130.5, 123.7, 106.0, 68.3, 63.6, 34.2, 21.1 ppm; HRMS (ESI-TOF) calcd for $C_{14}H_{14}INO_3H^+$ [M+H]$^+$ 372.0091, found 372.0084.

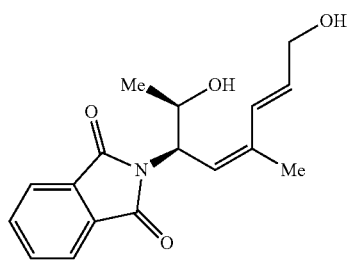

22

Diene 22: To a stirred solution of alcohol 19 (2.0 g, 5.4 mmol, 1.0 equiv) and stannane 20 (2.3 g, 6.5 mmol, 1.2 equiv) in NMP (90 mL) at 25° C. was added tris(dibenzylideneacetone)dipalladium (494 mg, 0.54 mmol, 0.1 equiv). After 18 h, the reaction mixture was filtered through a short silica plug, and rinsed thoroughly with ethyl acetate (300 mL). The resulting organic phase was washed with an aqueous solution of lithium chloride (1.0 M, 4×100 mL), dried with anhydrous sodium sulfate, and concentrated in vacuo. The obtained residue was purified by flash column chromatography (silica gel, 10→20→40→50→80% ethyl acetate in hexanes) to afford diene 22 (1.19 g, 3.9 mmol, 73% yield) as a white foam. 22: $R_f$=0.38 (silica gel, 70% ethyl acetate in hexanes); $[\alpha]_D^{25}$=+51.7 (c=0.3, CH$_2$Cl$_2$); FT-IR (neat) $\nu_{max}$=3440, 2973, 2922, 2857, 1769, 1702, 1614, 1467, 1453, 1387, 1332, 1260, 1187, 1172, 1141, 1112, 1089, 1073, 1014, 1000, 967, 912, 889, 868, 793, 720 cm$^{-1}$; $^1$H NMR (600 MHz, CDCl$_3$) δ 7.83-7.78 (m, 2H), 7.73-7.65 (m, 2H), 6.80 (d, J=15.6 Hz, 1H), 5.94 (dt, J=15.6, 5.6 Hz, 1H), 5.86 (d, J=9.8 Hz, 1H), 5.09 (dd, J=9.8, 8.2 Hz, 1H), 4.34 (qd, J=6.6, 6.6 Hz, 1H), 4.27 (d, J=5.6 Hz, 1H), 2.49 (br s, 1H) 1.87 (s, 3H), 1.22 (d, J=6.3 Hz, 3H) ppm; $^{13}$C NMR (151 MHz, CDCl$_3$) δ 168.9, 136.6, 134.2, 132.1, 131.8, 127.2, 124.0, 123.5, 68.3, 63.9, 54.8, 21.4, 20.7 ppm; HRMS (ESI-TOF) calcd for $C_{17}H_{19}NO_4Na^+$ [M+Na]$^+$ 324.1206, found 324.1194.

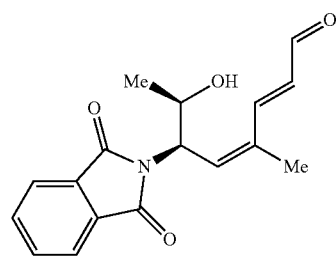

7

Aldehyde 7: Procedure A, MnO$_2$ oxidation: To a stirred solution of diene 22 (1.0 g, 3.32 mmol, 1.0 equiv) in CH$_2$Cl$_2$ (66 mL) was added MnO$_2$ (3.36 g, 33.4 mmol, 10 equiv) at 25° C. After 15 min, additional MnO$_2$ (3.36 g, 33.4 mmol, 10 equiv) was added, and stirring was continued for 30 min. The reaction mixture was then filtered through Celite®, rinsed thoroughly with ethyl acetate (150 mL), and concentrated in vacuo. The obtained white foam (894 mg, 2.99 mmol, 90%) was sufficiently pure for use in the following step.

Procedure B, Stille coupling: To a stirred solution of alcohol 19 (100 mg, 0.27 mmol, 1.0 equiv) and stannane 21 (140 mg, 0.41 mmol, 1.5 equiv) in NMP (4.5 mL) at 25° C. was added tris(dibenzylideneacetone)dipalladium (25 mg, 0.027 mmol, 0.1 equiv). After 18 h, the reaction mixture was filtered through a short silica plug, and rinsed thoroughly with ethyl acetate (30 mL). The resulting organic phase was washed with an aqueous solution of lithium chloride (1.0 M, 4×10 mL), dried with anhydrous sodium sulfate, and concentrated in vacuo. The obtained residue was purified by flash column chromatography (silica gel, 10→50% ethyl acetate in hexanes) to afford aldehyde 7 (48 mg, 0.16 mmol, 73% yield) as a white foam. 7: $R_f$=0.30 (silica gel, 50% ethyl acetate in hexanes); $[\alpha]_D^{25}$=+257 (c=0.7, $CH_2Cl_2$); FT-IR (neat) $v_{max}$=3463, 3060, 2970, 2925, 2854, 2729, 1769, 1705, 1632, 1613, 1597, 1467, 1453, 1385, 1333, 1262, 1188, 1172, 1135, 1111, 1080, 1059, 1019, 972, 919, 889, 863, 797, 719 $cm^{-1}$; $^1H$ NMR (600 MHz, $CDCl_3$) δ 9.70 (d, J=7.8 Hz, 1H), 7.86-7.84 (m, 2H), 7.75-7.73 (m, 2H), 7.72 (d, J=15.6 Hz, 1H), 6.30 (d, J=10.0 Hz, 1H), 6.23 (dd, J=15.6, 7.8 Hz, 1H), 5.16 (dd, J=10.0, 7.8 Hz, 1H), 4.42 (qd, J=6.5, 6.5 Hz, 1H), 2.46 (d, J=7.8 Hz, 1H), 1.26 (d, J=6.3 Hz, 3H) ppm; $^{13}C$ NMR (151 MHz, $CDCl_3$) δ 193.4, 168.7, 147.1, 135.8, 134.5, 132.9, 131.8, 131.4, 123.7, 67.9, 54.5, 21.4, 20.3 ppm; HRMS (ESI-TOF) calcd for $C_{17}H_{17}NO_4Na^+$ $[M+Na]^+$ 322.1050, found 322.1058.

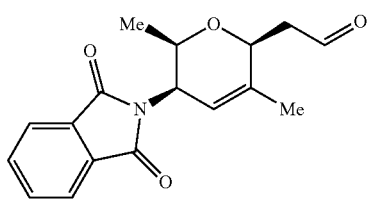

24

Dihydropyran 24: To a stirred solution of aldehyde 7 (860 mg, 2.77 mmol, 1.0 equiv) in $CH_2Cl_2$ (55 mL) at 0° C. was added benzoic acid (68 mg, 0.55 mmol, 0.20 equiv) followed by diphenyl prolinol catalyst 23 (339 mg, 0.55 mmol, 0.20 equiv). After 6.5 h, the reaction mixture was quenched with a saturated aqueous solution of sodium bicarbonate (40 mL), and allowed to warm to 25° C. The phases were separated, the aqueous layer was extracted with $CH_2Cl_2$ (3×15 mL), and the combined organic layers were dried with anhydrous sodium sulfate and concentrated in vacuo. The obtained residue was purified by flash column chromatography (silica gel, 20→30→50% ethyl acetate in hexanes) to afford pure dihydropyan 24 (640 mg, 2.13 mmol, 77%) as a white foam along with recovered 7 (149 mg, 0.50 mmol, 18%). 24: $R_f$=0.33 (silica gel, 25% ethyl acetate in hexanes); $[\alpha]_D^{25}$=-266 (c=1.0, $CH_2Cl_2$); FT-IR (neat) $v_{max}$=2977, 2920, 2855, 2730, 1770, 1712, 1611, 1556, 1467, 1443, 1386, 1363, 1351, 1327, 1291, 1193, 1165, 1125, 1088, 1072, 1041, 900, 871, 836, 795, 720, 689 $cm^{-1}$; $^1H$ NMR (600 MHz, $CDCl_3$) δ 9.98 (dd, J=2.2, 2.2 Hz, 1H), 7.83-7.80 (m, 2H), 7.72-7.69 (m, 2H), 5.59 (dt, J=5.8, 1.6 Hz, 1H), 4.66-4.61 (m, 1H), 4.60-4.55 (m, 1H), 3.94 (qd, J=6.4, 3.4 Hz, 1H), 2.98 (ddd, J=16.1, 8.2, 2.6 Hz, 1H), 2.75 (ddd, J=16.1, 3.6, 1.9 Hz, 1H), 1.74 (d, J=1.1 Hz, 3H), 1.08 (d, J=6.4 Hz, 3H) ppm; $^{13}C$ NMR (151 MHz, $CDCl_3$) δ 202.7, 168.5, 137.2, 131.9, 123.3, 74.0, 48.3, 45.9, 19.1, 17.1 ppm; HRMS (ESI-TOF) calcd for $C_{17}H_{17}NO_4Na^+$ $[M+Na]^+$ 322.1050, found 322.1048.

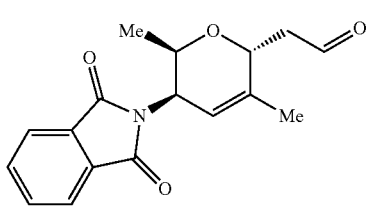

11-epi-24

Dihydropyran 11-epi-24: To a stirred solution was aldehyde 7 (100 mg, 0.33 mmol, 1.0 equiv) in $CH_2Cl_2$ (6.6 mL) at 0° C. was added benzoic acid (8.5 mg, 0.07 mmol, 0.20 equiv) followed by diphenyl prolinol catalyst ent-23 (42 mg, 0.07 mmol, 0.20 equiv). After 6.5 h, the reaction mixture was quenched with a saturated aqueous solution of sodium bicarbonate (5 mL) and allowed to warm to 25° C. The phases were separated, and the aqueous layer was extracted with $CH_2Cl_2$ (3×5 mL). The combined organic layers were dried with anhydrous sodium sulfate and concentrated in vacuo. The obtained residue was purified by flash column chromatography (silica gel, 20→30→50% ethyl acetate in hexanes) to afford pure dihydropyan 11-epi-24 (640 g, 2.13 mmol, 64%) as a white foam along with recovered 7 (149 mg, 0.50 mmol, 28%). 11-epi-24: $R_f$=0.16 (silica gel, 25% ethyl acetate in hexanes); $[\alpha]_D^{25}$=-331 (c=1.0, $CH_2Cl_2$); FT-IR (neat) $v_{max}$=2976, 2922, 2859, 2732, 1771, 1711, 1612, 1467, 1444, 1385, 1355, 1331, 1282, 1172, 1125, 1107, 1088, 1072, 1034, 898, 839, 795, 765, 720, 689 $cm^{-1}$; $^1H$ NMR (600 MHz, $CDCl_3$) δ 9.86 (dd, J=4.0, 1.4 Hz, 1H), 7.89-7.77 (m, 2H), 7.75-7.68 (m, 2H), 5.58 (dt, J=5.4, 1.6 Hz, 1H), 4.88 (dd, J=10.1, 10.1 Hz, 1H), 4.63-4.61 (m, 1H), 4.07 (qd, J=6.4, 3.6 Hz, 1H), 2.78 (ddd, J=15.8, 10.4, 4.0 Hz, 1H), 2.67 (ddd, J=15.8, 3.4, 1.4 Hz, 1H), 1.79 (s, 3H), 1.07 (d, J=6.4 Hz, 3H) ppm; $^{13}C$ NMR (151 MHz, $CDCl_3$) δ 201.2, 168.5, 139.4, 134.2, 131.9, 123.4, 117.6, 71.9, 66.4, 48.1, 45.1, 19.5, 16.8 ppm; HRMS (ESI-TOF) calcd for $C_{17}H_{17}NO_4Na^+$ $[M+Na]^+$ 322.1050, found 322.1041.

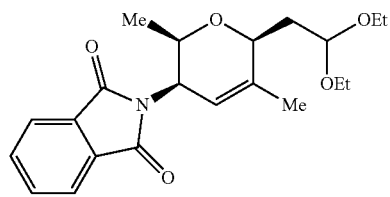

25

Acetal 25: To a stirred solution of dihydropyran 24 (511 mg, 1.71 mmol, 1.0 equiv) in EtOH (17.1 mL) at 25° C. was added triethylorthoformate (2.85 mL, 17.1 mmol, 10 equiv) followed by camphorsulfonic acid (40 mg, 0.17 mmol, 0.1 equiv). After 2 h, the reaction mixture was concentrated in vacuo, and the obtained residue was purified by flash column chromatography (silica gel, 10→15% ethyl acetate in hexanes) to provide acetal 25 (583 mg, 1.56 mmol, 91%) as a colorless oil. 25: $R_f$=0.32 (silica gel, 20% ethyl acetate in hexanes); $[\alpha]_D^{25}$=-366 (c=1.0, $CH_2Cl_2$); FT-IR (neat) $v_{max}$=2974, 2932, 2874, 1771, 1713, 1612, 1467, 1443, 1385, 1342, 1327, 1291, 1162, 1124, 1089, 1059, 1043, 1020, 950, 923, 899, 871, 834, 795, 749, 720, 704, 688 $cm^{-1}$; $^1H$ NMR (600 MHz, $CDCl_3$) δ 7.82-7.80 (m, 2H), 7.71-7.68 (m, 2H), 5.49 (dt, J=5.9, 1.8 Hz, 1H), 4.89 (dd, J=8.5, 3.3 Hz, 1H), 4.54 (ddq, J=6.2, 3.4, 1.6 Hz, 1H), 4.22 (dd, J=10.0, 10.0 Hz, 1H), 3.88 (qd, J=6.4, 3.3 Hz, 1H), 3.76-3.69 (m, 2H), 3.61 (dq, J=9.6, 7.0 Hz, 1H), 3.54 (dq, J=9.2, 7.0 Hz, 1H), 2.17-2.04 (m, 2H), 1.74 (d, J=0.9 Hz, 3H), 1.24 (t, J=7.0 Hz, 3H), 1.22 (t, J=7.0 Hz, 3H), 1.08 (d, J=6.4 Hz, 3H) ppm; $^{13}$C NMR (151 MHz, CDCl$_3$) δ 141.9, 133.8, 131.9, 123.1, 116.5, 100.9, 74.8, 71.5, 62.2, 62.0, 48.6, 36.4, 19.0, 17.1, 15.47, 15.46 ppm; HRMS (ESI-TOF) calcd for C$_{21}$H$_{27}$NO$_5$Na$^+$ [M+Na]$^+$ 396.1781, found 396.1783.

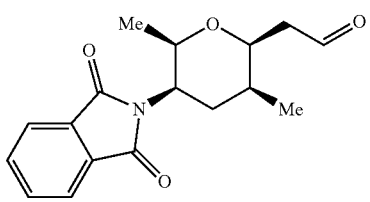

26

Tetrahydropyran 26: To a stirred solution of acetal 25 (50 mg, 0.13 mmol, 1.0 equiv) in EtOH (4.3 mL) at 25° C. was added 10% Pd/C (17.5 mg, 35%, w/w). The reaction mixture was placed in a bomb reactor, evacuated three times with H$_2$, and placed under a pressurized H$_2$ atmosphere (80 bar). After 24 h, the H$_2$ atmosphere was removed, the reaction mixture was filtered through a Celite® pad, rinsed thoroughly with ethyl acetate (30 mL), and concentrated in vacuo. The crude residue was redissolved in acetone (1.3 mL) with stirring, and an aqueous solution of hydrochloric acid (0.1 M, 3.9 mL, 0.39 mmol, 3.0 equiv) was added at 25° C. After 15 min, the reaction mixture was neutralized with solid sodium bicarbonate (200 mg) and diluted with ethyl acetate (5 mL) and water (5 mL). The phases were separated, the aqueous layer was extracted with ethyl acetate (3×3 mL), and the combined organic layers were concentrated in vacuo. The obtained residue was purified by flash chromatography (silica gel, 30% ethyl acetate in hexanes) to provide tetrahydropyran 26 (21 mg, 0.07 mmol, 54%) as a colorless oil. 26: R$_f$=0.29 (silica gel, 30% ethyl acetate in hexanes); $[α]_D^{25}$=4.2 (c=1.0, CH$_2$Cl$_2$); FT-IR (neat) $v_{max}$=2972, 2936, 2879, 2728, 1772, 1709, 1612, 1467, 1396, 1371, 1330, 1291, 1194, 1173, 1105, 1079, 1056, 980, 934, 881, 794, 719, 659 cm$^{-1}$; $^1$H NMR (600 MHz, CDCl$_3$) δ 9.92 (dd, J=2.2, 2.3 Hz, 1H), 7.87-7.79 (m, 2H), 7.76-7.66 (m, 2H), 4.52 (ddd, J=10.2, 7.1, 6.0 Hz, 1H), 4.43 (ddd, J=9.2, 6.5, 4.3 Hz, 1H), 4.11 (qd, J=6.5, 6.5 Hz, 1H), 2.86 (ddd, J=15.9, 9.2, 2.6 Hz, 1H), 2.52-2.43 (m, 3H), 2.24-2.15 (m, 1H), 1.77 (ddd, J=13.1, 7.0, 4.0 Hz, 1H), 1.07 (d, J=6.6 Hz, 3H), 0.93 (d, J=7.0 Hz, 3H) ppm; $^{13}$C NMR (151 MHz, CDCl$_3$) δ 202.7, 168.7, 134.2, 131.8, 123.4, 73.2, 70.6, 50.9, 45.0, 30.3, 28.1, 16.8, 16.3 ppm; HRMS (ESI-TOF) calcd for C$_{17}$H$_{19}$NO$_4$Na$^+$ [M+Na]$^+$ 324.1206, found 324.1211.

Procedure for the Direct Hydrogenation of 24:

To a stirred solution of dihydropyran 24 (100 mg, 0.33 mmol, 1.0 equiv) in hexafluoroisopropanol (7.3 mL) at 25° C. was added 10% Pd/C (50 mg, 50%, w/w). The reaction mixture was placed in a bomb reactor, evacuated three times with H$_2$, and placed under a pressurized H$_2$ atmosphere (80 bar). After 24 h, the H$_2$ atmosphere was removed, the reaction mixture was filtered through a Celite® pad, rinsed thoroughly with ethyl acetate (30 mL), and concentrated in vacuo. The obtained residue was purified by flash chromatography (silica gel, 35% t-butyl methyl ether in hexanes) to provide tetrahydropyran 26 (63 mg, 0.21 mmol, 65%) and tetrahydropyran 12-epi-26 (27 mg, 0.09 mmol, 28%) as colorless oils.

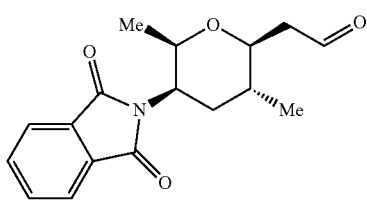

12-epi-26

Tetrahydropyran 12-epi-26: To a stirred solution of acetal 25 (120 mg, 0.32 mmol, 1.0 equiv) in CH$_2$Cl$_2$ (3.2 mL) was added [Ir(Py)(PCy$_3$)(COD)BARF] (24 mg, 0.016 mmol, 0.05 equiv) at 25° C. The reaction mixture was placed under an atmosphere of H$_2$ (1 atm), stirred for 10 h, and then concentrated in vacuo. The crude residue was redissolved in acetone (3.2 mL) with stirring, and an aqueous solution of hydrochloric acid (0.1 M, 9.6 mL, 0.96 mmol, 3.0 equiv) was added at 25° C. After 15 min, the reaction mixture was neutralized with solid sodium bicarbonate (600 mg) and diluted with ethyl acetate (12 mL) and water (12 mL). The phases were separated, the aqueous layer was extracted with ethyl acetate (3×5 mL), and the combined organic layers were concentrated in vacuo. The obtained residue was purified by flash chromatography (silica gel, 30% ethyl acetate in hexanes) to afford pure tetrahydropyran 12-epi-26 (69 mg, 0.23 mmol, 85%) as a colorless oil. 12-epi-26: R$_f$=0.34 (silica gel, 30% ethyl acetate in hexanes); $[α]_D^{25}$=+47.8 (c=0.6, CH$_2$Cl$_2$); FT-IR (neat) $v_{max}$=2973, 2936, 2872, 2848, 2732, 1771, 1709, 1611, 1467, 1437, 1404, 1371, 1356, 1328, 1285, 1241, 1207, 1184, 1170, 1142, 1094, 1067, 1044, 1030, 990, 958, 927, 897, 851, 795, 764, 721, 694 cm$^{-1}$; $^1$H NMR (600 MHz, CDCl$_3$) δ 9.95 (dd, J=2.8, 2.0 Hz, 1H), 7.87-7.80 (m, 2H), 7.76-7.69 (m, 2H), 4.43 (ddd, J=6.1, 3.2, 1.5 Hz, 1H), 3.83 (qd, J=6.4, 3.4 Hz, 1H), 3.62 (ddd, J=10.0, 8.1, 3.4 Hz, 1H), 2.76 (ddd, J=16.1, 8.1, 2.8 Hz, 1H), 2.68 (ddd, J=16.1, 3.3, 2.0 Hz, 1H), 2.61-2.49 (m, 2H), 2.00 (ddd, J=15.0, 4.8, 1.7 Hz, 1H), 1.78 (ddd, J=15.0, 12.3, 6.5 Hz, 1H), 1.04 (d, J=6.4 Hz, 3H), 0.84 (d, J=6.5 Hz, 3H) ppm; $^{13}$C NMR (151 MHz, CDCl$_3$) δ 202.9, 169.0, 134.2, 131.8, 123.4, 79.7, 74.1, 49.4, 47.3, 36.7, 30.2, 17.9, 17.7 ppm; HRMS (ESI-TOF) calcd for C$_{17}$H$_{19}$NO$_4$Na$^+$ [M+Na]$^+$ 324.1206, found 324.1216.

27

Olefin 27: To a stirred solution of tetrahydropyran 26 (86 mg, 0.29 mmol, 1.0 equiv) in THF (5.1 mL) at −20° C. was added Tebbe reagent (0.58 mL, 0.5 M in toluene, 0.29 mmol, 1.0 equiv) dropwise. The reaction mixture was allowed to slowly warm to 0° C. over 1 h, and was then quenched with a saturated aqueous solution of sodium bicarbonate (10 mL). The phases were separated, the aqueous layer was extracted with ethyl acetate (3×5 mL), and the combined organic layers were concentrated in vacuo. The obtained residue was purified by flash column chromatography (silica gel, 5→10% ethyl acetate in hexanes) to provide 27 (66 mg, 0.22 mmol, 76%) as a colorless oil. 27: R$_f$=0.24 (silica gel, 10% ethyl acetate in hexanes); $[\alpha]_D^{25}=-14.4$ (c=0.5, CH$_2$Cl$_2$); FT-IR (neat) $\nu_{max}$=3072, 2974, 2936, 2878, 1773, 1713, 1640, 1612, 1467, 1429, 1396, 1372, 1356, 1329, 1291, 1193, 1159, 1110, 1088, 1069, 1057, 1033, 994, 911, 874, 795, 718, 667 cm$^{-1}$; $^1$H NMR (600 MHz, CDCl$_3$) δ 7.84-7.81 (m, 2H), 7.73-7.70 (m, 2H), 6.00 (dddd, J=17.1, 10.2, 6.8, 6.8 Hz, 1H), 5.15-5.11 (m, 1H), 5.07-5.05 (m, 1H), 4.49 (ddd, J=10.1, 6.0, 6.0 Hz, 1H), 4.09 (qd, J=6.5, 6.5 Hz, 1H), 3.82 (ddd, J=8.6, 5.4, 5.4 Hz, 1H), 2.50-2.43 (m, 2H), 2.29-2.24 (m, 1H), 2.09-2.03 (m, 1H), 1.79 (ddd, J=13.2, 6.0, 4.8 Hz, 1H), 1.14 (d, J=6.7 Hz, 3H), 0.98 (d, J=7.0 Hz, 3H) ppm; $^{13}$C NMR (151 MHz, CDCl$_3$) δ 168.8, 136.4, 134.1, 132.0, 123.3, 116.4, 71.3, 51.1, 35.8, 31.2, 29.3, 17.1, 15.9 ppm; HRMS (ESI-TOF) calcd for C$_{18}$H$_{20}$NO$_3$Na$^+$ [M+Na]$^+$ 322.1414, found 322.1414.

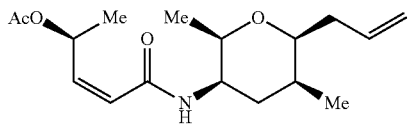

28

Amide 28: To a stirred solution of olefin 27 (52 mg, 0.17 mmol, 1.0 equiv) in benzene (8.5 mL) was added methylhydrazine (0.09 mL, 1.7 mmol, 10 equiv) at 25° C. After 2 h, the reaction mixture was washed with an aqueous solution of sodium hydroxide (0.1 M, 10 mL), and the phases were separated. The aqueous layer was extracted with ethyl acetate (3×4 mL), and the combined organic layers were dried with anhydrous sodium sulfate and concentrated in vacuo. The crude amine was redissolved in CH$_2$Cl$_2$ (2.4 mL) with stirring, and NMM (0.06 mL, 0.51 mmol, 3.0 equiv), EDCI (98 mg, 0.51 mmol, 3.0 equiv), and a solution of acid 8 (54 mg, 0.34 mmol, 2.0 equiv) in CH$_2$Cl$_2$ (0.3 mL) were added sequentially at 25° C. After 2 h, the reaction mixture was quenched with a saturated aqueous solution of ammonium chloride (2.5 mL), and the phases were separated. The aqueous layer was extracted with ethyl acetate (3×2 mL), and the combined organic layers were dried with anhydrous sodium sulfate and concentrated in vacuo. The obtained residue was purified by flash column chromatography (silica gel, 10→30% ethyl acetate in hexanes) to provide amide 28 (37 mg, 0.12 mmol, 73%) as a colorless oil. 28: R$_f$=0.31 (silica gel, 30% ethyl acetate in hexanes); $[\alpha]_D^{25}=-87.5$ (c=0.2, CH$_2$Cl$_2$); FT-IR (neat) $\nu_{max}$=3445, 3357, 3076, 2976, 2935, 2882, 2857, 1738, 1668, 1639, 1519, 1468, 1445, 1369, 1335, 1317, 1242, 1176, 1158, 1123, 1079, 1049, 1010, 972, 953, 914, 884, 859, 844, 813, 785, 742, 711 cm$^{-1}$; $^1$H NMR (600 MHz, CDCl$_3$) δ 6.29-6.24 (m, 1H), 5.97 (d, J=9.1 Hz, 1H), 5.89 (dd, J=11.6, 7.9 Hz, 1H), 5.79 (dddd, J=17.2, 10.2, 7.7, 6.1 Hz, 1H), 5.70 (dd, J=11.6, 1.3 Hz, 1H), 5.13-5.09 (m, 1H), 5.06-5.04 (m, 1H), 3.94 (ddd, J=11.7, 4.6, 2.5 Hz, 1H), 3.66 (qd, J=6.5, 2.3 Hz, 1H), 3.54 (ddd, J=7.2, 2.8, 2.8 Hz, 1H), 2.36-2.31 (m, 1H), 2.16-2.09 (m, 1H), 2.04 (s, 3H), 2.00-1.87 (m, 2H), 1.80-1.75 (m, 1H), 1.39 (d, J=6.5 Hz, 3H), 1.15 (d, J=6.5 Hz, 3H), 1.02 (d, J=7.4 Hz, 3H) ppm; $^{13}$C NMR (151 MHz, CDCl$_3$) δ 170.5, 165.0, 143.9, 134.9, 122.6, 116.9, 80.9, 76.1, 69.1, 47.3, 37.5, 36.1, 29.0, 21.4, 20.1, 18.0, 15.1 ppm; HRMS (ESI-TOF) calcd for C$_{17}$H$_{27}$NO$_4$Na$^+$ [M+Na]$^+$ 332.1832, found 332.1831.

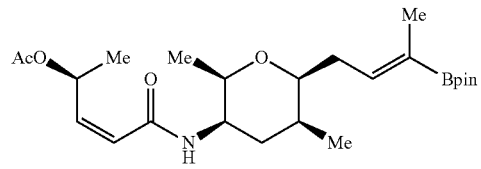

5

Boronate 5: To a stirred solution of amide 28 (90 mg, 0.29 mmol, 1.0 equiv) in ClCH$_2$CH$_2$Cl (3 mL) was added vinyl boronate 29 (243 mg, 1.45 mmol, 5.0 equiv) followed by Grubbs 2$^{nd}$ generation catalyst (25 mg, 0.03 mmol, 0.1 equiv). The reaction mixture was heated to 80° C., stirred for 1 h, and allowed to cool to 25° C. The solvent was removed in vacuo, and the obtained residue was purified by flash column chromatography (silica gel, 15→20% ethyl acetate in hexanes) to provide boronate 5 (95 mg, 0.21 mmol, 71%) as a white amorphous solid. 5: R$_f$=0.30 (silica gel, 30% ethyl acetate in hexanes); $[\alpha]_D^{25}=-137$ (c=1.0, CHCl$_3$); FT-IR (neat) $\nu_{max}$=3349, 2977, 2928, 1739, 1669, 1633, 1521, 1457, 1411, 1370, 1305, 1242, 1146, 1052, 859 cm$^{-1}$; $^1$H NMR (600 MHz, CDCl$_3$) δ 6.28-6.23 (m, 2H), 5.99 (d, J=9.1 Hz, 1H), 5.88 (dd, J=11.6, 7.9 Hz, 1H), 5.70 (dd, J=11.6, 1.3 Hz, 1H), 3.93 (ddd, J=11.7, 4.6, 2.5 Hz, 1H), 3.67 (qd, J=6.5, 2.3 Hz, 1H), 3.60 (ddd, J=7.4, 2.8, 2.8 Hz, 1H), 2.38-2.34 (m, 1H), 2.29-2.24 (m, 1H), 2.03 (s, 3H), 1.99-1.89 (m, 2H), 1.83-1.78 (m, 1H), 1.69 (br s, 3H), 1.38 (d, J=6.5 Hz, 3H), 1.25 (br s, 12H), 1.15 (d, J=6.4 Hz, 3H), 1.01 (d, J=7.4 Hz, 3H) ppm; $^{13}$C NMR (151 MHz, CDCl$_3$) δ 170.5, 165.0, 143.7, 141.1, 122.7, 83.4, 80.5, 76.1, 69.0, 47.3, 36.0, 32.5, 28.9, 25.0, 24.9, 21.4, 20.1, 18.0, 15.2, 14.4 ppm; HRMS (ESI TOF) calcd for C$_{24}$H$_{40}$BNO$_6$Na$^+$ [M+Na]$^+$ 472.2846, found 472.2845.

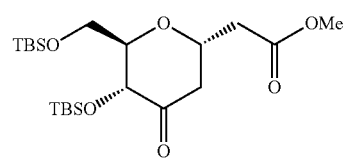

11

Ketone 11: To a stirred solution of enone 9 (10.0 g, 26.8 mmol, 1.0 equiv) in MeCN (150 mL) at −20° C. was added a solution of silyl enol ether 10 (7.84 g, 53.6 mmol, 2.0 equiv) in MeCN (50 mL) followed by iodine (68 mg, 0.1 mmol, 0.1 equiv). After 30 min, the reaction mixture was quenched with a saturated aqueous solution of sodium thiosulfate (50 mL), followed by a saturated aqueous solution of sodium bicarbonate (50 mL), and allowed to warm to 25° C. The phases were separated, and the aqueous layer was extracted with CH$_2$Cl$_2$ (3×50 mL). The combined organic layers were dried with anhydrous sodium sulfate and concentrated in vacuo. The crude material was redissolved in methanol (100 mL) with stirring, and potassium carbonate (100 mg, 0.7 mmol, 0.03 equiv) was added with stirring at 25° C. After 10 min, the reaction mixture was concentrated in vacuo, and the obtained residue was purified by flash column chromatography (silica gel, 3→5% ethyl acetate in hexanes) to provide ketone 11 (11.8 g, 26.3 mmol, 98%) as a colorless oil. 11: R$_f$=0.42 (silica gel, 15% ethyl acetate in hexanes); $[\alpha]_D^{25}=+51.3$ (c=1.0, CHCl$_3$); FT-IR (neat) $\nu_{max}$=2954, 2930, 2886, 2857, 1736, 1472, 1463, 1254, 1133, 1087, 1043, 1006, 865, 779 cm$^{-1}$; $^1$H NMR (600

MHz, CDCl₃) δ 4.80-4.76 (m, 1H), 4.33 (d, J=8.4 Hz, 1H), 3.86 (dd, J=11.3, 3.4 Hz, 1H), 3.82 (dd, J=11.3, 2.3 Hz, 1H), 3.71-3.67 (m, 1H), 3.68 (s, 3H), 2.75 (ddd, J=14.4, 6.3, 1.1 Hz, 1H), 2.66 (dd, J=15.2, 7.7 Hz, 1H), 2.48-2.43 (m, 2H), 0.91 (s, 9H), 0.90 (s, 9H), 0.14 (s, 3H), 0.08 (s, 3H), 0.06 (s, 3H), 0.03 (s, 3H) ppm; ¹³C NMR (151 MHz, CDCl₃) δ 206.2, 170.7, 78.7, 74.3, 71.2, 63.1, 52.0, 45.0, 38.2, 26.0, 25.9, 18.55, 18.54, −4.2, −5.0, −5.2, −5.4 ppm; HRMS (ESI-TOF) calcd for C₂₁H₄₂O₆Si₂Na⁺ [M+Na]⁺ 469.2418, found 469.2413.

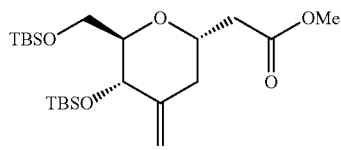

12

Olefin 12: To a stirred suspension of methyltriphenylphosphonium bromide (2.15 g, 6.02 mmol, 1.5 equiv) in THF (10 mL) at 0° C. was added t-BuOK (11 mg, 0.09 mmol, 1.3 equiv). After 30 min, the suspension was transferred via cannula to a stirred solution of ketone 11 (1.79 g, 4.0 mmol, 1.0 equiv) in THF (60 mL) at 0° C. The reaction mixture was allowed to slowly warm to 25° C. over 1 h. Then the reaction mixture was quenched with a saturated aqueous solution of ammonium chloride (25 mL). The phases were separated, and the aqueous layer was extracted with ethyl acetate (3×20 mL). The combined organic layers were dried with anhydrous sodium sulfate and concentrated in vacuo. The obtained residue was purified by flash column chromatography (silica gel, 3→5% ethyl acetate in hexanes) to provide olefin 12 (1.28 g, 2.88 mmol, 72%) as a colorless oil. 12: R_f=0.28 (silica gel, 5% ethyl acetate in hexanes); [α]_D^25=+51.5 (c=1.0, CHCl₃); FT-IR (neat) ν_max=2953, 2930, 2886, 2858, 1744, 1658, 1473, 1463, 1361, 1254, 1104, 1055, 1006, 864, 777 cm⁻¹; ¹H NMR (600 MHz, CDCl₃) δ 5.07 (s, 1H) 4.87 (s, 1H), 4.28-4.24 (m, 1H), 4.02 (d, J=6.6 Hz, 1H), 3.73 (dd, J=10.7, 4.7 Hz, 1H), 3.68 (dd, J=9.9, 4.7 Hz, 1H), 3.67 (s, 3H), 3.48-3.46 (m, 1H), 2.65 (dd, J=15.0, 7.3 Hz, 1H), 2.48 (dd, J=15.0, 6.7 Hz, 1H), 2.39 (dd, J=13.1, 4.8 Hz, 1H), 2.31 (dd, J=13.1, 4.8 Hz, 1H), 0.92 (s, 9H), 0.88 (s, 9H), 0.08 (s, 3H), 0.045 (s, 3H), 0.038 (s, 6H) ppm; ¹³C NMR (151 MHz, CDCl₃) δ 171.8, 143.9, 110.3, 79.0, 70.6, 70.3, 62.6, 51.8, 37.8, 37.5, 26.1, 26.0, 18.5, 18.4, −4.4, −4.87, −4.94, −5.2 ppm; HRMS (ESI-TOF) calcd for C₂₂H₄₄NO₅Si₂Na⁺ [M+Na]⁺ 467.2625, found 467.2618.

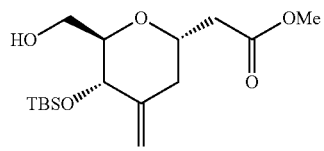

13

Alcohol 13: To a stirred solution of olefin 12 (1.0 g, 2.32 mmol, 1.0 equiv) in methanol (15 mL) was added pyridium p-toluenesulfonate (583 mg, 2.32 mmol, 1.0 equiv) at 25° C. After 12 h, the reaction mixture was quenched with a saturated aqueous solution of sodium bicarbonate (15 mL). The phases were separated, and the aqueous layer was extracted with ethyl acetate (3×10 mL). The combined organic layers were dried with anhydrous sodium sulfate and concentrated in vacuo. The obtained residue was purified by flash column chromatography (silica gel, 25→30% ethyl acetate in hexanes) to provide alcohol 13 (730 mg, 2.27 mmol, 98%) as a colorless oil. 13: R_f=0.30 (silica gel, 25% ethyl acetate in hexanes); [α]_D^25=+76.5. (c=1.0, CHCl₃); FT-IR (neat) ν_max=2953, 2930, 2887, 2858, 1739, 1658, 1473, 1463, 1437, 1389, 1253, 1166, 1098, 1047, 862, 837, 777 cm⁻¹; ¹H NMR (600 MHz, CDCl₃) δ 5.11 (s, 1H), 4.88 (s, 1H), 4.40-4.36 (m, 1H), 3.93 (d, J=7.4, 1H), 3.71-3.64 (m, 2H), 3.69 (s, 3H), 3.53 (ddd, J=7.4, 6.2, 3.4 Hz, 1H), 2.73 (dd, J=15.4, 8.8 Hz, 1H), 2.49-2.44 (m, 2H), 2.32 (dd, J=13.4, 3.7 Hz, 1H), 2.15 (t, J=6.8 Hz, 1H), 0.92 (s, 9H), 0.09 (s, 3H), 0.04 (s, 3H) ppm; ¹³C NMR (151 MHz, CDCl₃) δ 171.9, 143.6, 110.4, 77.7, 70.6, 69.9, 61.7, 51.9, 37.8, 36.8, 26.0, 18.3, −4.34, −5.0 ppm; HRMS (ESI-TOF) calcd for C₁₆H₃₀O₅SiNa⁺ [M+Na]⁺ 353.1760, found 353.1747.

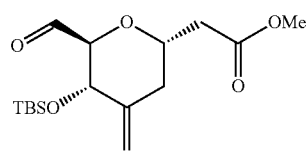

14

Aldehyde 14: To a stirred solution of oxalyl chloride (1.2 mL, 13.4 mmol, 1.5 equiv) in CH₂Cl₂ (21 mL) at −78° C. was slowly added dimethyl sulfoxide (1.9 mL, 26.8 mmol, 3.0 equiv) over 5 min, and the reaction mixture was allowed to slowly warm to −60° C. over an additional 20 min. Then a solution of alcohol 13 (2.95 g, 8.93 mmol, 1.0 equiv) in CH₂Cl₂ (41 mL) was added dropwise via cannula over 45 min, and the original flask was rinsed with additional CH₂Cl₂ (3×3 mL). The reaction mixture was allowed to slowly warm to −45° C. over 30 min, at which point triethylamine (7.2 mL, 51.6 mmol, 5.8 equiv) was added dropwise over 5 min, and the reaction mixture was warmed to 0° C. over 10 min. Then the reaction mixture was quenched with a saturated aqueous solution of ammonium chloride (75 mL), and the phases were separated. The aqueous layer was extracted with CH₂Cl₂ (3×15 mL), and the combined organic layers were washed with brine (25 mL), dried with anhydrous sodium sulfate, and concentrated in vacuo. The obtained residue was purified by flash column chromatography (silica gel, 10→30% ethyl acetate in hexanes) to provide aldehyde 14 (2.80 g, 8.5 mmol, 96%) as a colorless oil. 14: R_f=0.35 (silica gel, 30% ethyl acetate in hexanes); [α]_D^25=+68.2 (c=1.0, CHCl₃); FT-IR (neat) ν_max=2954, 2930, 2904, 2858, 1739, 1736, 1473, 1463, 1437, 1389, 1360, 1323, 1255, 1210, 1158, 1123, 1092, 1006, 907, 837, 777 cm⁻¹; ¹H NMR (600 MHz, CDCl₃) δ 9.74 (s, 1H), 5.02 (s, 1H), 4.89 (s, 1H), 4.36 (d, J=4.2 Hz, 1H), 4.26-4.22 (m, 1H), 4.10 (d, J=4.2 Hz, 1H), 3.71 (s, 3H), 2.72 (dd, J=15.4, 7.8 Hz, 1H), 2.53 (dd, J=15.4, 5.4 Hz, 1H), 2.44 (dd, J=13.0, 8.4 Hz, 1H), 2.25 (dd, J=13.0, 3.5 Hz, 1H), 0.89 (s, 9H), 0.06 (s, 3H), 0.04 (s, 3H) ppm; ¹³C NMR (151 MHz, CDCl₃) δ 201.6, 171.2, 142.5, 112.1, 84.6, 72.6, 70.5, 52.0, 39.3, 36.0, 25.9, 18.3, −4.5, −4.9 ppm; HRMS (ESI-TOF) calcd for C₁₆H₂₈NO₅SiNa⁺ [M+Na]⁺ 351.1604, found 351.1581.

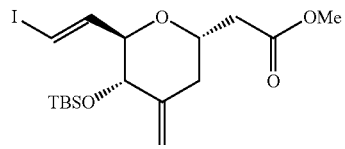

15

Vinyl iodide 15: To a stirred solution of anhydrous CrCl$_2$ (597 mg, 4.86 mmol, 6.0 equiv) and CHI$_3$ (957 mg, 2.43 mmol, 3.0 equiv) in THF (16 mL) at 25° C. was added a solution of aldehyde 14 (266 mg, 0.81 mmol, 1.0 equiv) in THF (8 mL) via cannula, and the original flask was rinsed with additional THF (3×1 mL). After 12 h, the reaction mixture was quenched with water (15 mL). The phases were separated, and the aqueous layer was extracted with Et$_2$O (3×10 mL). The combined organic layers were dried with anhydrous sodium sulfate and concentrated in vacuo. The obtained residue was purified by flash column chromatography (silica gel, 10% Et$_2$O in hexanes) to provide vinyl iodide 15 (213 mg, 0.47 mmol, 58%) as a colorless oil. 15: R$_f$=0.29 (silica gel, 10% Et$_2$O in hexanes); [α]$_D^{25}$=+93.3 (c=1.0, CH$_2$Cl$_2$); FT-IR (neat) $v_{max}$=2952, 2857, 1740, 1656, 1613, 1472, 1436, 1318, 1253, 1165, 1117, 1006, 859, 837, 777 cm$^{-1}$; $^1$H NMR (600 MHz, CDCl$_3$) δ 6.55 (dd, J=14.5, 6.2 Hz, 1H), 6.41 (dd, J=14.5, 1.1 Hz, 1H), 5.13 (s, 1H), 4.90 (s, 1H), 4.41-4.38 (m, 1H), 3.88-3.86 (m, 1H), 3.80-3.78 (m, 1H), 3.68 (s, 3H), 2.68 (dd, J=15.0, 7.7 Hz, 1H), 2.52-2.46 (m, 2H), 2.31 (dd, J=13.4, 3.6 Hz, 1H), 0.92 (s, 9H), 0.07 (s, 3H), 0.03 (s, 3H) ppm; $^{13}$C NMR (151 MHz, CDCl$_3$) δ 171.5, 143.8, 142.8, 110.6, 80.5, 80.1, 73.8, 70.4, 51.9, 37.7, 37.1, 25.9, 18.3, −4.5, −4.6 ppm; HRMS (ESI-TOF) calcd for C$_{17}$H$_{29}$O$_4$INa$^+$ [M+Na]$^+$ 475.0777, found 475.0772.

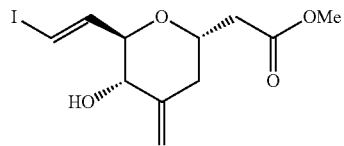

Alcohol 16: To a stirred solution of vinyl iodide 15 (200 mg, 0.44 mmol, 1.0 equiv) in THF (4.4. mL) at 0° C. was added tetra-n-butylammonium fluoride (1.0 M in THF, 0.52 mL, 0.52 mmol, 1.2 equiv) dropwise, and the reaction mixture was allowed to slowly warm to 25° C. After 3 h, the reaction mixture was quenched with a saturated aqueous solution of ammonium chloride (10 mL), and the two phases were separated. The aqueous layer was extracted with ethyl acetate (3×10 mL), and the combined organic layers were dried with anhydrous sodium sulfate and concentrated in vacuo. The obtained residue was purified by flash column chromatography (20→25% ethyl acetate in hexanes) to afford pure alcohol 16 (138 mg, 0.41 mmol, 93%) as a colorless oil. 16: R$_f$=0.33 (silica gel, 30% ethyl acetate in hexanes); [α]$_D^{25}$=+66.7 (c=1.0, CH$_2$Cl$_2$); FT-IR (neat) $v_{max}$=3451, 3073, 2990, 2949, 2904, 1735, 1655, 1609, 1472, 1437, 1382, 1321, 1272, 1203, 1165, 1089, 1045, 1002, 950, 908 cm$^{-1}$; $^1$H NMR (600 MHz, CDCl$_3$) δ 6.62 (dd, J=14.7, 5.7 Hz, 1H), 6.53 (dd, J=14.7, 1.3 Hz, 1H), 5.13 (s, 1H), 4.98 (s, 1H), 4.33-4.29 (m, 1H), 4.11-4.09 (m, 1H), 3.92 (d, J=5.4 Hz, 1H), 3.69 (s, 3H), 2.66 (dd, J=15.3, 7.9 Hz, 1H), 2.48 (dd, J=15.3, 5.9 Hz, 1H), 2.43-2.36 (m, 2H) ppm; $^{13}$C NMR (151 MHz, CDCl$_3$) δ 171.3, 142.4, 141.9, 111.9, 81.4, 79.9, 72.6, 69.4, 52.0, 38.5, 36.6 ppm; HRMS (ESI-TOF) calcd for C$_{11}$H$_{15}$O$_4$INa$^+$ [M+Na]$^+$ 360.9913, found 360.9909.

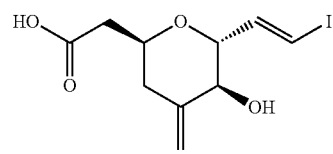

Acid 16a: To a stirred solution of alcohol 16 (107 mg, 0.32 mmol, 1.0 equiv) in 1:1 THF/H$_2$O (2.8 mL) at 0° C. was added LiOH (62 mg, 2.6 mmol, 8.0 equiv), and the reaction mixture was allowed to slowly warm to 25° C. After 12 h, the reaction mixture was neutralized with phosphate buffer (NaH$_2$PO$_4$, 1.0 M, 10 mL) and the phases were separated. The aqueous layer was extracted with ethyl acetate (3×7 mL), and the combined organic layers were dried with anhydrous sodium sulfate and concentrated in vacuo. The resulting acid 16a (101 mg, 0.34 mmol, 98%) was sufficiently pure for characterization and X-ray crystallographic purposes (FIG. 1). 16a: R$_f$=0.30 (silica gel, 10% methanol in CH$_2$Cl$_2$); m.p.=128-136° C. (ethyl acetate); [α]$_D^{25}$=+61.0 (c=1.0, MeOH); FT-IR (neat) $v_{max}$=3385, 3074, 2923, 1711, 1608, 1407, 1265, 1169, 1085, 1043, 1018, 951, 912, 838, 812 cm$^{-1}$; $^1$H NMR (600 MHz, CDCl$_3$) δ 6.63 (dd, J=14.7, 5.8 Hz, 1H), 6.56 (dd, J=14.7, 1.2 Hz, 1H), 5.15 (s, 1H), 5.01 (s, 1H), 4.34-4.30 (m, 1H), 4.17-4.08 (m, 1H), 3.95 (d, J=5.2 Hz, 1H), 2.71 (dd, J=15.6, 7.9 Hz, 1H), 2.55 (dd, J=15.6, 5.6 Hz, 1H), 2.49-2.38 (m, 2H) 1.25 (br s, 1H) ppm; $^{13}$C NMR (151 MHz, CDCl$_3$) δ 174.4, 142.1, 141.5, 112.3, 81.9, 80.0, 72.5, 69.2, 38.1, 36.4 ppm; HRMS (ESI-TOF) calcd for C$_{10}$H$_{12}$IO$_4^-$ [M−H$^+$]$^-$ 322.9786, found 322.9786.

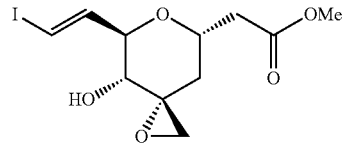

Epoxide 6a: To a stirred solution of alcohol 16 (120 mg, 0.35 mmol, 1.0 equiv) in CH$_2$Cl$_2$ (8 mL) at 0° C. was added vanadyl acetoacetonate (4.0 mg, 0.035 mmol, 0.1 equiv) followed by a solution of tert-butylhydroperoxide (5.5 M in decanes, 0.13 mL, 0.70 mmol, 2.0 equiv), and the reaction mixture was allowed to slowly warm to 25° C. After 3 h, the reaction mixture was filtered through a short silica plug, rinsed thoroughly with ethyl acetate (30 mL), and concentrated in vacuo. The obtained residue was purified by flash column chromatography (silica gel, 15→35%) to provide epoxide 6a (92 mg, 0.26 mmol, 74%) as a colorless oil. 6a: R$_f$=0.30 (silica gel, 40% ethyl acetate in hexanes); [α]$_D^{25}$=+61.7 (c=1.0, CH$_2$Cl$_2$); FT-IR (neat) $v_{max}$=3385, 2923, 1730, 1608, 1407, 1260, 1169, 1083, 1043, 1018, 953, 908 cm$^{-1}$; $^1$H NMR (600 MHz, CDCl$_3$) δ 6.70 (dd, J=14.6, 5.0 Hz, 1H), 6.53 (dd, J=14.6, 1.6 Hz, 1H), 4.54-4.46 (m, 1H), 4.14-4.08 (m, 1H), 3.70 (s, 3H), 3.50 (dd, J=9.2, 7.5 Hz, 1H), 2.98 (d, J=4.4 Hz, 1H), 2.91 (dd, J=15.5, 8.3 Hz, 1H), 2.68-2.61 (m, 2H), 2.17 (dd, J=14.3, 5.3 Hz, 1H), 1.85 (d, J=9.2 Hz, 1H), 1.72 (dd, J=14.3, 4.0 Hz, 1H) ppm; $^{13}$C NMR (151 MHz, CDCl$_3$) δ 171.4, 142.3, 80.2, 76.8, 69.1, 69.0, 57.1, 52.0, 49.5, 37.9, 34.4 ppm; HRMS (ESI-TOF) calcd for C$_{11}$H$_{15}$IO$_5$Na$^+$ [M+Na]$^+$ 376.9862, found 376.9859.

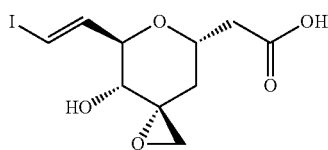

Acid 6: To a stirred solution of epoxide 6a (20 mg, 0.06 mmol, 1.0 equiv) in 10:1 THF/H$_2$O THF (1.2 mL) at 0° C. was added LiOH (2.2 mg, 0.09 mmol, 1.5 equiv), and the reaction mixture was allowed to slowly warm to 25° C. After 6 h, the reaction mixture was neutralized with phosphate buffer (NaH$_2$PO$_4$, 1.0 M, 3 mL) and the phases were separated. The aqueous layer was extracted with ethyl acetate (3×2 mL), and the combined organic layers were dried with anhydrous sodium sulfate and concentrated in vacuo. The resulting acid 6 (18 mg, 0.054 mmol, 90%) was sufficiently pure for direct use in the next step. 6: $R_f$=0.32 (silica gel, 1% acetic acid in 95:5 CH$_2$Cl$_2$/MeOH); $[\alpha]_D^{25}$=+61.7 (c=0.3, CH$_2$Cl$_2$); FT-IR (neat) $v_{max}$=3419, 3063, 2926, 1714, 1610, 1408, 1263, 1237, 1171, 1086, 1066, 1033, 944, 922, 856, 812, 742, 709 cm$^{-1}$; $^1$H NMR (600 MHz, CDCl$_3$) δ 6.70 (dd, J=14.6, 5.1 Hz, 1H), 6.55 (dd, J=14.6, 1.5 Hz, 1H), 4.56-4.46 (m, 1H), 4.14-4.07 (m, 1H), 3.52 (d, J=7.7 Hz, 1H), 3.01 (d, J=4.4 Hz, 1H), 2.96 (dd, J=15.7, 8.4 Hz, 1H), 2.71 (dd, J=15.7, 6.1 Hz, 1H), 2.66 (d, J=4.4 Hz, 1H), 2.20 (dd, J=14.3, 5.3 Hz, 1H), 1.74 (dd, J=14.3, 3.9 Hz, 1H) ppm; $^{13}$C NMR (151 MHz, CDCl$_3$) δ 174.8, 142.2, 80.5, 76.8, 69.0, 68.9, 57.1, 49.5, 37.6, 34.4 ppm; HRMS (ESI-TOF) calcd for C$_{11}$H$_{12}$IO$_5^-$ [M−H$^+$]$^-$ 338.9735, found 338.9740.

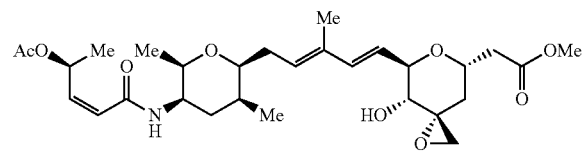

Thailanstatin A methyl ester (2): To a stirred solution of epoxide 6a (7 mg, 0.02 mmol, 1.0 equiv) and boronate 5 (27 mg, 0.06 mmol, 3.0 equiv) in rigorously degassed (freeze-pump-thaw technique×3) 3:1:1 1,4-dioxane/MeCN/H$_2$O (0.22 mL) at 25° C. was added tripotassium phosphate monohydrate (4.6 mg, 0.02 mmol, 1.0 equiv) followed by Pd(dppf)Cl$_2$.CH$_2$Cl$_2$ (0.32 mg, 0.04 μmol, 0.02 equiv). After 10 min, the reaction mixture was filtered through a layer of Celite®, and rinsed thoroughly with ethyl acetate (25 mL). The organic layer was washed with brine (5 mL), dried with anhydrous sodium sulfate, and concentrated in vacuo. The obtained residue was purified by flash column chromatography (silica gel, 45→20% hexanes in ethyl acetate) to provide methyl ester 2 (7.0 mg, 13 μmol, 64%) as a colorless oil. 2: $R_f$=0.18 (silica gel, 20% hexanes in ethyl acetate); $[\alpha]_D^{25}$=+3.0 (c=0.1, CH$_2$Cl$_2$); FT-IR (neat) $v_{max}$=3378, 2974, 2934, 1736, 1667, 1638, 1520, 1439, 1370, 1332, 1317, 1244, 1169, 1116, 1057, 1009, 972, 933, 898, 856, 814, 785, 720 cm$^{-1}$; $^1$H NMR (600 MHz, CDCl$_3$) δ 6.37 (d, J=15.8 Hz, 1H), 6.28-6.23 (m, 1H), 5.98 (d, J=9.0 Hz, 1H), 5.89 (dd, J=11.6, 7.9 Hz, 1H), 5.70 (dd, J=11.6, 1.3 Hz, 1H), 5.62 (dd, J=15.8, 6.2 Hz, 1H), 5.51 (dd, J=7.1, 7.1 Hz, 1H), 4.52-4.48 (m, 1H), 4.21 (dd, J=6.5, 6.5 Hz, 1H), 3.96-3.93 (m, 1H), 3.70 (s, 3H), 3.66 (qd, J=6.3, 2.1 Hz, 1H), 3.54-3.51 (m, 2H), 2.99 (d, J=4.6 Hz, 1H), 2.93 (dd, J=15.4, 7.8 Hz, 1H), 2.69 (dd, J=15.4, 6.6 Hz, 1H), 2.64 (d, J=4.6 Hz, 1H), 2.41-2.36 (m, 1H), 2.26-2.21 (m, 1H), 2.14 (dd, J=14.2, 5.2 Hz, 1H), 2.04 (s, 3H), 1.99-1.91 (m, 2H), 1.82-1.74 (m, 2H), 1.76 (s, 3H), 1.39 (d, J=6.5 Hz, 3H), 1.15 (d, J=6.4 Hz, 3H), 1.02 (d, J=7.4 Hz, 3H) ppm; $^{13}$C NMR (151 MHz, CDCl$_3$) δ 171.6, 170.5, 165.0, 143.8, 138.6, 134.7, 129.6, 123.1, 122.7, 80.9, 76.1, 75.8, 69.9, 69.1, 68.9, 57.3, 52.0, 49.8, 47.3, 38.2, 36.0, 34.7, 32.2, 29.1, 21.4, 20.1, 18.0, 15.3, 12.8 ppm; HRMS (ESI-TOF) calcd for C$_{29}$H$_{43}$NO$_9$Na$^+$ [M+Na]$^+$ 572.2830, found 572.2823.

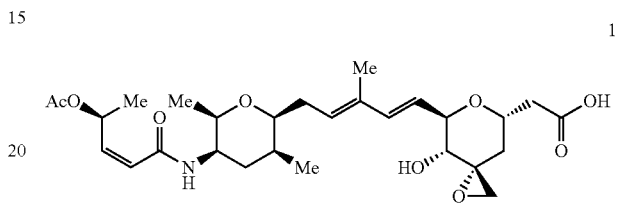

Thailanstatin A (1): To a stirred solution of epoxide 6 (4.0 mg, 0.012 mmol, 1.0 equiv) and boronate 5 (5.8 mg, 13 μmol, 1.1 equiv) in rigorously degassed (freeze-pump-thaw technique×3) 3:1:1 1,4-dioxane/MeCN/H$_2$O (0.64 mL,) at 25° C. was added tripotassium phosphate monohydrate (2.8 mg, 0.012 mmol, 1.0 equiv) followed by Pd(dppf)Cl$_2$.CH$_2$Cl$_2$ (0.1 mg, 0.125 μmol, 0.025 equiv). After 10 min, the reaction mixture was neutralized with phosphate buffer (NaH$_2$PO$_4$, 1.0 M, 2.5 mL), filtered through a layer of Celite®, and rinsed thoroughly with ethyl acetate (20 mL). Then the organic layer was dried with anhydrous sodium sulfate and concentrated in vacuo. The obtained residue was purified by reversed-phase HPLC (C18, φ19×150 mm, Atlantis, 40→50% aqueous MeCN containing 0.03% TFA) to afford thailanstatin A (1) (ca. 3.0 mg, 6.0 μmol, 52%) as a white foam. 1: $R_f$=0.35 (silica gel, 1% acetic acid in ethyl acetate); $[\alpha]_D^{25}$=+3.0 (c=0.1, CH$_2$Cl$_2$); FT-IR (neat) $v_{max}$=3347, 3036, 2976, 2933, 1731, 1667, 1634, 1523, 1442, 1370, 1333, 1317, 1244, 1116, 1051, 1008, 970, 957, 928, 894, 859, 812, 783, 710 cm$^{-1}$; $^1$H NMR (600 MHz, CD$_2$Cl$_2$) δ 6.36 (d, J=15.8 Hz, 1H), 6.30-6.25 (m, 1H), 6.24 (d, J=9.0 Hz, 1H), 5.90 (dd, J=11.6, 7.8 Hz, 1H), 5.75 (dd, J=11.6, 1.2 Hz, 1H), 5.62 (dd, J=15.8, 6.2 Hz, 1H), 5.51 (dd, J=7.0, 7.0 Hz, 1H), 4.48-4.44 (m, 1H), 4.25 (dd, J=6.4, 6.4 Hz, 1H), 3.92-3.89 (m, 1H), 3.68 (qd, J=6.5, 2.2 Hz, 1H), 3.55 (ddd, J=7.2, 7.2, 2.7 Hz, 1H), 3.48 (d, J=6.7 Hz, 1H), 2.95 (dd, J=15.6, 9.0 Hz, 1H), 2.95 (d, J=4.6 Hz, 1H), 2.65 (d, J=4.6 Hz, 1H), 2.62 (dd, J=15.6, 5.2 Hz, 1H), 2.39-2.34 (m, 1H), 2.24-2.19 (m, 1H), 2.05 (dd, J=14.0, 5.0 Hz, 1H), 2.01 (s, 3H), 1.94-1.93 (m, 2H), 1.79 (dd, J=14.0, 5.1 Hz, 1H), 1.78-1.76 (m, 1H), 1.76 (s, 3H), 1.34 (d, J=6.5 Hz, 3H), 1.12 (d, J=6.5 Hz, 3H), 1.00 (d, J=7.4 Hz, 3H) ppm; $^{13}$C NMR (151 MHz, CD$_2$Cl$_2$) δ 173.3, 170.7, 165.1, 144.0, 138.6, 134.9, 130.1, 123.2, 122.8, 81.4, 76.6, 76.5, 70.5, 68.96, 68.95, 57.5, 50.4, 47.4, 38.3, 36.2, 34.8, 32.3, 29.5, 21.4, 20.2, 17.9, 15.2, 12.7 ppm; HRMS (ESI-TOF) calcd for C$_{28}$H$_{41}$NO$_9$Na$^+$ [M+Na]$^+$ 558.2674, found 558.2671.

To approximate the yield of this step, the crude material from the aforementioned procedure was redissolved in 3:2 toluene/MeOH (0.5 mL) with stirring, and a solution of TMSCHN$_2$ (2.0 M in Et$_2$O, 18 μL, 0.036 mmol, 3.0 equiv) was added dropwise at 25° C. After 1 h, the reaction mixture was concentrated in vacuo and then purified directly by flash

2-[(2R,3R,6S)-6-Allyl-2,5-dimethyl-3,6-dihydro-2H-pyran-3-yl]-1H-isoindole-1,3(2H)-dione (48)

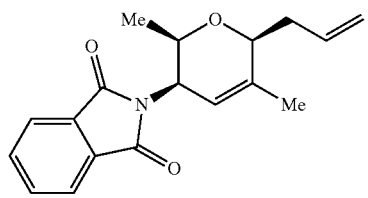

To a stirred suspension of methyltriphenylphosphonium bromide (447 mg, 1.25 mmol, 1.7 equiv) in tetrahydrofuran (8.0 mL) at 0° C. was added potassium tert-butoxide (116 mg, 1.03 mmol, 1.4 equiv). After stirring for 1 h, a solution of aldehyde 24 (220 mg, 0.740 mmol, 1.0 equiv) in tetrahydrofuran (6.0 mL) was added dropwise, and stirring was continued for an additional 1 h at the same temperature. Then the reaction mixture was quenched with a saturated aqueous solution of ammonium chloride (15 mL), and the two phases were separated. The aqueous layer was extracted with ethyl acetate (3×20 mL), and the combined organic layers were washed with brine (20 mL), dried over anhydrous sodium sulfate, and concentrated in vacuo. The obtained residue was purified by flash column chromatography (silica gel, 5→15% ethyl acetate in hexanes) to afford olefin 48 (180 mg, 0.61 mmol, 82%) as a colorless oil. 48: $R_f$=0.60 (silica gel, 25% ethyl acetate in hexanes); $[\alpha]_D^{22}$=−151.7 (c=1.0, CH$_2$Cl$_2$); FT-IR (neat) $v_{max}$=2977, 2937, 2917, 2855, 1711, 1712, 1639, 1612, 1386, 1349, 1325, 1122, 1043, 912, 897, 720 cm$^{-1}$; $^1$H NMR (600 MHz, CDCl$_3$) δ 7.81 (dd, J=5.4, 3.1 Hz, 2H), 7.69 (dd, J=5.4, 3.1 Hz, 2H), 6.17 (ddt, J=17.0, 10.3, 6.6 Hz, 1H), 5.51 (dq, J=5.8, 0.8 Hz, 1H), 5.16 (dq, J=17.0, 1.9 Hz, 1H), 5.11 (dddd, J=10.3, 1.9, 1.2, 1.2 Hz, 1H), 4.55 (ddq, J=5.8, 3.5, 1.6 Hz, 1H), 4.14 (ddq, J=7.4, 3.6, 1.8 Hz, 1H), 3.89 (qd, J=6.4, 3.5 Hz, 1H), 2.62-2.59 (m, 2H), 1.76 (s, 3H), 1.10 (d, J=6.4 Hz, 3H) ppm; $^{13}$C NMR (151 MHz, CDCl$_3$) δ 168.6, 141.9 136.2, 134.0, 132.0, 123.3, 117.2 116.2, 78.0, 71.9, 48.8, 36.8, 19.4, 17.2 ppm; HRMS (ESI-TOF) calcd for C$_{18}$H$_{19}$NO$_3$Na$^+$ [M+Na]$^+$ 320.1257, found 320.1269.

(2S,3Z)-5-{[(2R,3R,6S)-6-Allyl-2,5-dimethyl-3,6-dihydro-2H-pyran-3-yl]amino}-5-oxopent-3-en-2-yl acetate (49)

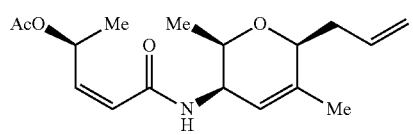

To a stirred solution of olefin 48 (174 mg, 0.58 mmol, 1.0 equiv) in ethanol (8.0 mL) at 25° C. was added ethylenediamine (0.08 mL, 1.2 mmol, 2.0 equiv) and the reaction mixture was heated to 80° C. After stirring for 15 h, the reaction mixture was allowed to cool to 25° C., and the solvent was removed in vacuo. The obtained crude amine was redissolved in dichloromethane (10 mL) with stirring at 25° C., and N-methylmorpholine (0.2 mL, 1.74 mmol, 3.0 equiv), N-(3-dimethylaminopropyl)-N'-ethylcarbodiimide hydrochloride (334 mg, 1.74 mmol, 3.0 equiv), and a solution of carboxylic acid 8 (183 mg, 1.16 mmol, 2.0 equiv) in dichloromethane (4.0 mL) were added successively. After stirring for 2 h, the reaction mixture was quenched with a saturated aqueous solution of ammonium chloride (10 mL), and the two phases were separated. The aqueous layer was extracted with ethyl acetate (3×10 mL), and the combined organic layers were washed with brine (10 mL), dried over anhydrous sodium sulfate, and concentrated in vacuo. The obtained residue was purified by flash column chromatography (silica gel, 10→30% ethyl acetate in hexanes) to afford pure amide 49 (97 mg, 0.31 mmol, 54%) as a colorless oil. 49: $R_f$=0.50 (silica gel, 30% ethyl acetate in hexanes); $[\alpha]_D^{22}$=−182.0 (c=1.0, CH$_2$Cl$_2$); FT-IR (neat) $v_{max}$=3334, 2981, 2934, 1724, 1670, 1527, 1448, 1371, 1241, 1120, 1048, 952, 815 cm$^{-1}$; $^1$H NMR (600 MHz, CDCl$_3$) δ 6.19 (m, 1H), 6.07 (d, J=9.2 Hz, 1H), 5.85 (ddt, J=17.0, 10.3, 6.6 Hz, 1H), 5.83 (dd, J=11.7, 8.2 Hz, 1H), 5.72 (dd, J=11.7, 1.2 Hz, 1H), 5.67 (d, J=6.2 Hz, 1H), 5.12 (dq, J=17.0, 1.8 Hz, 1H), 5.07 (dddd, J=10.3, 2.3, 1.1, 1.1 Hz, 1H), 4.27 (dd, J=9.2, 6.8 Hz, 1H), 4.12 (dd, J=3.6, 3.6 Hz, 1H), 3.72 (qd, J=6.4, 2.3 Hz, 1H), 2.48 (ddd, J=14.7, 6.6, 3.6 Hz, 1H), 2.35-2.30 (m, 1H), 2.03 (s, 3H), 1.64 (s, 3H), 1.37 (d, J=6.5 Hz, 3H), 1.14 (d, J=6.4 Hz, 3H) ppm; $^{13}$C NMR (151 MHz, CDCl$_3$) δ 170.6, 164.9, 142.5, 139.2, 134.4, 123.2, 122.5, 117.3, 77.5, 72.2, 69.1, 46.1, 36.9, 21.4, 20.2, 18.9, 17.2 ppm; HRMS (ESI-TOF) calcd for C$_{17}$H$_{25}$NO$_4$Na$^+$ [M+Na]$^+$ 330.1676, found 330.1685.

(2S,3Z)-5-(1{(2R,3R,6S)-2,5-Dimethyl-6-[(2E)-3-(4,4,5,5-tetramethyl-1,3,2-dioxaborolan-2-yl)but-2-en-1-yl]-3,6-dihydro-2H-pyran-3-yl}amino)-5-oxopent-3-en-2-yl acetate and (2S,3Z)-5-({(2R,3R,6S)-2,5-Dimethyl-6-[2Z]-3-(4,4,5,5-tetramethyl-1,3,2-dioxaborolan-2-yl)but-2-en-1-yl]-3,6-dihydro-2H-pyran-3-yl}amino)-5-oxopent-3-en-2-yl acetate (50 and 51)

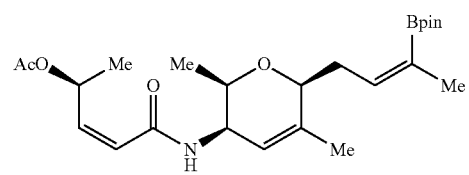

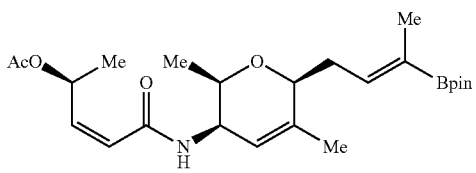

To a stirred solution of amide 49 (26 mg, 84 μmol, 1.0 equiv) in 1,2-dichloroethane (3.0 mL) at 25° C. was added isopropenylboronic acid pinacol ester (0.09 mL, 0.84 mmol, 10 equiv) followed by Grubbs II catalyst (8 mg, 0.01 mmol, 0.1 equiv), and the reaction mixture was heated to 80° C. After stirring for 2 h, the reaction mixture was allowed to cool to 25° C., and the solvent was removed in vacuo. The obtained residue was purified by flash column chromatography (silica gel, 10→30% ethyl acetate in hexanes) to afford pure (E) boronate 50 (2.5 mg, 5.5 μmol, 7%) and (Z) boronate 51 (13 mg, 29 μmol, 35%) as colorless oils. 50: $R_f$=0.50 (silica gel, 30% ethyl acetate in hexanes); $[\alpha]_D^{22}$=−109.4 (c=0.25, $CH_2Cl_2$); FT-IR (neat) $v_{max}$=3319, 2977, 2933, 2862, 1739, 1670, 1635, 1509, 1370, 1242, 1102, 1048, 862 $cm^{-1}$; $^1$H NMR (600 MHz, $CDCl_3$) δ 6.20-6.14 (m, 2H), 5.98 (d, J=9.5 Hz, 1H), 5.85 (dd, J=11.6, 8.0 Hz, 1H), 5.74 (dd, J=11.6, 1.2 Hz, 1H), 5.65 (dq, J=6.2, 0.8 Hz, 1H), 4.28 (dd, J=8.0, 7.1 Hz, 1H), 4.07 (m, 1H), 3.71 (qd, J=6.4, 2.4 Hz, 1H), 2.94-2.82 (m, 1H), 2.54-2.45 (m, 1H), 2.03 (s, 3H), 1.79 (s, 3H), 1.64 (s, 3H), 1.39 (d, J=6.6 Hz, 3H), 1.27 (s, 12H), 1.15 (d, J=6.4 Hz, 3H) ppm; $^{13}$C NMR (151 MHz, $CDCl_3$) δ 142.8, 142.2, 139.9, 123.1, 122.1, 83.1, 78.5, 77.3, 77.0, 72.2, 69.1, 46.2, 34.0, 25.1, 25.0, 22.7, 21.4, 20.2, 18.9, 17.3 ppm; HRMS (ESI-TOF) calcd for $C_{24}H_{38}BNO_6Na^+$ [M+Na]$^+$ 469.2721, found 469.2717. 51: $R_f$=0.40 (silica gel, 30% ethyl acetate in hexanes); $[\alpha]_D^{25}$=−146.0 (c=1.0, $CH_2Cl_2$); FT-IR (neat) $v_{max}$=3344, 2982, 2921, 2851, 1723, 1670, 1525, 1372, 1244, 1050 $cm^{-1}$; $^1$H NMR (600 MHz, $CDCl_3$) δ 6.27 (ddt, J=6.7, 4.8, 1.7 Hz, 1H), 6.25-6.17 (m, 1H), 5.83 (d, J=9.6 Hz, 1H), 5.80 (ddd, J=11.6, 7.8, 1.3 Hz, 1H), 5.68 (dd, J=11.6, 1.3 Hz, 1H), 5.62 (dt, J=6.2, 1.6 Hz, 1H), 4.26-4.19 (m, 1H), 4.17-4.10 (m, 1H), 3.65 (qd, J=6.4, 2.1 Hz, 1H), 2.54-2.43 (m, 1H), 2.36-2.28 (m, 1H), 1.96 (d, J=1.5 Hz, 3H), 1.64 (t, J=1.4 Hz, 3H), 1.56 (t, J=1.2 Hz, 3H), 1.32 (dd, J=6.5, 1.5 Hz, 3H), 1.19 (s, 12H), 1.07 (dd, J=6.5, 1.5 Hz, 3H) ppm; $^{13}$C NMR (151 MHz, $CDCl_3$) δ 170.4, 164.8, 143.5, 141.1, 139.3, 122.9, 122.5, 83.4, 72.2, 69.0, 46.1, 31.8, 25.00, 24.95, 21.4, 20.2, 18.9, 17.3, 14.5 ppm; HRMS (ESI-TOF) calcd for $C_{24}H_{38}BNO_6Na^+$ [M+Na]$^+$ 470.2689, found 470.2706.

Methyl [(3R,5S,7R,8R)-7-{(1E,3E)-5-[2S,5R,6R)-5-{[(2Z,4S)-4-acetoxypent-2-enoyl]amino}-3,6-dimethyl-5,6-dihydro-2H-pyran-2-yl]-3-methylpenta-1,3-dien-1-yl}-8-hydroxy-1,6-dioxaspiro[2.5]-oct-5-yl]acetate (32)

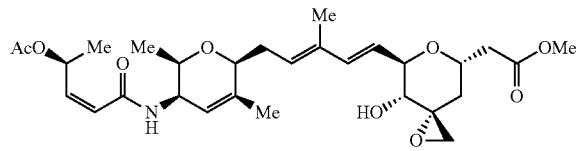

To a stirred solution of epoxide 6 (6.0 mg, 17 μmol, 1.4 equiv) and boronate 51 (6.0 mg, 13 μmol, 1.0 equiv) in rigorously degassed (freeze-pump-thaw technique×3) THF: $H_2O$ (1.0 mL, 3:1, v/v) at 25° C. was added Pd(dppf) $Cl_2.CH_2Cl_2$ (0.7 mg, 0.85 μmol, 0.1 equiv) followed by thallium(I) carbonate (30 mg, 65 μmol, 5.0 equiv). After stirring for 3 h, the reaction mixture was filtered through a layer of Celite, rinsed thoroughly with ethyl acetate (10 mL), and concentrated in vacuo. The obtained residue was purified by flash column chromatography (silica gel, 10→80% ethyl acetate in hexanes), and further purified by preparative thin layer chromatography (silica gel, 40% diethyl ether in dichloromethane) to afford pure thailanstatin analogue 32 (3.4 mg, 6.4 μmol, 48%) as a colorless oil. 32: $R_f$=0.40 (silica gel, 40% diethyl ether in dichloromethane); $[\alpha]_D^{22}$=−37.3 (c=0.42, $CH_2Cl_2$); FT-IR (neat) $v_{max}$=3378, 2974, 2934, 1736, 1667, 1638, 1520, 1439, 1370, 1332, 1317, 1244, 1169, 1116, 1057, 1009, 972, 933, 898, 856, 814, 785, 720 $cm^{-1}$; $^1$H NMR (600 MHz, $CDCl_3$) δ 6.40 (d, J=15.7 Hz, 1H), 6.18 (tt, J=7.3, 5.7 Hz, 1H), 5.95 (d, J=9.6 Hz, 1H), 5.84 (dd, J=11.6, 8.0 Hz, 1H), 5.71 (dd, J=11.6, 1.2 Hz, 1H), 5.67 (dt, J=6.2, 1.6 Hz, 1H), 5.64 (dd, J=15.8, 6.2 Hz, 1H), 5.59 (t, J=7.1 Hz, 1H), 4.49 (td, J=6.6, 6.1, 2.5 Hz, 1H), 4.33-4.27 (m, 1H), 4.20 (t, J=6.8 Hz, 1H), 4.14 (d, J=6.0 Hz, 1H), 3.69 (s, 3H), 3.52 (d, J=7.3 Hz, 1H), 2.98 (d, J=4.6 Hz, 1H), 2.92 (dd, J=15.4, 7.8 Hz, 1H), 2.70 (dd, J=15.4, 6.6 Hz, 1H), 2.67-2.57 (m, 2H), 2.38 (dt, J=15.8, 6.3 Hz, 1H), 2.15 (dd, J=14.2, 5.2 Hz, 1H), 2.04 (s, 3H), 1.79-1.74 (m, 4H), 1.64 (s, 3H), 1.38 (d, J=6.5 Hz, 3H), 1.12 (d, J=6.4 Hz, 3H) ppm; $^{13}$C NMR (151 MHz, $CDCl_3$) δ 171.6, 170.6, 164.9, 142.9, 139.2, 138.5, 135.2, 129.3, 123.2, 123.1, 122.6, 77.6, 75.8, 72.3, 69.9, 69.1, 68.9, 57.3, 52.0, 49.7, 46.1, 38.2, 34.6, 31.6, 21.4, 20.2, 18.9, 17.2, 12.9 ppm; HRMS (ESI-TOF) calcd for $C_{29}H_{41}NO_9Na^+$ [M+Na]$^+$ 570.2674, found 570.2684.

Methyl [(3R,5S,7R,8R)-7-{(1E,3Z)-5-[2S,5R,6R)-5-{[2Z,4S)-4-acetoxypent-2-enoyl]amino}-3,6-dimethyl-5,6-dihydro-2H-pyran-2-yl]-3-methylpenta-1,3-dien-1-yl}-8-hydroxy-1,6-dioxaspiro[2.5]-oct-5-yl] acetate (46)

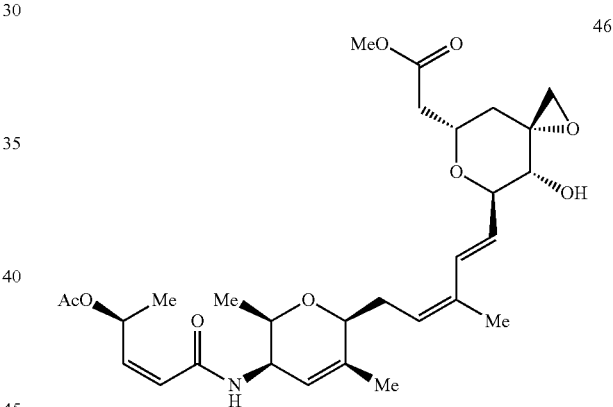

To a stirred solution of epoxide 6 (4.8 mg, 13 μmol, 1.5 equiv) and boronate 50 (4.0 mg, 9.0 μmol, 1.0 equiv) in rigorously degassed (freeze-pump-thaw technique×3) THF: $H_2O$ (1.0 mL, 3:1, v/v) at 25° C. was added Pd(dppf) $Cl_2.CH_2Cl_2$ (0.7 mg, 0.90 μmol, 0.1 equiv) followed by thallium(I) carbonate (21 mg, 45 μmol, 5.0 equiv). After stirring for 3 h, the reaction mixture was filtered through a layer of Celite, rinsed thoroughly with ethyl acetate (10 mL), and concentrated in vacuo. The obtained residue was purified by flash column chromatography (silica gel, 10→80% ethyl acetate in hexanes), and further purified by preparative thin layer chromatography (silica gel, 40% diethyl ether in dichloromethane) to afford pure thailanstatin analogue 46 (2.5 mg, 4.6 μmol, 51%) as a colorless oil. 46: $R_f$=0.30 (silica gel, 30% diethyl ether in dichloromethane); $[\alpha]_D^{22}$=−37.3 (c=0.42, $CH_2Cl_2$); FT-IR (neat) $v_{max}$=3378, 2974, 2934, 1736, 1667, 1638, 1520, 1439, 1370, 1332, 1317, 1244, 1169, 1116, 1057, 1009, 972, 933, 898, 856, 814, 785, 720 $cm^{-1}$; $^1$H NMR (600 MHz, $CDCl_3$) δ 6.78 (d, J=15.8 Hz, 1H), 6.14 (dqd, J=7.7, 6.5, 1.2 Hz, 1H), 6.03 (d, J=9.5 Hz, 1H), 5.85 (dd, J=11.6, 8.1 Hz, 1H), 5.76-5.73 (m, 1H), 5.71 (dd, J=3.7, 2.5 Hz, 1H), 5.68 (dt, J=6.2, 1.7 Hz, 1H), 5.48 (t, J=7.1 Hz, 1H), 4.51 (dq, J=7.2, 4.8 Hz, 1H), 4.32-4.28 (m, 1H), 4.13 (dd, J=6.4, 3.6 Hz, 1H), 3.75-3.67 (m, 5H), 3.52 (d, J=7.1 Hz, 1H), 2.98 (d, J=4.6 Hz, 1H), 2.92 (dd, J=15.5, 7.9 Hz, 1H), 2.74-2.63 (m, 3H), 2.42 (dt, J=14.8, 6.7 Hz, 1H), 2.16-2.11 (m, 1H), 2.04 (s, 3H), 1.85 (d, J=1.4 Hz, 3H), 1.80-1.76 (m, 1H), 1.64 (d, J=1.4 Hz, 3H), 1.38 (d, J=6.5 Hz, 3H), 1.13 (d, J=6.3 Hz, 3H) ppm; $^{13}$C NMR (151 MHz, CDCl$_3$) δ 171.5, 170.7, 165.0, 142.6, 139.3, 133.3, 131.0, 127.1, 126.0, 123.2, 122.5, 77.7, 76.0, 72.3, 69.9, 69.1, 68.8, 57.3, 52.0, 49.9, 46.1, 38.2, 34.6, 30.8, 21.4, 20.6, 20.2, 18.9, 17.2 ppm; HRMS (ESI-TOF) calcd for C$_{29}$H$_{41}$NO$_9$Na$^+$ [M+Na]$^+$ 570.2674, found 570.2670.

2-[(2R,3R,6R)-6-Allyl-2,5-dimethyl-3,6-dihydro-2H-pyran-3-yl]-1H-isoindole-1,3(2H)-dione (52)

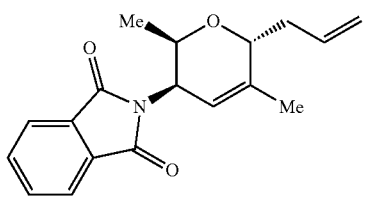

To a stirred suspension of trimethylphosphonium bromide (157 mg, 0.442 mmol. 1.7 equiv) in tetrahydrofuran (2.0 mL) at 0° C. was added potassium tert-butoxide (38 mg, 0.34 mmol, 1.3 equiv). After stirring for 1 h, a solution of the aldehyde 11-epi-24 (80 mg, 0.26 mmol, 1.0 equiv) in tetrahydrofuran (2.0 mL) was added dropwise, and stirring was continued for an additional 1 h at the same temperature. Then the reaction mixture was quenched with a saturated aqueous solution of ammonium chloride (5 mL), and the two phases were separated. The aqueous layer was extracted with ethyl acetate (3×10 mL), and the combined organic layers were washed with brine (10 mL), dried over anhydrous sodium sulfate, and concentrated in vacuo. The obtained residue was purified by flash column chromatography (silica gel, 5→15% ethyl acetate in hexanes) to afford olefin 52 (45 mg, 0.15 mmol, 57%) as a colorless oil. 52: R$_f$=0.50 (silica gel, 15% ethyl acetate in hexanes); [α]$_D^{22}$=−212.0 (c=1.0, CH$_2$Cl$_2$); FT-IR (neat) ν$_{max}$=2976, 2918, 1770, 1713, 1642, 1386, 1354, 1124, 1034, 902, 720 cm$^{-1}$; $^1$H NMR (600 MHz, CDCl$_3$) δ 7.81 (dd, J=5.4, 3.1 Hz, 2H), 7.70 (dd, J=5.5, 3.0 Hz, 2H), 5.96 (ddt, J=17.1, 10.2, 6.9 Hz, 1H), 5.51 (dt, J=5.3, 1.6 Hz, 1H), 5.21-5.02 (m, 2H), 4.60 (dq, J=3.7, 1.8 Hz, 1H), 4.37-4.23 (m, 1H), 4.17-4.06 (m, 1H), 2.56-2.37 (m, 2H), 1.78 (s, 3H), 1.07 (d, J=6.4 Hz, 3H) ppm; $^{13}$C NMR (151 MHz, CDCl$_3$) δ 168.6, 141.0, 135.5, 134.0, 132.0, 123.3, 116.8, 116.6, 75.8, 66.2, 48.6, 35.8, 19.90, 16.8 ppm; HRMS (ESI-TOF) calcd for C$_{18}$H$_{19}$NO$_3$Na$^+$ [M+Na]$^+$ 320.1257, found 320.1269.

(2S,3Z)-5-{[2R,3R,6R)-6-Allyl-2,5-dimethyl-3,6-dihydro-2H-pyran-3-yl]amino}-5-oxopent-3-en-2-yl acetate (53)

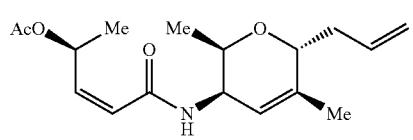

To a stirred solution of olefin 52 (40 mg, 0.13 mmol, 1.0 equiv) in ethanol (2.0 mL) at 25° C. was added ethylenediamine (0.02 mL, 0.26 mmol, 2.0 equiv), and the reaction mixture was heated to 80° C. After stirring for 15 h, the reaction mixture was allowed to cool to 25° C., and the solvent was removed in vacuo. The obtained crude amine was redissolved in dichloromethane (3 mL) with stirring at 25° C., and N-methylmorpholine (0.04 mL, 0.39 mmol, 3.0 equiv), N-(3-dimethylaminopropyl)-N'-ethylcarbodiimide hydrochloride (61 mg, 0.39 mmol, 3.0 equiv), and a solution of carboxylic acid 8 (32 mg, 0.20 mmol, 1.5 equiv) in dichloromethane (2.0 mL) were added successively. After stirring for 2 h, the reaction mixture was quenched with a saturated aqueous solution of ammonium chloride (10 mL), and the two phases were separated. The aqueous layer was extracted with ethyl acetate (3×10 mL), and the combined organic layers were washed with brine (10 mL), dried over anhydrous sodium sulfate, and concentrated in vacuo. The obtained residue was purified by flash column chromatography (silica gel, 10→30% ethyl acetate in hexanes) to afford pure amide 53 (28 mg, 0.090 mmol, 69%) as a colorless oil. 53: R$_f$=0.50 (silica gel, 30% ethyl acetate in hexanes); [α]$_D^{22}$=−232.0 (c=1.0, CH$_2$Cl$_2$); FT-IR (neat) ν$_{max}$=3311, 2977, 2934, 2881, 1738, 1671, 1640, 1521, 1370, 1242, 1095, 1050, 1016, 904, 814 cm$^{-1}$; $^1$H NMR (600 MHz, CDCl$_3$) δ 6.16 (dqd, J=7.9, 6.5, 1.2 Hz, 1H), 6.11 (d, J=10.4 Hz, 1H), 5.91 (dddd, J=17.1, 10.2, 6.9, 3.4 Hz, 1H), 5.84 (ddd, J=11.6, 8.0, 1.5 Hz, 1H), 5.73 (dd, J=11.6, 1.3 Hz, 1H), 5.58 (ddt, J=5.8, 3.1, 1.5 Hz, 1H), 5.15-5.06 (m, 2H), 4.30 (dddd, J=9.8, 5.7, 2.7, 1.3 Hz, 1H), 4.02 (dd, J=10.0, 3.6 Hz, 1H), 3.95 (qd, J=6.3, 2.5 Hz, 1H), 2.48-2.38 (m, 1H), 2.38-2.29 (m, 1H), 2.03 (s, 3H), 1.70-1.65 (m, 3H), 1.37 (d, J=6.5 Hz, 3H), 1.12 (d, J=6.4 Hz, 3H) ppm; $^{13}$C NMR (151 MHz, CDCl$_3$) δ 170.6, 164.9, 142.9, 135.4, 123.0, 120.9, 117.0, 76.6, 76.6, 69.0, 66.0, 45.9, 35.5, 21.4, 20.2, 19.8, 16.9 ppm; HRMS (ESI-TOF) calcd for C$_{17}$H$_{25}$NO$_4$Na$^+$ [M+Na]$^+$ 330.1676, found 330.1685.

(2S,3Z)-5-({(2R,3R,6R)-2,5-Dimethyl-6-[2Z)-3-(4,4,5,5-tetramethyl-1,3,2-dioxaborolan-2-yl)but-2-en-1-yl]-3,6-dihydro-2H-pyran-3-yl}amino)-5-oxopent-3-en-2-yl acetate (54)

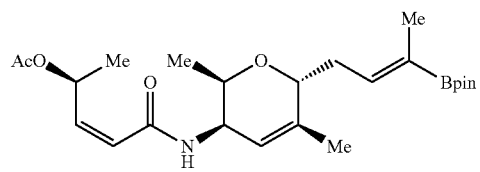

To a stirred solution of amide 53 (10 mg, 0.032 mmol, 1.0 equiv) in dichloroethane (1.0 mL) at 25° C. was added isopropenylboronic acid pinacol ester (0.06 mL, 0.32 mmol, 10 equiv) followed by Grubbs II generation catalyst (3.0 mg, 3.0 μmol, 0.1 equiv), and the reaction mixture was heated to 80° C. After stirring for 2 h, the reaction mixture was allowed to cool to 25° C., and the solvent was removed in vacuo. The obtained residue was purified by flash column chromatography (silica gel, 10→30% ethyl acetate in hexanes) to afford pure boronate 54 (5.0 mg, 11 μmol, 35%) as a colorless oil. 54: R$_f$=0.30 (silica gel, 30% ethyl acetate in hexanes); [α]$_D^{22}$=−109.4 (c=0.5, CH$_2$Cl$_2$); FT-IR (neat) ν$_{max}$=3312, 2978, 2934, 1739, 1671, 1636, 1520, 1370, 1305, 1242, 1215, 1120, 1050, 859 cm$^{-1}$; $^1$H NMR (600 MHz, CD$_2$Cl$_2$) δ 6.51-6.41 (m, 1H), 6.20-6.06 (m, 2H), 5.84 (dd, J=11.6, 8.1 Hz, 1H), 5.72 (dd, J=11.7, 1.2 Hz, 1H), 5.59 (dt, J=5.7, 1.6 Hz, 1H), 4.30 (t, J=7.3 Hz, 1H), 4.07 (dt, J=9.5, 2.5 Hz, 1H), 3.93 (dd, J=6.4, 2.6 Hz, 1H), 2.52 (ddd, J=16.6, 9.9, 7.7 Hz, 1H), 2.38 (ddd, J=15.8, 7.1, 3.4 Hz, 1H), 2.03 (s, 3H), 1.71 (d, J=1.6 Hz, 3H), 1.68 (s, 3H), 1.38 (d, J=6.5 Hz, 3H), 1.26 (s, 12H), 1.12 (d, J=6.4 Hz, 3H) ppm; $^{13}$C NMR (151 MHz, CD$_2$Cl$_2$) δ 170.6, 164.9, 142.7, 142.4, 139.5, 123.1, 120.9, 83.4, 69.0, 66.1, 46.0, 30.2, 25.0, 24.9, 24.97, 21.4, 20.2, 19.9, 17.1, 14.2 ppm; HRMS (ESI-TOF) calcd for C$_{24}$H$_{38}$BNO$_6$Na$^+$ [M+Na]$^+$ 469.2721, found 469.2717.

Methyl [3R,5S,7R,8R)-7-{(1E,3E)-5-[(2R,5R,6R)-5-{[2Z,4S)-4-acetoxypent-2-enoyl]amino}-3,6-dimethyl-5,6-dihydro-2H-pyran-2-yl]-3-methylpenta-1,3-dien-1-yl}-8-hydroxy-1,6-dioxaspiro[2.5]-oct-5-yl]acetate (30)

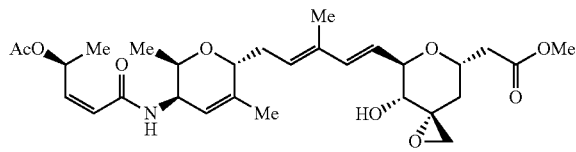

To a stirred solution of epoxide 6 (6.0 mg, 17 μmol, 1.4 equiv) and boronate 54 (5.0 mg, 11 μmol, 1.0 equiv) in rigorously degassed (freeze-pump-thaw technique×3) THF:H$_2$O (1.0 mL, 3:1, v/v) at 25° C. was added Pd(dppf)Cl$_2$·CH$_2$Cl$_2$ (0.9 mg, 1.1 μmol, 0.1 equiv), followed by thallium(I) carbonate (31 mg, 65 μmol, 5.0 equiv). After stirring for 3 h, the reaction mixture was filtered through a layer of Celite, rinsed thoroughly with ethyl acetate (10 mL), and concentrated in vacuo. The obtained residue was purified by flash column chromatography (silica gel, 10→80% ethyl acetate in hexanes), and further purified by preparative thin layer chromatography (silica gel, 40% diethyl ether in CH$_2$Cl$_2$) to afford pure methyl ester 30 (3.5 mg, 6.4 μmol, 51%) as a colorless oil. 3: R$_f$=0.40 (silica gel, 40% diethyl ether in dichloromethane); [α]$_D^{22}$=−37.0 (c=0.1, CH$_2$Cl$_2$); FT-IR (neat) ν$_{max}$=3378, 2974, 2934, 1736, 1667, 1638, 1520, 1439, 1370, 1332, 1317, 1244, 1169, 1116, 1057, 1009, 972, 933, 898, 856, 814, 785, 720 cm$^{-1}$; $^1$H NMR (600 MHz, CDCl$_3$) δ 6.40 (d, J=15.8 Hz, 1H), 6.16-6.06 (m, 2H), 5.84 (dd, J=11.6, 8.1 Hz, 1H), 5.72 (dd, J=11.7, 1.2 Hz, 1H), 5.69-5.59 (m, 3H), 4.50 (ddd, J=11.5, 8.6, 4.9 Hz, 1H), 4.31 (d, J=8.2 Hz, 1H), 4.23 (t, J=6.7 Hz, 1H), 4.06-4.00 (m, 1H), 3.92 (qd, J=6.4, 2.6 Hz, 1H), 3.70 (s, 3H), 3.52 (d, J=7.1 Hz, 1H), 2.98 (d, J=4.6 Hz, 1H), 2.93 (dd, J=15.4, 7.9 Hz, 1H), 2.69 (dd, J=15.5, 6.5 Hz, 1H), 2.65 (d, J=4.6 Hz, 1H), 2.56-2.47 (m, 1H), 2.43 (ddd, J=15.7, 7.4, 3.6 Hz, 1H), 2.12 (dd, J=14.2, 4.9 Hz, 1H), 2.03 (s, 3H), 1.80-1.76 (m, 4H), 1.69 (s, 3H), 1.38 (d, J=6.5 Hz, 3H), 1.11 (d, J=6.3 Hz, 3H) ppm; $^{13}$C NMR (151 MHz, CDCl$_3$) δ 171.6, 170.7, 165.0, 142.7, 139.3, 138.6, 134.5, 130.4, 123.1, 123.1, 121.1, 76.8, 76.0, 70.0, 69.0, 68.8, 66.2, 57.4, 52.0, 49.9, 45.9, 38.3, 34.6, 30.1, 21.4, 20.2, 19.9, 17.0, 12.7 ppm; HRMS (ESI-TOF) calcd for C$_{29}$H$_{41}$NO$_9$Na$^+$ [M+Na]$^+$ 570.2674, found 570.2691.

2-[2R,3R,6S)-6-(1,3-Dioxolan-2-ylmethyl)-2,5-dimethyl-3,6-dihydro-2H-pyran-3-yl]-1H-isoindole-1,3(2H-dione (55)

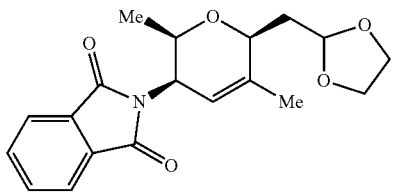

To a stirred solution of aldehyde 24 (100 mg, 0.334 mmol, 1.0 equiv) in benzene (5.0 mL) at 25° C. was added ethylene glycol (41 mg, 0.67 mmol, 2.0 equiv) followed by camphorsulfonic acid (8.0 mg, 33 μmol, 0.1 equiv), and the reaction mixture was heated to 80° C. After stirring for 16 h, the reaction mixture was allowed to cool to 25° C., and was quenched with a saturated aqueous solution of sodium bicarbonate (5 mL). The two phases were separated, and the aqueous layer was extracted with ethyl acetate (3×5 mL). The combined organic layers were washed with brine (10 mL), dried over anhydrous sodium sulfate, and concentrated in vacuo. The obtained residue was purified by flash column chromatography (silica gel, 10→30% ethyl acetate in hexanes) to afford pure acetal 55 (111 mg, 0.323 mmol, 97%) as a white foam. 55: R$_f$=0.40 (silica gel, 30% ethyl acetate in hexanes); [α]$_D^{22}$=−156.6 (c=1.5, CH$_2$Cl$_2$); FT-IR (film) ν$_{max}$=2975, 2940, 2886, 1770, 1713, 1467, 1386, 1344, 1327, 1125, 1040, 721 cm$^{-1}$; $^1$H NMR (600 MHz, CD$_2$Cl$_2$) δ 7.81 (dd, J=5.4, 3.1 Hz, 2H), 7.70 (dd, J=5.5, 3.0 Hz, 2H), 5.52 (dt, J=5.9, 1.7 Hz, 1H), 5.24 (dd, J=7.8, 2.5 Hz, 1H), 4.54 (dtd, J=6.1, 3.1, 1.5 Hz, 1H), 4.32 (dd, J=10.7, 2.6 Hz, 1H), 4.07-3.96 (m, 2H), 3.95-3.85 (m, 3H), 2.35 (ddd, J=13.4, 10.6, 2.6 Hz, 1H), 1.99 (ddd, J=13.8, 7.8, 2.5 Hz, 1H), 1.76 (d, J=1.4 Hz, 3H), 1.08 (d, J=6.4 Hz, 3H) ppm; $^{13}$C NMR (151 MHz, CD$_2$Cl$_2$) δ 168.6, 141.7, 134.0, 132.0, 123.2, 116.9, 102.5, 75.0, 71.6, 65.0, 64.8, 48.6, 36.7, 19.2, 17.2 ppm; HRMS (ESI-TOF) calcd for C$_{19}$H$_{21}$NO$_5$Na$^+$ [M+Na]$^+$ 366.1312, found 366.1317.

2-[2R,3R,5R,6S)-6-(1,3-Dioxolan-2-ylmethyl)-2,5-dimethyltetrahydro-2H-pyran-3-yl]-1H-iso-indole-1,3(2H)-dione (56)

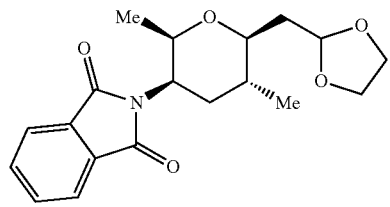

To a stirred solution of acetal 55 (73.0 mg, 0.213 mmol, 1.0 equiv) in dichloromethane (5.0 mL) at 25° C. was added Ir(py)(PCy$_3$)(COD)BARF (16.0 mg, 0.106 mmol, 0.05 equiv), and an atmosphere of hydrogen (1 atm) was introduced. After stirring for 15 h, the hydrogen atmosphere was removed, and the reaction mixture was concentrated in vacuo. The obtained residue was purified by flash column chromatography (silica gel, 10→30% ethyl acetate in hexanes) to afford pure tetrahydropyran 56 (59 mg, 0.17 mmol, 81%) as a colorless oil 56: $R_f$=0.40 (silica gel, 30% ethyl acetate in hexanes); $[α]_D^{22}$=+7.0 (c=1.0, $CH_2Cl_2$); FT-IR (neat) $ν_{max}$=2972, 2933, 2887, 1772, 1710, 1371, 1355, 1329, 1138, 1093, 1066, 1016, 721 $cm^{-1}$; $^1H$ NMR (600 MHz, $CD_2Cl_2$) δ 7.83 (dd, J=5.4, 3.0 Hz, 2H), 7.71 (dd, J=5.4, 3.0 Hz, 2H), 5.19 (dd, J=7.7, 2.7 Hz, 1H), 4.40 (ddd, J=6.7, 3.4, 1.6 Hz, 1H), 4.05-3.93 (m, 2H), 3.91-3.84 (m, 2H), 3.80 (qd, J=6.4, 3.4 Hz, 1H), 3.29 (td, J=10.0, 2.2 Hz, 1H), 2.54-2.41 (m, 1H), 2.10-2.03 (m, 1H), 2.00-1.88 (m, 2H), 1.75 (ddd, J=15.0, 12.4, 6.6 Hz, 1H), 1.04 (d, J=6.4 Hz, 3H), 0.84 (d, J=6.6 Hz, 3H) ppm; $^{13}C$ NMR (151 MHz, $CD_2Cl_2$) δ 169.5, 134.5, 132.3, 123.8, 102.9, 81.2, 74.2, 65.4, 65.2, 50.0, 38.5, 37.3, 31.0, 18.5, 18.2 ppm; HRMS (ESI-TOF) calcd for $C_{19}H_{23}NO_5Na^+$ $[M+Na]^+$ 368.1468, found 368.1472.

2-[(2R,3R,5R,6S)-6-Allyl-2,5-dimethyltetrahydro-2H-pyran-3-yl]-1H-isoindole-1,3(2H)-dione (57)

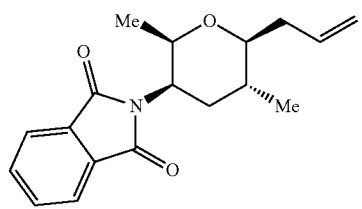

57

To a stirred solution of tetrahydropyran 56 (58.0 mg, 0.168 mmol, 1.0 equiv) in acetone (2.0 mL) at 25° C. was added aqueous 1N HCl (0.84 mL, 0.84 mmol, 5.0 equiv). After stirring for 15 h, the solvent was removed in vacuo, and the obtained crude aldehyde was used directly in the following step. To a stirred suspension of methyl triphenylphosphonium bromide (120 mg, 0.336 mmol, 2.0 equiv) in tetrahydrofuran (2.0 mL) at 0° C. was added potassium tert-butoxide (32 mg, 0.286 mmol, 1.7 equiv). After stirring for 1 h, a solution of the crude aldehyde (ca 58.0 mg, 0.168 mmol, 1.0 equiv) in tetrahydrofuran (3.0 mL) was added dropwise, and stirring was continued for an additional 1 h at the same temperature. Then the reaction mixture was quenched with a saturated aqueous solution of ammonium chloride (10 mL), and the two phases were separated. The aqueous layer was extracted with ethyl acetate (3×10 mL), and the combined organic layers were washed with brine (10 mL), dried over anhydrous sodium sulfate, and concentrated in vacuo. The obtained residue was purified by flash column chromatography (silica gel, 5→15% ethyl acetate in hexanes) to afford olefin 57 (40.0 mg, 0.133 mmol, 76%) as a colorless oil. 57: $R_f$=0.60 (silica gel, 20% ethyl acetate in hexanes); $[α]_D^{22}$=+35.3 (c=1.0, $CH_2Cl_2$); FT-IR (neat) $ν_{max}$=2977, 2937, 2917, 2855, 1711, 1712, 1639, 1612, 1386, 1349, 1325, 1122, 1043, 912, 897, 720 $cm^{-1}$; $^1H$ NMR (600 MHz, $CDCl_3$) δ 7.82 (dd, J=5.4, 3.1 Hz, 2H), 7.70 (dd, J=5.5, 3.0 Hz, 2H), 6.17 (ddt, J=17.0, 10.3, 6.6 Hz, 1H), 5.51 (d, J=5.8 Hz, 1H), 5.16 (dd, J=17.2, 1.9 Hz, 1H), 5.13-5.08 (m, 1H), 4.56 (ddq, J=6.4, 3.3, 1.6 Hz, 1H), 4.17-4.10 (m, 1H), 3.89 (qd, J=6.4, 3.5 Hz, 1H), 3.12 (ddd, J=10.3, 7.8, 2.9 Hz, 1H), 2.60 (ddd, J=7.1, 4.4, 1.5 Hz, 2H), 2.42-2.37 (m, 1H), 1.97 (d, J=4.7 Hz, 1H), 1.95 (d, J=4.7 Hz, 1H), 1.76 (s, 3H), 1.10 (d, J=6.4 Hz, 3H) ppm; $^{13}C$ NMR (151 MHz, $CDCl_3$) δ 168.6, 141.9, 136.2, 134.0, 132.0, 123.3, 117.2, 116.2, 78.0, 71.9, 48.8, 36.8, 19.4, 17.2 ppm; HRMS (ESI-TOF) calcd for $C_{18}H_{21}NO_3Na^+$ $[M+Na]^+$ 322.1414, found 322.1414.

(2S,3Z)-5-{[(2R,3R,5R,6S)-6-Allyl-2,5-dimethyltetrahydro-2H-pyran-3-yl]amino}-5-oxopent-3-en-2-yl acetate (58)

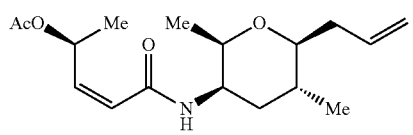

58

To a stirred solution of olefin 57 (206 mg, 0.688 mmol, 1.0 equiv) in ethanol (9.0 mL) at 25° C. was added ethylenediamine (0.09 mL, 1.4 mmol, 2.0 equiv), and the reaction mixture was heated to 80° C. After stirring for 15 h, the reaction mixture was allowed to cool to 25° C., and the solvent was removed in vacuo. The obtained crude amine was redissolved in dichloromethane (10 mL) with stirring at 25° C., and N-methylmorpholine (0.31 mL, 2.8 mmol, 6.0 equiv), N-(3-dimethylaminopropyl)-N'-ethylcarbodiimide hydrochloride (272 mg, 1.74 mmol, 3.0 equiv), and a solution of carboxylic acid 8 (223 mg, 1.74 mmol, 3.0 equiv) in dichloromethane (4.0 mL) were added successively. After stirring for 2 h, the reaction mixture was quenched with a saturated aqueous solution of ammonium chloride (10 mL), and the two phases were separated. The aqueous layer was extracted with ethyl acetate (3×10 mL), and the combined organic layers were washed with brine (10 mL), dried over anhydrous sodium sulfate, and concentrated in vacuo. The obtained residue was purified by flash column chromatography (silica gel, 10→30% ethyl acetate in hexanes) to afford pure amide 58 (108 mg, 0.35 mmol, 51%) as a colorless oil. 58: $R_f$=0.50 (silica gel, 30% ethyl acetate in hexanes); $[α]_D^{22}$=-65.3 (c=1.0, $CH_2Cl_2$); FT-IR (neat) $ν_{max}$=3314, 2977, 2933, 2851, 1739, 1669, 1634, 1525, 1369, 1242, 1087, 1048, 1017, 814 $cm^{-1}$; $^1H$ NMR (600 MHz, $CDCl_3$) δ 6.53 (d, J=9.1 Hz, 1H), 6.14-6.04 (m, 1H), 5.93 (ddt, J=17.1, 10.2, 6.9 Hz, 1H), 5.87-5.72 (m, 2H), 5.07 (dq, J=17.2, 1.7 Hz, 1H), 5.03 (ddt, J=10.2, 2.3, 1.3 Hz, 1H), 4.00 (ddt, J=10.9, 5.0, 2.2 Hz, 1H), 3.59 (qd, J=6.4, 1.8 Hz, 1H), 3.07 (ddd, J=10.2, 7.5, 3.1 Hz, 1H), 2.41 (dddd, J=12.7, 6.4, 3.1, 1.5 Hz, 1H), 2.23-2.14 (m, 1H), 2.04 (s, 3H), 1.95 (ddd, J=13.7, 4.0, 3.0 Hz, 1H), 1.56-1.49 (m, 1H), 1.44-1.40 (m, 1H), 1.38 (d, J=6.5 Hz, 3H), 1.12 (d, J=6.4 Hz, 3H), 0.83 (d, J=6.5 Hz, 3H) ppm; $^{13}C$ NMR (151 MHz, $CDCl_3$) δ 170.7, 165.2, 141.8, 135.4, 123.6, 116.4, 83.8, 75.0, 69.2, 48.2, 38.2, 37.5, 29.7, 21.4, 20.2, 18.0, 17.4 ppm; HRMS (ESI-TOF) calcd for $C_{17}H_{27}NO_4Na^+$ $[M+Na]^+$ 332.1832, found 332.1839.

(2S,3Z)-5-({(2R,3R,5R,6S)-2,5-Dimethyl-6-[(2Z)-3-(4,4,5,5-tetramethyl-1,3,2-dioxaborolan-2-yl)but-2-en-1-yl]tetrahydro-2H-pyran-3-yl}amino)-5-oxopent-3-en-2-yl acetate and (2S,3Z)-5-({(2R,3R,5R,6S)-2,5-Dimethyl-6-[2E)-3-(4,4,5,5-tetramethyl-1,3,2-dioxaborolan-2-yl)but-2-en-1-yl]tetrahydro-2H-pyran-3-yl}amino)-5-oxopent-3-en-2-yl acetate (60 and 61)

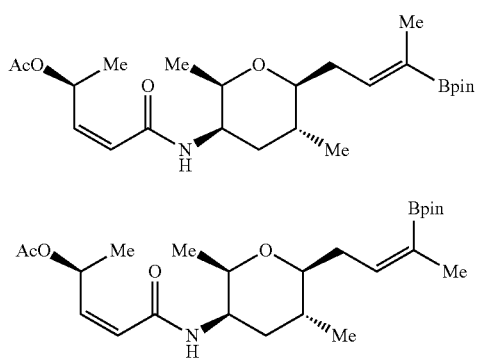

To a stirred solution of amide 58 (17 mg, 55 µmol, 1.0 equiv) in dichloromethane (2.0 mL) at 25° C. was added isopropenylboronic acid pinacol ester (0.11 mL, 0.55 mmol, 10 equiv) followed by Grela's catalyst 59 (5.0 mg, 6.0 µmol, 0.1 equiv), and the reaction mixture was heated to 50° C. After stirring for 7 h, the reaction mixture was allowed to cool to 25° C., and the solvent was removed in vacuo. The obtained residue was purified by flash column chromatography (silica gel, 10→80% ethyl acetate in hexanes) to afford pure (Z) boronate 60 (13 mg, 29 µmol, 52%) and (E) boronate 61 (2.5 mg, 5.5 µmol, 10%) as colorless oils. 60: $R_f$=0.40 (silica gel, 10% diethyl ether in dichloromethane); $[\alpha]_D^{22}$=−69.6 (c=0.9, $CH_2Cl_2$); FT-IR (neat) $\nu_{max}$=3315, 2977, 2932, 2851, 1739, 1670, 1632, 1524, 1370, 1242, 1088, 1048, 859 $cm^{-1}$; $^1H$ NMR (600 MHz, $CDCl_3$) δ 6.51-6.35 (m, 2H), 6.23-6.12 (m, 1H), 5.85 (dd, J=11.5, 8.1 Hz, 1H), 5.77 (dd, J=11.7, 1.1 Hz, 1H), 3.99 (d, J=9.4 Hz, 1H), 3.59 (qd, J=6.5, 1.5 Hz, 1H), 3.13 (ddd, J=10.5, 8.1, 3.1 Hz, 1H), 2.54-2.41 (m, 1H), 2.25 (dt, J=15.6, 7.3 Hz, 1H), 2.05 (s, 3H), 1.95 (dt, J=13.7, 3.6 Hz, 1H), 1.69 (d, J=1.6 Hz, 3H), 1.55-1.50 (m, 1H), 1.39 (d, J=6.5 Hz, 3H), 1.26 (s, 12H), 1.12 (d, J=6.4 Hz, 3H), 0.84 (d, J=6.5 Hz, 3H) ppm; $^{13}C$ NMR (151 MHz, $CDCl_3$) δ 170.6, 165.1, 142.54, 142.46, 123.3, 83.7, 83.3, 75.0, 69.1, 48.2, 38.2, 32.7, 30.3, 24.99, 24.95, 21.4, 20.2, 18.1, 17.7, 14.4 ppm; HRMS (ESI-TOF) calcd for $C_{24}H_{40}BNO_6Na^+$ $[M+Na]^+$ 472.2845, found 472.2856. 61: $R_f$=0.50 (silica gel, 10% diethyl ether in dichloromethane); $[\alpha]_D^{22}$=−100.8 (c=0.25, $CH_2Cl_2$); FT-IR (neat) $\nu_{max}$=3320, 2979, 2931, 2851, 1736, 1670, 1635, 1523, 1371, 1244, 1143, 1089, 1049, 860 $cm^{-1}$; $^1H$ NMR (600 MHz, $CDCl_3$) δ 6.48 (d, J=9.0 Hz, 1H), 6.27 (t, J=7.2 Hz, 1H), 6.12 (q, J=7.0 Hz, 1H), 5.86-5.82 (m, 1H), 5.78 (d, J=11.7 Hz, 1H), 4.01-3.95 (m, 1H), 3.58 (qd, J=6.7, 2.0 Hz, 1H), 3.01 (ddt, J=12.8, 8.0, 4.0 Hz, 1H), 2.90-2.81 (m, 1H), 2.34 (dt, J=14.9, 7.5 Hz, 1H), 2.05 (s, 3H), 1.97-1.92 (m, 1H), 1.78 (d, J=1.6 Hz, 3H), 1.52-1.46 (m, 1H), 1.39 (d, J=6.3 Hz, 3H), 1.26 (s, 12H), 1.13 (d, J=6.4 Hz, 3H), 0.85 (d, J=6.6 Hz, 3H) ppm; $^{13}C$ NMR (151 MHz, $CDCl_3$) δ 170.7, 165.2, 143.7, 142.1, 123.5, 85.0, 83.0, 74.9, 69.2, 48.3, 38.3, 34.7, 30.2, 25.1, 25.0, 22.6, 21.4, 20.2, 18.1, 17.4 ppm; HRMS (ESI-TOF) calcd for $C_{24}H_{40}BNO_6Na^+$ $[M+Na]^+$ 472.2845, found 472.2847.

Methyl [(3R,5S,7R,8R)-7-{(1E,3E)-5-[(2S,3R,5R,6R)-5-{[(2Z,4S)-4-acetoxypent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetate (34)

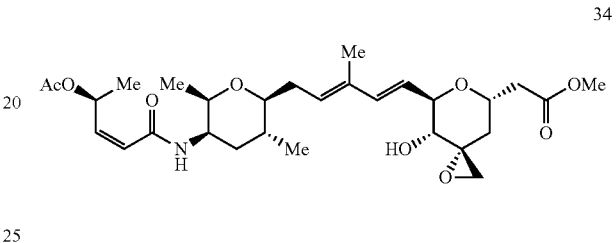

To a stirred solution of epoxide 6 (9.0 mg, 26 µmol, 1.5 equiv) and boronate 60 (8.0 mg, 18 µmol, 1.0 equiv) in rigorously degassed (freeze-pump-thaw technique×3) THF:$H_2O$ (2 mL, 3:1, v/v) at 25° C. was added Pd(dppf)$Cl_2 \cdot CH_2Cl_2$ (1.5 mg, 1.7 µmol, 0.1 equiv) followed by thallium(I) carbonate (42 mg, 90 µmol, 5.0 equiv). After stirring for 3 h, the reaction mixture was filtered through a layer of Celite, rinsed thoroughly with ethyl acetate (10 mL), and concentrated in vacuo. The obtained residue was purified by flash column chromatography (silica gel, 10→80% hexanes in ethyl acetate), and further purified by preparative thin layer chromatography (silica gel, 50% diethyl ether in dichloromethane) to afford pure methyl ester 34 (4.3 mg, 8.0 µmol, 44%) as a colorless oil. 34: $R_f$=0.40 (silica gel, 40% diethyl ether in dichloromethane); $[\alpha]_D^{22}$=−23.7 (c=0.43, $CH_2Cl_2$); FT-IR (neat) $\nu_{max}$=3367, 2926, 1735, 1671, 1664, 1632, 1523, 1439, 1371, 1244, 1081, 1050 $cm^{-1}$; $^1H$ NMR (600 MHz, $CDCl_3$) δ 6.51 (d, J=9.1 Hz, 1H), 6.39 (d, J=15.8 Hz, 1H), 6.10 (p, J=6.7 Hz, 1H), 5.85-5.78 (m, 2H), 5.70 (t, J=7.0 Hz, 1H), 5.61 (dd, J=15.8, 6.2 Hz, 1H), 4.54-4.46 (m, 1H), 4.22 (t, J=6.7 Hz, 1H), 4.05-3.97 (m, 1H), 3.70 (s, 3H), 3.62-3.57 (m, 1H), 3.52 (t, J=7.6 Hz, 1H), 3.06 (ddd, J=10.4, 7.8, 3.1 Hz, 1H), 2.99 (d, J=4.6 Hz, 1H), 2.93 (dd, J=15.4, 7.8 Hz, 1H), 2.69 (dd, J=15.4, 6.6 Hz, 1H), 2.65 (d, J=4.6 Hz, 1H), 2.51 (ddd, J=15.9, 7.3, 2.9 Hz, 1H), 2.26 (dt, J=15.4, 7.3 Hz, 1H), 2.16-2.10 (m, 1H), 2.05 (s, 3H), 1.95 (dt, J=13.7, 3.7 Hz, 1H), 1.86 (d, J=8.4 Hz, 1H), 1.80-1.74 (m, 4H), 1.53 (ddt, J=13.4, 6.5, 3.9 Hz, 1H), 1.44-1.40 (m, 1H), 1.39 (d, J=6.5 Hz, 3H), 1.12 (d, J=6.4 Hz, 3H), 0.84 (d, J=6.4 Hz, 3H) ppm; $^{13}C$ NMR (151 MHz, $CDCl_3$) δ 171.6, 170.7, 165.2, 141.9, 138.8, 134.1, 130.6, 123.5, 122.6, 84.1, 76.0, 75.1, 60.0, 69.2, 68.8, 57.4, 52.0, 49.9, 48.2, 38.3, 38.2, 34.6, 32.2, 30.2, 21.4, 20.2, 18.0, 17.6, 12.7 ppm; HRMS (ESI-TOF) calcd for $C_{29}H_{43}NO_9Na^+$ $[M+Na]^+$ 572.2830, found 572.2841.

Methyl [(3R,5S,7R,8R)-7-{(1E,3Z)-5-[(2S,3R,5R,6R)-5-{[(2Z,4S)-4-acetoxypent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetate (47)

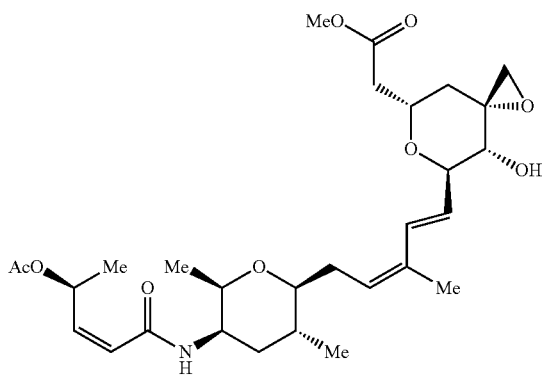

To a stirred solution of epoxide 6 (5.9 mg, 17 µmol, 1.5 equiv) and boronate 61 (4.0 mg, 9.0 µmol, 1.0 equiv) in rigorously degassed (freeze-pump-thaw technique×3) THF:H$_2$O (1 mL, 3:1, v/v) at 25° C. was added Pd(dppf)Cl$_2$·CH$_2$Cl$_2$ (0.7 mg, 0.90 µmol, 0.1 equiv) followed by thallium(I) carbonate (21 mg, 45 µmol, 5.0 equiv). After stirring for 3 h, the reaction mixture was filtered through a layer of Celite, rinsed thoroughly with ethyl acetate (10 mL), and concentrated in vacuo. The obtained residue was purified by flash column chromatography (silica gel, 10→80% hexanes in ethyl acetate), and further purified by preparative thin layer chromatography (silica gel, 50% diethyl ether in dichloromethane) to afford pure methyl ester 47 (2.0 mg, 3.6 µmol, 41%) as a colorless oil. 47: R$_f$=0.30 (silica gel, 45% diethyl ether in dichloromethane); [α]$_D^{22}$=−5.5 (c=0.2, CH$_2$Cl$_2$); FT-IR (neat) ν$_{max}$=3359, 2925, 2854, 1736, 167, 1635, 1524, 137, 1244, 1086, 1048, 813 cm$^{-1}$; $^1$H NMR (600 MHz, CDCl$_3$) δ 6.75 (d, J=15.7 Hz, 1H), 6.52 (d, J=9.0 Hz, 1H), 6.11 (p, J=6.7 Hz, 1H), 5.86-5.78 (m, 2H), 5.70 (dd, J=15.8, 6.1 Hz, 1H), 5.57 (t, J=7.0 Hz, 1H), 4.54-4.48 (m, 1H), 4.27 (t, J=6.6 Hz, 1H), 4.00 (d, J=9.1 Hz, 1H), 3.69 (s, 3H), 3.59 (dd, J=6.3, 1.6 Hz, 1H), 3.52 (d, J=7.1 Hz, 1H), 3.06 (ddd, J=10.4, 8.1, 3.0 Hz, 1H), 2.99 (d, J=4.6 Hz, 1H), 2.93 (dd, J=15.5, 7.9 Hz, 1H), 2.70 (dd, J=15.5, 6.4 Hz, 1H), 2.65 (d, J=4.6 Hz, 1H), 2.57 (dd, J=16.5, 6.9 Hz, 1H), 2.30 (dt, J=15.8, 7.8 Hz, 1H), 2.14-2.09 (m, 1H), 2.05 (s, 3H), 1.95 (dt, J=13.6, 3.5 Hz, 1H), 1.84 (d, J=1.4 Hz, 3H), 1.79 (dd, J=14.1, 4.6 Hz, 1H), 1.53 (d, J=3.2 Hz, 1H), 1.41 (d, J=2.8 Hz, 1H), 1.43 (d, J=5.5 Hz, 1H), 1.39 (d, J=6.5 Hz, 3H), 1.12 (d, J=6.4 Hz, 3H), 0.85 (d, J=6.4 Hz, 3H) ppm; $^{13}$C NMR (151 MHz, CDCl$_3$) δ 171.6, 170.7, 165.2, 141.9, 132.4, 131.1, 128.3, 125.5, 123.5, 84.1, 77.0, 76.2, 75.1, 70.0, 69.2, 68.8, 57.3, 52.0, 50.0, 48.2, 38.3, 38.2, 34.6, 31.3, 30.2, 21.4, 20.6, 20.3, 18.1, 17.6 ppm; HRMS (ESI-TOF) calcd for C$_{29}$H$_{43}$NO$_9$Na$^+$ [M+Na]$^+$ 572.2830, found 572.2833.

(2Z,4S)-N-[(2R,3R,5R,6S)-6-Allyl-2,5-dimethyltetrahydro-2H-pyran-3-yl]-4-hydroxypent-2-en-amide (62)

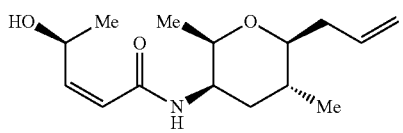

To a stirred solution of amide 58 (45.0 mg, 0.146 mmol, 1.0 equiv) in methanol (2.0 mL) at 25° C. was added potassium carbonate (60.0 mg, 0.436 mmol, 3.0 equiv). After stirring for 2 h, the solvent was removed in vacuo, and the obtained residue was purified by flash column chromatography (silica gel, 10→50% ethyl acetate in hexanes) to afford pure alcohol 62 (38.0 mg, 0.142 mmol, 98%) as a colorless oil. 62: R$_f$=0.40 (silica gel, 50% ethyl acetate in hexanes); [α]$_D^{22}$=−3.4 (c=0.8, CH$_2$Cl$_2$); FT-IR (neat) ν$_{max}$=3303, 2976, 2930, 2852, 1655, 1623, 1533, 1457, 1328, 1243, 1087, 912, 816 cm$^{-1}$; $^1$H NMR (600 MHz, CDCl$_3$) δ 6.17 (dt, J=13.1, 6.6 Hz, 2H), 5.91 (ddt, J=17.1, 10.3, 6.8 Hz, 1H), 5.79 (dd, J=12.0, 1.7 Hz, 1H), 5.15-5.02 (m, 2H), 4.79 (tt, J=6.8, 5.2 Hz, 1H), 3.97 (dtd, J=8.5, 3.1, 1.6 Hz, 1H), 3.61 (qd, J=6.5, 1.7 Hz, 1H), 3.11-3.06 (m, 1H), 2.43 (dddt, J=14.9, 6.4, 3.1, 1.4 Hz, 1H), 2.21-2.13 (m, 1H), 1.94 (dt, J=13.5, 3.4 Hz, 1H), 1.49 (dtt, J=9.9, 6.5, 2.7 Hz, 1H), 1.45-1.40 (m, 1H), 1.35 (d, J=6.7 Hz, 3H), 1.11 (d, J=6.4 Hz, 3H), 0.84 (d, J=6.4 Hz, 3H) ppm; $^{13}$C NMR (151 MHz, CDCl$_3$) δ 166.4, 150.5, 135.1, 122.8, 116.7, 83.8, 74.9, 64.7, 48.6, 38.0, 37.4, 29.9, 22.9, 18.0, 17.3 ppm; HRMS (ESI-TOF) calcd for C$_{15}$H$_{25}$NO$_3$Na$^+$ [M+Na]$^+$ 290.1727, found 290.1729.

(2S,3Z)-5-{[(2R,3R,5R,6S)-6-Allyl-2,5-dimethyltetrahydro-2H-pyran-3-yl]amino}-5-oxopent-3-en-2-yl piperidine-1-carboxylate (63)

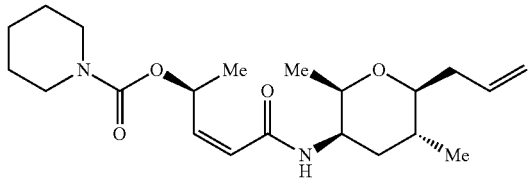

To a stirred solution of the alcohol 62 (12 mg, 45 µmol, 1.0 equiv) in dichloromethane (1.0 mL) at 25° C. were added triethylamine (25 µL, 0.18 mmol, 4.0 equiv), N,N'-carbonyldiimidazole (29 mg, 0.18 mmol, 4.0 equiv), and 4-dimethylaminopyridine (1 mg, 9 µmol, 0.2 equiv) successively. After stirring for 2 h, piperidine (0.088 mL, 0.89 mmol, 20 equiv) was added dropwise, and stirring was continued for an additional 3 h at the same temperature. Then the reaction mixture was quenched with water (5 mL), and the two phases were separated. The aqueous layer was extracted with ethyl acetate (3×10 mL), and the combined organic layers were washed with brine (10 mL), dried over anhydrous sodium sulfate, and concentrated in vacuo. The obtained residue was purified by flash column chromatography (silica gel, 10→40% ethyl acetate in hexanes) to afford pure carbamate 63 (15.7 mg, 41 µmol, 92%) as a pale yellow amorphous solid. 63: $R_f$=0.50 (silica gel, 40% ethyl acetate in hexanes); $[\alpha]_D^{22}$=+12.2 (c=1.0, CH$_2$Cl$_2$); FT-IR (neat) $v_{max}$=3334, 2934, 2854, 1685, 1667, 1638, 1528, 1431, 1234, 1087, 911 cm$^{-1}$; $^1$H NMR (600 MHz, CDCl$_3$) δ 7.30 (d, J=8.9 Hz, 1H), 6.02-5.90 (m, 1H), 5.86-5.71 (m, 3H), 5.06 (dt, J=17.2, 1.7 Hz, 1H), 5.01 (ddd, J=10.1, 2.3, 1.2 Hz, 1H), 4.02 (dq, J=8.4, 2.8 Hz, 1H), 3.58 (dtd, J=8.1, 6.5, 5.8, 1.7 Hz, 1H), 3.41 (t, J=5.5 Hz, 4H), 3.06 (ddd, J=10.1, 7.2, 3.1 Hz, 1H), 2.41 (dddd, J=16.1, 6.2, 3.0, 1.4 Hz, 1H), 2.21 (dtd, J=14.7, 7.3, 1.4 Hz, 1H), 1.94 (dt, J=13.8, 3.4 Hz, 1H), 1.63 (d, J=3.1 Hz, 1H), 1.59 (q, J=5.5 Hz, 2H), 1.52 (s, 4H), 1.44-1.39 (m, 1H), 1.39-1.35 (m, 3H), 1.13 (d, J=6.4 Hz, 3H), 0.82 (d, J=6.4 Hz, 3H) ppm; $^{13}$C NMR (151 MHz, CDCl$_3$) δ 165.6, 155.0, 140.8, 135.4, 123.7, 116.0, 83.5, 74.9, 69.5, 48.1, 44.7, 38.0, 37.3, 29.3, 25.7, 24.4, 20.4, 17.9, 17.3 ppm; HRMS (ESI-TOF) calcd for C$_{21}$H$_{34}$N$_2$O$_4$Na$^+$ [M+Na]$^+$ 401.2411, found 401.2416.

(2S,3Z)-5-({(2R,3R,5R,6S)-2,5-Dimethyl-6[(2Z)-3-(4,4,5,5-tetramethyl-1,3,2-dioxaborolan-2-yl)but-2-en-1-yl]tetrahydro-2H-pyran-3-yl}amino)-5-oxo-pent-3-en-2-yl piperidine-1-carboxylate (64)

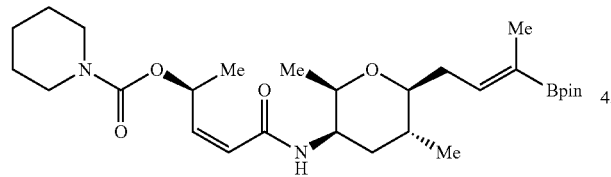

To a stirred solution of carbamate 63 (14.0 mg, 37.0 µmol, 1.0 equiv) in dichloromethane (2.0 mL) at 25° C. was added isopropenylboronic acid pinacol ester (0.07 mL, 0.37 mmol, 10 equiv) followed by Grela's catalyst (59) (2.4 mg, 3.7 µmol, 0.1 equiv), and the reaction mixture was heated to 50° C. After stirring for 6 h, the reaction mixture was allowed to cool to 25° C., and the solvent was removed in vacuo. The obtained residue was purified by flash column chromatography (silica gel, 10→40% ethyl acetate in hexanes) and further purified by preparative thin layer chromatography [silica gel, methanol/diethyl ether/dichloromethane (1:9:90)] to afford pure boronate 64 (12 mg, 23 µmol, 63%) as a colorless oil. 64: $R_f$=0.40 (silica gel, 40% ethyl acetate in hexanes); $[\alpha]_D^{22}$=−31.2 (c=0.6, CH$_2$Cl$_2$); FT-IR (neat) $v_{max}$=3324, 2977, 2932, 2834, 1686, 1668, 1632, 1528, 1431, 1371, 1234, 1147, 859 cm$^{-1}$; $^1$H NMR (600 MHz, CDCl$_3$) δ 7.00 (d, J=9.2 Hz, 1H), 6.47-6.42 (m, 1H), 5.87 (p, J=6.6 Hz, 1H), 5.83-5.76 (m, 2H), 4.05-4.00 (m, 1H), 3.57 (qd, J=6.4, 1.7 Hz, 1H), 3.40 (t, J=5.5 Hz, 4H), 3.10 (ddd, J=9.9, 8.4, 3.0 Hz, 1H), 2.51-2.43 (m, 1H), 2.31-2.20 (m, 1H), 1.93 (ddd, J=13.7, 4.1, 2.9 Hz, 1H), 1.68 (d, J=1.6 Hz, 3H), 1.62 (dd, J=6.2, 3.7 Hz, 1H), 1.58 (q, J=5.7 Hz, 2H), 1.54-1.49 (m, 4H), 1.44-1.39 (m, 1H), 1.38 (d, J=6.4 Hz, 3H), 1.26 (s, 12H), 1.11 (d, J=6.4 Hz, 3H), 0.83 (d, J=6.5 Hz, 3H) ppm; $^{13}$C NMR (151 MHz, CDCl$_3$) δ 143.1, 142.0, 123.4, 83.7, 83.3, 75.0, 69.7, 48.1, 44.9, 38.3, 32.9, 30.3, 25.8, 25.0, 24.9, 24.5, 20.5, 18.1, 17.8, 14.4 ppm; HRMS (ESI-TOF) (541.3419) calcd for C$_{28}$H$_{47}$BN$_2$O$_6$Na$^+$ [M+Na]$^+$ 541.3424, found 541.3431.

(2S,3Z)-5-{[(2R,3R,5R,6S)-6-{(2E,4E)-5-[(3R,4R,5R,7S)-4-Hydroxy-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]-amino}-5-oxopent-3-en-2-yl piperidine-1-carboxylate (38)

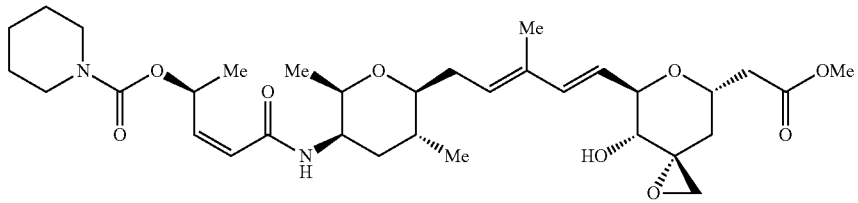

To a stirred solution of epoxide 6 (6.1 mg, 17 µmol, 1.5 equiv) and boronate 64 (6.0 mg, 12 µmol, 1.0 equiv) in rigorously degassed (freeze-pump-thaw technique×3) THF:H$_2$O (1.0 mL, 3:1, v/v) at 25° C. was added Pd(dppf)Cl$_2$.CH$_2$Cl$_2$ (2.0 mg, 2.3 µmol, 0.2 equiv) followed by thallium(I) carbonate (27 mg, 60 µmol, 5.0 equiv). After stirring for 6 h, the reaction mixture was filtered through a layer of Celite, rinsed thoroughly with ethyl acetate (10 mL), and concentrated in vacuo. The obtained residue was purified by flash column chromatography (silica gel, 2% methanol in diethyl ether), and further purified by preparative thin layer chromatography (silica gel, 5% methanol in diethyl ether) to afford pure thailanstatin A analogue 38 (3.0 mg, 4.8 µmol, 40%) as a colorless oil. 38: $R_f$=0.30 (silica gel, 2% methanol in diethyl ether); $[\alpha]_D^{22}$=+1.0 (c=0.3, CH$_2$Cl$_2$); FT-IR (neat) $v_{max}$=3345, 2928, 2856, 1738, 1683, 1668, 1528, 1434, 1263, 1235, 1086, 1052, 814 cm$^{-1}$; $^1$H NMR (600 MHz, CDCl$_3$) δ 7.13 (d, J=9.1 Hz, 1H), 6.39 (d, J=15.8 Hz, 1H), 5.85-5.80 (m, 1H), 5.79 (d, J=3.0 Hz, 2H), 5.71 (t, J=7.1 Hz, 1H), 5.59 (dd, J=15.8, 6.3 Hz, 1H), 4.49 (ddd, J=12.0, 7.1, 4.8 Hz, 1H), 4.23 (t, J=6.7 Hz, 1H), 4.02 (dd, J=9.4, 4.1 Hz, 1H), 3.70 (s, 3H), 3.57 (qd, J=6.5, 1.8 Hz, 1H), 3.52 (t, J=7.6 Hz, 1H), 3.41 (t, J=5.5 Hz, 4H), 3.04 (ddd, J=10.4, 8.1, 3.0 Hz, 1H), 2.98 (d, J=4.6 Hz, 1H), 2.92 (dd, J=15.5, 7.7 Hz, 1H), 2.70 (dd, J=15.4, 6.6 Hz, 1H), 2.65 (d, J=4.6 Hz, 1H), 2.49 (ddd, J=15.7, 7.5, 3.0 Hz, 1H), 2.26 (dt, J=15.4, 7.5 Hz, 1H), 2.13-2.10 (m, 1H), 1.94 (dt, J=13.7, 3.6 Hz, 1H), 1.85 (d, J=8.4 Hz, 1H), 1.79 (dd, J=14.1, 4.5 Hz, 1H), 1.75 (s, 3H), 1.57 (d, J=5.6 Hz, 2H), 1.54-1.50 (m, 4H), 1.44-1.41 (m, 1H), 1.38 (d, J=6.1 Hz, 3H), 1.12 (d, J=6.4 Hz, 3H), 0.84 (d, J=6.5 Hz, 3H) ppm; $^{13}$C NMR (151 MHz, CDCl$_3$) δ 171.6, 165.6, 155.2, 141.5, 139.0, 133.9, 131.1, 123.7, 122.4, 84.0, 76.1, 75.1, 70.0, 69.7, 68.8, 57.4, 52.0, 50.0, 48.2, 44.9, 38.3, 38.3, 34.6, 32.3, 30.1, 25.8, 24.5, 20.5, 18.1, 17.7, 12.7 ppm; HRMS (ESI-TOF) calcd for C$_{33}$H$_{50}$N$_2$O$_9$Na$^+$ [M+Na]$^+$ 641.3409, found 641.3415.

133

(2S,3Z)-5-{[(2R,3R,5R,6S)-6-Allyl-2,5-dimethyltetrahydro-2H-pyran-3-yl]amino}-5-oxopent-3-en-2-yl morpholine-4-carboxylate (65)

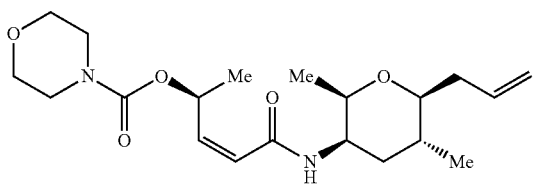

65

To a stirred solution of alcohol 62 (8 mg, 30 µmol, 1.0 equiv) in dichloromethane (1.0 mL) at 25° C. were added triethylamine (20 µL, 0.12 mmol, 4.0 equiv), N,N'-carbonyldiimidazole (15 mg, 90 µmol, 3.0 equiv), and 4-dimethylaminopyridine (1.0 mg, 6.0 µmol, 0.2 equiv). After stirring for 2 h, morpholine (0.03 mL, 0.30 mmol, 10 equiv) was added dropwise, and stirring was continued for an additional 3 h at the same temperature. Then the reaction mixture was quenched with water (5 mL), and the two phases were separated. The aqueous layer was extracted with ethyl acetate (3×10 mL), and the combined organic layers were washed with brine (10 mL), dried over anhydrous sodium sulfate, and concentrated in vacuo. The obtained residue was purified by flash column chromatography (silica gel, 10→60% ethyl acetate in hexanes) to afford pure carbamate 65 (11.0 mg, 29 µmol, 96%) as a pale yellow amorphous solid. 65: $R_f$=0.40 (silica gel, 60% ethyl acetate in hexanes); $[\alpha]_D^{22}$=−1.9 (c=1.1, $CH_2Cl_2$); FT-IR (film) $\nu_{max}$=3334, 2975, 2931, 2855, 1691, 1668, 1638, 1527, 1427, 1241, 1117, 1088, 908 $cm^{-1}$; $^1$H NMR (600 MHz, $CDCl_3$) δ 6.97 (d, J=9.0 Hz, 1H), 5.98-5.87 (m, 2H), 5.83-5.77 (m, 2H), 5.06 (dd, J=17.2, 1.8 Hz, 1H), 5.03-4.98 (m, 1H), 4.04-3.97 (m, 1H), 3.65 (t, J=5.0 Hz, 4H), 3.58 (qd, J=6.4, 1.8 Hz, 1H), 3.51-3.41 (m, 4H), 3.06 (ddd, J=10.2, 7.3, 3.2 Hz, 1H), 2.45-2.37 (m, 1H), 2.23-2.15 (m, 1H), 1.94 (ddd, J=13.7, 4.0, 2.9 Hz, 1H), 1.62-1.54 (m, 1H), 1.44-1.40 (m, 1H), 1.39 (d, J=6.5 Hz, 3H), 1.12 (d, J=6.4 Hz, 3H), 0.82 (d, J=6.5 Hz, 3H) ppm; $^{13}$C NMR (151 MHz, $CDCl_3$) δ 165.4, 155.1, 141.4, 135.4, 123.8, 116.3, 83.6, 75.0, 70.2, 66.7, 48.3, 44.4, 43.9, 38.1, 37.5, 29.6, 20.4, 18.0, 17.4 ppm; HRMS (ESI-TOF) calcd for $C_{20}H_{32}N_2O_5Na^+$ [M+Na]$^+$ 403.2203, found 403.2208.

134

(2S,3Z)-5-({(2R,3R,5R,6S)-2,5-Dimethyl-6-[(2Z)-3-(4,4,5,5-tetramethyl-1,3,2-dioxaborolan-2-yl)but-2-en-1-yl]tetrahydro-2H-pyran-3-yl}amino)-5-oxopent-3-en-2-yl morpholine-4-carboxylate (66)

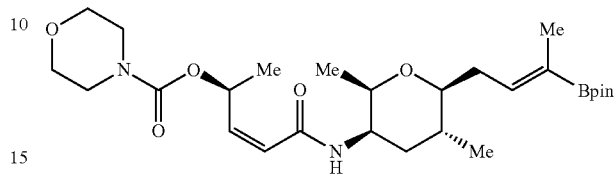

66

To a stirred solution of carbamate 65 (10.0 mg, 26.0 µmol, 1.0 equiv) in dichloromethane (1.0 mL) at 25° C. was added isopropenylboronic acid pinacol ester (50 µL 0.26 mmol, 10 equiv) followed by Grela's catalyst (1.8 mg, 2.6 µmol, 0.1 equiv) and the reaction mixture was heated to 50° C. After stirring for 6 h, the reaction mixture was allowed to cool to 25° C., and the solvent was removed in vacuo. The obtained residue was purified by flash column chromatography (silica gel, 10→60% ethyl acetate in hexanes) to afford pure boronate 66 (7.0 mg, 13 µmol, 52%) as a colorless oil. 66: $R_f$=0.50 (silica gel, 60% ethyl acetate in hexanes); $[\alpha]_D^{22}$=−33.1 (c=0.7, $CH_2Cl_2$); FT-IR (neat) $\nu_{max}$=3336, 2976, 2931, 2857, 1702, 1669, 1632, 1525, 1370, 1241, 1117, 1089, 859 $cm^{-1}$; $^1$H NMR (600 MHz, $CDCl_3$) δ 6.77 (d, J=9.2 Hz, 1H), 6.50-6.40 (m, 1H), 6.00 (p, J=6.6 Hz, 1H), 5.83 (dd, J=11.6, 7.8 Hz, 1H), 5.79 (d, J=11.7 Hz, 1H), 4.01 (dt, J=9.4, 2.5 Hz, 1H), 3.65 (t, J=4.8 Hz, 4H), 3.58 (qd, J=6.4, 1.7 Hz, 1H), 3.46 (dd, J=5.9, 3.9 Hz, 4H), 3.11 (ddd, J=9.9, 8.3, 3.0 Hz, 1H), 2.51-2.44 (m, 1H), 2.26-2.20 (m, 1H), 1.97-1.92 (m, 1H), 1.68 (s, 3H), 1.57 (ddt, J=12.6, 6.2, 2.5 Hz, 1H), 1.43-1.38 (m, 4H), 1.28-1.25 (m, 13H), 1.11 (d, J=6.4 Hz, 3H), 0.83 (d, J=6.5 Hz, 3H) ppm; $^{13}$C NMR (151 MHz, $CDCl_3$) δ 165.3, 155.1, 142.8, 142.2, 123.4, 83.7, 83.3, 75.0, 70.2, 66.7, 48.2, 44.4, 38.3, 32.8, 30.3, 25.0, 24.9, 20.5, 18.1, 17.7, 14.4 ppm; HRMS (ESI-TOF) calcd for $C_{27}H_{45}BN_2O_7Na^+$ [M+Na]$^+$ 543.3217, found 543.3226.

(2S,3Z)-5-{[2R,3R,5R,6S)-6-{(2E,4E)-5-[(3R,4R,5R,7S)-4-Hydroxy-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]-amino}-5-oxopent-3-en-2-yl morpholine-4-carboxylate (40)

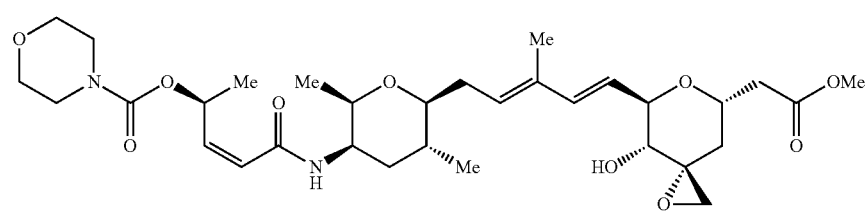

40

To a stirred solution of epoxide 6 (4.0 mg, 12 µmol, 1.5 equiv) and boronate 66 (4.0 mg, 7.7 µmol, 1.0 equiv) in rigorously degassed (freeze-pump-thaw technique×3) THF:H$_2$O (1.0 mL, 3:1, v/v) at 25° C. was added Pd(dppf)Cl$_2$·CH$_2$Cl$_2$ (2.0 mg, 1.5 µmol, 0.2 equiv) followed by thallium(I) carbonate (18 mg, 38 µmol, 5.0 equiv). After stirring for 6 h, the reaction mixture was filtered through a layer of Celite, rinsed thoroughly with ethyl acetate (10 mL), and concentrated in vacuo. The obtained residue was purified by flash column chromatography (silica gel, 10→100% ethyl acetate in hexanes), and further purified by preparative thin layer chromatography [silica gel, 3% methanol in diethyl ether/dichloromethane (1:1)] to afford pure thailanstatin analogue 40 (3.0 mg, 4.8 µmol, 63%) as a colorless oil. 40: R$_f$=0.30 (silica gel, ethyl acetate); [α]$_D^{22}$=−1.0 (c=0.3, CH$_2$Cl$_2$); FT-IR (neat) ν$_{max}$=3333, 2956, 2926, 2855, 1736, 1691, 1668, 1434, 1242, 1115, 1088, 1075, 731 cm$^{-1}$; $^1$H NMR (600 MHz, CDCl$_3$) δ 6.86 (d, J=9.1 Hz, 1H), 6.38 (d, J=15.8 Hz, 1H), 5.98-5.92 (m, 1H), 5.85-5.78 (m, 2H), 5.70 (t, J=7.0 Hz, 1H), 5.60 (dd, J=15.7, 6.3 Hz, 1H), 4.50 (ddd, J=12.1, 7.4, 4.9 Hz, 1H), 4.22 (t, J=6.7 Hz, 1H), 4.01 (d, J=9.1 Hz, 1H), 3.70 (s, 3H), 3.66 (q, J=5.6 Hz, 5H), 3.58 (qd, J=6.4, 1.7 Hz, 1H), 3.52 (d, J=7.1 Hz, 1H), 3.46 (d, J=5.0 Hz, 4H), 3.05 (ddd, J=10.3, 8.0, 3.0 Hz, 1H), 2.99 (d, J=4.6 Hz, 1H), 2.92 (dd, J=15.5, 7.7 Hz, 1H), 2.70 (dd, J=15.4, 6.6 Hz, 1H), 2.65 (d, J=4.6 Hz, 1H), 2.50 (ddd, J=15.4, 7.4, 2.9 Hz, 1H), 2.25 (dt, J=15.4, 7.4 Hz, 1H), 2.16-2.11 (m, 1H), 1.95 (dt, J=13.7, 3.5 Hz, 1H), 1.77 (dd, J=14.0, 4.5 Hz, 1H), 1.74 (d, J=1.2 Hz, 3H), 1.44-1.41 (m, 1H), 1.40 (d, J=6.5 Hz, 3H), 1.11 (d, J=6.4 Hz, 3H), 0.84 (d, J=6.5 Hz, 3H) ppm; $^{13}$C NMR (151 MHz, CDCl$_3$) δ 171.6, 165.4, 155.1, 141.8, 138.9, 134.0, 130.8, 123.6, 122.6, 84.0, 76.0, 75.1, 70.3, 70.0, 68.9, 66.7, 57.4, 52.0, 49.9, 48.2, 44.4, 38.3, 38.2, 34.6, 32.2, 30.2, 20.5, 18.1, 17.6, 12.7 ppm; HRMS (ESI-TOF) calcd for C$_{32}$H$_{48}$N$_2$O$_{10}$Na$^+$ [M+Na]$^+$ 643.3201, found 643.3204.

(2Z,4S)-N-[(2R,3R,5S,6S)-6-Allyl-2,5-dimethyltetrahydro-2H-pyran-3-yl]-4-hydroxypent-2-en-amide (68)

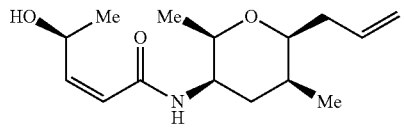

68

To a stirred solution of enamide 28 (59 mg, 0.191 mmol, 1.0 equiv) in MeOH (3 mL) at 25° C. was added potassium carbonate (80 mg, 0.573 mmol, 3.0 equiv). After stirring for 1 h, the solvent was removed in vacuo, and the obtained residue was purified by flash column chromatography (silica gel, 10→50% ethyl acetate in hexanes) to afford pure alcohol 68 (46 mg, 0.172 mmol, 90%) as a colorless oil. 68: R$_f$=0.40 (silica gel, 50% ethyl acetate in hexanes); [α]$_D^{22}$=+36.2 (c=1.0, CH$_2$Cl$_2$); FT-IR (neat) ν$_{max}$=3315, 2975, 2931, 2851, 1655, 1620, 1516, 1444, 1317, 1059, 914 cm$^{-1}$; $^1$H NMR (600 MHz, CDCl$_3$) δ 6.21-6.14 (m, 1H), 5.94 (d, J=9.2 Hz, 1H), 5.85-5.73 (m, 1H), 5.71 (dt, J=11.9, 1.5 Hz, 1H), 5.11 (ddq, J=17.1, 3.3, 1.6 Hz, 1H), 5.07-5.02 (m, 1H), 4.81-4.76 (m, 1H), 3.93 (dq, J=9.1, 3.0 Hz, 1H), 3.69-3.63 (m, 1H), 3.57-3.52 (m, 1H), 2.33 (dddd, J=14.0, 7.6, 3.9, 1.7 Hz, 1H), 2.16-2.09 (m, 1H), 1.94 (dt, J=6.1, 2.9 Hz, 2H), 1.79 (tdd, J=7.6, 5.0, 2.2 Hz, 1H), 1.34 (dd, J=7.1, 2.7 Hz, 3H), 1.13 (dd, J=6.5, 2.5 Hz, 3H), 1.01 (dd, J=7.4, 2.4 Hz, 3H) ppm; $^{13}$C NMR (151 MHz, CDCl$_3$) δ 166.2, 150.8, 134.7, 122.6, 117.0, 80.9, 76.0, 64.7, 47.6, 37.5, 35.9, 29.0, 22.9, 18.0, 15.3 ppm; HRMS (ESI-TOF) calcd for C$_{15}$H$_{25}$NO$_3$Na$^+$ [M+Na]$^+$ 290.1727, found 290.1730.

(2S,3Z)-5-{[2R,3R,5S,6S)-6-Allyl-2,5-dimethyltetrahydro-2H-pyran-3-yl]amino}-5-oxopent-3-en-2-yl piperidine-1-carboxylate (69)

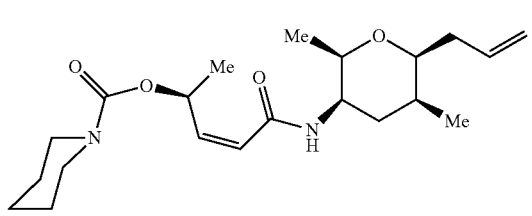

69

To a stirred solution of the alcohol 68 (13 mg, 0.049 mmol, 1.0 equiv) were added Et$_3$N (0.03 mL, 0.19 mmol, 4.0 equiv), DMAP (1 mg, 9 µmol, 0.2 equiv) and N,N'-carbonyldiimidazole (24 mg, 0.15 mmol, 3.0 equiv) in dichloromethane (1 mL) at 25° C. and allowed to stir for 2 h. After consumption of the starting material (monitored through TLC) piperidine (0.04 mL, 0.49 mmol, 10 equiv) was introduced into the reaction mixture and allowed to stir at 25° C. After 3 h, the reaction mixture was quenched with water (5 mL) and extracted with ethyl acetate (3×10 mL). The combined organic layer was washed with brine (10 mL), dried over anhydrous sodium sulfate, and concentrated in vacuo. The obtained residue was purified by flash column chromatography (silica gel, 10→40% ethyl acetate in hexanes) to afford pure carbamate 69 (15.7 mg, 0.041 mmol, 92%) as a colorless oil. 69: R$_f$=0.60 (silica gel, 50% ethyl acetate in hexanes); [α]$_D^{22}$=+0.3 (c=1.0, CH$_2$Cl$_2$); FT-IR (neat) ν$_{max}$=3355, 2976, 2934, 2854, 1685, 1640, 1518, 1428, 1262, 1233, 1151, 1067, 915 cm$^{-1}$; $^1$H NMR (600 MHz, CDCl$_3$) δ 6.24 (d, J=9.0 Hz, 1H), 6.10-6.01 (m, 1H), 5.91 (dd, J=11.6, 7.9 Hz, 1H), 5.79 (dddd, J=16.6, 10.2, 7.7, 6.1 Hz, 1H), 5.68 (dd, J=11.6, 1.3 Hz, 1H), 5.10 (dd, J=17.2, 1.8 Hz, 1H), 5.06-5.01 (m, 1H), 4.00-3.89 (m, 1H), 3.65 (qd, J=6.5, 2.4 Hz, 1H), 3.52 (td, J=7.1, 2.7 Hz, 1H), 3.40 (t, J=5.5 Hz, 4H), 2.32 (dddt, J=13.9, 7.7, 6.3, 1.6 Hz, 1H), 2.16-2.07 (m, 1H), 1.99-1.89 (m, 2H), 1.76 (ddt, J=7.6, 5.1, 2.6 Hz, 1H), 1.57 (d, J=4.7 Hz, 2H), 1.54-1.48 (m, 4H), 1.39 (d, J=6.5 Hz, 3H), 1.15 (d, J=6.5 Hz, 3H), 1.02 (d, J=7.4 Hz, 3H) ppm; $^{13}$C NMR (151 MHz, CDCl$_3$) δ 165.1, 155.0, 144.5, 134.8, 122.0, 116.7, 80.7, 75.9, 69.6, 47.0, 44.7, 37.4, 35.9, 28.8, 25.7, 24.4, 20.2, 17.8, 14.9 ppm; HRMS (ESI-TOF) calcd for C$_{21}$H$_{34}$N$_2$O$_4$Na$^+$ [M+Na]$^+$ 401.2411, found 401.2416.

(2S,3Z)-5-({(2R,3R,5S,6S)-2,5-Dimethyl-6-[(2Z)-3-(4,4,5,5-tetramethyl-1,3,2-dioxaborolan-2-yl)but-2-en-1-yl]tetrahydro-2H-pyran-3-yl}amino)-5-oxo-pent-3-en-2-yl piperidine-1-carboxylate (70)

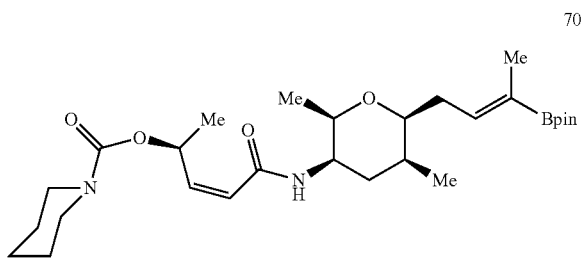

To a stirred solution of eneamide 69 (15.0 mg, 0.04 mmol, 1.0 equiv) in dichloromethane (2 mL) was added isopropenylboronic acid pinacol ester (0.07 mL, 0.39 mmol, 10 equiv) followed by Grela's catalyst (2.6 mg, 3.9 µmol, 0.1 equiv) and stirred at 50° C. for 6 h. After completion of the reaction it was allowed to cool to 25° C. The solvent was removed in vacuo, and the obtained residue was purified by flash column chromatography (silica gel, 10→50% ethyl acetate in hexanes) and further purified by preparative thin layer chromatography (silica gel, 55% ethyl acetate in hexanes) to afford pure boronate 70 (12 mg, 0.023 mmol, 63%) as a colorless oil. 70: $R_f$=0.50 (silica gel, 50% ethyl acetate in hexanes); $[\alpha]_D^{22}$=−0.3 (c=1.0, $CH_2Cl_2$); FT-IR (neat) $\nu_{max}$=3324, 2976, 2935, 2857, 1698, 1669, 1633, 1521, 1429, 1370, 1263, 1234, 1147, 1069, 857 cm$^{-1}$; $^1$H NMR (600 MHz, $CD_2Cl_2$) δ 6.30 (d, J=9.0 Hz, 1H), 6.25 (ddd, J=7.7, 5.9, 1.9 Hz, 1H), 6.08-6.01 (m, 1H), 5.90 (dd, J=11.6, 7.9 Hz, 1H), 5.68 (dd, J=11.6, 1.3 Hz, 1H), 3.94 (ddt, J=9.1, 4.6, 2.3 Hz, 1H), 3.67 (qd, J=6.5, 2.3 Hz, 1H), 3.59 (td, J=7.3, 2.7 Hz, 1H), 3.40 (t, J=5.5 Hz, 4H), 2.40-2.33 (m, 1H), 2.26 (dt, J=15.3, 7.5 Hz, 1H), 1.99-1.90 (m, 2H), 1.79 (td, J=5.1, 2.5 Hz, 1H), 1.69 (d, J=1.6 Hz, 3H), 1.57 (d, J=4.9 Hz, 2H), 1.51 (d, J=5.6 Hz, 4H), 1.39 (d, J=6.5 Hz, 3H), 1.25 (s, 13H), 1.15 (d, J=6.5 Hz, 3H), 1.01 (d, J=7.3 Hz, 3H) ppm; $^{13}$C NMR (151 MHz, $CD_2Cl_2$) δ 165.2, 155.1, 144.4, 141.2, 122.3, 83.3, 80.4, 76.1, 69.8, 47.2, 44.9, 36.0, 32.5, 28.9, 25.8, 25.0, 24.9, 24.5, 20.4, 18.0, 15.1, 14.4 ppm; HRMS (ESI-TOF) calcd for $C_{28}H_{47}BN_2O_6Na^+$ [M+Na]$^+$ 540.3456, found 540.3458.

(2S,3Z)-5-{[2R,3R,5S,6S)-6-{(2E,4E)-5-[(3R,4R,5R,7S)-4-Hydroxy-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]-amino}-5-oxopent-3-en-2-yl piperidine-1-carboxylate (42)

To a stirred solution of epoxide 6 (6.1 mg, 0.017 mmol, 1.5 equiv) and boronate 70 (6.0 mg, 12 µmol, 1.0 equiv) in rigorously degassed (freeze-pump-thaw technique×3) THF:H$_2$O (1 mL, 3:1, v/v) at 25° C. was added Pd(dppf)Cl$_2$.CH$_2$Cl$_2$ (2.0 mg, 2.3 µmol, 0.2 equiv) followed by Tl$_2$CO$_3$ (27 mg, 0.058 mmol, 5.0 equiv). After 6 h, the reaction mixture was filtered through a layer of Celite, and rinsed thoroughly with ethyl acetate (10 mL) and the combined organic layer was concentrated in vacuo. The obtained residue was purified by flash column chromatography (silica gel, 2% methanol in diethyl ether), and further purified by preparative thin layer chromatography (silica gel, 5% methanol in diethyl ether) to afford pure thailanstatin A analogue 42 (3.0 mg, 4.8 µmol, 41%) as a colorless oil. 42: $R_f$=0.30 (silica gel, ethyl acetate); $[\alpha]_D^{22}$=+1.0 (c=0.3, $CH_2Cl_2$); FT-IR (neat) $\nu_{max}$=3385, 2928, 2855, 136, 1682, 1670, 1516, 1433, 1261, 1234, 1078, 812 cm$^{-1}$; $^1$H NMR (600 MHz, CDCl$_3$) δ 6.37 (d, J=15.8 Hz, 1H), 6.31 (d, J=9.0 Hz, 1H), 6.08-6.01 (m, 1H), 5.91 (dd, J=11.6, 7.9 Hz, 1H), 5.69 (dd, J=11.7, 1.2 Hz, 1H), 5.62 (dd, J=15.8, 6.2 Hz, 1H), 5.52 (t, J=7.2 Hz, 1H), 4.49 (dq, J=6.8, 4.8 Hz, 1H), 4.21 (t, J=6.7 Hz, 1H), 3.95 (d, J=8.7 Hz, 1H), 3.70 (s, 3H), 3.69-3.65 (m, 1H), 3.52 (tt, J=4.4, 2.6 Hz, 2H), 3.40 (t, J=5.5 Hz, 4H), 2.99 (d, J=4.6 Hz, 1H), 2.93 (dd, J=15.4, 7.9 Hz, 1H), 2.69 (dd, J=15.4, 6.6 Hz, 1H), 2.64 (d, J=4.6 Hz, 1H), 2.39 (dt, J=14.5, 7.0 Hz, 1H), 2.27-2.19 (m, 1H), 2.15 (dd, J=14.1, 5.2 Hz, 1H), 1.95 (dtd, J=14.3, 10.7, 9.5, 3.5 Hz, 2H), 1.84 (d, J=8.6 Hz, 1H), 1.78-1.75 (m, 4H), 1.58 (d, J=4.9 Hz, 2H), 1.54-1.50 (m, 5H), 1.39 (d, J=6.4 Hz, 3H), 1.15 (d, J=6.4 Hz, 3H), 1.02 (d, J=7.3 Hz, 3H) ppm; $^{13}$C NMR (151 MHz, CDCl$_3$) δ 171.4, 165.1, 155.0, 144.3, 138.5, 134.5, 129.6, 122.9, 122.2, 80.7, 76.0, 75.7, 69.8, 69.6, 68.7, 57.2, 51.8, 49.7, 47.0, 44.7, 38.1, 35.9, 34.5, 32.0, 29.7, 29.0, 25.7, 24.4, 20.3, 17.8, 15.0, 12.6 ppm; HRMS (ESI-TOF) calcd for $C_{33}H_{50}N_2O_9Na^+$ [M+Na]$^+$ 641.3409, found 641.3422.

(2S,3Z)-5-{[(2R,3R,5S,6S)-6-Allyl-2,5-dimethyltetrahydro-2H-pyran-3-yl]amino}-5-oxopent-3-en-2-yl dimethylcarbamate (71)

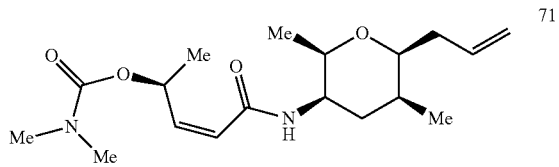 [SMILES: C=CC[C@@H]1O[C@H](C)[C@H](NC(=O)/C=C\[C@H](C)OC(=O)N(C)C)C[C@@H]1C]

To a stirred solution of the alcohol 68 (13 mg, 0.049 mmol, 1.0 equiv) were added Et$_3$N (0.03 mL, 0.194 mmol, 4.0 equiv), DMAP (1.2 mg, 0.010 mmol, 0.2 equiv) and

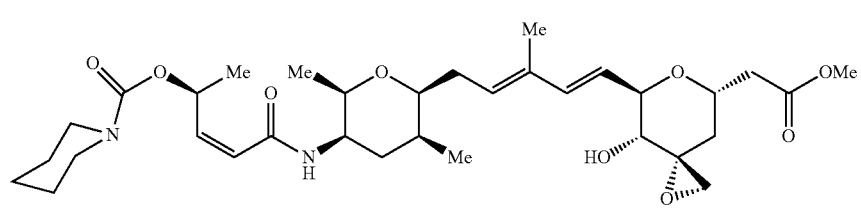

N,N'-carbonyldiimidazole (24 mg, 0.15 mmol, 3.0 equiv) in dichloromethane (1 mL) at 25° C. and allowed to stir for 2 h. After consumption of the starting material (monitored through TLC) dimethylamine [0.4 mL (2.0 M solution in THF), 0.877 mmol, 20 equiv] was introduced into the reaction mixture and allowed to stir at 25° C. After 3 h, the reaction mixture was quenched with water (5 mL) and extracted with ethyl acetate (3×10 mL). The combined organic layer was washed with brine (10 mL), dried over anhydrous sodium sulfate, and concentrated in vacuo. The obtained residue was purified by flash column chromatography (silica gel, 10→50% ethyl acetate in hexanes) to afford pure carbamate 71 (15 mg, 0.044 mmol, 92%) as a colorless oil. 71: $R_f$=0.50 (silica gel, 50% ethyl acetate in hexanes); $[\alpha]_D^{22}$=−16.2 16.2 (c=1.5, $CH_2Cl_2$); FT-IR (neat) $v_{max}$=3354, 2973, 2932, 1692, 1667, 1639, 1515, 1392, 1191, 1059, 914 cm$^{-1}$; $^1$H NMR (600 MHz, $CDCl_3$) δ 6.22 (d, J=9.0 Hz, 1H), 6.09-6.03 (m, 1H), 5.91 (ddd, J=11.5, 7.8, 2.1 Hz, 1H), 5.84-5.74 (m, 1H), 5.68 (dd, J=11.6, 1.4 Hz, 1H), 5.10 (dt, J=17.0, 1.8 Hz, 1H), 5.07-5.01 (m, 1H), 3.94 (ddt, J=9.3, 4.7, 2.5 Hz, 1H), 3.65 (qd, J=6.4, 2.3 Hz, 1H), 3.52 (td, J=7.1, 2.7 Hz, 1H), 2.89 (d, J=2.0 Hz, 6H), 2.36-2.29 (m, 1H), 2.12 (dt, J=14.4, 7.3 Hz, 1H), 1.99-1.90 (m, 2H), 1.76 (dqd, J=6.9, 4.7, 2.4 Hz, 1H), 1.40 (dd, J=6.6, 2.1 Hz, 3H), 1.15 (dd, J=6.5, 2.0 Hz, 3H), 1.02 (d, J=7.5, 1.9 Hz, 3H) ppm; $^{13}$C NMR (151 MHz, $CDCl_3$) δ 165.2, 156.3, 144.6, 134.9, 122.2, 116.8, 80.8, 76.1, 69.9, 47.1, 37.5, 36.4, 36.1, 29.0, 20.4, 18.0, 15.0 ppm; HRMS (ESI-TOF) calcd for $C_{18}H_{30}N_2O_4Na^+$ [M+Na]$^+$ 361.2098, found 361.2104.

(2S,3Z)-5-({(2R,3R,5S,6S)-2,5-Dimethyl-6-[(2Z)-3-(4,4,5,5-tetramethyl-1,3,2-dioxaborolan-2-yl)but-2-en-1-yl]tetrahydro-2H-pyran-3-yl}amino)-5-oxo-pent-3-en-2-yldimethylcarbamate (72)

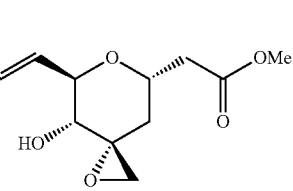

72

To a stirred solution of eneamide 71 (13.0 mg, 0.039 mmol, 1.0 equiv) in dichloromethane (2 mL) was added isopropenylboronic acid pinacol ester (0.07 mL, 0.39 mmol, 10 equiv) followed by Grela's catalyst (59) (2.6 mg, 3.9 μmol, 0.1 equiv) and stirred at 50° C. for 6 h. After completion of the reaction it was allowed to cool to 25° C. The solvent was removed in vacuo, and the obtained residue was purified by flash column chromatography (silica gel, 10→50% ethyl acetate in hexanes) and further purified by preparative thin layer chromatography (silica gel, 65% ethyl acetate in hexanes) to afford pure boronate 72 (10 mg, 0.021 mmol, 54%) as a colorless oil. 72: $R_f$=0.50 (silica gel, 50% ethyl acetate in hexanes); $[\alpha]_D^{22}$=−11.8 (c=1.0, $CH_2Cl_2$); FT-IR (neat) $v_{max}$=3350, 2977, 2932, 1694, 1668, 1633, 1515, 1370, 1304, 1191, 1059, 858 cm$^{-1}$; $^1$H NMR (600 MHz, $CD_2Cl_2$) δ 6.29-6.22 (m, 2H), 6.09-6.02 (m, 1H), 5.91 (dd, J=11.6, 7.9 Hz, 1H), 5.68 (dd, J=11.7, 1.3 Hz, 1H), 3.94 (ddt, J=9.3, 4.6, 2.4 Hz, 1H), 3.67 (qd, J=6.4, 2.2 Hz, 1H), 3.59 (td, J=7.3, 2.7 Hz, 1H), 2.89 (d, J=0.7 Hz, 6H), 2.40-2.33 (m, 1H), 2.26 (dt, J=15.3, 7.5 Hz, 1H), 1.99-1.90 (m, 2H), 1.81-1.77 (m, 1H), 1.69 (d, J=1.6 Hz, 3H), 1.39 (d, J=6.5 Hz, 3H), 1.25 (s, 12H), 1.16 (d, J=6.4 Hz, 3H), 1.01 (d, J=7.3 Hz, 3H) ppm; $^{13}$C NMR (151 MHz, $CD_2Cl_2$) δ 165.2, 156.3, 144.4, 141.2, 122.3, 83.3, 80.4, 76.1, 69.9, 47.2, 36.4, 36.0, 32.5, 28.9, 25.0, 24.9, 20.4, 18.0, 15.1, 14.4 ppm; HRMS (ESI-TOF) calcd for $C_{25}H_{43}BN_2O_6Na^+$ [M+Na]$^+$ 500.3143, found 500.3148.

Methyl [(3R,5S,7R,8R)-7-{(1E,3E)-5-[(2S,3S,5R,6R)-5-({(2Z,4S)-4-[(dimethylcarbamoyl)oxy]pent-2-enoyl}amino)-3,6-dimethyltetrahydro-2H-pyran-2-yl]-3-methylpenta-1,3-dien-1-yl}-8-hydroxy-1,6-dioxaspiro[2.5]oct-5-yl]acetate (36)

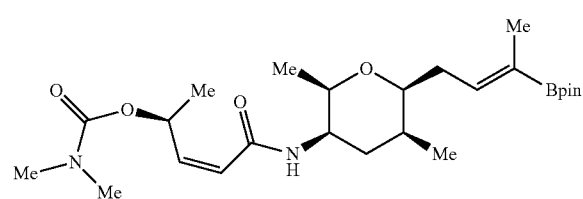

36

To a stirred solution of epoxide 6 (5.5 mg, 0.016 mmol, 1.5 equiv) and boronate 72 (5.0 mg, 10 μmol, 1.0 equiv) in rigorously degassed (freeze-pump-thaw technique×3) THF:$H_2O$ (1 mL, 3:1, v/v) at 25° C. was added Pd(dppf)$Cl_2 \cdot CH_2Cl_2$ (2.0 mg, 2.1 μmol, 0.2 equiv) followed by $Tl_2CO_3$ (25 mg, 0.052 mmol, 5.0 equiv). After 6 h, the reaction mixture was filtered through a layer of Celite, and rinsed thoroughly with ethyl acetate (10 mL) and the combined organic layer was concentrated in vacuo. The obtained residue was purified by flash column chromatography (silica gel, 5% methanol in diethyl ether), and further purified by preparative thin layer chromatography (silica gel, 10% methanol in diethyl ether) to afford pure thailanstatin A analogue 36 (3.0 mg, 52 μmol, 50%) as a colorless oil. 36: $R_f$=0.30 (silica gel, ethyl acetate); $[\alpha]_D^{22}$=+24.0 (c=0.3, $CH_2Cl_2$); FT-IR (neat) $v_{max}$=3372, 2929, 1737, 1691, 1669, 1638, 1514, 1441, 1393, 1195, 1061, 813 cm$^{-1}$; $^1$H NMR (600 MHz, $CDCl_3$) δ 6.37 (d, J=15.8 Hz, 1H), 6.27 (d, J=9.0 Hz, 1H), 6.09-6.02 (m, 1H), 5.91 (dd, J=11.6, 7.9 Hz, 1H), 5.69 (dd, J=11.6, 1.3 Hz, 1H), 5.62 (dd, J=15.8, 6.2 Hz, 1H), 5.52 (t, J=7.2 Hz, 1H), 4.50 (ddd, J=11.9, 7.0, 4.8 Hz, 1H), 4.21 (t, J=6.7 Hz, 1H), 3.94 (dd, J=7.7, 3.5 Hz, 1H), 3.70 (s, 3H), 3.67 (dq, J=6.5, 3.6, 2.2 Hz, 1H), 3.52 (dq, J=7.2, 3.6, 3.0 Hz, 2H), 2.99 (d, J=4.6 Hz, 1H), 2.95-2.91 (m, 1H), 2.90 (s, 7H), 2.69 (dd, J=15.4, 6.6 Hz, 1H), 2.64 (d, J=4.6 Hz, 1H), 2.39 (dt, J=14.5, 7.0 Hz, 1H), 2.23 (dt, J=15.0, 7.4 Hz, 1H), 2.17-2.12 (m, 1H), 2.00-1.90 (m, 2H), 1.84 (d, J=8.3 Hz, 1H), 1.78-1.75 (m, 4H), 1.40 (d, J=6.5 Hz, 3H), 1.16 (d, J=6.4 Hz, 3H), 1.02 (d, J=7.4 Hz, 3H) ppm; $^{13}$C NMR (151 MHz, CDCl$_3$) δ 171.6, 165.2, 156.3, 144.4, 138.6, 134.6, 129.7, 123.0, 122.4, 80.9, 76.1, 75.8, 69.91, 69.89, 68.9, 57.3, 52.0, 49.8, 47.2, 38.2, 36.5, 36.0, 34.6, 32.2, 29.1, 20.4, 18.0, 15.2, 12.8 ppm; HRMS (ESI-TOF) calcd for C$_{30}$H$_{46}$N$_2$O$_9$Na$^+$ [M+Na]$^+$ 601.3096, found 601.3096.

(2S,3Z)-5-{[(2R,3R,5S,6S)-6-Allyl-2,5-dimethyltetrahydro-2H-pyran-3-yl]amino}-5-oxopent-3-en-2-yl morpholine-4-carboxylate (73)

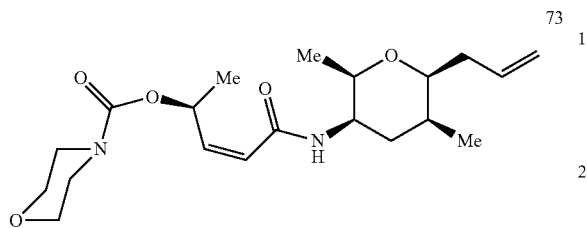

To a stirred solution of the alcohol 68 (10 mg, 0.037 mmol, 1.0 equiv) were added Et$_3$N (0.02 mL, 0.15 mmol, 4.0 equiv), DMAP (1 mg, 8 μmol, 0.2 equiv) and N,N'-carbonyldiimidazole (18 mg, 0.112 mmol, 3.0 equiv) in dichloromethane (1 mL) at 25° C. and allowed to stir for 2 h. After consumption of the starting material (monitored through TLC) morpholine (0.03 mL, 0.374 mmol, 10 equiv) was introduced into the reaction mixture and allowed to stir at 25° C. After 3 h, the reaction mixture was quenched with water (5 mL) and extracted with ethyl acetate (3×10 mL). The combined organic layer was washed with brine (10 mL), dried over anhydrous sodium sulfate, and concentrated in vacuo. The obtained residue was purified by flash column chromatography (silica gel, 10→60% ethyl acetate in hexanes) to afford pure carbamate 73 (10 mg, 0.026 mmol, 70%) as a colorless oil. 73: R$_f$=0.35 (silica gel, 50% ethyl acetate in hexanes); [α]$_D^{22}$=−9.3 (c=1.0, CH$_2$Cl$_2$); FT-IR (neat) ν$_{max}$=3357, 2974, 2929, 2856, 1702, 1668, 1640, 1516, 1425, 1241, 1117, 1068, 910 cm$^{-1}$; $^1$H NMR (600 MHz, CDCl$_3$) δ 6.16 (dtd, J=7.8, 6.5, 1.3 Hz, 1H), 6.13-6.09 (m, 1H), 5.92 (dd, J=11.6, 7.8 Hz, 1H), 5.79 (dddd, J=16.5, 10.2, 7.7, 6.1 Hz, 1H), 5.69 (dd, J=11.6, 1.3 Hz, 1H), 5.11 (dq, J=17.2, 1.7 Hz, 1H), 5.04 (ddt, J=10.2, 2.1, 1.2 Hz, 1H), 3.94 (ddt, J=9.1, 4.7, 2.6 Hz, 1H), 3.65 (dt, J=8.6, 3.4 Hz, 5H), 3.53 (td, J=7.1, 2.7 Hz, 1H), 3.48-3.44 (m, 4H), 2.33 (dddt, J=13.9, 7.6, 6.1, 1.6 Hz, 1H), 2.12 (dddt, J=14.4, 7.9, 6.7, 1.2 Hz, 1H), 1.99-1.91 (m, 2H), 1.77 (ddd, J=7.5, 5.0, 2.5 Hz, 1H), 1.40 (d, J=6.6 Hz, 3H), 1.15 (d, J=6.4 Hz, 3H), 1.02 (d, J=7.3 Hz, 3H) ppm; $^{13}$C NMR (151 MHz, CDCl$_3$) δ 165.0, 155.0, 144.4, 134.9, 122.3, 116.9, 80.8, 76.1, 70.3, 66.7, 47.2, 44.3, 37.5, 36.0, 29.0, 20.3, 18.0, 15.1 ppm; HRMS (ESI-TOF) calcd for C$_{20}$H$_{32}$N$_2$O$_5$Na$^+$ [M+Na]$^+$ 403.2203, found 403.2209.

(2S,3Z)-5-({(2R,3R,5S,6S)-2,5-Dimethyl-6-[(2Z)-3-(4,4,5,5-tetramethyl-1,3,2-dioxaborolan-2-yl)but-2-en-1-yl]tetrahydro-2H-pyran-3-yl}amino)-5-oxopent-3-en-2-yl morpholine-4-carboxylate (74)

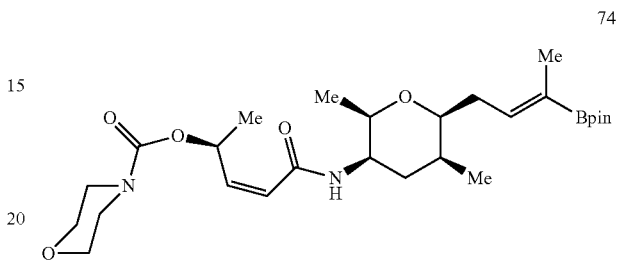

To a stirred solution of eneamide 73 (11 mg, 0.029 mmol, 1.0 equiv) in dichloromethane (1.5 mL) was added isopropenylboronic acid pinacol ester (0.05 mL, 0.29 mmol, 10 equiv) followed by Grela's catalyst (59) (2.0 mg, 2.9 μmol, 0.1 equiv) and stirred at 50° C. for 6 h. After completion of the reaction it was allowed to cool to 25° C. The solvent was removed in vacuo, and the obtained residue was purified by flash column chromatography (silica gel, 10→60% ethyl acetate in hexanes) and further purified by preparative thin layer chromatography (silica gel, 70% ethyl acetate in hexanes) to afford pure boronate 74 (8.5 mg, 0.016 mmol, 57%) as a colorless oil. 74: R$_f$=0.50 (silica gel, 50% ethyl acetate in hexanes); [α]$_D^{22}$=−3.8 (c=0.8, CH$_2$Cl$_2$); FT-IR (neat) ν$_{max}$=3348, 2976, 2857, 1702, 1671, 1635, 1509, 1370, 1240, 1117, 1058, 856 cm$^{-1}$; $^1$H NMR (600 MHz, CD$_2$Cl$_2$) δ 6.25 (ddq, J=7.7, 5.7, 1.8 Hz, 1H), 6.18-6.12 (m, 2H), 5.91 (dd, J=11.6, 7.8 Hz, 1H), 5.70 (dd, J=11.6, 1.3 Hz, 1H), 3.94 (ddt, J=9.2, 4.6, 2.4 Hz, 1H), 3.66 (dt, J=16.2, 5.7 Hz, 5H), 3.59 (td, J=7.3, 2.7 Hz, 1H), 3.46 (t, J=4.9 Hz, 4H), 2.41-2.33 (m, 1H), 2.26 (dt, J=15.3, 7.5 Hz, 1H), 1.99-1.90 (m, 2H), 1.80 (td, J=5.0, 2.5 Hz, 1H), 1.70 (d, J=1.7 Hz, 3H), 1.41 (d, J=6.5 Hz, 3H), 1.26 (s, 12H), 1.15 (d, J=6.4 Hz, 3H), 1.01 (d, J=7.3 Hz, 3H) ppm; $^{13}$C NMR (151 MHz, CD$_2$Cl$_2$) δ 165.1, 155.0, 144.2, 141.1, 122.4, 83.4, 80.4, 76.1, 70.3, 66.8, 47.2, 44.4, 36.0, 32.5, 28.9, 25.0, 24.9, 20.4, 18.0, 15.2, 14.4 ppm; HRMS (ESI-TOF) calcd for C$_{27}$H$_{45}$BN$_2$O$_7$Na$^+$ [M+Na]$^+$ 542.3248, found 542.3254.

(2S,3Z)-5-{[2R,3R,5S,6S)-6-{(2E,4E)-5-[(3R,4R,5R,7S)-4-Hydroxy-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]-amino}-5-oxopent-3-en-2-yl morpholine-4-carboxylate (44)

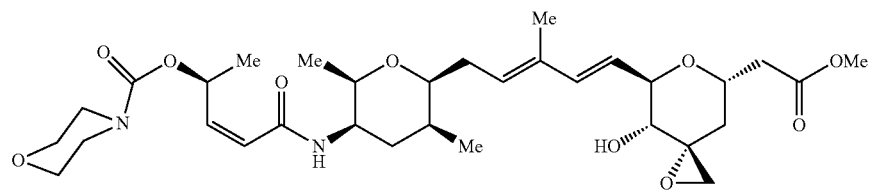

To a stirred solution of epoxide 6 (4.0 mg, 0.012 mmol, 1.5 equiv) and boronate 74 (4.0 mg, 7.7 µmol, 1.0 equiv) in rigorously degassed (freeze-pump-thaw technique×3) THF:H$_2$O (1 mL, 3:1, v/v) at 25° C. was added Pd(dppf)Cl$_2$.CH$_2$Cl$_2$ (1.3 mg, 1.5 µmol, 0.2 equiv) followed by Tl$_2$CO$_3$ (18 mg, 0.038 mmol, 5.0 equiv). After 6 h, the reaction mixture was filtered through a layer of Celite, and rinsed thoroughly with ethyl acetate (10 mL) and the combined organic layer was concentrated in vacuo. The obtained residue was purified by flash column chromatography (silica gel, 30→100% ethyl acetate in hexanes), and further purified by preparative thin layer chromatography (silica gel, 15% methanol in diethyl ether) to afford pure thailanstatin A analogue 44 (2.5 mg, 4.0 µmol, 53%) as a colorless oil. 44: R$_f$=0.30 (silica gel, ethyl acetate); [α]$_D^{22}$=+1.0 (c=0.3, CH$_2$Cl$_2$); FT-IR (neat) ν$_{max}$=3385, 2924, 2853, 1737, 1703, 1672, 1515, 1431, 1242, 1116, 1072, 810 cm$^{-1}$; $^1$H NMR (600 MHz, CDCl$_3$) δ 6.37 (d, J=15.8 Hz, 1H), 6.18-6.12 (m, 2H), 5.92 (dd, J=11.6, 7.8 Hz, 1H), 5.70 (dd, J=11.6, 1.3 Hz, 1H), 5.62 (dd, J=15.8, 6.2 Hz, 1H), 5.52 (t, J=7.2 Hz, 1H), 4.50 (p, J=5.5 Hz, 1H), 4.21 (t, J=6.8 Hz, 1H), 3.94 (dd, J=8.0, 3.8 Hz, 1H), 3.70 (s, 3H), 3.66 (dt, J=9.5, 3.6 Hz, 5H), 3.55-3.50 (m, 2H), 3.47 (t, J=4.8 Hz, 4H), 2.99 (d, J=4.6 Hz, 1H), 2.93 (dd, J=15.5, 7.9 Hz, 1H), 2.70 (dd, J=15.4, 6.5 Hz, 1H), 2.64 (d, J=4.6 Hz, 1H), 2.39 (dt, J=14.7, 7.1 Hz, 1H), 2.28-2.20 (m, 1H), 2.16 (dd, J=14.2, 5.2 Hz, 1H), 1.99-1.91 (m, 2H), 1.83 (d, J=8.5 Hz, 1H), 1.76 (s, 4H), 1.41 (d, J=6.5 Hz, 3H), 1.15 (d, J=6.4 Hz, 3H), 1.02 (d, J=7.4 Hz, 3H) ppm; $^{13}$C NMR (151 MHz, CDCl$_3$) δ 171.6, 165.1, 155.1, 144.3, 138.6, 134.7, 129.6, 123.1, 122.4, 80.9, 76.1, 75.8, 70.3, 69.86, 68.90, 66.8, 57.3, 52.0, 49.8, 47.2, 44.4, 38.2, 36.0, 34.7, 32.2, 29.1, 20.4, 18.0, 15.2, 12.8 ppm; HRMS (ESI-TOF) calcd for C$_{32}$H$_{48}$N$_2$O$_{10}$Na$^+$ [M+Na]$^+$ 643.3210, found 643.3208.

N-Cyclopropyl-2-{(2S,5S,6R)-5-hydroxy-6-[(E)-2-iodovinyl]-4-methylenetetrahydro-2H-pyran-2-yl}acetamide (75)

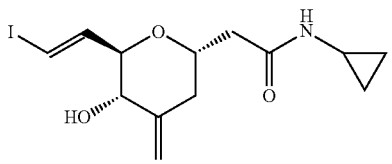

To a stirred solution of alcohol 16 (18 mg, 0.053 mmol, 1.0 equiv) in THF/H$_2$O (1 mL, 4:1) at 0° C. was added LiOH (10 mg, 0.43 mmol, 8.0 equiv), and the reaction mixture was allowed to slowly warm to 25° C. After 15 h, the reaction mixture was neutralized with phosphate buffer (NaH$_2$PO$_4$, 1.01 M, 5 mL) and the phases were separated. The aqueous layer was extracted with ethyl acetate (3×5 mL), and the combined organic layers were dried over anhydrous sodium sulfate and concentrated in vacuo, to afford crude acid which was dissolved in dichloromethane (1 mL) followed by the addition of NMM (0.018 mL, 0.16 mmol, 3.0 equiv), EDC.HCl (20 mg, 0.107 mmol, 2 equiv) and cyclopropylamine (8.0 µL, 0.107 mmol, 2.0 equiv) at 25° C. and allowed to stir for 15 h. After completion of the reaction the reaction mixture was quenched with water (5 mL) and the phases were separated. The aqueous layer was extracted with ethyl acetate (3×5 mL), and the combined organic layers were dried over anhydrous sodium sulfate and concentrated in vacuo. The obtained residue was purified by flash column chromatography (silica gel, 30→100% ethyl acetate in hexanes) to afford pure amide 75 (13 mg, 0.035 mmol, 68% for two steps) as a colorless oil. 75: R$_f$=0.50 (silica gel, ethyl acetate); [α]$_D^{22}$=+47.0 (c=0.5, MeOH); FT-IR (neat) ν$_{max}$=3319, 2919, 2878, 1649, 1536, 1430, 1092, 1072, 916 cm$^{-1}$; $^1$H NMR (600 MHz, CD$_3$OD) δ 6.64 (dd, J=14.6, 5.5 Hz, 1H), 6.52 (dd, J=14.6, 1.4 Hz, 1H), 5.12 (d, J=1.5 Hz, 1H), 4.94 (t, J=1.5 Hz, 1H), 4.24 (dq, J=8.9, 5.3 Hz, 1H), 4.03 (td, J=5.7, 1.4 Hz, 1H), 3.85 (dt, J=5.8, 1.2 Hz, 1H), 2.64 (ddq, J=5.2, 3.7, 1.8 Hz, 1H), 2.48 (dd, J=14.2, 8.9 Hz, 1H), 2.37 (dd, J=5.3, 3.1 Hz, 2H), 2.28-2.23 (m, 1H), 0.74-0.68 (m, 2H), 0.45 (qd, J=4.7, 3.3 Hz, 2H) ppm; $^{13}$C NMR (151 MHz, CD$_3$OD) δ (rotamers) 174.8, 174.7, 144.5, 111.3, 80.7, 80.3, 73.4, 71.5, 40.6, 40.6, 37.7, 23.4, 23.3, 6.6, 6.53, 6.47, 6.4 ppm; HRMS (ESI-TOF) calcd for C$_{13}$H$_{18}$INO$_3$Na$^+$ [M+Na]$^+$ 386.0224, found 386.0228.

N-Cyclopropyl-2-{(3R,5S,7R,8R)-8-hydroxy-7-[(E)-2-iodovinyl]-1,6-dioxaspiro[2.5]oct-5-yl}acetamide (76)

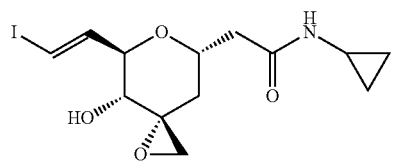

To a stirred solution of alcohol 75 (8 mg, 0.022 mmol, 1.0 equiv) in CH$_2$Cl$_2$ (1 mL) at 0° C. was added vanadyl acetoacetonate (0.6 mg, 2 µmol, 0.1 equiv) followed by a solution of tert-butyl hydroperoxide (5.5 M decanes, 0.01 mL, 0.044 mmol, 2.0 equiv), and the reaction mixture was allowed to slowly warm to 25° C. After 2 h, the reaction mixture was filtered through a short silica plug, rinsed thoroughly with ethyl acetate (15 mL), and concentrated in vacuo. The obtained residue was purified by flash column chromatography (silica gel, 1→5% methanol in ethyl acetate) to provide epoxide 76 (7.0 mg, 0.018 mmol, 87%) as a colorless oil. 76: R$_f$=0.20 (silica gel, ethyl acetate); [α]$_D^{22}$=+41.7 (c=0.4, MeOH); FT-IR (neat) ν$_{max}$=3303, 2919, 2851, 1645, 1548, 1425, 1359, 1196, 1096, 1075, 950 cm$^{-1}$; $^1$H NMR (600 MHz, CD$_3$CN) δ 6.65 (dd, J=14.6, 5.1 Hz, 1H), 6.58 (dd, J=14.7, 1.5 Hz, 1H), 6.53 (s, 1H), 4.33 (ddt, J=9.0, 7.2, 4.4 Hz, 1H), 4.19 (td, J=5.2, 1.5 Hz, 1H), 3.34 (dd, J=6.6, 5.2 Hz, 1H), 3.07 (d, J=6.7 Hz, 1H), 2.78 (dd, J=4.8, 0.9 Hz, 1H), 2.63 (td, J=7.2, 3.6 Hz, 1H), 2.60 (d, J=4.8 Hz, 1H), 2.47 (dd, J=14.7, 9.0 Hz, 1H), 2.26 (dd, J=14.7, 4.6 Hz, 1H), 1.81 (dd, J=13.5, 7.2 Hz, 1H), 1.65 (dd, J=13.5, 4.2 Hz, 1H), 0.67-0.61 (m, 2H), 0.40 (dtd, J=6.3, 3.8, 3.1, 1.6 Hz, 2H) ppm; $^{13}$C NMR (151 MHz, CD$_3$CN) δ 172.0, 143.9, 80.5, 79.7, 70.9, 69.9, 57.9, 51.0, 41.3, 34.8, 23.2, 6.44, 6.35 ppm; HRMS (ESI-TOF) calcd for C$_{13}$H$_{18}$INO$_4$Na$^+$ [M+Na]$^+$ 402.0173, found 402.0180.

Methyl {(5S,7R,8S)-8-hydroxy-7-[(E)-2-iodovinyl]-6-oxaspiro[2.5]oct-5-yl}acetate (77)

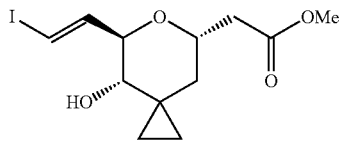

To a pre-cooled (0° C.) solution of ClCH$_2$I (0.014 mL, 0.19 mmol, 4.0 equiv) in dichloromethane (1 mL) was added diethylzinc (1.0 M solution in hexanes, 0.10 mL, 0.095 mmol, 2.0 equiv) and was stirred for 1 h. A solution of the vinyl iodide 16 (16 mg, 0.047 mmol) in dichloromethane (1 mL) was added drop wise to the reaction mixture at the same temperature. After 2 h, the reaction mixture was quenched with a saturated solution of ammonium chloride (5 mL) and extracted with EtOAc (2×10 mL). The combined organic layers were washed with brine (10 mL) and dried over anhydrous Na$_2$SO$_4$. Evaporation of the solvent gave the crude residue which on purification by flash column chromatography (silica gel, 10→30% ethyl acetate in hexanes) provided 77 (9 mg, 0.026 mmol, 54%) as a colorless oil. 77: R$_f$=0.30 (silica gel, 30% ethyl acetate in hexanes); $[\alpha]_D^{22}$=+36.3 (c=0.9, CH$_2$Cl$_2$); FT-IR (neat) $v_{max}$=3439, 2922, 2852, 1735, 1608, 1437, 1165, 1088, 1045, 946 cm$^{-1}$; $^1$H NMR (600 MHz, CDCl$_3$) δ 6.65 (dd, J=14.6, 5.6 Hz, 1H), 6.51 (dd, J=14.6, 1.7 Hz, 1H), 4.29 (dt, J=5.6, 2.1 Hz, 1H), 4.25 (dddd, J=10.8, 8.0, 4.9, 2.8 Hz, 1H), 3.64 (s, 3H), 2.85 (d, J=2.4 Hz, 1H), 2.57 (dd, J=15.6, 8.3 Hz, 1H), 2.37 (dd, J=15.6, 5.0 Hz, 1H), 1.95 (dd, J=13.5, 10.5 Hz, 1H), 0.86 (dd, J=13.6, 2.8 Hz, 1H), 0.52-0.43 (m, 3H), 0.31-0.24 (m, 1H) ppm; $^{13}$C NMR (151 MHz, CDCl$_3$) δ 171.6, 141.9, 80.9, 80.5, 74.6, 67.2, 51.9, 40.3, 35.3, 18.9, 11.4, 9.05 ppm; HRMS (ESI-TOF) calcd for C$_{12}$H$_{17}$IO$_4$Na$^+$ [M+Na]$^+$ 375.0064, found 375.0067.

Methyl 3-[({(2S,5S,6R)-5-hydroxy-6-[(E)-2-iodovinyl]-4-methylenetetrahydro-2H-pyran-2-yl}-acetyl)amino]propanoate (79)

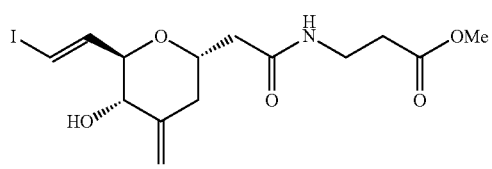

To a stirred solution of alcohol 16 (11 mg, 0.033 mmol, 1.0 equiv) in 4:1 THF/H$_2$O (1 mL) at 0° C. was added LiOH (6 mg, 0.26 mmol, 8.0 equiv), and the reaction mixture was allowed to slowly warm to 25° C. After 15 h, the reaction mixture was neutralized with phosphate buffer (NaH$_2$PO$_4$, 1.0 M, 5 mL) and the phases were separated. The aqueous layer was extracted with ethyl acetate (3×5 mL), and the combined organic layers were dried over anhydrous sodium sulfate and concentrated in vacuo, to afford crude acid which was dissolved in dichloromethane (1 mL) followed by the addition of NMM (0.013 mL, 0.12 mmol, 4.0 equiv), EDC.HCl (12 mg, 0.062 mmol, 2 equiv) and β-alanine methyl ester 78 (7 mg, 0.046 mmol, 1.5 equiv) at 25° C. and allowed to stir for 15 h. After completion of the reaction, the reaction mixture was quenched with water (5 mL) and the phases were separated. The aqueous layer was extracted with ethyl acetate (3×5 mL), and the combined organic layers were dried over anhydrous sodium sulfate and concentrated in vacuo. The obtained residue was purified by flash column chromatography (silica gel, 30→100% ethyl acetate in hexanes) to afford pure amide 79 (9 mg, 0.022 mmol, 72% for two steps) as a colorless oil. 79: R$_f$=0.50 (silica gel, ethyl acetate); $[\alpha]_D^{22}$=+40.9 (c=0.9, CH$_2$Cl$_2$); FT-IR (neat) $v_{max}$=3312, 2949, 1733, 1647, 1544, 1438, 1367, 1199, 1175, 1090, 908 cm$^{-1}$; $^1$H NMR (600 MHz, CDCl$_3$) δ 6.73 (s, 1H), 6.64 (dd, J=14.7, 6.0 Hz, 1H), 6.55 (dd, J=14.6, 1.2 Hz, 1H), 5.11 (s, 1H), 4.99 (s, 1H), 4.23-4.19 (m, 1H), 4.17 (dt, J=7.9, 3.9 Hz, 1H), 3.96 (d, J=4.3 Hz, 1H), 3.71 (s, 3H), 3.55 (dtd, J=13.5, 6.9, 5.1 Hz, 1H), 3.48 (dddd, J=13.6, 7.1, 5.9, 4.6 Hz, 1H), 2.59-2.50 (m, 2H), 2.48 (dd, J=15.2, 7.7 Hz, 1H), 2.43 (dd, J=13.8, 8.2 Hz, 1H), 2.38 (dd, J=15.3, 4.4 Hz, 1H), 2.31 (dd, J=13.7, 3.9 Hz, 1H), 2.02 (s, 1H) ppm; $^{13}$C NMR (151 MHz, CDCl$_3$) δ 173.2, 170.1, 141.9, 141.6, 112.6, 81.8, 80.2, 72.3, 69.3, 52.0, 40.8, 35.9, 34.8, 33.8 ppm; HRMS (ESI-TOF) calcd for C$_{14}$H$_{20}$INO$_5$Na$^+$ [M+Na]$^+$ 432.0278, found 432.0279.

Methyl 3-[{(3R,5S,7R,8R)-8-hydroxy-7-[(E)-2-iodovinyl]-1,6-dioxaspiro[2.5]oct-5-yl}acetyl)-amino]propanoate (80)

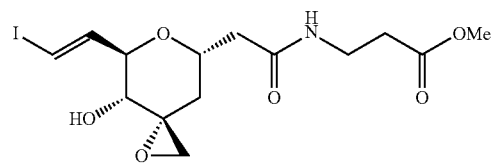

To a stirred solution of alcohol 79 (40 mg, 0.098 mmol, 1.0 equiv) in CH$_2$Cl$_2$ (3 mL) at 0° C. was added vanadyl acetoacetonate (2.6 mg, 0.01 mmol, 0.1 equiv) followed by a solution of tert-butyl hydroperoxide (5.5 M decanes, 0.04 mL, 0.19 mmol, 2.0 equiv), and the reaction mixture was allowed to slowly warm to 25° C. After 2 h, the reaction mixture was filtered through a short silica plug, rinsed thoroughly with ethyl acetate (30 mL), and concentrated in vacuo. The obtained residue was purified by flash column chromatography (silica gel, 1→5% methanol in ethyl acetate) to provide epoxide 80 (20 mg, 0.047 mmol, 49%) as a colorless oil. 80: R$_f$=0.60 (silica gel, 5% methanol in ethyl acetate); $[\alpha]_D^{25}$=+29.2 (c=1.0, CH$_2$Cl$_2$); FT-IR (neat) $v_{max}$=3349, 2951, 2925, 1732, 1647, 1547, 1438, 1368, 1198, 1177, 1072, 943 cm$^{-1}$; $^1$H NMR (600 MHz, CD$_3$CN) δ 6.65 (ddd, J=14.5, 5.1, 1.4 Hz, 2H), 6.57 (dt, J=14.6, 1.4 Hz, 1H), 4.32 (td, J=4.7, 2.5 Hz, 1H), 4.24-4.15 (m, 1H), 3.64 (s, 3H), 3.37 (dt, J=6.2, 1.6 Hz, 1H), 3.36-3.33 (m, 1H), 3.10 (t, J=6.3 Hz, 1H), 2.79 (d, J=4.8 Hz, 1H), 2.60 (dd, J=4.8, 1.3 Hz, 1H), 2.52 (ddd, J=14.7, 8.8, 1.5 Hz, 1H), 2.49-2.42 (m, 2H), 2.32 (ddd, J=14.8, 4.9, 1.4 Hz, 1H), 1.82 (dd, J=13.5, 7.1 Hz, 1H), 1.66 (dd, J=13.5, 3.7 Hz, 1H) ppm; $^{13}$C NMR (151 MHz, CD$_3$CN) δ 173.2, 171.0, 143.8, 80.6, 79.7, 70.9, 70.0, 57.9, 52.2, 51.0, 41.4, 35.8, 34.7 (2C) ppm; HRMS (ESI-TOF) calcd for C$_{14}$H$_{20}$INO$_6$Na$^+$ [M+Na]$^+$ 448.0228, found 448.0225.

Methyl {(3R,5S,7R,8R)-7-[(E)-2-iodovinyl]-8-[(methylcarbamoyl)oxy]-1,6-dioxaspiro[2.5]oct-5-yl}-acetate (81)

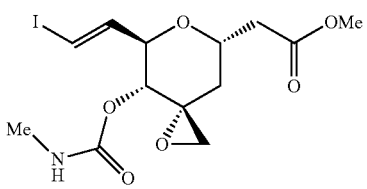

To a stirred solution of the alcohol 6 (10 mg, 0.028 mmol, 1.0 equiv) were added Et$_3$N (0.02 mL, 0.112 mmol, 4.0 equiv), DMAP (0.7 mg, 6 μmol, 0.2 equiv) and N,N'-carbonyldiimidazole (14 mg, 0.085 mmol, 3.0 equiv) in dichloromethane (1.5 mL) at 25° C. and allowed to stir for 2 h. After consumption of the starting material (monitored through TLC), a solution of methylamine (2.0 M in THF, 0.14 mL, 0.282 mmol, 10 equiv) was introduced into the reaction mixture and allowed to stir at 25° C. After 3 h, the reaction mixture was quenched with water (5 mL) and extracted with ethyl acetate (3×10 mL). The combined organic layer was washed with brine (10 mL), dried over anhydrous sodium sulfate, and concentrated in vacuo. The obtained residue was purified by flash column chromatography (silica gel, 10→60% ethyl acetate in hexanes) to afford pure carbamate 81 (9 mg, 0.022 mmol, 77%) as a white foam. 81: R$_f$=0.30 (silica gel, 50% ethyl acetate in hexanes); [α]$_D^{25}$=+51.1 (c=0.9, CH$_2$Cl$_2$); FT-IR (neat) ν$_{max}$=3366, 2952, 2924, 1725, 1528, 1259, 1164, 1134, 1007, 946, 820 cm$^{-1}$; $^1$H NMR (600 MHz, CDCl$_3$) δ 6.57 (dd, J=14.7, 1.5 Hz, 1H), 6.50 (dd, J=14.7, 4.9 Hz, 1H), 4.72 (d, J=6.2 Hz, 1H), 4.47-4.44 (m, 1H), 4.43 (d, J=3.9 Hz, 1H), 4.35 (dtd, J=8.7, 5.2, 2.6 Hz, 1H), 3.64 (s, 3H), 2.75-2.71 (m, 4H), 2.71-2.66 (m, 2H), 2.48 (dd, J=15.7, 5.0 Hz, 1H), 1.99-1.93 (m, 1H), 1.53-1.49 (m, 1H) ppm; $^{13}$C NMR (151 MHz, CDCl$_3$) δ 171.2, 156.0, 140.4, 81.5, 78.0, 72.7, 68.4, 55.5, 52.1, 51.9, 39.7, 34.6, 27.7 ppm; HRMS (ESI-TOF) calcd for C$_{13}$H$_{18}$INO$_6$Na$^+$ [M+Na]$^+$ 434.0071, found 434.0079.

Methyl {(3R,5S,7R,8R)-8-acetoxy-7-[(E)-2-iodovinyl]-1,6-dioxaspiro[2.5]oct-5-yl}acetate (82)

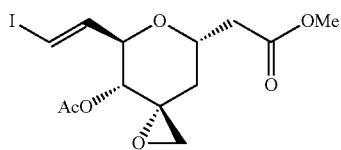

To a stirred solution of 6 (10 mg, 0.028 mmol, 1.0 equiv) in CH$_2$Cl$_2$ (1 mL) was added triethylamine (0.012 mL, 0.085 mmol, 3.0 equiv), followed by acetic anhydride (5 μL 0.056 mmol, 2.0 equiv) and DMAP (0.3 mg, 2.8 μmol, 0.1 equiv) at 25° C. After 1 h, the reaction mixture was quenched with a saturated aqueous solution of ammonium chloride (5 mL), and the phases were separated. The aqueous layer was extracted with ethyl acetate (3×5 mL), and the combined organic layers were dried over anhydrous sodium sulfate and concentrated in vacuo. The obtained residue was purified by flash column chromatography (silica gel, 10→40% ethyl acetate in hexanes) to provide acetate 82 (9 mg, 0.023 mmol, 81%) as a colorless oil. 82: R$_f$=0.50 (silica gel, 40% ethyl acetate in hexanes); [α]$_D^{25}$=+48.5 (c=0.9, CH$_2$Cl$_2$); FT-IR (neat) ν$_{max}$=2952, 2925, 2848, 1735, 1605, 1437, 1371, 1235, 1163, 102, 944, 816 cm$^{-1}$; $^1$H NMR (600 MHz, CDCl$_3$) δ 6.67 (ddd, J=14.7, 1.8, 1.0 Hz, 1H), 6.56 (ddd, J=14.8, 4.9, 1.0 Hz, 1H), 4.54-4.52 (m, 1H), 4.51 (tt, J=4.5, 2.0 Hz, 1H), 4.42 (dtd, J=12.2, 8.2, 4.0 Hz, 1H), 3.72 (s, 3H), 2.78 (qd, J=4.5, 2.1 Hz, 2H), 2.76-2.72 (m, 1H), 2.54 (ddd, J=15.8, 4.8, 0.9 Hz, 1H), 2.18-2.14 (m, 1H), 2.13 (s, 3H), 1.49 (dd, J=13.3, 3.2 Hz, 1H) ppm; $^{13}$C NMR (151 MHz, CDCl$_3$) δ 171.1, 140.1, 81.7, 78.2, 77.2, 72.8, 68.2, 55.2, 52.2, 52.1, 39.9, 34.4, 21.2 ppm; HRMS (ESI-TOF) calcd for C$_{13}$H$_{17}$IO$_6$Na$^+$ [M+Na]$^+$ 418.9962, found 418.9965.

tert-Butyl({(2R,3S,6R)-2-[(E)-2-iodovinyl]-6-methyl-4-methylenetetrahydro-2H-pyran-3-yl}oxy)di-methylsilane (84)

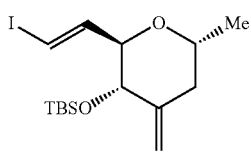

To a stirred solution of ester 15 (95 mg, 0.210 mmol, 1.0 equiv) in THF/H$_2$O (3 mL, 4:1) at 0° C. was added LiOH (40 mg, 1.681 mmol, 8.0 equiv), and the reaction mixture was allowed to slowly warm to 25° C. After 15 h, the reaction mixture was neutralized with phosphate buffer (NaH$_2$PO$_4$, 1.01 M, 5 mL) and the phases were separated. The aqueous layer was extracted with ethyl acetate (3×5 mL), and the combined organic layers were dried over anhydrous sodium sulfate and concentrated in vacuo, to afford crude acid which was dissolved in dichloromethane (2 mL) followed by addition of oxalyl chloride (0.05 mL, 0.546 mmol, 3.0 equiv), at 25° C. and allowed to stir for 20 min. The volatiles were evaporated in vacuo to afford acid chloride which was used as such in the next reaction.

To a stirred solution of 2-mercaptopyridine-N-oxide sodium salt (40 mg, 0.273 mmol, 1.5 equiv), DMAP (2 mg, 0.018 mmol, 0.1 equiv), and tert-butyl mercaptan (83) (0.2 mL, 1.82 mmol, 10 eq) in benzene (3 mL) was added a solution of acid chloride (obtained above) in benzene (2 mL) at 25° C. while irradiating with a 400 W tungsten lamp. After 1 h, the volatiles were evaporated off in vacuo and the obtained residue was purified by flash column chromatography (silica gel, 2% diethyl ether in hexanes) to afford vinyl iodide 84 (36 mg, 0.082 mmol, 51% for three steps) as a colorless oil. 84: R$_f$=0.40 (silica gel, 2% ethyl acetate in hexanes); [α]$_D^{25}$=+93.0 (c=1.0, CH$_2$Cl$_2$); FT-IR (neat) ν$_{max}$=2954, 2929, 2857, 1613, 1377, 1253, 1117, 902, 837 cm$^{-1}$; $^1$H NMR (600 MHz, CDCl$_3$) δ 6.56 (dd, J=14.5, 6.6 Hz, 1H), 6.36 (dd, J=14.5, 1.2 Hz, 1H), 5.07 (d, J=2.3 Hz, 1H), 4.83 (d, J=1.9 Hz, 1H), 4.14-4.07 (m, 1H), 3.87-3.82 (m, 1H), 3.73 (dt, J=7.4, 1.5 Hz, 1H), 2.43 (dd, J=13.2, 5.4 Hz, 1H), 2.16 (dd, J=13.2, 3.4 Hz, 1H), 1.14 (d, J=6.6 Hz, 3H), 0.89 (s, 9H), 0.04 (s, 3H), −0.00 (s, 3H) ppm; $^{13}$C NMR (151 MHz, CDCl$_3$) δ 144.5, 143.5, 109.9, 80.1, 79.4, 74.2, 69.7, 39.4, 26.0, 18.4, 17.9, −4.5, −4.6 ppm; HRMS (ESI-TOF) calcd for $C_{15}H_{27}IO_2SiNa^+$ [M+Na]$^+$ 417.0717, found 417.0722.

(2R,3S,6R)-2-[(E)-2-Iodovinyl]-6-methyl-4-methyl-enetetrahydro-2H-pyran-3-ol (85)

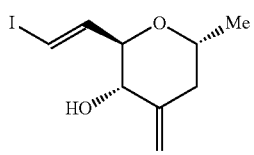

To a stirred solution of vinyl iodide 84 (33 mg, 0.084 mmol, 1.0 equiv) in THF (3 mL) at 0° C. was added tetra-n-butylammonium fluoride (1.0 M in THF, 0.11 mL, 0.114 mmol, 1.5 equiv), and the reaction mixture was allowed to slowly warm to 25° C. After 2 h, the reaction mixture was quenched with a saturated aqueous solution of ammonium chloride (5 mL), and the two phases were separated. The aqueous layer was extracted with ethyl acetate (3×5 mL), and the combined organic layers were dried over anhydrous sodium sulfate and concentrated in vacuo. The obtained residue was purified by flash column chromatography (10→25% ethyl acetate in hexanes) to afford pure alcohol 85 (21 mg, 0.075 mmol, 93%) as a white amorphous solid. 85: $R_f$=0.60 (silica gel, 25% ethyl acetate in hexanes); $[\alpha]_D^{25}$=+77.7 (c=1.0, CH$_2$Cl$_2$); FT-IR (neat) $\nu_{max}$=3410, 2971, 2929, 2902, 1655, 1610, 1379, 1133, 1112, 1090, 1074, 1034, 907, 816 cm$^{-1}$; $^1$H NMR (600 MHz, CDCl$_3$) δ 6.68 (ddd, J=14.7, 6.4, 1.5 Hz, 1H), 6.50 (dq, J=14.6, 1.3 Hz, 1H), 5.10 (d, J=1.8 Hz, 1H), 4.95 (dq, J=2.5, 1.3 Hz, 1H), 4.12-4.06 (m, 1H), 4.02 (td, J=6.4, 4.1 Hz, 1H), 3.92-3.86 (m, 1H), 2.37 (dd, J=13.6, 4.2 Hz, 1H), 2.30-2.25 (m, 1H), 1.85 (s, 1H), 1.20 (d, J=6.4 Hz, 3H) ppm; $^{13}$C NMR (151 MHz, CDCl$_3$) δ 143.2, 142.7, 111.2, 81.2, 79.5, 72.8, 68.9, 38.5, 19.4 ppm; HRMS (ESI-TOF) calcd for $C_{11}H_{15}O_4INa^+$ [M+Na]$^+$ 360.9913, found 360.9909.

(3R,4R,5R,7R)-5-[(E)-2-Iodovinyl]-7-methyl-1,6-dioxaspiro[2.5]octan-4-ol (86)

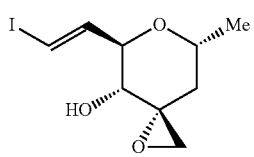

To a stirred solution of alcohol 85 (11 mg, 39 μmol, 1.0 equiv) in CH$_2$Cl$_2$ (1.5 mL) at 0° C. was added vanadyl acetoacetonate (1.0 mg, 4.0 μmol, 0.1 equiv) followed by a solution of tert-butyl hydroperoxide (5.5 M decanes, 0.02 mL, 0.118 mmol, 3.0 equiv), and the reaction mixture was allowed to slowly warm to 25° C. After 1.5 h, the reaction mixture was filtered through a short silica plug, rinsed thoroughly with ethyl acetate (10 mL), and concentrated in vacuo. The obtained residue was purified by flash column chromatography (silica gel, 15→40% ethyl acetate in hexanes) to provide epoxide 86 (9.5 mg, 0.032 mmol, 82%) as a white amorphous solid. 86: $R_f$=0.30 (silica gel, 25% ethyl acetate in hexanes); $[\alpha]_D^{25}$=+68.6 (c=0.5, CH$_2$Cl$_2$); FT-IR (neat) $\nu_{max}$=3427, 2972, 2927, 1609, 1382, 1296, 1201, 1172, 1105, 1085, 1044, 953, 818 cm$^{-1}$; $^1$H NMR (600 MHz, CDCl$_3$) δ 6.68 (dd, J=14.6, 5.3 Hz, 1H), 6.43 (dd, J=14.6, 1.5 Hz, 1H), 4.19-4.11 (m, 1H), 4.06 (ddd, J=7.2, 5.3, 1.5 Hz, 1H), 3.39 (t, J=7.9 Hz, 1H), 2.88 (d, J=4.5 Hz, 1H), 2.54 (d, J=4.5 Hz, 1H), 2.04 (ddd, J=14.1, 5.2, 1.4 Hz, 1H), 1.88 (d, J=8.8 Hz, 1H), 1.59-1.55 (m, 1H), 1.29 (d, J=6.7 Hz, 3H) ppm; $^{13}$C NMR (151 MHz, CDCl$_3$) δ 143.1, 79.8, 77.3, 77.1, 76.9, 76.2, 69.3, 68.5, 57.3, 49.4, 36.0, 19.2 ppm; HRMS (ESI-TOF) calcd for $C_{11}H_{15}IO_5Na^+$ [M+Na]$^+$ 376.9862, found 376.9859.

Methyl 3,7-anhydro-6-O-[tert-butyl(dimethyl)silyl]-2,4-dideoxy-D-arabino-oct-5-ulosonate (88)

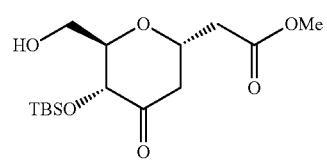

To a stirred solution of bis-TBS protected ketone 11 (1.76 g, 4.68 mmol, 1.0 equiv) in dichloromethane (94 mL) at 0° C. was added trifluoroacetic acid (3.58 mL, 46.8 mmol, 10 equiv), and the reaction mixture was allowed to slowly warm to 25° C. After stirring for 7 h, the reaction mixture was quenched with a saturated aqueous solution of sodium bicarbonate (100 mL), and the two phases were separated. The aqueous layer was extracted with ethyl acetate (3×20 mL), and the combined organic layers were dried over anhydrous sodium sulfate and concentrated under reduced pressure. The obtained residue was purified by flash column chromatography (silica gel, 40% ethyl acetate in hexanes) to afford pure alcohol 88 (1.21 g, 3.65 mmol, 78%) as a colorless oil. 88: $R_f$=0.33 (silica gel, 40% ethyl acetate in hexanes); $[\alpha]_D^{22}$=±64.8 (c=1.0, CH$_2$Cl$_2$); FT-IR (neat) $\nu_{max}$ 3500, 2954, 2930, 2887, 2857, 1731, 1472, 1463, 1438, 1388, 1361, 1318, 1254, 1190, 1168, 1135, 1074, 1047, 1030, 1006, 939, 839, 780, 703, 672 cm$^{-1}$; $^1$H NMR (600 MHz, CDCl$_3$) δ=4.84 (m, 1H), 4.34 (d, J=8.9 Hz, 1H), 3.85-3.74 (m, 3H), 3.70 (s, 3H), 2.81 (dd, J=14.5, 6.5 Hz, 1H), 2.69 (dd, J=15.7, 9.2 Hz, 1H), 2.48 (dd, J=15.7, 5.6 Hz, 1H), 2.45 (dd, J=14.5, 3.5 Hz, 1H), 2.22 (dd, J=6.6, 6.4 Hz, 1H), 0.91 (s, 9H), 0.15 (s, 3H), 0.04 (s, 3H) ppm; $^{13}$C NMR (151 MHz, CDCl$_3$) δ=205.6, 170.9, 77.7, 74.5, 71.0, 62.3, 52.2, 44.9, 37.6, 25.9, 18.6, −4.25, −5.47 ppm; HRMS (ESI) calcd for $C_{15}H_{29}O_6Si^+$ [M+H]$^+$ 333.1728, found 333.1730.

Methyl {(2S,5R,6R)-5-{[tert-butyl(dimethyl)silyl]oxy}-6-[(E)-2-iodovinyl]-4-oxotetrahydro-2H-pyran-2-yl}acetate (89)

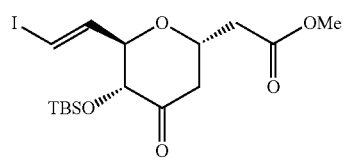

To a stirred solution of oxalyl chloride (63 μL, 0.73 mmol, 1.5 equiv) in dichloromethane (1.3 mL) at 78° C. was slowly added dimethyl sulfoxide (0.10 mL, 1.46 mmol, 3.0 equiv), and the reaction mixture was allowed to slowly warm to 60° C. over an additional 20 min. Then a solution of alcohol 88 (161 mg, 0.484 mmol, 1.0 equiv) in dichloromethane (0.83 mL) was added dropwise via cannula, and the original flask was rinsed with additional dichloromethane (3×0.2 mL). The stirred reaction mixture was allowed to slowly warm to 45° C. over 30 min, at which point N,N'-diisopropylethylamine (0.49 mL, 2.8 mmol, 5.8 equiv) was added dropwise over 1 min, and the reaction mixture was allowed to warm to 0° C. Then the reaction mixture was quenched with a saturated aqueous solution of ammonium chloride (10 mL), and the two phases were separated. The aqueous layer was extracted with ethyl acetate (3×5 mL), and the combined organic layers were dried over anhydrous sodium sulfate and concentrated under reduced pressure. Due to product instability, the obtained crude aldehyde was used directly in the following step.

To a stirred solution of anhydrous chromium(II) chloride (359 mg, 2.92 mmol, 6.0 equiv) and iodoform (575 mg, 1.46 mmol, 3.0 equiv) in tetrahydrofuran (48 mL) at 25° C. was added a solution of crude aldehyde (ca 159 mg, 0.484 mmol, 1.0 equiv) in tetrahydrofuran (5.2 mL) dropwise via cannula, and the original flask was rinsed with additional tetrahydrofuran (3×0.3 mL). After stirring for 3 h, the reaction mixture was quenched with water (25 mL) and filtered through Celite. The two phases were separated, and the aqueous layer was extracted with diethyl ether (3×10 mL). The combined organic layers were dried over anhydrous sodium sulfate and concentrated in vacuo. The obtained residue was purified by flash column chromatography (silica gel, 3→10% ethyl acetate in hexanes) to afford pure vinyl iodide 89 (1.21 g, 3.65 mmol, 20% over two steps) as a colorless oil. 89: $R_f$=0.14 (silica gel, 10% ethyl acetate in hexanes); $[\alpha]_D^{22}$=+42.5 (c=1.0, $CH_2Cl_2$); FT-IR (neat) $v_{max}$ 2953, 2929, 2887, 2856, 1733, 1615, 1471, 1462, 1437, 1387, 1361, 1317, 1254, 1219, 1172, 1135, 1092, 1006, 940, 917, 837, 780, 672 $cm^{-1}$; $^1$H NMR (600 MHz, $CDCl_3$) δ=6.63 (dd, J=14.6, 5.8 Hz, 1H), 6.52 (dd, J=14.6, 0.7 Hz, 1H), 4.77 (ddd, J=8.5, 5.8, 0.7 Hz, 1H), 4.14 (dd, J=8.2, 6.4 Hz, 1H), 3.98 (d, J=8.5 Hz, 1H), 3.69 (s, 3H), 2.81 (dd, J=14.2, 6.4 Hz, 1H), 2.68 (dd, J=15.3, 8.2 Hz, 1H), 2.50 (dd, J=14.2, 3.3 Hz, 1H), 2.48 (dd, J=15.3, 6.5 Hz, 1H), 0.91 (s, 9H), 0.12 (s, 3H), 0.03 (s, 3H) ppm; $^{13}$C NMR (151 MHz, $CDCl_3$) δ=204.1, 170.4, 142.4, 80.9, 79.8, 77.9, 71.2, 52.2, 45.0, 37.9, 25.8, 18.6, −4.4, −5.2 ppm; HRMS (ESI) calcd for $C_{16}H_{27}IO_5SiNa^+$ $[M+Na]^+$ 477.0565, found 477.0570.

Methyl {(2S,5R,6R)-5-hydroxy-6-[(E)-2-iodovinyl]-4-oxotetrahydro-2H-pyran-2-yl}acetate (90)

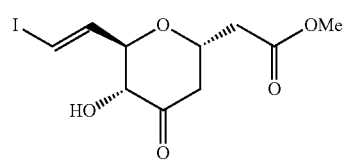

90

To a stirred solution of vinyl iodide 89 (25 mg, 55 μmol, 1.0 equiv) in tetrahydrofuran (1.5 mL) at 0° C. was added hydrogen fluoride pyridine complex (70%, 0.20 mL, 7.7 mmol, excess), and the reaction mixture was allowed to slowly warm to 25° C. After stirring for 20 h, the reaction mixture was carefully quenched with a saturated aqueous solution of sodium bicarbonate (20 mL), and the two phases were separated. The aqueous layer was extracted with ethyl acetate (3×10 mL), and the combined organic layers were dried over anhydrous sodium sulfate and concentrated in vacuo. The obtained residue was purified by flash column chromatography (silica gel, 40% ethyl acetate in hexanes) to afford pure α-hydroxy ketone 90 (18.1 mg, 53.2 μmol, 96%) as a colorless oil. 90: $R_f$=0.33 (silica gel, 40% ethyl acetate in hexanes); $[\alpha]_D^{22}$=−28.8 (c=1.0, $CH_2Cl_2$); FT-IR (neat) $v_{max}$ 3456, 3073, 2952, 2921, 2850, 1725, 1613, 1554, 1437, 1384, 1358, 1319, 1263, 1226, 1170, 1105, 1005, 953, 913, 849, 785, 752, 711, 667 $cm^{-1}$; $^1$H NMR (600 MHz, $CDCl_3$) δ=6.74 (dd, J=14.6, 4.8 Hz, 1H), 6.58 (dd, J=14.6, 1.2 Hz, 1H), 4.89 (qd, J=7.4, 1.9 Hz, 1H), 4.01 (br d, J=9.6 Hz, 1H), 3.98 (ddd, J=9.6, 4.8, 0.9 Hz, 1H), 3.70 (s, 3H), 3.58 (br s, 1H), 2.98 (ddd, J=14.4, 7.2, 0.7 Hz, 1H), 2.64 (dd, J=15.4, 8.2 Hz, 1H), 2.57 (dd, J=14.4, 2.0 Hz, 1H), 2.47 (dd, J=15.4, 6.9 Hz, 1H) ppm; $^{13}$C NMR (151 MHz, $CDCl_3$) δ=206.0, 170.1, 141.9, 80.2, 79.1, 76.5, 71.5, 52.3, 44.0, 37.4 ppm; HRMS (ESI) calcd for $C_{10}H_{14}IO_5^+$ $[M+H]^+$ 340.9880, found 340.9883.

(2S,3Z)-5-({(2R,3R,5S,6S)-6-[(2E,4E)-5-{(3R,4R,5R,7S)-7-[2-(Cyclopropylamino)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (31)

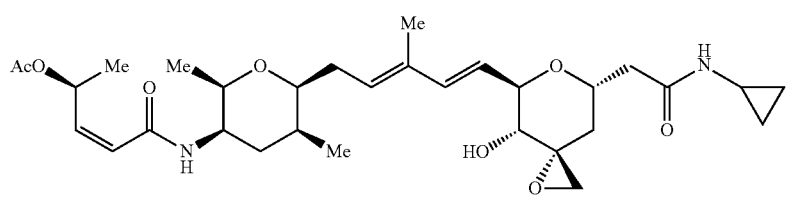

31

To a stirred solution of epoxide 76 (4.0 mg, 11 μmol, 1.0 equiv) and boronate 5 (7.0 mg, 16 μmol, 1.5 equiv) in rigorously degassed (freeze-pump-thaw technique×3) THF:H$_2$O (1 mL, 3:1, v/v) at 25° C. was added Pd(dppf)Cl$_2$·CH$_2$Cl$_2$ (1.0 mg, 1.1 μmol, 0.1 equiv) followed by Tl$_2$CO$_3$ (24 mg, 0.053 mmol, 5.0 equiv). After 3 h, the reaction mixture was filtered through a layer of Celite, and rinsed thoroughly with ethyl acetate (15 mL) and the combined organic layer was concentrated in vacuo. The obtained residue was purified by flash column chromatography (silica gel, 5% methanol in ethyl acetate), and further purified by preparative thin layer chromatography (silica gel, 5% methanol in 1:1 mixture of diethyl ether/dichloromethane) to afford pure thailanstatin A analogue 31 (3.4 mg, 5.9 μmol, 54%) as a colorless oil. 31: R$_f$=0.25 (silica gel, 5% methanol in ethyl acetate); [α]$_D^{22}$=+1.0 (c=0.3, CH$_2$Cl$_2$); FT-IR (neat) $v_{max}$=3325, 2982, 2933, 1724, 1659, 1534, 1371, 1246, 1050, 814, 700 cm$^{-1}$; $^1$H NMR (600 MHz, CDCl$_3$) δ6.39-6.29 (m, 2H), 6.26 (tt, J=6.8, 5.6 Hz, 1H), 6.00 (d, J=9.1 Hz, 1H), 5.89 (dd, J=11.6, 7.9 Hz, 1H), 5.71 (dd, J=11.6, 1.3 Hz, 1H), 5.62 (dd, J=15.8, 6.3 Hz, 1H), 5.53 (t, J=7.3 Hz, 1H), 4.40 (dd, J=8.3, 5.0 Hz, 1H), 4.24 (t, J=6.3 Hz, 1H), 3.94 (ddd, J=9.3, 4.3, 2.3 Hz, 1H), 3.67 (qd, J=6.3, 2.3 Hz, 1H), 3.53 (td, J=7.2, 2.7 Hz, 1H), 3.49 (t, J=6.5 Hz, 1H), 2.97 (d, J=4.5 Hz, 1H), 2.72 (dt, J=7.2, 3.6 Hz, 1H), 2.70-2.64 (m, 2H), 2.50 (dd, J=14.9, 5.6 Hz, 1H), 2.40 (dt, J=14.5, 7.0 Hz, 1H), 2.24 (dt, J=15.0, 7.4 Hz, 1H), 2.04 (s, 3H), 1.98-1.92 (m, 4H), 1.84 (dd, J=14.0, 5.7 Hz, 1H), 1.76 (s, 3H), 1.39 (d, J=6.5 Hz, 4H), 1.15 (d, J=6.4 Hz, 3H), 1.02 (d, J=7.4 Hz, 3H), 0.77-0.72 (m, 2H), 0.45 (dt, J=6.8, 2.5 Hz, 2H) ppm; $^{13}$C NMR (151 MHz, CDCl$_3$) δ 171.8, 170.5, 165.0, 143.8, 138.9, 134.4, 130.1, 122.6, 122.4, 80.9, 76.4, 76.1, 70.5, 69.1, 69.0, 57.5, 50.7, 47.2, 40.3, 36.0, 34.3, 32.2, 29.2, 22.6, 21.4, 20.1, 18.0, 15.2, 12.8, 6.7 ppm;

HRMS (ESI-TOF) calcd for C$_{31}$H$_{46}$N$_2$O$_8$Na$^+$ [M+Na]$^+$ 597.3146, found 597.3147.

Ethyl 3-({[(3R,5S,7R,8R)-7-{(1E,3E)-5-[(2S,3R,5R,6R)-5-{[(2Z,4S)-4-acetoxypent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)propanoate (33)

33

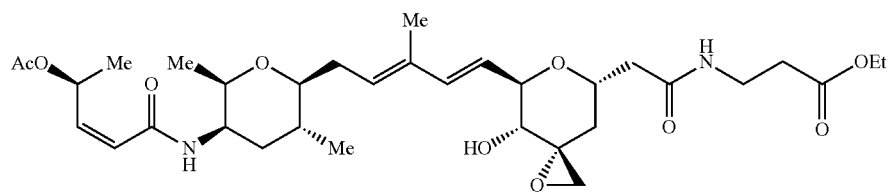

To a stirred solution of epoxide 80 (5.0 mg, 0.012 mmol, 1.0 equiv) and boronate 60 (8.0 mg, 18 µmol, 1.5 equiv) in rigorously degassed (freeze-pump-thaw technique×3) THF: H$_2$O (1 mL, 3:1, v/v) at 25° C. was added Pd(dppf) Cl$_2$·CH$_2$Cl$_2$ (2.0 mg, 2.4 µmol, 0.2 equiv) followed by Tl$_2$CO$_3$ (28 mg, 59 µmol, 5.0 equiv). After 3 h, the reaction mixture was filtered through a layer of Celite, and rinsed thoroughly with ethyl acetate (20 mL) and the combined organic layer was concentrated in vacuo. The obtained residue was purified by flash column chromatography (silica gel, 5% methanol in ethyl acetate), and further purified by preparative thin layer chromatography (silica gel, 5% methanol in 1:1 mixture of diethyl ether/dichloromethane) to afford pure thailanstatin A analogue 33 (3.5 mg, 5.5 µmol, 47%) as a colorless oil. 33: R$_f$=0.25 (silica gel, 5% methanol in 1:1 mixture of diethyl ether/dichloromethane); [α]$_D^{25}$=−35.4 (c=0.35, CH$_2$Cl$_2$); FT-IR (neat) $v_{max}$=3319, 2927, 2854, 1735, 1658, 1530, 1439, 1370, 1244, 1072, 1050, 971, 814 cm$^{-1}$; $^1$H NMR (600 MHz, CD$_2$Cl$_2$) δ 6.55 (s, 1H), 6.45 (d, J=9.2 Hz, 1H), 6.37 (d, J=15.8 Hz, 1H), 6.18-6.12 (m, 1H), 5.85 (dd, J=11.6, 7.8 Hz, 1H), 5.79 (dd, J=11.6, 1.1 Hz, 1H), 5.70 (t, J=7.0 Hz, 1H), 5.60 (dd, J=15.8, 6.2 Hz, 1H), 4.37 (dq, J=7.9, 5.5 Hz, 1H), 4.25 (t, J=6.0 Hz, 1H), 4.00-3.94 (m, 1H), 3.66 (s, 3H), 3.59 (qd, J=6.4, 1.8 Hz, 1H), 3.48 (d, J=6.3 Hz, 1H), 3.48-3.42 (m, 2H), 3.08 (ddd, J=10.5, 7.8, 3.1 Hz, 1H), 2.91 (d, J=4.6 Hz, 1H), 2.67 (d, J=4.6 Hz, 1H), 2.60 (dd, J=14.6, 7.9 Hz, 1H), 2.53-2.47 (m, 4H), 2.27 (dt, J=15.5, 7.5 Hz, 1H), 2.02 (s, 3H), 1.92-1.89 (m, 1H), 1.87-1.83 (m, 2H), 1.75 (s, 3H), 1.55-1.51 (m, 1H), 1.45-1.41 (m, 1H), 1.34 (d, J=6.4 Hz, 3H), 1.08 (d, J=6.4 Hz, 3H), 0.84 (d, J=6.5 Hz, 3H) ppm; $^{13}$C NMR (151 MHz, CD$_2$Cl$_2$) δ 173.1, 170.8, 170.4, 165.2, 142.7, 138.9, 134.3, 131.1, 123.4, 122.6, 84.2, 77.1, 75.3, 71.2, 69.1, 69.1, 57.6, 52.1, 51.0, 48.4, 41.0, 38.5, 35.2, 34.4, 34.3, 32.3, 30.3, 21.4, 20.3, 18.1, 17.5, 12.7 ppm; HRMS (ESI-TOF) calcd for C$_{32}$H$_{48}$N$_2$O$_{10}$Na$^+$ [M+Na]$^+$ 643.3201, found 643.3215.

Ethyl 3-({[(3R,5S,7R,8R)-7-{(1E,3E)-5-[(2S,3S,5R, 6R)-5-{[(2Z,4S)-4-acetoxypent-2-enoyl]amino}-3,6-dimethyltetrahydro-2H-pyran-2-yl]-3-methylpenta-1, 3-dien-1-yl}-8-hydroxy-1,6-dioxaspiro-[2.5]oct-5-yl]acetyl}amino)propanoatee (35)

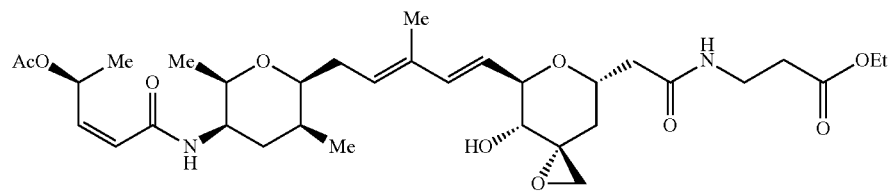

35

To a stirred solution of epoxide 80 (7.0 mg, 0.017 mmol, 1.5 equiv) and boronate 5 (5.0 mg, 11 µmol, 1.0 equiv) in rigorously degassed (freeze-pump-thaw technique×3) THF: H$_2$O (1.5 mL, 3:1, v/v) at 25° C. was added Pd(dppf) Cl$_2$·CH$_2$Cl$_2$ (2.0 mg, 2.2 µmol, 0.2 equiv) followed by Tl$_2$CO$_3$ (26 mg, 56 µmol, 5.0 equiv). After 3 h, the reaction mixture was filtered through a layer of Celite, and rinsed thoroughly with ethyl acetate (20 mL) and the combined organic layer was concentrated in vacuo. The obtained residue was purified by flash column chromatography (silica gel, 5% methanol in ethyl acetate), and further purified by preparative thin layer chromatography (silica gel, 5% methanol in 1:1 mixture of diethyl ether/dichloromethane) to afford pure thailanstatin A analogue 35 (3.0 mg, 5.8 µmol, 43%) as a colorless oil. 35: R$_f$=0.50 (silica gel, 5% methanol in ethyl acetate); [α]$_D^{25}$=−10.7 (c=0.30, CH$_2$Cl$_2$); FT-IR (neat) $v_{max}$=3351, 2925, 2855, 1736, 1662, 1641, 1527, 1370, 1245, 1052, 974, 815 cm$^{-1}$; $^1$H NMR (600 MHz, CDCl$_3$) δ 6.57 (s, 1H), 6.29 (d, J=15.7 Hz, 1H), 6.19 (ddd, J=7.9, 6.5, 1.4 Hz, 1H), 5.93 (d, J=9.1 Hz, 1H), 5.82 (dd, J=11.6, 7.9 Hz, 1H), 5.64 (dd, J=11.6, 1.3 Hz, 1H), 5.56 (dd, J=15.8, 6.3 Hz, 1H), 5.45 (t, J=7.2 Hz, 1H), 4.36 (p, J=6.0 Hz, 1H), 4.17 (t, J=6.4 Hz, 1H), 3.87 (d, J=9.1 Hz, 1H), 3.64 (d, J=4.8 Hz, 1H), 3.62 (s, 3H), 3.60 (dd, J=6.5, 2.2 Hz, 1H), 3.48-3.41 (m, 5H), 2.90 (d, J=4.5 Hz, 1H), 2.63 (d, J=4.6 Hz, 1H), 2.61-2.58 (m, 1H), 2.52 (dd, J=14.6, 6.3 Hz, 1H), 2.47-2.45 (m, 2H), 2.32 (dt, J=14.5, 6.9 Hz, 1H), 2.17 (dt, J=15.1, 7.4 Hz, 1H), 1.97 (s, 4H), 1.92 (d, J=5.1 Hz, 1H), 1.89 (d, J=3.0 Hz, 2H), 1.79-1.75 (m, 1H), 1.69 (s, 4H), 1.32 (d, J=6.6 Hz, 4H), 1.08 (d, J=6.4 Hz, 4H), 0.95 (d, J=7.3 Hz, 3H) ppm; $^{13}$C NMR (151 MHz, CDCl$_3$) δ 173.0, 170.5, 170.4, 165.0, 143.8, 138.7, 134.5, 129.9, 122.7, 122.6, 80.9, 76.5, 76.1, 70.4, 69.1, 69.0, 57.5, 52.0, 50.6, 47.2, 40.5, 36.0, 35.0, 34.1, 34.0, 32.2, 29.1, 21.4, 20.1, 18.0, 15.2, 12.8 ppm; HRMS (ESI-TOF) calcd for C$_{32}$H$_{48}$N$_2$O$_{10}$Na$^+$ [M+Na]$^+$ 643.3201, found 643.3217.

Methyl {(5S,7R,8S)-7-{(1E,3E)-5-[(2S,3S,5R,6R)-5-{[(2Z,4S)-4-acetoxypent-2-enoyl]amino}-3,6-dimethyltetrahydro-2H-pyran-2-yl]-3-methylpenta-1, 3-dien-1-yl}-8-[(methylcarbamoyl)oxy]-6-oxaspiro [2.5]oct-5-yl}acetate (37)

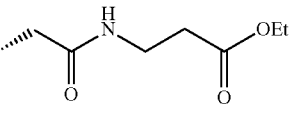

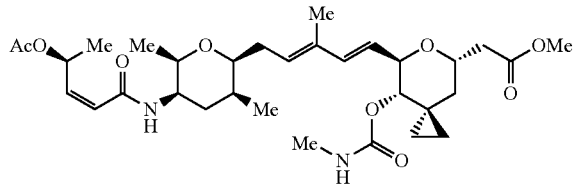

To a stirred solution of epoxide 81 (5.5 mg, 13 µmol, 1.2 equiv) and boronate 5 (4.0 mg, 9.0 µmol, 1.0 equiv) in rigorously degassed (freeze-pump-thaw technique×3) THF: H$_2$O (1.5 mL, 3:1, v/v) at 25° C. was added Pd(dppf) Cl$_2$CH$_2$Cl$_2$ (1.5 mg, 1.8 µmol, 0.2 equiv) followed by Tl$_2$CO$_3$ (21 mg, 55 µmol, 5.0 equiv). After 3 h, the reaction mixture was filtered through a layer of Celite, and rinsed thoroughly with ethyl acetate (20 mL) and the combined organic layer was concentrated in vacuo. The obtained residue was purified by flash column chromatography (silica gel, ethyl acetate), and further purified by preparative thin layer chromatography (silica gel, 5% methanol in diethyl ether) to afford pure thailanstatin A analogue 37 (2.3 mg, 3.7 µmol, 43%) as a colorless oil. 37: $R_f$=0.50 (silica gel, 5% methanol in ethyl acetate); $[\alpha]_D^{25}$=−8.7 (c=0.23, $CH_2Cl_2$); FT-IR (neat) $\nu_{max}$=3356, 2926, 2857, 1732, 1667, 1638, 1521, 1370, 1246, 1053, 1010, 972, 817 $cm^{-1}$; $^1H$ NMR (600 MHz, $CDCl_3$) δ 6.37 (d, J=15.8 Hz, 1H), 6.26 (dqd, J=7.9, 6.6, 1.2 Hz, 1H), 6.00 (d, J=9.1 Hz, 1H), 5.89 (dd, J=11.6, 7.9 Hz, 1H), 5.71 (dd, J=11.6, 1.3 Hz, 1H), 5.58-5.49 (m, 2H), 4.77 (d, J=5.4 Hz, 1H), 4.61 (d, J=5.3 Hz, 1H), 4.53 (d, J=3.7 Hz, 1H), 4.47-4.39 (m, 1H), 3.95 (ddt, J=9.1, 4.5, 2.4 Hz, 1H), 3.70 (s, 3H), 3.67 (tt, J=6.4, 3.5 Hz, 1H), 3.54 (td, J=7.2, 2.7 Hz, 1H), 2.82-2.77 (m, 5H), 2.73 (d, J=4.7 Hz, 1H), 2.56 (dd, J=15.5, 5.6 Hz, 1H), 2.39 (dt, J=14.5, 7.0 Hz, 1H), 2.24 (dt, J=15.1, 7.4 Hz, 1H), 2.09-2.06 (m, 1H), 2.04 (s, 3H), 2.00-1.97 (m, 1H), 1.96-1.92 (m, 1H), 1.79-1.76 (m, 1H), 1.74 (s, 3H), 1.56 (d, J=12.1 Hz, 1H), 1.39 (d, J=6.5 Hz, 3H), 1.16 (d, J=6.4 Hz, 3H), 1.02 (d, J=7.3 Hz, 3H) ppm; $^{13}C$ NMR (151 MHz, $CDCl_3$) δ 171.3, 170.5, 165.0, 156.3, 143.8, 138.9, 134.5, 129.8, 122.7, 120.9, 80.9, 76.1, 74.0, 69.0, 67.9, 55.7, 52.3, 52.0, 47.3, 40.0, 36.0, 34.8, 32.2, 29.1, 27.7, 21.4, 20.1, 18.0, 15.2, 12.8 ppm; HRMS (ESI-TOF) calcd for $C_{31}H_{47}N_2O_{10}^+$ $[M+H]^+$ 607.3225, found 607.3231.

(2S,3Z)-5-{[(2R,3R,5S,6S)-6-{(2E,4E)-5-[(3R,4R,5R,7R)-4-Hydroxy-7-methyl-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (39)

39

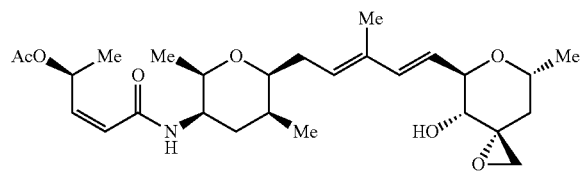

To a stirred solution of epoxide 86 (4.3 mg, 0.014 mmol, 1.3 equiv) and boronate 5 (5.0 mg, 11 µmol, 1.0 equiv) in rigorously degassed (freeze-pump-thaw technique×3) THF: $H_2O$ (1.5 mL, 3:1, v/v) at 25° C. was added Pd(dppf) $Cl_2CH_2Cl_2$ (2.0 mg, 2.2 µmol, 0.2 equiv) followed by $Tl_2CO_3$ (26 mg, 55 µmol, 5.0 equiv). After 3 h, the reaction mixture was filtered through a layer of Celite, and rinsed thoroughly with ethyl acetate (20 mL) and the combined organic layer was concentrated in vacuo. The obtained residue was purified by flash column chromatography (silica gel, 20→100% ethyl acetate in hexanes), and further purified by preparative thin layer chromatography (silica gel, 2% methanol in diethyl ether) to afford pure thailanstatin A analogue 39 (3.0 mg, 6.1 µmol, 55%) as a colorless oil. 39: $R_f$=0.40 (silica gel, 1% methanol in diethyl ether); $[\alpha]_D^{25}$=−13.2 (c=0.25, $CH_2Cl_2$); FT-IR (neat) $\nu_{max}$=3364, 2927, 2855, 1736, 1667, 1637, 1520, 1369, 1243, 1124, 1049, 973, 814 $cm^{-1}$; $^1H$ NMR (600 MHz, $CDCl_3$) δ 6.37 (d, J=15.8 Hz, 1H), 6.26 (dqd, J=7.8, 6.5, 1.3 Hz, 1H), 5.98 (d, J=9.1 Hz, 1H), 5.89 (dd, J=11.6, 7.9 Hz, 1H), 5.71 (dd, J=11.6, 1.3 Hz, 1H), 5.67 (d, J=15.8, 6.4 Hz, 1H), 5.51 (t, J=7.2 Hz, 1H), 4.28-4.19 (m, 2H), 3.94 (ddt, J=9.1, 4.5, 2.4 Hz, 1H), 3.66 (tt, J=6.4, 3.2 Hz, 1H), 3.52 (td, J=7.2, 2.7 Hz, 1H), 3.49 (dd, J=8.6, 7.1 Hz, 1H), 2.95 (d, J=4.7 Hz, 1H), 2.62 (d, J=4.6 Hz, 1H), 2.39 (dt, J=14.4, 7.0 Hz, 1H), 2.24 (dt, J=15.1, 7.5 Hz, 1H), 2.07 (dd, J=14.0, 5.0 Hz, 1H), 2.04 (s, 3H), 1.97 (dt, J=14.4, 2.4 Hz, 1H), 1.93 (dt, J=14.4, 4.9 Hz, 1H), 1.88 (d, J=8.6 Hz, 1H), 1.77 (d, J=1.2 Hz, 3H), 1.68 (dd, J=14.0, 4.5 Hz, 1H), 1.39 (dd, J=6.6, 4.2 Hz, 6H), 1.15 (d, J=6.4 Hz, 3H), 1.02 (d, J=7.4 Hz, 3H) ppm; $^{13}C$ NMR (151 MHz, $CDCl_3$) δ 170.5, 165.0, 143.8, 138.3, 134.6, 129.4, 123.6, 122.7, 81.0, 76.1, 75.2, 70.3, 69.1, 68.2, 57.5, 49.7, 47.3, 36.3, 36.0, 32.1, 29.1, 21.4, 20.1, 19.5, 18.0, 15.2, 12.8 ppm; HRMS (ESI-TOF) calcd for $C_{27}H_{41}NO_7Na^+$ $[M+Na]^+$ 514.2775, found 514.2789.

Methyl [(2S,5R,6R)-6-{(1E,3E)-5-[(2S,3S,5R,6R)-5-{[(2Z,4S)-4-acetoxypent-2-enoyl]amino}-3,6-dimethyltetrahydro-2H-pyran-2-yl]-3-methylpenta-1,3-dien-1-yl}-5-hydroxy-4-oxotetrahydro-2H-pyran-2-yl]acetate (41)

41

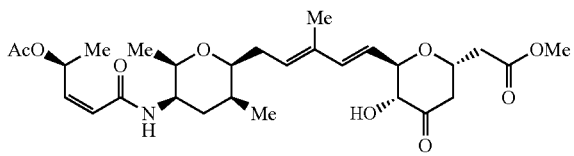

To a stirred solution of epoxide 90 (5.7 mg, 17 µmol, 1.5 equiv) and boronate 5 (5.0 mg, 11 µmol, 1.0 equiv) in rigorously degassed (freeze-pump-thaw technique×3) THF: $H_2O$ (1.5 mL, 3:1, v/v) at 25° C. was added Pd(dppf) $Cl_2.CH_2Cl_2$ (2.0 mg, 2.2 µmol, 0.2 equiv) followed by $Tl_2CO_3$ (26 mg, 55 µmol, 5.0 equiv). After 3 h, the reaction mixture was filtered through a layer of Celite, and rinsed thoroughly with ethyl acetate (20 mL) and the combined organic layer was concentrated in vacuo. The obtained residue was purified by flash column chromatography (silica gel, 20→100% ethyl acetate in hexanes), and further purified by preparative thin layer chromatography (silica gel, 1% methanol in diethyl ether) to afford pure thailanstatin A analogue 41 (2.5 mg, 4.7 µmol, 42%) as a colorless oil. 41: $R_f$=0.40 (silica gel, 1% methanol in diethyl ether); $[\alpha]_D^{25}$=−18.0 (c=0.10, $CH_2Cl_2$); FT-IR (neat) $\nu_{max}$=3370, 2930, 1734, 1668, 1518, 1439, 1370, 1317, 1244, 1109, 1052 $cm^{-1}$; $^1H$ NMR (600 MHz, $CDCl_3$) δ 6.40 (d, J=15.6 Hz, 1H), 6.29-6.24 (m, 1H), 6.01 (d, J=9.1 Hz, 1H), 5.89 (dd, J=11.6, 7.9 Hz, 1H), 5.74-5.66 (m, 2H), 5.55 (t, J=7.2 Hz, 1H), 4.90 (qd, J=7.5, 1.9 Hz, 1H), 4.06 (d, J=4.1 Hz, 2H), 3.94 (dq, J=6.8, 2.0 Hz, 1H), 3.70 (s, 3H), 3.69-3.64 (m, 1H), 3.56 (d, J=2.9 Hz, 1H), 3.52 (td, J=7.2, 2.7 Hz, 1H), 3.01 (dd, J=14.1, 7.2 Hz, 1H), 2.69 (dd, J=15.3, 7.8 Hz, 1H), 2.59 (dd, J=14.1, 1.9 Hz, 1H), 2.50 (dd, J=15.4, 7.2 Hz, 1H), 2.39 (dt, J=14.6, 7.0 Hz, 1H), 2.24 (dt, J=15.1, 7.4 Hz, 1H), 2.04 (s, 3H), 2.00-1.96 (m, 1H), 1.93 (dt, J=9.6, 4.8 Hz, 1H), 1.78 (s, 3H), 1.39 (d, J=6.5 Hz, 3H), 1.15 (d, J=6.4 Hz, 3H), 1.02 (d, J=7.3 Hz, 31-1) ppm; $^{13}C$ NMR (151 MHz, $CDCl_3$) δ 206.6, 170.5, 170.3, 165.0, 143.8, 138.4, 134.5, 130.2, 123.2, 122.7, 80.9, 78.6, 76.1, 71.6, 69.1, 52.2, 47.2, 44.1, 37.5, 36.0, 32.2, 29.2, 25.0, 21.4, 20.1, 18.0, 15.2, 12.7 ppm; HRMS (ESI-TOF) calcd for $C_{28}H_{41}NO_9Na^+$ $[M+Na]^+$ 535.6340, found.

Methyl [(5S,7R,8S)-7-{(1E,3E)-5-[(2S,3S,5R,6R)-5-{[(2Z,4S)-4-acetoxypent-2-enoyl]amino}-3,6-dimethyltetrahydro-2H-pyran-2-yl]-3-methylpenta-1,3-dien-1-yl}-8-hydroxy-6-oxaspiro[2.5]oct-5-yl]acetate (43)

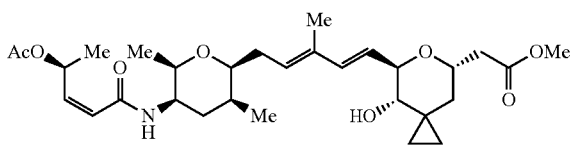

43

To a stirred solution of epoxide 77 (4.7 mg, 13 µmol, 1.2 equiv) and boronate 5 (5.0 mg, 11 µmol, 1.0 equiv) in rigorously degassed (freeze-pump-thaw technique×3) THF:H$_2$O (1.5 mL, 3:1, v/v) at 25° C. was added Pd(dppf)Cl$_2$.CH$_2$Cl$_2$ (2.0 mg, 2.2 µmol, 0.2 equiv) followed by Tl$_2$CO$_3$ (26 mg, 55 µmol, 5.0 equiv). After 3 h, the reaction mixture was filtered through a layer of Celite, and rinsed thoroughly with ethyl acetate (20 mL) and the combined organic layer was concentrated in vacuo. The obtained residue was purified by flash column chromatography (silica gel, 20→100% ethyl acetate in hexanes), and further purified by preparative thin layer chromatography (silica gel, 90% ethyl acetate in hexanes) to afford pure thailanstatin A analogue 43 (3.2 mg, 5.8 µmol, 53%) as a colorless oil. 43: R$_f$=0.40 (silica gel, 70% ethyl acetate in hexanes); [α]$_D^{25}$=−17.2 (c=0.32, CH$_2$Cl$_2$); FT-IR (neat) ν$_{max}$=3379, 2976, 2927, 2854, 1737, 1667, 1636, 1517, 1369, 1243, 1049, 976, 814 cm$^{-1}$; $^1$H NMR (600 MHz, CDCl$_3$) δ 6.34 (d, J=15.8 Hz, 1H), 6.26 (tt, J=6.5, 1.3 Hz, 1H), 6.00 (d, J=9.0 Hz, 1H), 5.89 (dd, J=11.6, 7.9 Hz, 1H), 5.76 (dd, J=15.8, 6.6 Hz, 1H), 5.71 (dd, J=11.6, 1.3 Hz, 1H), 5.50 (t, J=7.2 Hz, 1H), 4.41-4.37 (m, 1H), 4.35 (ddd, J=13.2, 7.6, 3.0 Hz, 1H), 3.98-3.91 (m, 1H), 3.69 (s, 3H), 3.67 (dd, J=6.5, 2.2 Hz, 1H), 3.54 (td, J=7.2, 2.7 Hz, 1H), 2.96 (d, J=2.8 Hz, 1H), 2.68 (dd, J=15.3, 7.7 Hz, 1H), 2.48 (dd, J=15.3, 5.7 Hz, 1H), 2.40 (dt, J=14.3, 6.9 Hz, 1H), 2.25 (dt, J=15.2, 7.6 Hz, 1H), 2.04 (s, 4H), 2.00-1.92 (m, 4H), 1.81-1.76 (m, 4H), 1.39 (d, J=6.5 Hz, 3H), 1.16 (d, J=6.4 Hz, 3H), 1.02 (d, J=7.4 Hz, 3H), 0.62-0.53 (m, 2H), 0.50 (ddd, J=9.7, 5.2, 4.0 Hz, 1H), 0.34-0.30 (m, 1H) ppm; $^{13}$C NMR (151 MHz, CDCl$_3$) δ 171.8, 170.5, 165.0, 143.8, 138.2, 134.8, 129.1, 122.7, 122.6, 80.9, 79.6, 76.1, 75.2, 69.1, 67.1, 51.9, 47.3, 40.3, 36.0, 35.8, 32.2, 29.1, 21.4, 20.1, 18.8, 18.0, 15.2, 12.8, 11.3, 8.9 ppm; HRMS (ESI-TOF) calcd for C$_{30}$H$_{45}$NO$_8$Na$^+$ [M+Na]$^+$ 570.3037, found 570.3042.

Methyl [(3R,5S,7R,8R)-8-acetoxy-7-{(1E,3E)-5-[(2S,3S,5R,6R)-5-{[(2Z,4S)-4-acetoxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (45)

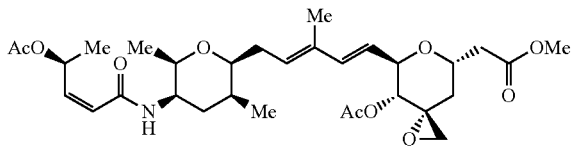 [SMILES: COC(=O)C[C@@H]1C[C@@]2(CO2)[C@H](O)[C@@H](/C=C/C(C)=C/C[C@@H]2O[C@H](C)[C@H](NC(=O)/C=C\[C@H](C)OC(C)=O)C[C@@H]2C)O1]

45

To a stirred solution of epoxide 82 (5.2 mg, 13 µmol, 1.2 equiv) and boronate 5 (5.0 mg, 11 µmol, 1.0 equiv) in rigorously degassed (freeze-pump-thaw technique×3) THF:H$_2$O (1.5 mL, 3:1, v/v) at 25° C. was added Pd(dppf)Cl$_2$.CH$_2$Cl$_2$ (2.0 mg, 2.2 µmol, 0.2 equiv) followed by Tl$_2$CO$_3$ (26 mg, 55 µmol, 5.0 equiv). After 3 h, the reaction mixture was filtered through a layer of Celite, and rinsed thoroughly with ethyl acetate (20 mL) and the combined organic layer was concentrated in vacuo. The obtained residue was purified by flash column chromatography (silica gel, 20→80% ethyl acetate in hexanes), and further purified by preparative thin layer chromatography (silica gel, 45% diethyl ether in dichloromethane) to afford pure thailanstatin A analogue 45 (3.9 mg, 6.6 µmol, 59%) as a colorless oil. 45: R$_f$=0.40 (silica gel, 30% diethyl ether in dichloromethane); [α]$_D^{25}$=−17.9 (c=0.39, CH$_2$Cl$_2$); FT-IR (neat) ν$_{max}$=2973, 2927, 2857, 1737, 1669, 1641, 1515, 1371, 1240, 1162, 1049, 1029, 815 cm$^{-1}$; $^1$H NMR (600 MHz, CDCl$_3$) δ 6.37 (d, J=15.8 Hz, 1H), 6.25 (ddd, J=7.8, 6.5, 1.3 Hz, 1H), 6.00 (d, J=9.1 Hz, 1H), 5.89 (dd, J=11.6, 7.9 Hz, 1H), 5.71 (dd, J=11.6, 1.3 Hz, 1H), 5.57-5.50 (m, 2H), 4.60 (d, J=4.0 Hz, 2H), 4.49-4.38 (m, 1H), 4.01-3.91 (m, 1H), 3.71 (s, 3H), 3.70-3.64 (m, 1H), 3.54 (td, J=7.2, 2.7 Hz, 1H), 2.81-2.74 (m, 3H), 2.56 (dd, J=15.6, 5.4 Hz, 1H), 2.39 (dt, J=14.5, 7.0 Hz, 1H), 2.25 (dt, J=15.1, 7.4 Hz, 1H), 2.17-2.13 (m, 1H), 2.12 (s, 3H), 2.04 (s, 3H), 2.01-1.97 (m, 1H), 1.97-1.91 (m, 1H), 1.78 (ddd, J=7.7, 5.1, 2.5 Hz, 1H), 1.74 (s, 3H), 1.51 (dd, J=13.1, 3.2 Hz, 1H), 1.39 (d, J=6.5 Hz, 3H), 1.16 (d, J=6.4 Hz, 3H), 1.02 (d, J=7.3 Hz, 3H) ppm; $^{13}$C NMR (151 MHz, CDCl$_3$) δ 171.2, 170.4 (2C), 143.6, 138.8, 134.3, 130.0, 122.5, 120.5, 80.7, 77.1, 76.7, 76.0, 73.7, 68.9, 67.7, 55.3, 52.3, 51.8 (2C), 47.1, 40.0, 35.9, 34.6, 32.0, 29.0, 21.3, 21.1, 20.0, 17.8, 15.1, 12.6 ppm; HRMS (ESI-TOF) calcd for C$_{31}$H$_{45}$NO$_{10}$Na$^+$ [M+Na]$^+$ 614.2936, found 614.2944.

Example 4

NMR Spectascopic Comparison of Synthetic and Natural Thailanstatin A

Tables 1-2 show the comparison of the $^1$H (Table 1) and $^{13}$C (Table 2) NMR spectra for natural and synthetic thailanstatin A.

TABLE 1

Comparison of $^1$H NMR spectroscopic data of natural and synthetic thailanstatin A (1)

| position | reported natural (Liu, et al., 2013) δ $^1$H [ppm; mult; J (Hz)] 600 MHz | synthetic δ $^1$H [ppm; mult; J (Hz)] 600 MHz | deviation (natural-synthetic) Δδ (ppm)[a] |
|---|---|---|---|
| 1 | 4.51; m | 4.46, m | 0.05 |
| 2[b] | 2.12; d; (not reported) | 2.05; dd; 14.0, 5.0 | 0.07 |
|  | 1.80; m | 1.79; dd; 14.0, 5.1 | 0.01 |
| 4 | 3.51; d; 7.3 | 3.48; d; 6.7 | 0.03 |
| 5 | 4.27; t; 6.3 | 4.25; dd; 6.4, 6.4 | 0.02 |
| 6 | 5.66; dd; 16.0, 6.0 | 5.62; dd; 15.8, 6.2 | 0.04 |
| 7 | 6.37; d; 16.0 | 6.36; d; 15.8 | 0.01 |
| 9 | 5.48; t; 7.0 | 5.51; dd; 7.0, 7.0 | −0.03 |
| 10 | 2.38; m | 2.36; m | 0.02 |
|  | 2.24; m | 2.22; m | 0.02 |
| 11 | 3.59; td; 7.4, 2.5 | 3.55; ddd; 7.2, 7.2, 2.7 | 0.04 |
| 12 | 1.78 (overlap) | 1.77; m (overlap) | 0.01 |
| 13 | 1.95; m | 1.93; m | 0.02 |
| 14 | 3.92; m | 3.90; m | 0.02 |
| 15 | 3.74; qd; 6.5, 2.0 | 3.68; qd; 6.5, 2.2 | 0.06 |
| 16 | 1.16; d; 6.5 | 1.12; d; 6.5 | 0.04 |
| 17[b] | 3.02; dd; 15.0, 9.0 | 2.95; dd; 15.6, 9.0 | 0.07 |
|  | 2.60; dd; 15.0, 5.0 | 2.62; dd; 15.6, 5.2 | 0.02 |
| 19 | 2.99; d; 4.6 | 2.95; d; 4.6 | 0.04 |
|  | 2.67; d; 4.5 | 2.65; d; 4.6 | 0.02 |
| 20 | 1.77; s | 1.76; s | 0.01 |
| 21 | 1.01; d; 7.3 | 1.00; d; 7.4 | 0.01 |
| 2' | 5.84; dd; 11.6, 1.0 | 5.75; dd; 11.6, 1.2 | 0.09 |
| 3' | 5.95; dd; 11.6, 8.0 | 5.90; dd; 11.6, 7.8 | 0.05 |
| 4' | 6.33; m | 6.27, m | 0.06 |
| 5' | 1.36; d; 6.5 | 1.34; d; 6.5 | 0.02 |
| 2" | 2.06; s | 2.01; s | 0.05 |
| NH[c] | 6.69; d; 8.7 | 6.24; d; 9.0 | 0.45 |

[a]These deviations may be partly due to the fact that the chemical shifts of the reported $^1$H NMR signals were based on a slightly different calibration (δH = 5.36 for CHDCl$_2$, see Liu, et al., 2013) than the one used in this work (δH = 5.32 for CHDCl$_2$, see Fulmer, et al., 2010).
[b]The chemical shifts (δ) for the $^{13}$C NMR signals at these positions appear to have been inadvertently interchanged in the original report (Fulmer, et al., 2010).
[c]Two hydroxy groups were not oberservable in the $^1$H NMR spectrum.

TABLE 2

Comparison of $^{13}$C NMR spectroscopic data of natural and synthetic thailanstatin A (1)

| position | reported natural (Liu, et al., 2013) δ $^{13}$C [ppm] 151 MHz | Synthetic δ $^{13}$C [ppm] 151 MHz | deviation (natural-synthetic) Δδ (ppm)[a] |
|---|---|---|---|
| 1 | 68.6 | 69.0 | −0.4 |
| 2[b] | 34.4 | 34.8 | −0.4 |
| 3 | 57.1 | 57.5 | −0.4 |
| 4 | 70.1 | 70.5 | −0.4 |

TABLE 2-continued

Comparison of $^{13}C$ NMR spectroscopic data of natural and synthetic thailanstatin A (1)

| position | reported natural (Liu, et al., 2013) δ $^{13}C$ [ppm] 151 MHz | Synthetic δ $^{13}C$ [ppm] 151 MHz | deviation (natural-synthetic) Δδ (ppm)[a] |
|---|---|---|---|
| 5 | 75.9 | 76.5 | −0.6 |
| 6 | 123.0 | 123.2 | −0.2 |
| 7 | 138.0 | 138.6 | −0.6 |
| 8 | 134.5 | 134.9 | −0.4 |
| 9 | 129.4 | 130.1 | −0.7 |
| 10 | 31.8 | 32.3 | −0.5 |
| 11 | 81.1 | 81.4 | −0.3 |
| 12 | 29.1 | 29.5 | −0.4 |
| 13 | 35.7 | 36.2 | −0.5 |
| 14 | 47.0 | 47.4 | −0.4 |
| 15 | 76.2 | 76.6 | −0.4 |
| 16 | 17.4 | 17.9 | −0.5 |
| 17[b] | 38.1 | 38.3 | −0.2 |
| 18 | 173.8 | 173.3 | −0.5 |
| 19 | 49.9 | 50.4 | −0.5 |
| 20 | 12.3 | 12.7 | −0.4 |
| 21 | 14.7 | 15.2 | −0.5 |
| 1' | 164.9 | 165.1 | −0.2 |
| 2' | 122.4 | 122.8 | −0.4 |
| 3' | 143.6 | 144.0 | −0.4 |
| 4' | 68.6 | 69.0 | −0.4 |
| 5' | 19.8 | 20.2 | −0.4 |
| 1" | 170.3 | 170.7 | −0.4 |
| 2" | 21.0 | 21.4 | −0.4 |

[a]These deviations may be partly due to the fact that the chemical shifts of the reported $^1H$ NMR signals were based on a slightly different calibration (δc = 53.44 for CHDCl$_2$, see Liu, et al., 2013) than the one used in this work (δc = 53.84) for CHDCl$_2$, see Fulmer, et al., 2010).
[b]The chemical shifts (δ) for the $^{13}C$ NMR signals at these positions appear to have been inadvertently interchanged in the original report (Fulmer, et al., 2010)

Example 5

Biological Activity

Table 3 shows the cytotoxicity data for the thailanstatin analogs described above. The related 72 hour killing assays can be found in FIG. 3.

TABLE 3

Cytotoxicity Data against the Cancer Cell Lines MES SA, MES SA DX, and HEK 293T for Thailanstatin A Analogues.

| | Cancer cell lines IC$_{50}$ (nM)[a] | | |
|---|---|---|---|
| Compound | MES SA[b] | MES SA DX[c] | HEK 293T[d] |
| MMAE | 0.096 | 88.2 | 0.068 |
| NAC | 0.364 | 15.3 | 0.166 |
| paclitaxel | 2.47 | >400 | 1.76 |
| 1 | 419 | >400 | 296 |
| 2 | 0.32 | 3.60 | 0.36 |
| 30 | >1000 | >1000 | >1000 |
| 31 | 1.04 | 105 | 0.739 |
| 32 | >1000 | >1000 | >1000 |
| 33 | 512 | >2500 | 1477 |
| 34 | 649 | >1000 | >1000 |
| 35 | 6.90 | 261 | 2.20 |
| 36 | 0.92 | 1.09 | 0.08 |
| 37 | — | — | — |
| 38 | >2500 | >2500 | >400 |
| 39 | — | — | — |
| 40 | >2500 | >2500 | >400 |
| 41 | — | — | — |
| 42 | 3.68 | 3.45 | 0.24 |
| 43 | >2500 | >2500 | 88.3 |
| 44 | 2.66 | 3.71 | 0.15 |
| 45 | 6.82 | 6.73 | 0.58 |
| 46 | >1000 | >1000 | >1000 |
| 47 | >1000 | >1000 | >1000 |

[a]IC$_{50}$ is the 50% inhibitory concentration of the compound against cell growth.
[b]Human uterine sarcoma cell line.
[c]MES SA cell line with marked multidrug resistance.
[d]Human embryonic kidney cancer cell line.
These data were obtained at Abbvie Stemcentrx. The highlighted background rows highlight notably potent compounds.

i. Cytotoxicity Assay.

Cells were cultured in a T75 flask to ~50-80% confluency and harvested with trypsin into a single cell suspension. Five hundred (500) cells per well were seeded in tissue culture plates in 50 µL/well culture media and incubated at 37° C. for 18-24 h. Compounds were diluted as 400× final desired concentrations in DMSO. Serial dilutions in DMSO were then diluted in culture media for a final DMSO concentration of 0.25% and 50 µL/well of the final dilution was added to the cells (Vf=100 µL). Upon plating and treatment, cells were returned to the incubator for an additional 72 hours. CellTiter-Glo reagent was prepared per manufacturer's instructions and added at 100 µL/well to the cultures. CellTiter-Glo allows for relative enumeration of metabolically active cells by quantifying intracellular ATP concentrations. After 5 minutes of incubation with CellTiter-Glo at ambient room temperature, 125 µL/well of the Cell Titer glo/cell lysate solution was transferred into black assay plates, which were then read in a luminometer within 30 minutes. Luminescence readings obtained from cultures that did not receive any treatment (cell culture media only) were set as 100% control and all other luminescence values were normalized to these controls (e.g., Normalized RLU, relative luminescence unit).

ii. Cell Lines Used in the Assay

MES SA and MES SA/Dx cells are uterine sarcoma. MES SA Dx cell line was generated from MES SA to achieve upregulation of MDR1. MES-SA/Dx cells exhibit marked cross-resistance to a number of chemotherapeutic agents (including daunorubicin, dactinomycin, vincristine, taxol, colchicine) and moderate cross-resistance to mitomycin C and melphalan.

293T cells are human embryonic kidney cell line.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference:

U.S. Patent Publication No. 2004/0005647
U.S. Patent Publication No. 2006/0034925
U.S. Patent Publication No. 2006/0115537
U.S. Patent Publication No. 2006/0223114
U.S. Patent Publication No. 2006/0234299
U.S. Patent Publication No. 2007/0148095
U.S. Patent Publication No. 2012/0141550
U.S. Patent Publication No. 2013/0138032
U.S. Patent Publication No. 2014/0024610
U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 6,232,287
U.S. Pat. No. 6,528,481
U.S. Pat. No. 7,452,964
U.S. Pat. No. 7,671,010
U.S. Pat. No. 7,781,565
U.S. Pat. No. 8,507,445
U.S. Pat. No. 8,450,278
PCT Publication No. 2008/121949
PCT Publication No. 2011/053435
PCT Publication No. 2014/087413
Albert, et al., *J. Am. Chem. Soc.*, 128:2792, 2006.
Albert, et al., *J. Am. Chem. Soc.*, 129:2648-2659, 2007.
Anderson, N. G., *Practical Process Research & Development—A Guide For Organic Chemists*, $2^{nd}$ ed., Academic Press, New York, 2012.
Austin-Ward and Villaseca, *Rev. Med. Chil.*, 126:838-845, 1998.
Barclay et al. (eds.), The Leucocyte Antigen Facts Book, 1993, Academic Press.
Bukowski et al., *Clin. Cancer Res.*, 4:2337-2347, 1998.
Burkly et al.: TWEAKing tissue remodeling by a multifunctional cytokine: role of TWEAK/Fn14 pathway in health and disease. *Cytokine* 40: 1-16, 2007.
Campbell et al., *Cancer Res.*, 51:5329-5338 1991.
Chen, et al., *Tetrahedron Lett.*, 35:2827, 1994.
Christodoulides et al., *Microbiology*, 144:3027-3037, 1998.
Davidson et al., *J. Immunother.*, 21:389-398, 1998.
Deuri and Phukan, *J. Phys. Org. Chem.*, 25:1228, 2012.
Dondoni and Perrone, *Org. Synth.*, 77:320, 2004.
Frank, et al., *Org. Lett.*, 2:2691, 2000.
Fujiwara and Hayashi, *J. Org. Chem.*, 73:9161-9163, 2008.
Fulmer, et al., *Organometallics*, 29:2176, 2010.
Hanibuchi et al., *Int. J. Cancer*, 78:480-485, 1998.
He, et al., *J. Nat. Prod.*, 77:1864-1870, 2014.
Helfrich and Piel, *Nat. Prod. Rep.*, 33:231, 2016.
Hellstrand et al., *Acta Oncol.*, 37:347-353, 1998.
Huang and Negishi, *Org. Lett.*, 8:3675, 2008.
Hui and Hashimoto, *Infect. Immun.*, 66:5329-5336, 1998.
Itoh, et al., *J. Am. Chem. Soc.*, 101:159, 1979.
Johnson and Kadow, *J. Org. Chem.*, 52:1493, 1987.
Ju et al., *Gene Ther.*, 7:1672-1679, 2000.
Lee, et al., *Org. Lett.*, 13:2722, 2011.
Lightfoot, et al., *Angew. Chem. Int. Ed.*, 37:2897, 1998.
Liu, et al., *J. Nat. Prod.*, 76:685-693, 2013.
*March's Advanced Organic Chemistry: Reactions, Mechanisms, and Structure*, 2007.
Mitchell et al., *Ann. N.Y. Acad. Sci.*, 690:153-166, 1993.
Mitchell et al., *J. Clin. Oncol.*, 8:856-869, 1990.
Morton et al., *Arch. Surg.*, 127:392-399, 1992.
Nechushtan et al., *J. Biol. Chem.*, 272(17):11597-11603, 1997
Nicolaou et al. *J. Am. Chem. Soc.* 138:7532-7535, 2016.
Nising and Bräse, *Chem. Soc. Rev.*, 37:1218, 2008.
Nising and Bräse, *Chem. Soc. Rev.*, 41:988, 2012.
Onda et al., *Cancer Res.*, 64:1419-1424, 2004.
Osman, et al., *Chem. Eur. J.*, 17:895-904, 2011.
Pietras et al., *Oncogene*, 17:2235-49, 1998.
Pilli, et al., *J. Org. Chem.*, 63:7811, 1998.
Qin et al., *Proc. Natl. Acad. Sci. USA*, 95:14411-14416, 1998.
Ravindranath and Morton, *Intern. Rev. Immunol.*, 7: 303-329, 1991.
Remington's Pharmaceutical Sciences, $15^{th}$ Ed., 1035-1038 and 1570-1580, 1990.
Remington's Pharmaceutical Sciences, $15^{th}$ Ed., 3:624-652, 1990.
Rosenberg et al., *Ann. Surg.* 210:474-548, 1989.
Rosenberg et al., *N. Engl. J. Med.*, 319:1676, 1988.

Stork and Zhao, *Tetrahedron Lett.*, 30:2173, 1989.
Takai, et al., *J. Am. Chem. Soc.*, 108:7408, 1986.
Thompson (ed.), 1994, The Cytokine Handbook, Academic Press, San Diego.
Trost, *Angew. Chem. Int. Ed.*, 34:259, 1995.
Weitman et al., *Cancer Res.*, 52:3396-3401, 1992b.
Weitman et al., *Cancer Res.*, 52:6708-6711, 1992a.
Winkles, *Nat. Rev. Drug Discov.*, 7:411-425, 2008.
Winthrop et al., *Clin. Cancer Res.*, 9:3845s-3853s, 2003.
Zhou, *Mol. Cancer Ther.*, 10:1276-1288, 2011.
What is claimed:
1. A compound further defined as:
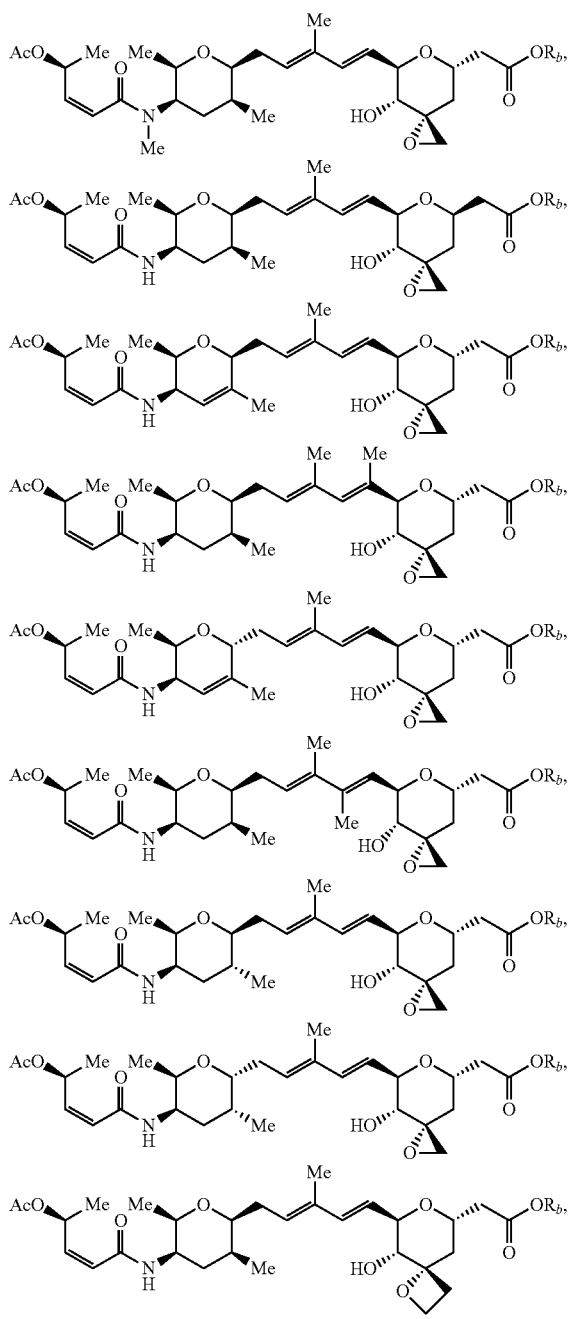
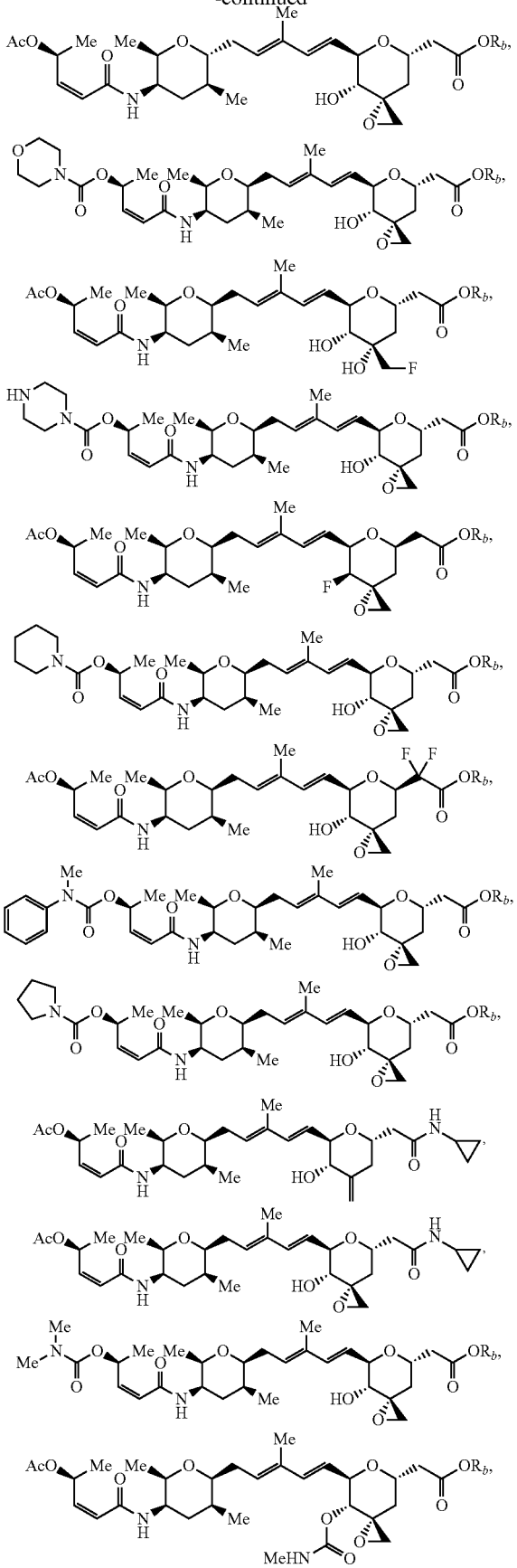

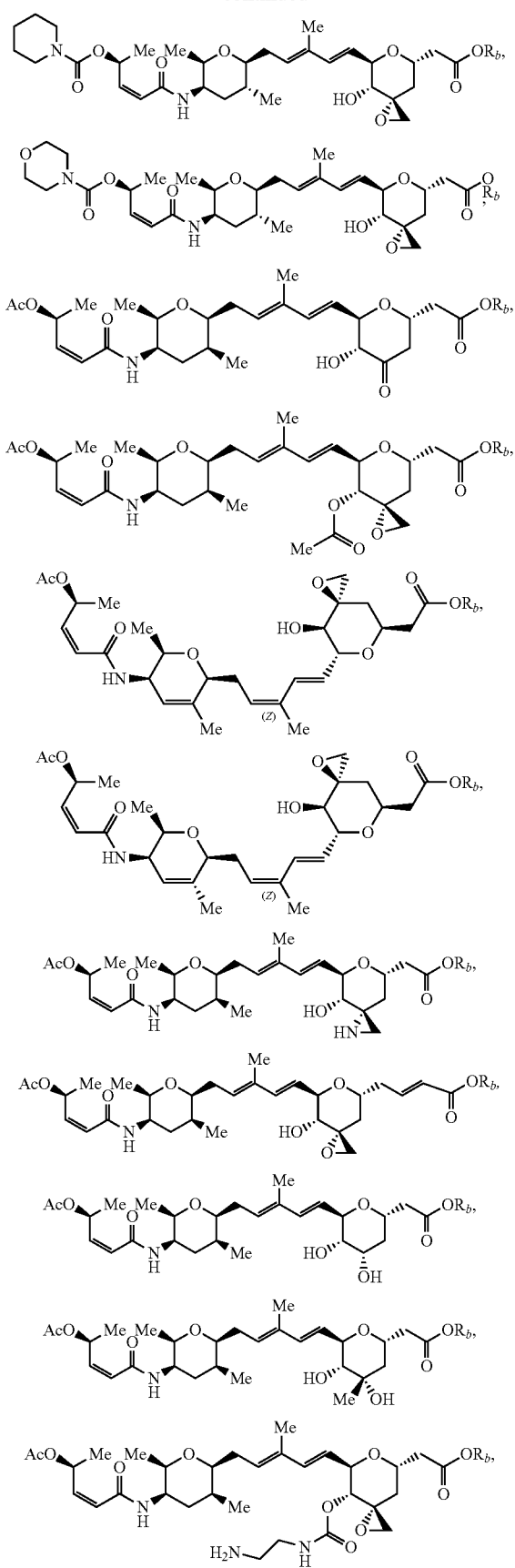
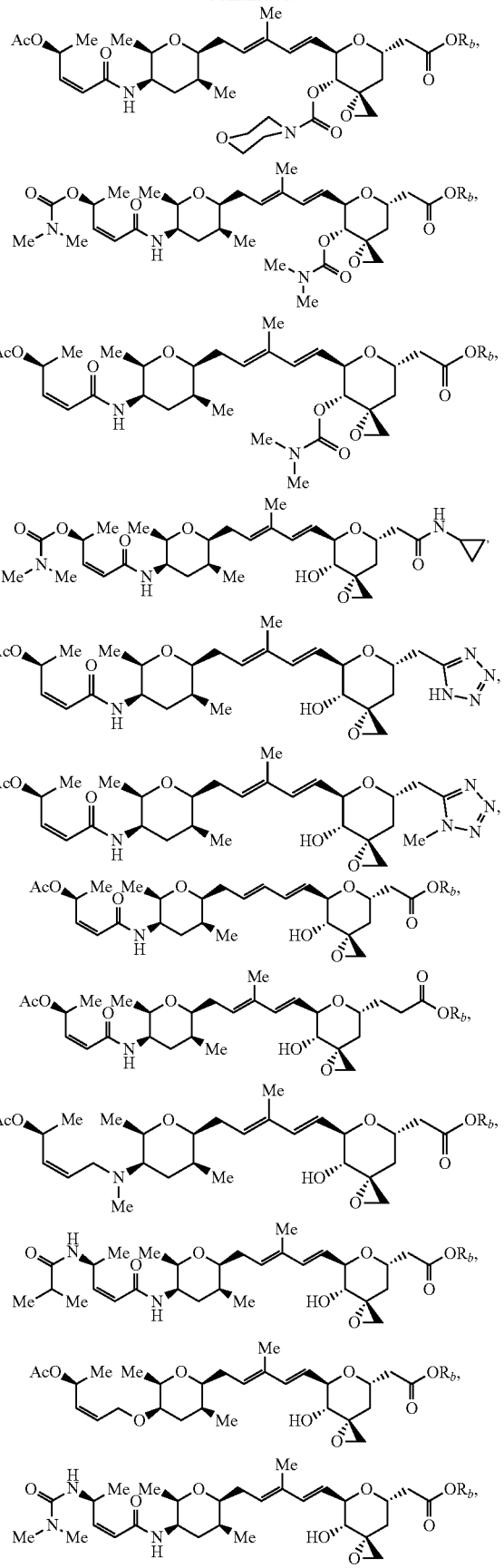

-continued

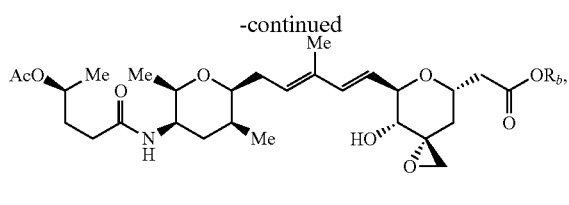

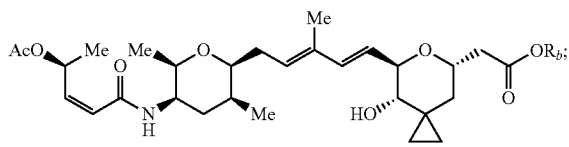

wherein:

$R_b$ is alkyl$_{(C≤6)}$, substituted alkyl$_{(C≤6)}$, aryl$_{(C≤8)}$, aralkyl$_{(C≤6)}$, or substituted aralkyl$_{(C≤6)}$;

provided that the compound is not:

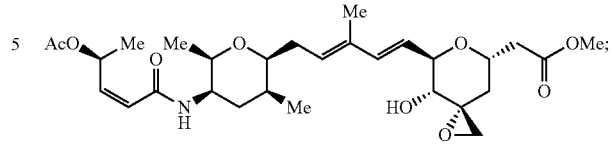

or a pharmaceutically acceptable salt thereof.

2. A cell targeting linked composition comprising:
(a) a compound of claim 1;
(b) a cell targeting moiety;
wherein the cell targeting moiety is linked to the compound.

3. A pharmaceutical composition comprising:
(a) a compound of claim 1; and
(b) a pharmaceutically acceptable carrier.

4. A method of treating a disease or disorder in a patient comprising administering to the patient in need thereof a therapeutically effective amount of a compound or composition of claim of claim 1, wherein the disease or disorder is cancer.

* * * * *